(12) United States Patent
Johnson et al.

(10) Patent No.: US 11,390,621 B2
(45) Date of Patent: Jul. 19, 2022

(54) CHIRAL INDOLE COMPOUNDS AND THEIR USE

(71) Applicant: ARIAGEN, INC., Menlo Park, CA (US)

(72) Inventors: Graham Johnson, Sanbornton, NH (US); Peter Colabuono, Half Moon Bay, CA (US); Paul Gerard Pearson, Westlake Village, CA (US); David Douglas Manning, Orchard Park, NY (US)

(73) Assignee: ARIAGEN, INC., Menlo Park, CA (US)

( * ) Notice: Subject to any disclaimer, the term of this patent is extended or adjusted under 35 U.S.C. 154(b) by 0 days.

(21) Appl. No.: 17/179,323

(22) Filed: Feb. 18, 2021

(65) Prior Publication Data

US 2021/0188834 A1 Jun. 24, 2021

Related U.S. Application Data

(63) Continuation of application No. PCT/US2020/028371, filed on Apr. 15, 2020.

(60) Provisional application No. 62/834,140, filed on Apr. 15, 2019, provisional application No. 62/861,123, filed on Jun. 13, 2019.

(51) Int. Cl.
    *C07D 417/06* (2006.01)

(52) U.S. Cl.
    CPC .................. *C07D 417/06* (2013.01)

(58) Field of Classification Search
    CPC ................................. C07D 417/06
    USPC ....................................... 514/365
    See application file for complete search history.

(56) References Cited

U.S. PATENT DOCUMENTS

| | | | |
|---|---|---|---|
| 3,946,029 A | 3/1976 | Descamps et al. | |
| 4,046,774 A | 9/1977 | Napier | |
| 6,916,834 B2 | 7/2005 | DeLuca et al. | |
| 7,002,019 B2 | 2/2006 | DeLuca et al. | |
| 7,419,992 B2 | 9/2008 | DeLuca et al. | |
| 9,205,148 B2 | 12/2015 | Langermann et al. | |
| 2002/0177594 A1 | 11/2002 | Curtin et al. | |
| 2002/0183524 A1 | 12/2002 | DeLuca et al. | |
| 2007/0043092 A1 | 2/2007 | DeLuca et al. | |
| 2008/0221070 A1 | 9/2008 | William et al. | |
| 2010/0197708 A1 | 8/2010 | Talley et al. | |
| 2012/0214853 A1 | 8/2012 | Song | |
| 2013/0338201 A1 | 12/2013 | Song | |
| 2020/0354353 A1* | 11/2020 | Colabuono | C07D 209/12 |

FOREIGN PATENT DOCUMENTS

| | | |
|---|---|---|
| EP | 1842541 A1 | 3/2006 |
| GB | 1318300 | 5/1973 |
| WO | WO 1998/039330 | 9/1998 |
| WO | WO 2002/028832 | 4/2002 |
| WO | WO 2002/064138 | 8/2002 |
| WO | WO 2003/068742 | 8/2003 |
| WO | WO 2003/105847 | 12/2003 |
| WO | WO 2004/060888 | 7/2004 |
| WO | WO 2006/029862 | 3/2006 |
| WO | WO 2008/019357 | 2/2008 |
| WO | WO 2009/067349 | 5/2009 |
| WO | WO 2009/070645 | 6/2009 |
| WO | WO 2009/117597 | 9/2009 |
| WO | WO 2010/089327 | 8/2010 |
| WO | WO2011/053466 | 5/2011 |
| WO | WO 2012/015914 | 2/2012 |
| WO | WO 2012/145493 | 10/2012 |
| WO | WO 2013/033003 | 3/2013 |
| WO | WO 2013/041468 | 3/2013 |
| WO | WO 2013/116182 | 8/2013 |
| WO | WO2013/163279 | 10/2013 |
| WO | WO 2015/035606 | 3/2015 |
| WO | WO 2015/112800 | 7/2015 |
| WO | WO 2015/112900 | 7/2015 |
| WO | WO2015/131035 | 9/2015 |
| WO | WO2016/023106 | 2/2016 |
| WO | WO2016/040553 | 3/2016 |
| WO | WO 2016/092419 | 6/2016 |
| WO | WO2018/085348 | 5/2018 |
| WO | WO 2018/120009 | 7/2018 |
| WO | WO2018/121434 | 7/2018 |
| WO | WO 2018/153893 | 8/2018 |
| WO | WO 2019/057744 | 3/2019 |
| WO | WO 2019/099977 | 5/2019 |

OTHER PUBLICATIONS

Patani et al., "Bioisosterism: A Rational, etc.," Chem. Rev.,95, 3147-3176. (Year: 1996).*
Fuganti et al., "A general method for the synthesis of the most powerful naturally occurring Maillard flavors," Tetrahedron 63:4762-4767 (2007).
Ishida et al., "Activation of the aryl hydrocarbon receptor pathway enhances cancer cell invasion by upregulating the MMP expression and is associated with poor prognosis in upper urinary tract urothelial cancer," Carcinogenesis 31(2):287-295 (2010).
Ramanjulu et al., "Design of amidobenzimidazole STING receptor agonists with systemic activity," Nature 564(7736):439-443 (2018).
Yoshida et al., "Effects of AhR ligands on the production of immunoglobulins in purified mouse B cells," Biomedical Research 33:67-74 (2012).
Zhang et al., "A Simple Statistical Parameter for Use in Evaluation and Validation of High Throughput Screening Assays," J Biomol Screen 4(2):67-73 (1999).
Zhang et al., "A tryptophan derivative, ITE, enhances liver cell metabolic functions in vitro," Int J Mol Med. 39(1): 101-112(2017).
Akahoshi et al., "Synthesis, structure-activity relationships, and pharmacokinetic profiles of nonpeptidic α-Keto Heterocycles as novel inhibitors of human chymase," J. Med. Chem. 44:1286-1296 (2001).

(Continued)

*Primary Examiner* — Nizal S Chandrakumar

(74) *Attorney, Agent, or Firm* — Steptoe & Johnson LLP

(57) ABSTRACT

The present disclosure relates to indole compounds and pharmaceutical compositions thereof, and their use in stimulating the immune system of patients in need thereof and in treating cancer.

20 Claims, 27 Drawing Sheets

(56) References Cited

OTHER PUBLICATIONS

Alarma-Estrany et al., "Design of novel melatonin analogs for the reduction of intraocular pressure in normotensive rabbits," J Pharmacol Exp Ther 337(3):703-9 (2011).

Bankoti et al., "Functional and phenotypic effects of AhR activation in inflammatory dendritic cells," Toxicol Appl Pharmacol 246:18-28 (2010).

Baud'Huin et al., "Factor VIII-von Willebrand factor complex inhibits osteoclastogenesis and controls cell survival," J Biol Chem. 284(46):31704-13(2009).

Bermúdez et al., "Beta-naphthoflavone represses dystrophin Dp71 expression in hepatic cells," Biochim. Biophys. Acta. 1759(3-4):152-158 (2006).

Bock et al., "Ah receptor- and TCDD-mediated liver tumor promotion: clonal selection and expansion of cells evading growth arrest and apoptosis," Biochem. Pharmacol. 69(10):1403-1408 (2005).

Boldron et al., "N-[6-(4-Butanoyl-5-methyl-1H-pyrazol-1-yl) pyridazin-3-yl]-5-chloro-1-[2-(4-methylpiperazin-1-yl)-2-oxoethyl]-1H-indole-3-carboxamide (SAR216471), a Novel Intravenous and Oral, Reversible, and Directly Acting P2Y12 Antagonist," Journal of Medical Chemistry 57(17):7293-7316 (2014).

Brauze et al., "The effect of aryl hydrocarbon receptor ligands on the expression of AhR, AhRR, ARNT, Hif1alpha, CYP1A1 and NQO1 genes in rat liver," Toxicol. Lett. 167(3):212-220 (2006).

Brozic et al., "Selective inhibitors of aldo-keto reductases AKR1C1 and AKR1C3 discovered by virtual screening of a fragment library," J. Med. Chem 55(17):7417-24 (2012).

Cavalluzzo et al., "De novo design of small molecule inhibitors targeting the LEDGF/P75-HIV integrase interaction," RSC Advances 2:974-984 (2012).

Cheng et al., "Tryptophan derivatives regulate the transcription of Oct4 in stem-like cancer cells." Nat Commun 6:7209 (2015).

Cook et al., "Angiogenesis Inhibitors: Current Strategies and Future Prospects," http://cajournal.org (2010).

Crestey et al., "Design and synthesis of a new indazole library: direct conversion of N-methoxy-N-methylamides (Weinreb amides) to 3-keto and 3-formylindazoles," Tetrahedron 63(2):419-428 (2007).

Dickson et al., "Rapid synthesis of indole cis-enamides via hydroamidation of indolic alkynes," Tetrahed Letts 54(38):5239-42 (2013).

Dietrich et al., "The aryl hydrocarbon receptor (AhR) in the regulation of cell-cell contact and tumor growth," Carcinogenesis 31(8):1319-1328 (2010).

Dolciami et al., "Binding Mode and Structure-Activity Relationships of ITE as Aryl Hydrocarbon Receptor (AhR) Agonist," ChemMedChem 13(3):270-279 (2018).

Dorbritsa et al., "Development of a High-Throughput Cell-Based Assay for Identifcation of IL-17 Inhibitors," Journal of Biomolecular Screening 18(1):75-84 (2013).

Duarte et al., "Differential influences of the aryl hydrocarbon receptor on Th17 mediated responses in vitro and in vivo," PLoS One 8:e79819 (2013).

Ebos et al., "Accelerated metastasis after short-term treatment with a potent inhibitor of tumor angiogenesis," Cancer Cell 15(3):232-239 (2009).

Elizondo et al., "Altered cell cycle control at the G(2)/M phases in aryl hydrocarbon receptor-null embryo fibroblast," Mol Pharmacol 57(5):1056-63 (2000).

Ellis, "Role of Angiogenesis Inhibitors in Cancer Treatment," Oncology 15:39-46 (2001).

Emtenäs et al., "An enantioselective ketene-imine cycloaddition method for synthesis of substituted ring-fused 2-pyridinones," J Org Chem 66(20):6756-61 (2001).

English et al., "VEGF inhibition and metastasis: possible implications for antiangiogenic therapy," Cancer Biol. Ther. 8(13):1214-1225 (2009).

Forrester et al., "Induction of a chloracne phenotype in an epidermal equivalent model by 2,3,7,8-tetrachlorodibenzo-p-dioxin (TCDD) is dependent on aryl hydrocarbon receptor activation and is not reproduced by aryl hydrocarbon receptor knock down," J Dermatol Sci 73:10-22 (2014).

Fritz et al., "The selective aryl hydrocarbon receptor modulator 6-methyl-1,3,8-trichlorodibenzofuran inhibits prostate tumor metastasis in TRAMP mice," Biochem. Pharmacol. 77(7):1151-1160 (2009).

Funcke et al., "The Effect of Alkyl Substitution in Drugs—IV. Pharmacological Properties of Tropinyl 2-Methyl-benzhydryl Ether Hydrobromide (BS 6825)," Journal of Medicinal and Pharmaceutical Chemistry 4(2): 215-224 (1961).

Gierthy et al., "Correlation of in vitro and in vivo growth suppression of MCF-7 human breast cancer by 2,3,7,8-tetrachlorodibenzo-p-dioxin," Cancer Res 53(13):3149-3153 (1993).

Gluschnaider et al., "beta-TrCP inhibition reduces prostate cancer cell growth via upregulation of the aryl hydrocarbon receptor," PLoS ONE 5(2):e9060 (2010).

Gruber et al., "Correlation between the tumoral expression of B33-integrin and outcome in cervical cancer patients who had undergone radiotherapy," Br. J. Cancer 92(1):41-46(2005).

Grzywacz et al., "A concise synthesis of an AHR endogenous ligand with the indolecarbonylthiazole skeleton," Heterocycles 60:5:1219 (2003).

Hall et al., "Activation of the Aryl-Hydrocarbon Receptor Inhibits Invasive and Metastatic Features of Human Breast Cancer Cells and Promotes Breast Cancer Cell Differentiation," Mol Endocrinol 24:359-369 (2010).

Hao et al., "Inhibitory effect and its mechanism of ITE, an endogenous aryl hydrocarbon receptor (AhR) ligand, on the proliferation of human placental trophoblast cells," Fudan Univ J Med Sci 41:488-493 (2014).

Hawerkamp et al., "Vemurafenib acts as an aryl hydrocarbon receptor antagonist: Implications for inflammatory cutaneous adverse events," Allergy. 74(12):2437-2448 (2019).

Henry et al., "A potential endogenous ligand for the aryl hydrocarbon receptor has potent agonist activity in vitro and in vivo," Arch. Biochem. Biophys. 450(1):67-77 (2006).

Henry et al., "TCDD and a Putative Endogenous AhR Ligand, ITE, Elicit the Same Immediate Changes in Gene Expression in Mouse Lung Fibroblasts," Toxicological Sciences 114:90-100 (2010).

Heravi et al., "An efficient synthesis of thiazol-2-imine derivatives via a onepot, three-component reaction," Tetrahedron Letters 53:392-394 (2012).

Holcomb et al., "Inhibition of 7,12-dimethylbenzanthracene-induced rat mammary tumor growth by 2,3,7,8-tetrachlorodibenzo-p-dioxin," Cancer Lett 82(1):43-7 (1994).

Hu et al., "Synthetic RORg agonists regulate multiple pathways to enhance antitumor immunity," Oncoimmunology 5(12) (2016).

Jana et al., "Cross-talk between 2,3,7,8-tetrachlorodibenzo-p-dioxin and testosterone signal transduction pathways in LNCaP prostate cancer cells," Biochem Biophys Res Commun 256(3):462-8 (1999).

Jin et al., "Copper-catalyzed oxidative cross-coupling of H-phosphonates and amides to N-acylphosphoramidates," Organic Letters 15(2) (2013).

John et al., "Antiangiogenic therapy and surgical practice," Br J Surg 95(3):281-293 (2008).

Johnson, et al., "Total synthesis of (–)-Rhazinilam: asymmetric C—H bond activation via the use of chiral auxiliary," J. Am. Chem. Soc. 124:6900-6903 (2002).

Jux et al., "Langerhans cell maturation and contact hypersensitivity are impaired in aryl hydrocarbon receptor-null mice," J. Immunol. 182(11):6709-6717 (2009).

Kajta et al., "Aryl hydrocarbon receptor-mediated apoptosis of neuronal cells: a possible interaction with estrogen receptor signaling," Neuroscience 158(2):811-822 (2009).

Kang et al., "Genome-wide transcriptional profiling of human glioblastoma cells in response to ITE treatment," Genomics Data 5:281-283 (2015).

Katner, "An Improved Synthesis of Indole-3-Carboxylic Acids," Organic Preparations and Procedures 2(4):297-303 (1970).

(56) References Cited

OTHER PUBLICATIONS

Kashani et al., "Expression of the aryl hydrocarbon receptor (AhR) and the aryl hydrocarbon receptor nuclear translocator (ARNT) in fetal, benign hyperplastic, and malignant prostate," Prostate 37(2):98-108 (1998).
Kawajiri, et al., "Aryl hydrocarbon receptor suppresses intestinal carcinogenesis in ApcMin/+ mice with natural ligands," Proc. Natl. Acad. Sci. U.S.A. 106(32):13481-13486 (2009).
Kerbel, "Tumor angiogenesis: past, present and the near future," Carcinogenesis 21:505-515 (2000).
King, "Bioisosteres, conformational restriction, and pro-drugs—case history: an example of a conformational restriction approach," Med Chem Principle and Practice 206-208 (1994).
Knerr et al., "Carcinogenicity of 2,3,7,8-tetrachlorodibenzo-p-dioxin in experimental models," Mol Nutr Food Res 50(10):897-907 (2006).
Knölker et al., "Isolation and synthesis of biologically active carbazole alkaloids," Chem Rev. 102(11):4303-427 (2002).
Koliopanos et al., "Increased aryl hydrocarbon receptor expression offers a potential therapeutic target for pancreatic cancer," Oncogene 21(39):6059-70 (2002).
Kurihara et al., "Synthesis and Cycloaddition Reaction of 2-Cyano-3-indoleacetonitriles," Chemical & Pharmaceutical Bulletin 34(11) (1986).
La Regina et al., New Arylthioindoles and Related Bioisosteres at the Sulfur Bridging Group. 4. Synthesis, Tubulin Polymerization, Cell Growth Inhibition, and Molecular Modeling Studies, J Med Chem. 52(23):7512-7527 (2009).
Lehmann et al., "The Aryl Hydrocarbon Receptor Ligand ITE Inhibits TGFβ1-Induced Human Myofibroblast Differentiation," Am J Pathol 178(4):1556-1567 (2011).
Leong et al., "In vitro, in vivo, and in silico analyses of the antitumor activity of 2-(4-amino-3-methylphenyl)-5-fluorobenzothiazoles," Mol Cancer Ther 3(12):1565-75 (2004).
Lin et al., "Overexpression of aryl hydrocarbon receptor in human lung carcinomas," Toxicol Pathol 31(1):22-30 (2003).
Liu et al., "AhR expression is increased in hepatocellular carcinoma," J Mol Histol 44(4):455-61 (2013).
Loges et al., "Silencing or fueling metastasis with VEGF inhibitors: antiangiogenesis revisited," Cancer Cell 15(3):167-170 (2009).
Loughlin et al., "Approaches to the high-throughput synthesis of analogues of dihydroaeruginoic acid," Aust. J. Chem 53:6:457-462 (2000).
Manegold et al., "The Potential of Combined Immunotherapy and Antiangiogenesis for the Synergistic Treatment of Advanced NSCLC," J Thorac Oncol. 12(2):194-207 (2017).
Marlowe et al., "The aryl hydrocarbon receptor displaces p300 from E2F-dependent promoters and represses S phase-specific gene expression," J Biol Chem 279(28):29013-22 (2004).
McDougal, "Methyl-substituted diindolylmethanes as inhibitors of estrogen-induced growth of T47D cells and mammary tumors in rats," Breast Cancer Research and Treatment 66:147-157 (2001).
McDougal et al., "Tamoxifen-induced antitumorigenic/antiestrogenic action synergized by a selective aryl hydrocarbon receptor modulator," Cancer Res 61(10):3902-3907 (2001).
McDougal et al., "Inhibition of 7,12-dirnethylbenz [a] anthracene-induced rat mammary tumor growth by aryl hydrocarbon receptor agonists," Cancer Lett 120(1):53-63 (1997).
Medjakovic et al., "Indolylfuran, a potent aryl hydrocarbon receptor agonist from sauerkraut, interacts with the oestrogen pathway," Food Chemistry 127(4): 1764-1772 (2011).
Milen et al., "A study on the phosphorylation of indole, imidazole, carbazole, and phenothiazine derivatives," Phosphorus, Sulfur and Silicon and The Related Elements 187(9) (2012).
Milinkevich et al., "Synthesis of 5-(Thiazol-5-yl)-4,5-dihydroisoxazoles from 3-Chloropentane-2,4-dione," J. Comb. Chem. 10:521-525 (2008).
Miyagi et al., "Binding affinity between AhR and exogenous/endogenous ligands: molecular simulations and biological experiment," Molecular Simulation 41(7) (2015).
Miyake et al., "Synthesis of 5-(3-indolyl) oxazole natural products. Structure revision of Almazole D," Tetrahed 66(26):4888-4893 (2010).
Mizzoni et al., "Some thiazolines and thiazolidinones with antituberculous activity," (Jul. 5, 1958).
Mjambili et al., "Synthesis and biological evaluation of 2-aminothiazole derivatives as antimycobacterial and antiplasmodial agents," Biorganic & Medicinal Chemistry Letters 24:560-564 (2014).
Morrow et al., "Aryl hydrocarbon receptor-mediated inhibition of LNCaP prostate cancer cell growth and hormone-induced transactivation," J. Steroid Biochem. Mol. Biol. 88(1):27-36 (2004).
Mouchlis et al., "Molecular docking and 3D-QSAR CoMFA studies on indole inhibitors of GIIA secreted phospholipase A(2)," Chem Inf Model 50(9):1589-1601 (2010).
Murray et al., "Aryl hydrocarbon receptor ligands in cancer: friend and foe," Nat Rev Cancer 14(12):801-14 (2014).
Narender et al., "Aqueous phase synthesis of thiazoles and aminothiazoles in the presence of β-cyclodextrin," Tetrahedron letters 46:5953-5955 (2005).
Neumann et al., "Exploring the oxidative cyclization of substituted N-aryl enamines: Pd-catalyzed formation of indoles from anilines," Chem. Eur. J 17(26):7298-7303 (2011).
Nugent et al., "ITE, A Novel Endogenous Nontoxic Aryl Hydrocarbon Receptor Ligand, Efficiently Suppresses EAU and T-Cell-Mediated Immunity," Invest Ophthalmol Vis Sci 54:7463-7469 (2013).
O'Donnell et al., "The aryl hydrocarbon receptor mediates leflunomide-induced growth inhibition of melanoma cells," PLoS ONE 7(7) (2012).
Oenga et al., "TCDD and PCBs inhibit breast cancer cell proliferation in vitro," Toxicol In Vitro. 18(6):811-9 (2004).
Okino et al., "Toxic and chemopreventive ligands preferentially activate distinct aryl hydrocarbon receptor pathways: implications for cancer prevention," Cancer Prev Res (Phila Pa). 2(3):251-256 (2009).
Ott et al., "Inhibition of immune checkpoints and vascular endothelial growth factor as combination therapy for metastatic melanoma: an overview of rationale, preclinical evidence, and initial clinical data," Frontiers in Oncology, 5:1-7 (2015).
Ozawa et al., "A new synthesis of glutathione via the thiazoline peptide," Bull. Chem. Soc. Jpn., 53:2592-2593 (1980).
Paez-Ribes et al., "Antiangiogenic therapy elicits malignant progression of tumors to increased local invasion and distant metastasis," Cancer Cell 15(3):220-231 (2009).
Park et al., "The aryl hydrocarbon receptor predisposes hepatocytes to Fas mediated apoptosis," Mol Pharmacol. 67(3):612-22 (2005).
Peng et al., "Potential therapeutic significance of increased expression of aryl hydrocarbon receptor in human gastric cancer," World J. Gastroenterol. 15(14):1719-1729 (2009).
Piparo et al., "Virtual screening for aryl hydrocarbon receptor binding prediction," J Med Chem 49(19):5702-5709 (2006).
Poellinger, "Mechanistic aspects—the dioxin (aryl hydrocarbon) receptor," Food Addit Contam 17(4):261-6 (2000).
Poland et al., "2,3,7,8-tetrachlorodibenzo-p-dioxin and related halogenated aromatic hydrocarbons: examination of the mechanism of toxicity," Annu. Rev. Pharmacol. Toxicol. 22:517-554 (1982).
Potewar et al., "Efficient synthesis of 2,4-disubstituted thiazoles using ionic liquid under ambient conditions: a practical approach towards the synthesis of Fanetizole," Tetrahedron 63:45:11066-11069 (2007).
Puga et al., "Ah receptor signals cross-talk with multiple developmental pathways," Biochem Pharmacol. 69(2):199-207 (2005).
Puga et al., "Role of the aryl hydrocarbon receptor in cell cycle regulation," Toxicology 181-182:171-7 (2002).
Quintana et al., "Control of T(reg) and T(H)17 cell differentiation by the aryl hydrocarbon receptor," Nature 453(7191):65-71 (2008).
Quintana et al., "An endogenous aryl hydrocarbon receptor ligand acts on dendritic cells and T cells to suppress experimental autoimmune encephalomyelitis," Proc Natl Acad Sci U S A 107:20768-73 (2010).
Quintana et al., "Aryl Hydrocarbon Receptor Control of Adaptive Immunity," Pharmacol Rev. 65(4):1148-61 (2013).

(56) References Cited

OTHER PUBLICATIONS

Radspieler, "Studies on the synthesis of diazonamide A and phorbazol A and C," Sel. Org. React. Database (SORD), no pp. given (2007).
Rajniak, et al., "A new cyanogenic metabolite in *Arabidiposis* required for inducible pathogen defense," Nature 525(7569):376-379 (2015).
Ramjiawan et al., "Anti-angiogenesis for cancer revisited: Is there a role for combinations with immunotherapy?" Angiogenesis. 20(2):185-204 (2017).
Rasool et al., "Convenient one-pot synthesis and biological evaluation of phosphoramidates and phosphonates containing heterocycles," Phosphorus, Sulfur and Silicon and The Related Elements 193(7) (2018).
Ray et al., "Activation of the aryl hydrocarbon receptor by TCDD inhibits senescence: a tumor promoting event?" Biochem. Pharmacol 77(4):681-688 (2009).
Reji et al., "Synthesis and Cytotoxicity Studies of Thiazole Analogs of the Anticancer Marine Alkaloid Dendrodoine," Indian Journal of Chemistry, Section B: Organic Chemistry Including Medicinal Chemistry 47:7:2: 1145-1150 (2011).
Rose, "A theory of the action of cancer chemotherapeutic drugs," Clin. Exp. Immunol. 2:361-373 (1967).
Safe et al., "Mechanism of action and development of selective aryl hydrocarbon receptor modulators for treatment of hormone dependent cancers," Int J Oncol 20(6):1123-1128 (2002).
Sanderson et al., "2,3,7,8-Tetrachlorodibenzo-p-dioxin and diindolylmethanes differentially induce cytochrome P450 1A1, 1B1, and 19 in H295R human adrenocortical carcinoma cells," Toxicol. Sci. 61(1):40-48 (2001).
Schmidt, "Developing combination strategies using PD-1 checkpoint inhibitors to treat cancer," Semin Immunopathol. 41(1):21-30 (2019).
Schmidt et al., "Occurrence, biogenesis, and synthesis of biologically active carbazole alkaloids," Chem Rev. 112(6):3193-328 (2012).
Schulz et al., "Activation of the aryl hydrocarbon receptor suppresses sensitization in a mouse peanut allergy model," Toxicol Sci 123:491-500 (2011).
Shih et al., "Bevacizumab: an angiogenesis inhibitor for the treatment of solid malignancies," Clin Ther(11): 1779-802 (2006).
Shiizaki et al., "Identification of amino acid residues in the ligand-binding domain of the aryl hydrocarbon receptor causing the species-specific response to omeprazole: possible determinants for binding putative endogenous ligands," Molecular Pharmacology Fast Forward (2013).
Simon et al., "Estimates of cancer potency of 2,3,7,8-tetrachlorixlibenzo(p)dioxin using linear and nonlinear dose-response modeling and toxicokinetics," Toxicological sciences 112(2):490-506 (2009).
Simones et al., "Consequences of AhR Activation in Steady-State Dendritic Cells," Toxicological Sciences 119:293-307 (2011).
Singh et al. "Primary peripheral T cells become susceptible to 2,3,7,8-tetrachlorodibenzo-p-dioxin-mediated apoptosis in vitro upon activation and in the presence of dendritic cells," Mol. Pharmacol. 73(6):1722-1735 (2008).
Smith et al., "Tapinarof is a natural AhR agonist that resolves skin inflammation in mice and humans," J Invest Dermatol. 137(10):2110-2119 (2017).
Solankee, et al., "Thiazoline: synthesis and antitubercular activity of 2-Alkyl/Aryl/-5-(w-carboxy pentyl) thiazolin-4-one," Part II, J. Inst. Chemists (India) vol. 66 (1994).
Song et al., "A ligand for the aryl hydrocarbon receptor isolated from lung," Proc Natl Acad Sci USA. 99(23):14694-9 (2002).
Stevens et al., "The aryl hydrocarbon receptor: a perspective on potential roles in the immune system," Immunology 127(3):299-311 (2009).
Sutter et al., "EGF receptor signaling blocks aryl hydrocarbon receptor mediated transcription and cell differentiation in human epidermal keratinocytes," Proc. Natl. Acad. Sci. U.S.A. 106(11):4266-4271 (2009).

Tchaicha et al., "Abstract 4131: Overcoming aryl hydrocarbon receptor mediated tumor immunosuppression," Immunology, 4131-4131 (2019).
Trapani et al., "DNA damage and cell cycle arrest induced by 2-(4-amino-3-methylphenyl)-5-fluorobenzothiazole (5F 203, NSC 703786) is attenuated in aryl hydrocarbon receptor deficient MCF-7 cells," Br J Cancer. 88(4): 599-605 (2003).
Tsai et al., "Aryl hydrocarbon receptor (AhR) agonists increase airway epithelial matrix metalloproteinase activity," J Mol Med 92:615-628 (2014).
Van Zandt et al., "Discovery of 3-[(4,5,7-Trifluorobenzothiazol-2-yl)methyl]indole-N-acetic acid (lidorestat) and congeners as highly potent and selective inhibitors of aldose reductase for treatment of chronic diabetic complications," J. Med. Chem. 48:3141-3152 (2005).
Veale et al., "Synthesis and MRSA PK inhibitory activity of thiazole containing deoxytopsentin analogues," Tetrahedron 70:43:7845-7853 (2014).
Veldhoen et al., "The aryl hydrocarbon receptor links TH17-cell-mediated autoimmunity to environmental toxins," Nature 453(7191):106-109 (2008).
Wang et al., "The first design and synthesis of [11C]MKC-1 ([11C]Ro 31-7453), a new potential PET cancer imaging agent," Nucl Med Biol 37(7):763-75 (2010).
Wang et al., "The first synthesis of [(11)C]SB-216763, a new potential PET agent for imaging of glycogen synthase kinase-3 (GSK-3)," Bioorg Med Chem Lett 21(1):245-9(2011).
Wang, et al., "An endogenous aryl hydrocarbon receptor ligand inhibits proliferation and migration of human ovarian cancer cells," Cancer Letters 340:63-71 (2013).
Wang et al., "Activation of the aryl hydrocarbon receptor affects activation and function of human monocyte-derived dendritic cells," Clinical and Experimental Immunology 177:521-530 (2014).
Wang et al., "Decreased Expression of the Aryl Hydrocarbon Receptor in Ocular Behcet's Disease," Mediators Inflamm 2014:195094 (2014).
Wang et al., "Discovery of the Human Immunodeficiency Virus Type 1 (HIV-1) Attachment Inhibitor Temsavir and Its Phosphonooxymethyl Prodrug Fostemsavir," J Med Chem. 61(14):6308-6327 (2018).
Wei et al., "Role of the Aryl Hydrocarbon Receptor in the Pathogenesis of Chronic Rhinosinusitis with Nasal Polyps," Inflammation 37:387-95 (2013).
Wei et al., "An aryl hydrocarbon receptor ligand acts on dendritic cells and T cells to suppress the Th17 response in allergic rhinitis patients," Laboratory Investigation 94:528-535 (2014).
Wei et al., "Increased aryl hydrocarbon receptor expression in patients with allergic rhinitis," QJM 107:107-113 (2014).
Wille et al., "Malassezin—A novel agonist of the arylhydrocarbon receptor from the yeast *Malassezia furfur*," Bioorg Med Chem. 9(4):955-60 (2001).
Wincent et al., "The suggested physiologic aryl hydrocarbon receptor activator and cytochrome P4501 substrate 6-formylindolo[3,2-b] carbazole is present in humans," J Biol Chem. 284(5):2690-6(2009).
Wu et al., "ITE and TCDD Differentially Regulate the Vascular Remodeling of Rat Placenta via the Activation of AhR," PLoS One 9:e86549 (2014).
Yan et al., "Synthesis, evaluation, and mechanism study of novel indole-chalcone derivatives exerting effective antitumor activity through microtubule destabilization in vitro and in vivo," J. Med. Chem. 59(11) 5264-5283 (2016).
Yeste et al., "Nanoparticle-mediated codelivery of myelin antigen and a tolerogenic small molecule suppresses experimental autoimmune encephalomyelitis," Proc Natl Acad Sci U S A 109:11270-5 (2012).
Yeste et al., "IL-21 induces IL-22 production in CD4 þ T cells," Nat Commun. 5:3753 (2014).
Yeste et al., "Tolerogenic nanoparticles inhibit T cell-mediated autoimmunity through SOCS2," Sci Signal. 9(433):ra61 (2016).

(56) References Cited

OTHER PUBLICATIONS

Yu et al., "In utero exposure of mice to dibenzo[a,l] pyrene produces lymphoma in the offspring: role of the aryl hydrocarbon receptor," Cancer Res 66(2):755-762 (2006).

Zhao et al., "Akt-mediated phosphorylation of Oct4 is associated with the proliferation of stem-like cancer cells," Oncology Reports 33:1621-1629 (2015).

Zhang et al., "The aryl hydrocarbon receptor as a target for estrogen receptor-negative breast cancer chemotherapy," Endocr Relat Cancer 16(3):835-844 (2009).

Zhang et al., "Induction of cytochromes P450 1A1 and 1A2 by tanshinones in human HepG2 hepatoma cell line," Toxicol Appl Pharmacol. 252(1):18-27 (2011).

Zhang et al., "Activation of aryl hydrocarbon receptor suppresses invasion of esophageal squamous cell carcinoma cell lines," Tumori 98(1):152-157 (2012).

Zhang et al., "Rhodium(I)-catalyzed cycloisomerization of nitrogen-tethered indoles and alkylidenecyclopropanes: convenient access to polycyclic indole derivatives," Chemistry 19(41):13668-73 (2013).

Zhang et al., "A novel assay for screening inhibitors targeting HIV integrase LEDGF/p75 interaction based on Ni2+ coated magnetic agarose beads," Sci Rep. 6:33477 (2016).

Zimmerman et al., "N-substituted prodrugs of mebendazole provide improved aqueous solubility and oral bioavailability in mice and dogs," J Med Chem. 61(9):3918-3929 (2018).

"Fruit juice and medications don't mix," Consumer Reports News (Sep. 2, 2008).

USPTO, PTAB decision on the appeal of U.S. Appl. No. 13/954,834, 17 pages (dated May 30, 2018).

Classic Bioelectronic isosteres.

* cited by examiner

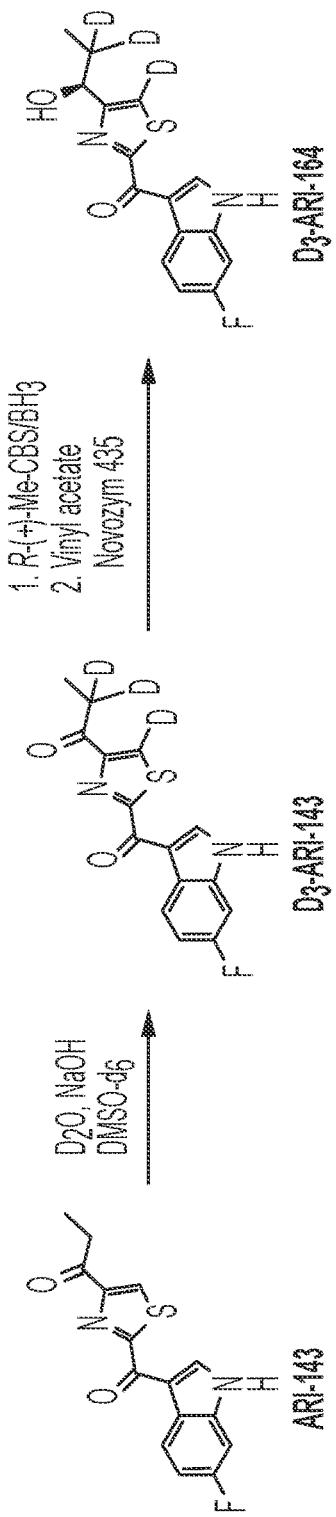
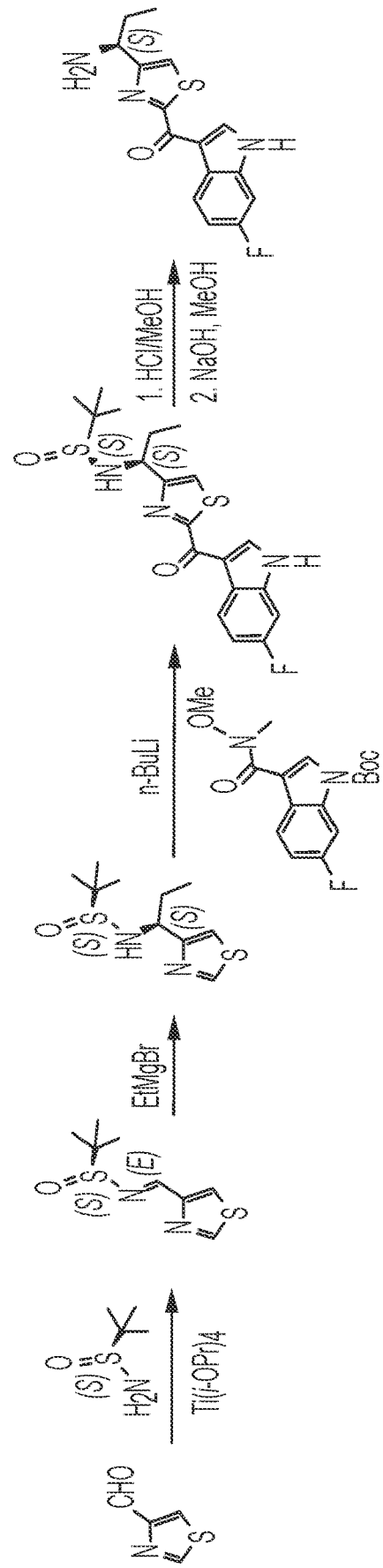
FIG. 14
FIG. 15A

CHIRAL INDOLE COMPOUNDS AND THEIR USE

CROSS-REFERENCE TO RELATED APPLICATION

This application is a continuation of International Application PCT/US2020/028371, filed Apr. 15, 2020, which claims priority from U.S. Provisional Application 62/834,140, filed Apr. 15, 2019, and U.S. Provisional Application 62/861,123, filed Jun. 13, 2019. The disclosures of the aforementioned priority applications are incorporated herein by reference in their entirety.

FIELD OF THE INVENTION

The present disclosure relates to chiral indole compounds and their use in treating patients in need thereof, such as patients with cancer or in need of immune stimulation.

BACKGROUND OF THE INVENTION

The aryl hydrocarbon (Ah) receptor (AhR) is a ligand-inducible transcription factor and a member of the basic helix-loop-helix/Per-Arnt-Sim (bHLH/PAS) superfamily. Upon binding to its ligand, AhR mediates a series of biological processes, including cell division, apoptosis, cell differentiation, adipose differentiation, hypothalamus actions, angiogenesis, immune system modulation, teratogenicity, tumorigenicity, tumor progression, chloracne, wasting, actions of hormonal systems (e.g., estrogen and androgen), and expression of genes of the P450 family (Poland et al., Annu. Rev. Pharmacol. Toxicol. 22:517-554 (1982); Poellinger et al., Food Addit Contam. 17(4):261-6 (2000); Bock et al., Biochem. Pharmacol. 69(10):1403-1408 (2005); Stevens et al., Immunology 127(3):299-311 (2009); Puga et al., Biochem Pharmacol. 69(2):199-207 (2005); Safe et al., Int J Oncol. 20(6):1123-8 (2002); Dietrich et al., Carcinogenesis 31(8):1319-1328 (2010); U.S. Pat. No. 7,419,992). The liganded receptor participates in biological processes through translocation from cytoplasm into the nucleus, heterodimerization with another factor named Ah receptor nuclear translocator, and binding of the heterodimer to the Ah response element of AhR-regulated genes, resulting in enhancement or inhibition of transcription of those genes.

The AhR is able to bind, with different affinities, to several groups of exogenous chemicals, or artificial ligands, including polycyclic aromatic hydrocarbons, e.g., 3-methylchoranthrene (3-MC), and halogenated aromatic hydrocarbons, e.g., 2,3,7,8-tetrachlorodibenzo-p-dioxin (TCDD). Studies with those AhR artificial ligands have helped in advancing the understanding of the AhR system. An endogenous or physiological ligand for the AhR has been identified as 2-(1'H-indole-3'-carbonyl)-thiazole-4-carboxylic acid methyl ester (ITE), with the following structure:

Structural Formula 1

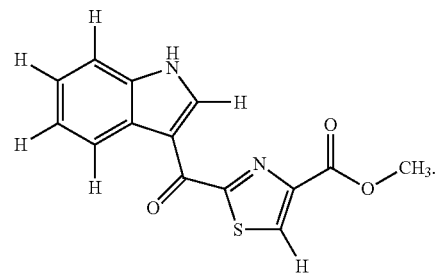

See, e.g., Song et al., PNAS USA 99(23):14694-9 (2002); and U.S. Pat. No. 6,916,834.

SUMMARY OF THE INVENTION

The present disclosure provides indole compounds useful in modulating an activity of human aryl hydrocarbon receptor (AhR), pharmaceutical compositions comprising one or more of these compounds, or use of these compounds and compositions in treating diseases and conditions in patients who can benefit from modulation of AhR activities.

Provided herein is a compound having the structure of formula 2, or a pharmaceutically acceptable salt thereof:

Structural Formula 2

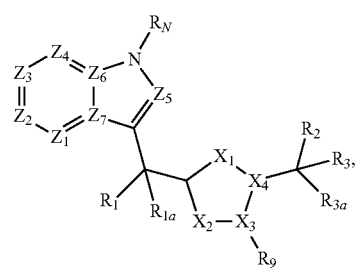

wherein:

$X_1$ is N (nitrogen), O (oxygen), S (sulfur), or C (carbon); $X_2$ is N (nitrogen), O (oxygen), S (sulfur), or C (carbon); $X_3$ is N (nitrogen), O (oxygen), S (sulfur), or C (carbon); and $X_4$ is N (nitrogen), O (oxygen), S (sulfur), or C (carbon), such that at least one of $X_1$, $X_2$, $X_3$ and $X_4$ is N, each of $X_1$, $X_2$, $X_3$ and $X_4$ is optionally selected to form a heteroaromatic, wherein the bond between $X_1$ and the adjacent carbon, between $X_2$ and the adjacent carbon, between $X_1$ and $X_4$, between $X_2$ and $X_3$, and between $X_3$ and $X_4$, can be a single bond or a double bond and the valence of $X_1$, $X_2$, $X_3$ and $X_4$ is completed with H or $C_1$-$C_6$ alkyl (i.e., the ring can be aromatic, partially saturated, or saturated);

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_2$ is $OR_O$, $N(R_N)_2$, or $SR_S$;

$R_O$ is H, CN, substituted or unsubstituted alkyl, alkenyl, alkynyl, aryl, alkanoyl, carbonyloxy, carbonylthio, or carbonylamino, wherein the alkyl, alkenyl, alkynyl, or alkanoyl is optionally interrupted by O, S, or NR (in which NR can be N—C1-C6 alkyl), or a phosphate moiety;

$R_S$ is H, CN, alkyl, alkenyl, alkynyl, aryl, alkanoyl, carbonyloxy, carbonylthio, carbonylamino, or a phosphate moiety;

each $R_N$ is H, CN, alkyl, alkenyl, alkynyl, aryl, alkanoyl, carbonyloxy, carbonylthio, carbonylamino, or a phosphate moiety; and $R_{3a}$ is selected from the group consisting of hydrogen, deuterium, cyano, or $C_1$-$C_6$ alkyl;

$R_3$ is selected from the group consisting of deuterium, cyano, formyl, furyl, nitro, alkyl, haloalkyl, alkenyl, haloalkenyl, alkynyl, haloalkynyl, $C_1$-$C_6$ acyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_4$, $R_5$, $R_6$, $R_7$, $R_8$, and $R_9$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_1$ and $R_{1a}$ are taken together to form =NR$_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, $R_2$ preferably can be =O, $R_3$ preferably can be —OR, wherein R is H or $C_1$-$C_6$ alkyl, or $R_1$ and $R_{1a}$ are taken together to form =CR$_b$R$_c$, wherein $R_b$ and $R_c$ are each independently H, $C_1$-$C_6$ alkyl, alkoxy (—O-alkyl), thioalkoxy (—S-alkyl), cyano (—CN), or amino, $R_2$ preferably can be =O, $R_3$ preferably can be —OR, wherein R is H or $C_1$-$C_6$ alkyl, or $R_1$ and $R_{1a}$ are taken together to form =O, =NOR$_a$, or =S, $R_2$ and $R_3$ preferably can be each independently —OR or —NR$_a$R$_b$, wherein R, $R_a$, and $R_b$ are each independently H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, carbonylthio, carbonylamino, thiocarbonyloxy, halothiocarbonyloxy, thiocarbonylthio, and halothiocarbonylthio;

wherein the compound is enantiomerically pure at the carbon substituted with $R_2$/$R_3$/$R_{3a}$, and optionally, adjacent R groups, together, can form a three- to twelve-membered ring.

Also provided herein is a compound having the structure of formula 2a, or a pharmaceutically acceptable salt thereof:

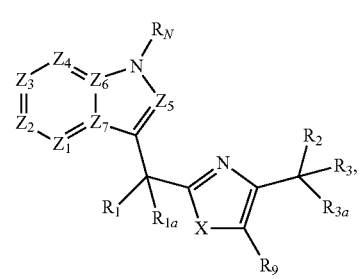

Structural Formula 2a wherein:

X is either O (oxygen) or S (sulfur);

$Z_1$ is N or CR$_4$, $Z_2$ is N or CR$_5$, $Z_3$ is N or CR$_6$, $Z_4$ is N or CR$_7$, $Z_5$ is N or CR$_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_2$ is OR$_O$, N(R$_N$)$_2$, or SR$_S$;

$R_O$ is H, CN, substituted or unsubstituted alkyl, alkenyl, alkynyl, aryl, alkanoyl, carbonyloxy, carbonylthio, or carbonylamino, wherein the alkyl, alkenyl, alkynyl, or alkanoyl is optionally interrupted by O, S, or NR (in which NR can be N—$C_1$-$C_6$ alkyl), or a phosphate moiety;

$R_S$ is H, CN, alkyl, alkenyl, alkynyl, aryl, alkanoyl, carbonyloxy, carbonylthio, carbonylamino, or a phosphate moiety;

each $R_N$ is H, CN, alkyl, alkenyl, alkynyl, aryl, alkanoyl, carbonyloxy, carbonylthio, carbonylamino, or a phosphate moiety; and $R_{3a}$ is selected from the group consisting of hydrogen, deuterium, cyano, or C1-C6 alkyl;

$R_3$ is selected from the group consisting of deuterium, cyano, formyl, furyl, nitro, alkyl, haloalkyl, alkenyl, haloalkenyl, alkynyl, haloalkynyl, $C_1$-$C_6$ acyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_4$, $R_5$, $R_6$, $R_7$, $R_8$, and $R_9$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and $—S(O)_nR_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_1$ and $R_{1a}$ are taken together to form $=NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, $R_2$ preferably can be =O, $R_3$ preferably can be —OR, wherein R is H or $C_1$-$C_6$ alkyl, or $R_1$ and $R_{1a}$ are taken together to form $=CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, $R_2$ preferably can be =O, $R_3$ preferably can be —OR, wherein R is H or $C_1$-$C_6$ alkyl, or $R_1$ and $R_{1a}$ are taken together to form =O, $=NOR_a$, or =S, $R_2$ and $R_3$ preferably can be each independently —OR or $—NR_aR_b$, wherein R, $R_a$, and $R_b$ are each independently H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and $—S(O)_nR_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

wherein the compound is enantiomerically pure at the carbon substituted with $R_2/R_3/R_{3a}$, and optionally, adjacent R groups, together, can form a three- to twelve-membered ring.

Also provided herein is a compound having the structure of formula 3, or a pharmaceutically acceptable salt thereof:

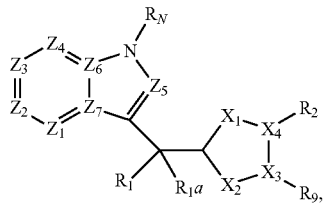

Structural Formula 3 wherein:

$X_1$ is N (nitrogen), O (oxygen), S (sulfur), or C (carbon); $X_2$ is N (nitrogen), O (oxygen) S (sulfur), or C (carbon); $X_3$ is N (nitrogen), O (oxygen), S (sulfur) or C (carbon); and $X_4$ is N (nitrogen) O (oxygen), S (sulfur), or C (carbon), such that at least one of $X_1$, $X_2$, $X_3$ and $X_4$ is N, each of $X_1$, $X_2$, $X_3$ and $X_4$ is optionally selected to form a heteroaromatic, wherein the bond between $X_1$ and the adjacent carbon, between $X_2$ and the adjacent carbon, between $X_1$ and $X_4$, between $X_2$ and $X_3$, and between $X_3$ and $X_4$ can be a single bond or a double bond and the valence of $X_1$, $X_2$, $X_3$ and $X_4$ is completed with H or $C_1$-$C_6$ alkyl (i.e., the ring can be aromatic, partially saturated, or saturated);

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_1$ and $R_{1a}$ are taken together to form $=NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, or $R_1$ and $R_{1a}$ are taken together to form $=CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, or $R_1$ and $R_{1a}$ are taken together to form =O, $=NOR_a$, or =S, wherein $R_a$ is H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and $—S(O)_nR_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and $R_2$ and $R_9$ are each independently selected from the group consisting of hydrogen, aryl, heteroaryl, cycloalkyl, heterocycloalkyl, alkyl, $—NR_{2a}C(O)OR_{2b}$, $—NR_{2a}C(O)R_{2b}$, $—(C_0$-$C_6$ alkyl)-$CONHSO_2R_{2a}$, $—(C_0$-$C_6$ alkyl)-$CONHSO_2NR_{2a}R_{2b}$, $—(C_0$-$C_6$ alkyl)-$SO_2NHCOR_{2a}$, $—(C_0$-$C_6$ alkyl)-$SO_2NHR_{2a}$, $—(C_0$-$C_6$ alkyl)-$CONR_{2a}OR_{2b}$,

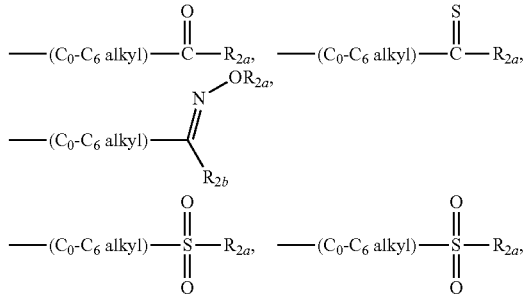

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and $—S(O)_nR_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino, wherein the compound is enantiomerically pure in the $R_2$ or $R_9$ moiety;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, alkyl, alkenyl, alkynyl, aryl, alkanoyl, carbonyloxy, carbonylthio, carbonylamino, or a phosphate moiety; and optionally, adjacent R groups, together, can form a three- to twelve-membered ring.

Further provided herein is a compound having the structure of formula 3a, or a pharmaceutically acceptable salt thereof:

Structural Formula 3a

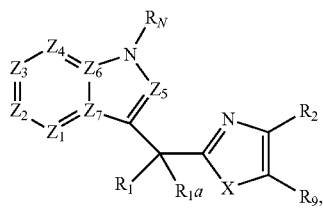

wherein:

X is either O (oxygen) or S (sulfur);

$Z_1$ is N or CR$_4$, $Z_2$ is N or CR$_5$, $Z_3$ is N or CR$_6$, $Z_4$ is N or CR$_7$, $Z_5$ is N or CR$_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_1$ and $R_{1a}$ are taken together to form =NR$_b$, wherein R$_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, or $R_1$ and $R_{1a}$ are taken together to form =CR$_b$R$_c$, wherein $R_b$ and $R_c$ are each independently H, $C_1$-$C_6$ alkyl, alkoxy (—O-alkyl), thioalkoxy (—S-alkyl), cyano (—CN), or amino, or $R_1$ and $R_{1a}$ are taken together to form =O, =NOR$_a$, or =S, wherein $R_a$ is H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and $R_2$ and $R_9$ are each independently selected from the group consisting of hydrogen, aryl, heteroaryl, cycloalkyl, heterocycloalkyl, alkyl, —NR$_{2a}$C(O)OR$_{2b}$, —NR$_{2a}$C(O)R$_{2b}$, —(C$_0$-C$_6$ alkyl)-CONHSO$_2$R$_{2a}$, —(C$_0$-C$_6$ alkyl)-CONHSO$_2$NR$_{2a}$R$_{2b}$, —(C$_0$-C$_6$ alkyl)-SO$_2$NHCOR$_{2a}$, —(C$_0$-C$_6$ alkyl)-SO$_2$NHR$_{2a}$, —(C$_0$-C$_6$ alkyl)-CONR$_{2a}$OR$_{2b}$,

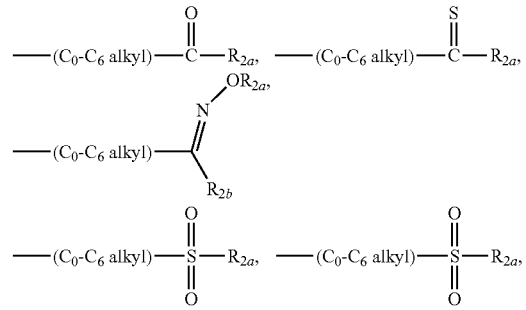

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino, wherein the compound is enantiomerically pure in the $R_2$ or $R_9$ moiety;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, alkyl, alkenyl, alkynyl, aryl, alkanoyl, carbonyloxy, carbonylthio, carbonylamino, or a phosphate moiety; and optionally, adjacent R groups, together, can form a three- to twelve-membered ring.

Provided further herein is a compound having the structure of formula 3b, or a pharmaceutically acceptable salt thereof:

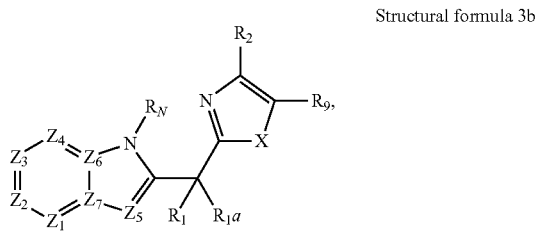

Structural formula 3b wherein:

X is either O (oxygen) or S (sulfur);

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_1$ and $R_{1a}$ are taken together to form =$NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, or $R_1$ and $R_{1a}$ are taken together to form =$CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, or $R_1$ and $R_{1a}$ are taken together to form =O, =$NOR_a$, or =S, wherein $R_a$ is H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and $R_2$ and $R_9$ are each independently selected from the group consisting of hydrogen, aryl, heteroaryl, cycloalkyl, heterocycloalkyl, alkyl, —NR$_{2a}$C(O)OR$_{2b}$, —NR$_{2a}$C(O)R$_{2b}$, —(C$_0$-C$_6$ alkyl)-CONHSO$_2$R$_{2a}$, —(C$_0$-C$_6$ alkyl)-CONHSO$_2$NR$_{2a}$R$_{2b}$, —(C$_0$-C$_6$ alkyl)-SO$_2$NHCOR$_{2a}$, —(C$_0$-C$_6$ alkyl)-SO$_2$NHR$_{2a}$, —(C$_0$-C$_6$ alkyl)-CONR$_{2a}$OR$_{2b}$,

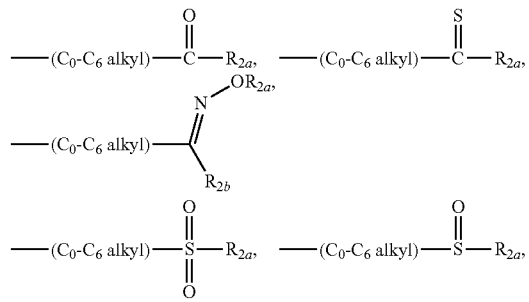

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino, wherein the compound is enantiomerically pure in the $R_2$ or $R_9$ moiety;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, alkyl, alkenyl, alkynyl, aryl, alkanoyl, carbonyloxy, carbonylthio, carbonylamino, or a phosphate moiety; and optionally, adjacent R groups, together, can form a three- to twelve-membered ring.

Provided herein is also a compound having the structure of formula 3c, or a pharmaceutically acceptable salt thereof:

Structural Formula 3c

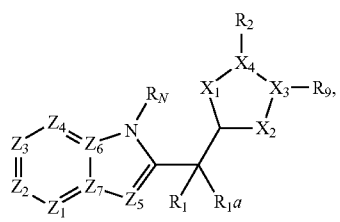

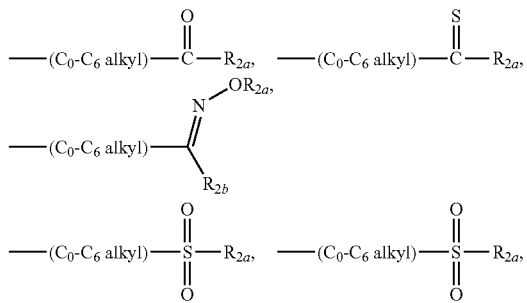

wherein:

$X_1$ is N (nitrogen), O (oxygen), S (sulfur), or C (carbon); $X_2$ is N (nitrogen), O (oxygen) S (sulfur), or C (carbon); $X_3$ is N (nitrogen), O (oxygen), S (sulfur) or C (carbon); and $X_4$ is N (nitrogen) O (oxygen), S (sulfur), or C (carbon), such that at least one of $X_1$, $X_2$, $X_3$ and $X_4$ is N, each of $X_1$, $X_2$, $X_3$ and $X_4$ is optionally selected to form a heteroaromatic, wherein the bond between $X_1$ and the adjacent carbon, between $X_2$ and the adjacent carbon, between $X_1$ and $X_4$, between $X_2$ and $X_3$, and between $X_3$ and $X_4$ can be a single bond or a double bond and the valence of $X_1$, $X_2$, $X_3$ and $X_4$ is completed with H or $C_1$-$C_6$ alkyl (i.e., the ring can be aromatic, partially saturated, or saturated);

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_1$ and $R_{1a}$ are taken together to form =$NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, or $R_1$ and $R_{1a}$ are taken together to form =$CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, or $R_1$ and $R_{1a}$ are taken together to form =O, =$NOR_a$, or =S, wherein $R_a$ is H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and $R_2$ and $R_9$ are each independently selected from the group consisting of hydrogen, aryl, heteroaryl, cycloalkyl, heterocycloalkyl, alkyl, —$NR_{2a}C(O)OR_{2b}$, —$NR_{2a}C(O)R_{2b}$, —($C_0$-$C_6$ alkyl)-$CONHSO_2R_{2a}$, —($C_0$-$C_6$ alkyl)-$CONHSO_2NR_{2a}R_{2b}$, —($C_0$-$C_6$ alkyl)-$SO_2NHCOR_{2a}$, —($C_0$-$C_6$ alkyl)-$SO_2NHR_{2a}$, —($C_0$-$C_6$ alkyl)-$CONR_{2a}OR_{2b}$, deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino, wherein the compound is enantiomerically pure in the $R_2$ or $R_9$ moiety;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, alkyl, alkenyl, alkynyl, aryl, alkanoyl, carbonyloxy, carbonylthio, carbonylamino, or a phosphate moiety; and optionally, adjacent R groups, together, can form a three- to twelve-membered ring.

Also provided herein is a compound having the structure of formula 4, or a pharmaceutically acceptable salt thereof:

Structural Formula 4

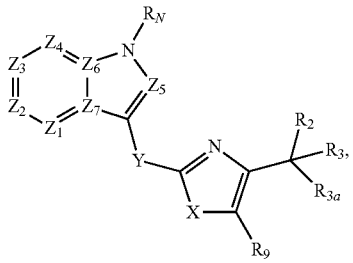

wherein:
X is O (oxygen) or S (sulfur);
Y is a bond, O (oxygen), S (sulfur), or

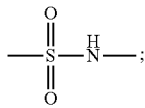

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, Z is N or C, wherein no more than two of $Z_1$, $Z_2$, $Z_3$, $Z_4$, $Z_5$, $Z_6$, and $Z_7$ are N;

$R_4$, $R_5$, $R_6$, $R_7$, $R_8$, and $R_9$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, R$_{11}$ is directly connected to S), wherein R$_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_2$ is $OR_O$, $N(R_N)_2$, or $SR_S$;

$R_O$ is H, CN, substituted or unsubstituted alkyl, alkenyl, alkynyl, aryl, alkanoyl, carbonyloxy, carbonylthio, or carbonylamino, wherein the alkyl, alkenyl, alkynyl, or alkanoyl is optionally interrupted by O, S, or NR (in which NR can be N—C1-C6 alkyl), or a phosphate moiety;

$R_S$ is H, CN, alkyl, alkenyl, alkynyl, aryl, alkanoyl, carbonyloxy, carbonylthio, carbonylamino, or a phosphate moiety;

each $R_N$ is H, CN, alkyl, alkenyl, alkynyl, aryl, alkanoyl, carbonyloxy, carbonylthio, carbonylamino, or a phosphate moiety;

$R_{3a}$ is selected from the group consisting of hydrogen, deuterium, cyano, or C1-C6 alkyl;

$R_3$ is selected from the group consisting of deuterium, cyano, formyl, furyl, nitro, alkyl, haloalkyl, alkenyl, haloalkenyl, alkynyl, haloalkynyl, $C_1$-$C_6$ acyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, R$_{10}$ is directly connected to S), wherein R$_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

wherein the compound is enantiomerically pure at the carbon substituted with $R_2/R_3/R_{3a}$; and optionally, adjacent R groups, together, can form a three- to twelve-membered ring.

Further provided herein is a compound having the structure of formula 5, or a pharmaceutically acceptable salt thereof:

Structural Formula 5

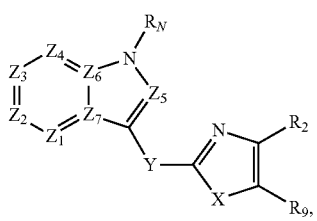

wherein:
X is O (oxygen) or S (sulfur);
Y is a bond, O (oxygen), S (sulfur), or

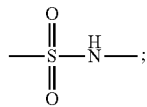

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_2$ and $R_9$ are each independently selected from the group consisting of hydrogen, aryl, heteroaryl, cycloalkyl, heterocycloalkyl, alkyl, —NR$_{2a}$C(O)OR$_{2b}$, —NR$_{2a}$C(O)R$_{2b}$, —(C$_0$-C$_6$ alkyl)-CONHSO$_2$R$_{2a}$, —(C$_0$-C$_6$ alkyl)-CONHSO$_2$NR$_{2a}$R$_{2b}$, —(C$_0$-C$_6$ alkyl)-SO$_2$NHCOR$_{2a}$, —(C$_0$-C$_6$ alkyl)-SO$_2$NHR$_{2a}$, —(C$_0$-C$_6$ alkyl)-CONR$_{2a}$OR$_{2b}$,

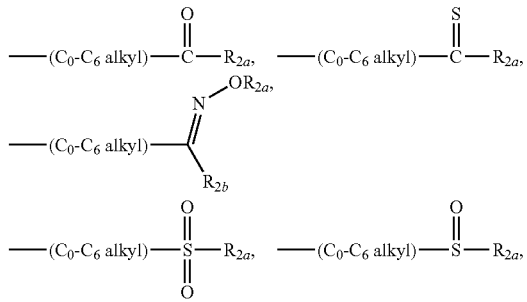

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and $-S(O)_nR_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino, wherein the compound is enantiomerically pure in the $R_2$ or $R_9$ moiety;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and $-S(O)_nR_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN; alkyl, alkenyl, alkynyl, aryl, alkanoyl, carbonyloxy, carbonylthio, carbonylamino, or a phosphate moiety; and optionally, adjacent R groups, together, can form a three- to twelve-membered ring.

Also provided herein is a compound having the structure of formula 6, or a pharmaceutically acceptable salt thereof:

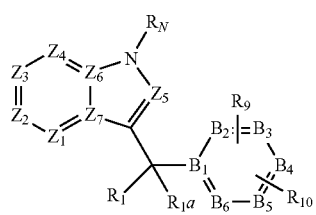

Structural Formula 6 wherein:

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_1$ and $R_{1a}$ are taken together to form $-NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, or $R_1$ and $R_{1a}$ are taken together to form $=CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, or $R_1$ and $R_{1a}$ are taken together to form =O, =$NOR_a$, or =S, wherein $R_a$ is H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and $-S(O)_nR_{14}$ (n=0 to 2, $R_{14}$ is directly connected to S), wherein $R_{14}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and $-S(O)_nR_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, alkyl, alkenyl, alkynyl, aryl, alkanoyl, carbonyloxy, carbonylthio, carbonylamino, or a phosphate moiety;

$B_1$, $B_2$, $B_3$, $B_4$, $B_5$, and $B_6$ are each independently C or N;

$R_9$ and $R_{10}$, the number of which, together, complete the valence of each of $B_1$, $B_2$, $B_3$, $B_4$, $B_5$, and $B_6$, are each independently selected from the group consisting of hydrogen, aryl, heteroaryl, cycloalkyl, heterocycloalkyl, alkyl, $-NR_{2a}C(O)OR_{2b}$, $-NR_{2a}C(O)R_{2b}$, $-(C_0$-$C_6$ alkyl)-$CONHSO_2R_{2a}$, $-(C_0$-$C_6$ alkyl)-$CONHSO_2NR_{2a}R_{2b}$, $-(C_0$-$C_6$ alkyl)-$SO_2NHCOR_{2a}$, $-(C_0$-$C_6$ alkyl)-$SO_2NHR_{2a}$, $-(C_0$-$C_6$ alkyl)-$CONR_{2a}OR_{2b}$,

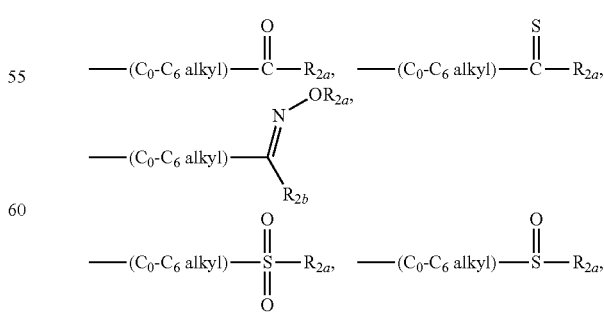

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{12}$ (n=0 to 2, R$_{12}$ is directly connected to S), wherein R$_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and

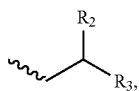

wherein R$_{2a}$ and R$_{2b}$ are each independently H, C$_1$-C$_6$ alkyl, alkoxy (—O-alkyl), hydroxy, thioalkoxy (—S-alkyl), cyano (—CN), or amino, R$_2$ and R$_3$ are each independently selected from the group consisting of —NR$_a$R$_b$ (R$_a$ and R$_b$ are each independently H, C$_1$-C$_6$ alkyl, or C$_1$-C$_6$ acyl), hydrogen, deuterium, halo, amino, hydroxy, cyano, formyl, furyl, nitro, alkyl, haloalkyl, alkenyl, haloalkenyl, alkynyl, haloalkynyl, C$_1$-C$_6$ acyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{13}$ (n=0 to 2, R$_{13}$ is directly connected to S), wherein R$_{13}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein the compound is enantiomerically pure in the R$_9$ or R$_{10}$ moiety; and optionally, adjacent R groups, together, can form a three- to twelve-membered ring.

In each of formulae 2, 2a, 3, 3a, 3b, 3c, 4, 5, and 6, in some embodiments, each of R$_4$, R$_5$, R$_6$, and R$_7$ is hydrogen. In other embodiments, at least one of R$_4$, R$_5$, R$_6$, and R$_7$ can be F, Cl, or Br, and the others of R$_4$, R$_5$, R$_6$, and R$_7$ are hydrogen. In still other embodiments, at least two of R$_4$, R$_5$, R$_6$, and R$_7$, independently, can be F, Cl, or Br, and the others of R$_4$, R$_5$, R$_6$, and R$_7$ are hydrogen. The F, Cl, or Br can be at the indole ring carbon 5, 6, or 7.

In each of formulae 2a, 3, 3a, 3b, 3c, 4, 5, and 6, in certain embodiments, R$_9$ can be hydrogen. R$_2$ can be acyl, cyano, hydroxyl-substituted C1-C6 alkyl, amino-substituted C1-C6 alkyl, aryl, or heteroaryl. The aryl or heteroaryl can be substituted or unsubstituted. The substituted aryl or heteroaryl can be substituted with halo, amino, hydroxyl, or C1-C6 alkyl. The amino can be unsubstituted.

In each of formulae 2, 2a, and 4, in certain embodiments, R$_2$ can be ester.

In each of formulae 2, 2a, and 4, in certain embodiments, R$_2$ can be hydroxyl or amino and R$_3$ can be alkyl, aryl, nitro, or cyano. R$_9$ can be hydrogen. The amino can be substituted or unsubstituted.

In some embodiments, the invention provides a compound having the structure of formula 8a, 8b, 8c, or 8d, or a pharmaceutically acceptable salt thereof:

Structural Formula 8a

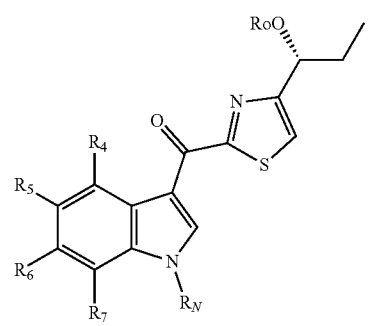

Structural Formula 8b

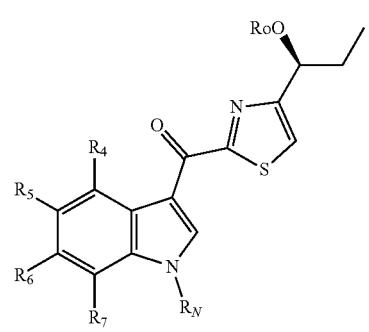

Structural Formula 8c

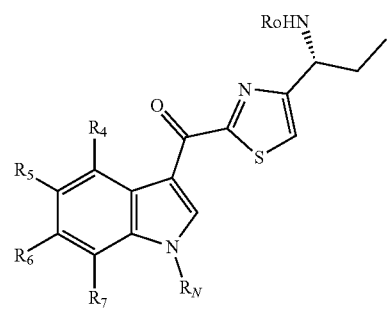

Structural Formula 8d

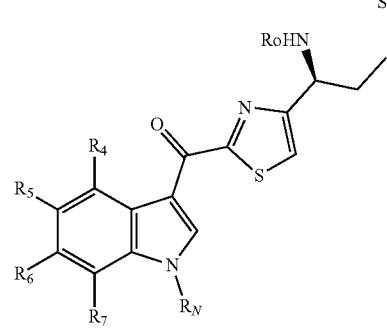

wherein:

R$_4$, R$_5$, R$_6$, and R$_7$, are each independently selected from the group consisting of hydrogen and halo;

R$_o$ is hydrogen, deuterium, alkyl, aryl, or acyl; and

R$_N$ is H, CN, alkyl, alkenyl, alkynyl, aryl, alkanoyl, carbonyloxy, carbonylthio, carbonylamino, or a phosphate moiety.

In one embodiment, $R_o$ is H or alkyl. In another embodiment, $R_o$ is acyl, for example, a substituted or unsubstituted $C_1$-$C_6$ acyl. The substituted or unsubstituted $C_1$-$C_6$ acyl can be a substituted $C_2$, $C_3$, $C_4$, $C_5$, or $C_6$ acyl, optionally interrupted by O, S, or NR (in which NR can be N—C1-C6 alkyl). The substituent can be a halo, carboxyl, amino, hydroxyl, alkoxy, or phosphonate moiety. The amino moiety can be a dialkylamino moiety, for example, dimethylamino, morpholino, piperazinyl or bipiperidinyl.

In one embodiment of the compound of structural formula 8a or 8b, at least one of $R_4$, $R_5$, $R_6$, and $R_7$ is F, Cl, or Br, and the others of $R_4$, $R_5$, $R_6$, and $R_7$ are hydrogen. In another embodiment, at least two of $R_4$, $R_5$, $R_6$, and $R_7$ are F, Cl, or Br, and the others of $R_4$, $R_5$, $R_6$, and $R_7$ are hydrogen.

In one embodiment, R is F, and $R_4$, $R_6$, and $R_7$ are hydrogen. In another embodiment, $R_6$ is F, and $R_4$, $R_5$, and $R_7$ are hydrogen. In still another embodiment, $R_7$ is F, and $R_4$, $R_5$, and $R_6$ are hydrogen.

In one embodiment, $R_5$ is Cl, and $R_4$, $R_6$, and $R_7$ are hydrogen. In another embodiment, $R_6$ is Cl, and $R_4$, $R_5$, and $R_7$ are hydrogen. In still another embodiment, $R_7$ is Cl, and $R_4$, $R_5$, and $R_6$ are hydrogen.

In one embodiment, $R_5$ and $R_6$ are F, and $R_4$ and $R_7$ are hydrogen. In another embodiment, $R_5$ and $R_7$ are F, and $R_4$ and $R_6$ are hydrogen. In still another embodiment, $R_6$ and $R_7$ are F, and $R_4$ and $R_5$ are hydrogen.

In one embodiment, $R_5$ and $R_6$ are Cl, and $R_4$ and $R_7$ are hydrogen. In another embodiment, $R_5$ and $R_7$ are Cl, and $R_4$ and $R_6$ are hydrogen. In still another embodiment, $R_6$ and $R_7$ are Cl, and $R_4$ and $R_5$ are hydrogen.

In some embodiments, each of $R_4$, $R_5$, $R_6$, and $R_7$ is hydrogen.

In some embodiments, $R_N$ can be a phosphate moiety. The phosphate moiety can have the structure

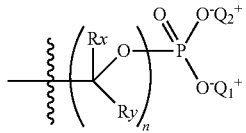

wherein n can be 0, 1, 2, 3, 4, 5, or 6, $R_x$ can be H or C1-C6 alkyl, $R_y$ can be H or C1-C6 alkyl, or, together, $R_x$ and $R_y$ form a C3-C8 cycloalkyl, and $Q_1^+$ and $Q_2^+$ can be each, independently, a monocation, or together can be a dication or one of $Q_1^+$ or $Q_2^+$ can be C1-C6 alkyl, benzyl, allyl or —(CR$_2$R$_3$—O)—R$_{23}$, and each of $R_2$, $R_3$, and $R_{23}$ can be, independently, H, or C1-C6 alkyl. In certain embodiments, the phosphate moiety can be a phosphorous-containing aralkyl group, for example a benzyl group.

In some embodiments, n can be 0 or 1.

In certain circumstances, $Q_1^+$ and $Q_2^+$ can be each, independently, an alkali metal.

In certain circumstances, $Q_1^+$ and $Q_2^+$ can be each, independently, selected from the group consisting of lithium, sodium, potassium, ammonium, alkyl ammonium, and phosphonium.

In certain circumstances, $Q_1^+$ and $Q_2^+$ together can be selected from the group consisting of an alkaline earth metal salt.

In certain circumstances, $Q_1^+$ and $Q_2^+$ can be each independently selected from the group consisting of zinc, calcium and magnesium.

In some embodiments, the present disclosure provides a compound selected from a compound in Table 1 (ARI-164), or a pharmaceutically acceptable salt thereof. In some embodiments, the present disclosure provides a compound selected from a compound in Table 1 (ARI-165), or a pharmaceutically acceptable salt thereof. In some embodiments, the present disclosure provides a compound selected from a compound in Table 1 (ARI-186), or a pharmaceutically acceptable salt thereof. In some embodiments, the present disclosure provides a compound selected from a compound in Table 1 (ARI-092), or a pharmaceutically acceptable salt thereof. In some embodiments, the present disclosure provides a compound selected from a compound in Table 1 (ARI-192), or an enantiomer or pharmaceutically acceptable salt thereof. In some embodiments, the present disclosure provides a compound selected from a compound in Table 1 (ARI-193), or an enantiomer or pharmaceutically acceptable salt thereof. In some embodiments, the present disclosure provides a compound selected from a compound in Table 1 (ARI-196), or an enantiomer or pharmaceutically acceptable salt thereof. In some embodiments, the present disclosure provides a compound selected from a compound in Table 1 (ARI-197), or an enantiomer or pharmaceutically acceptable salt thereof. In some embodiments, the present disclosure provides a compound selected from a compound in Table 1 (ARI-198), or an enantiomer or pharmaceutically acceptable salt thereof. In some embodiments, the present disclosure provides a compound selected from a compound in Table 1 (ARI-199), or an enantiomer or pharmaceutically acceptable salt thereof. In some embodiments, the present disclosure provides a compound selected from a compound in Table 1 (ARI-205), or an enantiomer or pharmaceutically acceptable salt thereof.

The present disclosure also provides a pharmaceutical composition comprising a compound described herein and a pharmaceutically acceptable carrier.

The present disclosure provides a method of stimulating the immune system in a patient in need thereof, comprising administering to the patient a therapeutically effective amount of a compound or pharmaceutical composition described herein. In some embodiments, the patient has an increased count of cells selected from the group consisting of white blood cells, macrophages, neutrophils, lymphocytes (e.g., B lymphocytes and/or T lymphocytes), natural killer (NK) cells, dendritic cells, and platelets, or increased levels of cytokines indicative of a stimulated immune system after the administering step. In some embodiments, the compound decreases IL-21 level in the patient. In some embodiments, the patient has cancer.

The present disclosure also provides a method of treating cancer in a patient, comprising administering to the patient a therapeutically effective amount of a compound described herein. In some embodiments, the cancer is a hematological malignancy (e.g., a lymphoma, leukemia, or myeloma), or a solid tumor. In some embodiments, the cancer may be selected from the group consisting of diffuse large B-cell lymphoma, marginal zone lymphoma, chronic lymphocytic leukemia (CLL), small lymphocytic lymphoma, prolymphocytic leukemia, acute lymphocytic leukemia, Waldenström's Macroglobulinemia (WM), follicular lymphoma, mantle cell lymphoma (MCL), Hodgkin lymphoma, non-Hodgkin lymphoma, multiple myeloma, prostate cancer, ovarian cancer, fallopian tube cancer, cervical cancer, breast cancer, lung cancer (e.g., non-small cell lung cancer), skin cancer (e.g., melanoma), colorectal cancer, stomach cancer, pancreatic cancer, liver cancer, kidney cancer, bladder cancer, soft tissue cancer, glioma, and head and neck cancer. In some embodiments, the method further comprises administering to the patient another cancer therapeutic agent, e.g., an immune checkpoint inhibitor (e.g., a PD-1, PD-L1, and/or PD-L2 inhibitor). In some embodiments, the method further comprises administering one or more maintenance doses of the compound while the patient is in remission.

Also provided herein is a compound or pharmaceutical composition described herein for use in modulating or stimulating the immune system (e.g., in patients with immune dysregulation or autoimmune diseases such as multiple sclerosis, rheumatoid arthritis, systemic lupus erythematosus, Crohn's disease, ulcerative colitis, or psoriasis) or treating cancer in a patient in need thereof in a treatment method described herein.

The present disclosure further provides the use of a compound described herein for the manufacture of a medicament for modulating or stimulating the immune system or treating cancer in a patient in need thereof in a treatment method described herein.

The present disclosure also provides articles of manufacture, including kits, that comprise a compound described herein.

The present disclosure also provides a method of making a compound of Structural Formula 9, or an enantiomer, diastereomer, or pharmaceutically acceptable salt thereof:

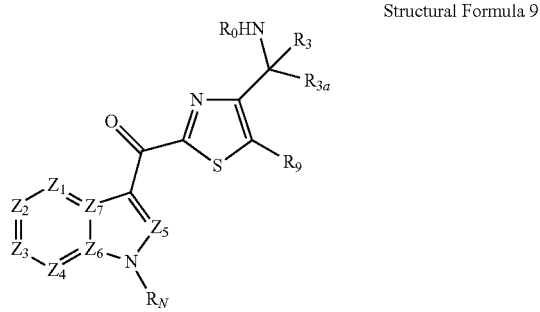

Structural Formula 9 wherein:

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_4$, $R_5$, $R_6$, $R_7$, $R_8$, and $R_9$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_3$ is selected from the group consisting of deuterium, cyano, formyl, furyl, nitro, alkyl, haloalkyl, alkenyl, haloalkenyl, alkynyl, haloalkynyl, $C_1$-$C_6$ acyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_{3a}$ is selected from the group consisting of hydrogen, deuterium, cyano, or C1-C6 alkyl;

$R_o$ is hydrogen, deuterium, alkyl, aryl, or acyl;

each $R_N$ is H, CN, alkyl, alkenyl, alkynyl, aryl, alkanoyl, carbonyloxy, carbonylthio, carbonylamino, or a phosphate moiety;

and optionally, adjacent R groups, together, can form a three- to twelve-membered ring; comprising:

(i) contacting a compound of Structural Formula 10 with with (S)-2-methylpropane-2-sulfinamide in the presence of a catalyst to yield a compound of Structural Formula 11;

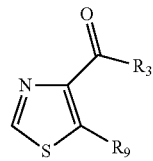

Structural Formula 10

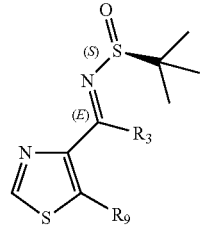

Structural Formula 11

(ii) contacting a compound of Structural Formula 11 with a one or more alkylating agent(s) to yield a compound of Structural Formula 12;

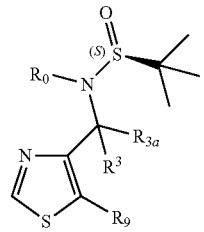

Structural Formula 12

(iii) contacting a compound of Structural Formula 12 with a compound of Structural Formula 13 in the presence of an organolithium base to yield a compound of Structural Formula 14;

Structural Formula 13

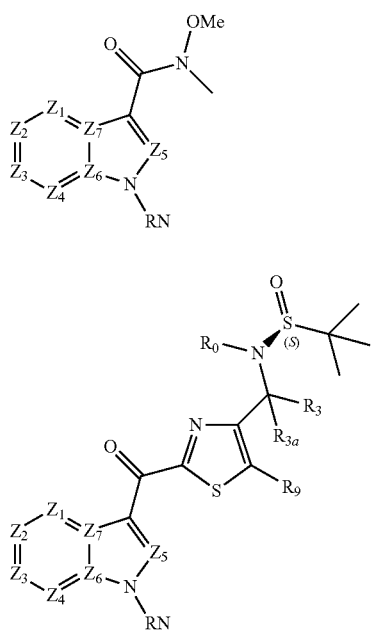

Structural Formula 14

(iv) subjecting a compound of Structural Formula 14 to acid-base hydrolysis to obtain a compound of Structural Formula 9.

In some embodiments, each of $R_4$, $R_5$, $R_6$, $R_7$, $R_8$, $R_9$, and $R_N$ is hydrogen.

In some embodiments, at least one of $R_4$, $R_5$, $R_6$, and $R_7$ is F, Cl, or Br and the others of $R_4$, $R_5$, $R_6$, and $R_7$ are hydrogen.

In some embodiments, $R_o$, $R_3$, and $R_{3a}$ are independently H or alkyl.

In some embodiments, at least one of $Z_1$, $Z_2$, $Z_3$, $Z_4$, $Z_5$, $Z_6$, or $Z_7$ is N.

In some embodiments, the compound of Structural formula 9 is enantiomerically pure at the carbon substituted with $NHR_o/R_3/R_{3a}$.

In some embodiments, $R_3$ and $R_{3a}$ together form a three- to twelve-membered ring, including a cyclopropyl, cyclobutyl, cyclopentyl, or cyclohexyl ring.

In some embodiments, the catalyst is a transition metal alkoxide.

In particular embodiments, the transition metal alkoxide is a titanium alkoxide.

The present disclosure also provides a method of making (S)-(4-(1-aminopropyl)thiazol-2-yl)(6-fluoro-1H-indol-3-yl)methanone, comprising:

contacting thiazole-4-carbaldehyde with (S)-2-methylpropane-2-sulfinamide in the presence of titanium isopropoxide to yield (SE)-2-methyl-N-(thiazol-4-ylmethylene)propane-2-sulfinamide;

contacting (S,E)-2-methyl-N-(thiazol-4-ylmethylene)propane-2-sulfinamide with ethylmagnesium bromide to yield (S)-2-methyl-N-(1-(thiazol-4-yl)propyl)propane-2-sulfinamide;

contacting (S)-2-methyl-N-(1-(thiazol-4-yl)propyl)propane-2-sulfinamide with tert-butyl 6-fluoro-3-(methoxy (methyl)carbamoyl)-1H-indole-1-carboxylate in the presence of an organolithium base to yield (S)—N—((S)-1-(2-(6-fluoro-1H-indole-3-carbonyl)thiazol-4-yl)propyl)-2-methylpropane-2-sulfinamide; and subjecting (S)—N—((S)-1-(2-(6-fluoro-1H-indole-3-carbonyl)thiazol-4-yl)propyl)-2-methylpropane-2-sulfinamide to acid-base hydrolysis to obtain (S)-(4-(1-aminopropyl) thiazol-2-yl)(6-fluoro-1H-indol-3-yl)methanone.

BRIEF DESCRIPTION OF THE DRAWINGS

FIG. 14 shows a synthesis scheme for compound ARI-217 according to Example 25.

FIG. 15A shows a synthesis scheme for compound ARI-186 according to Example 26.

DETAILED DESCRIPTION OF THE INVENTION

Figure 1:
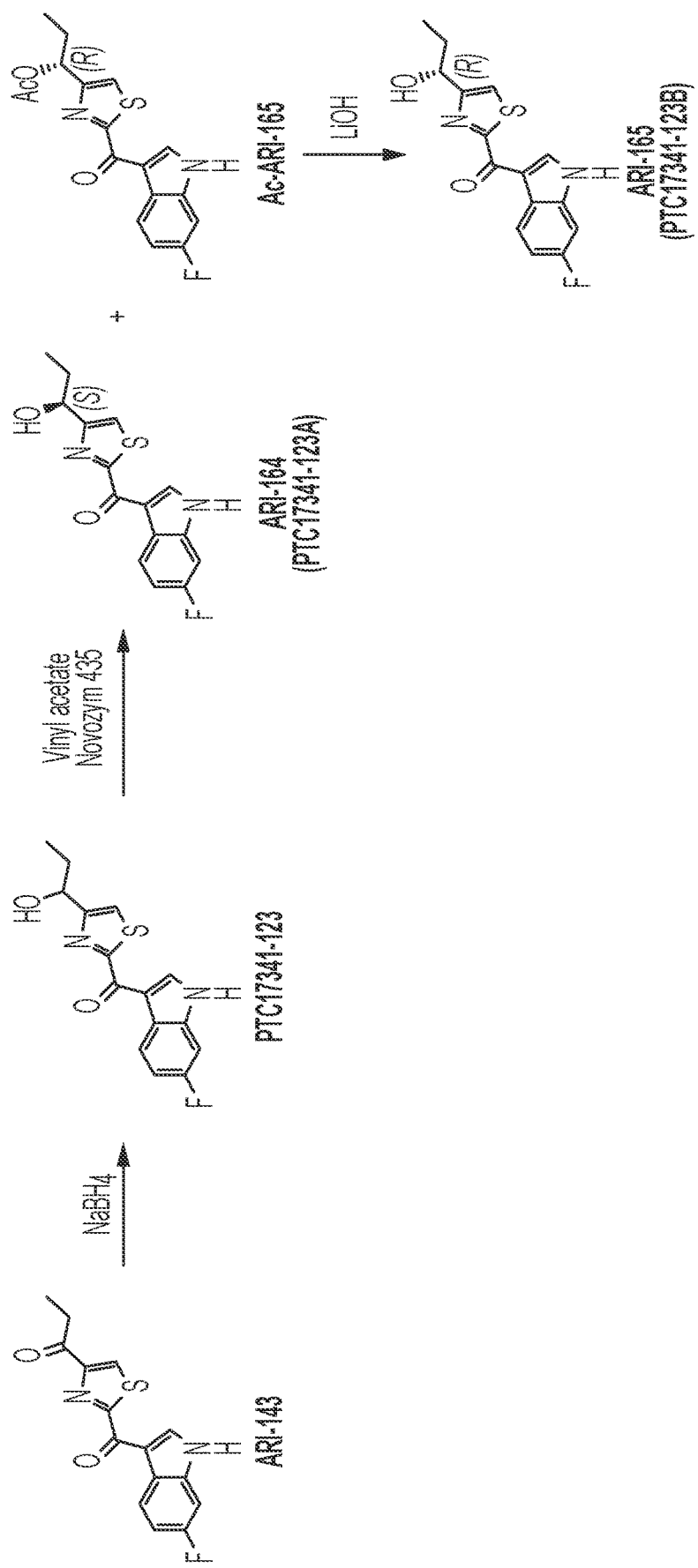
FIG. 1 shows a synthesis scheme for ARI-164 and ARI-165 according to Example 1.
Figure 2:
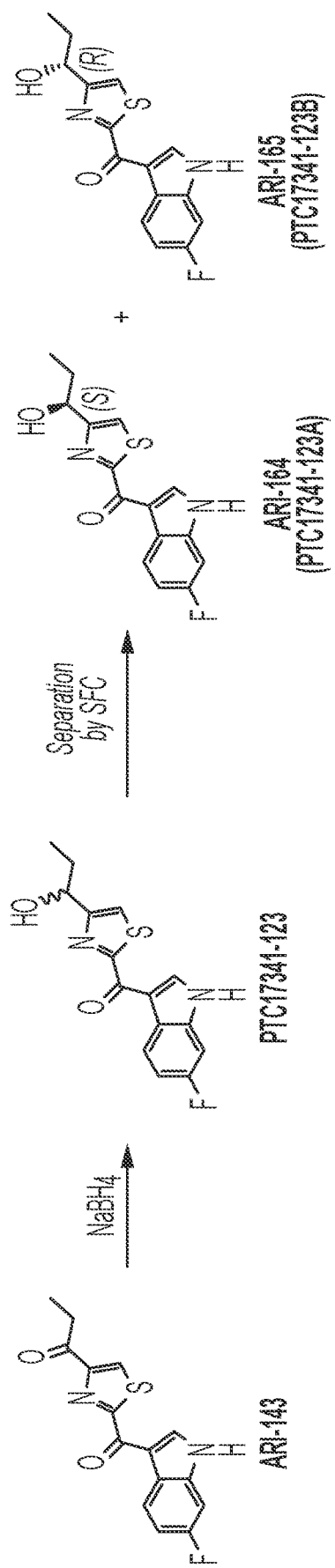
FIG. 2 shows a synthesis scheme for ARI-164 and ARI-165 according to Example 2
Figure 3:
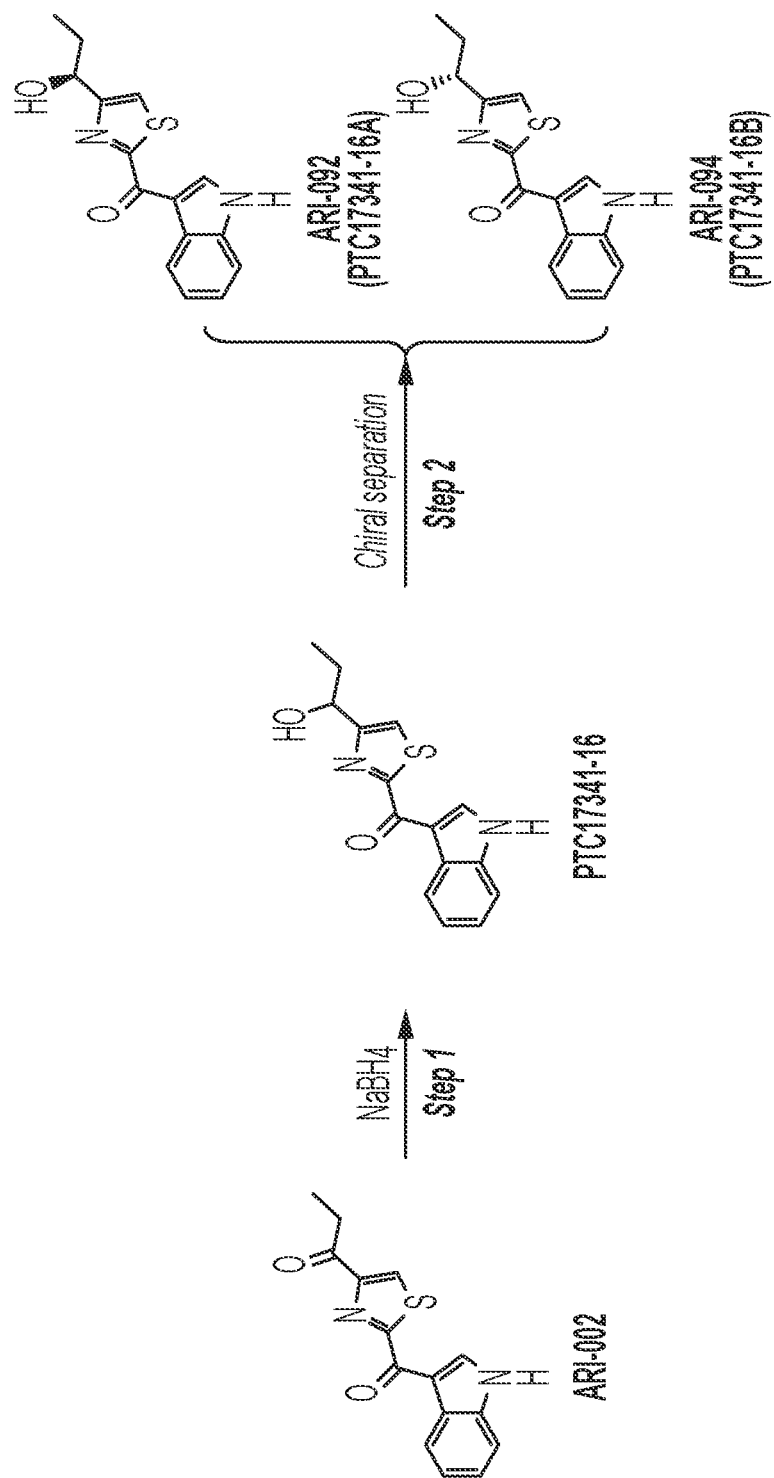
FIG. 3 shows a synthesis scheme for ARI-092 and ARI-094 according to Example 3.
Figure 4:
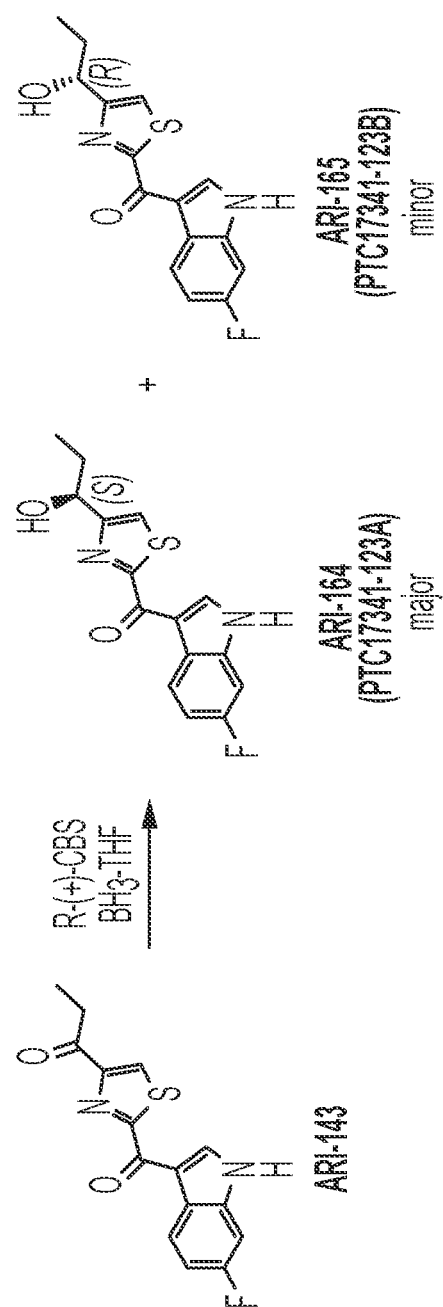
FIG. 4 shows a chiral synthesis scheme for ARI-164 and ARI-165 according to Example 4.
Figure 5:
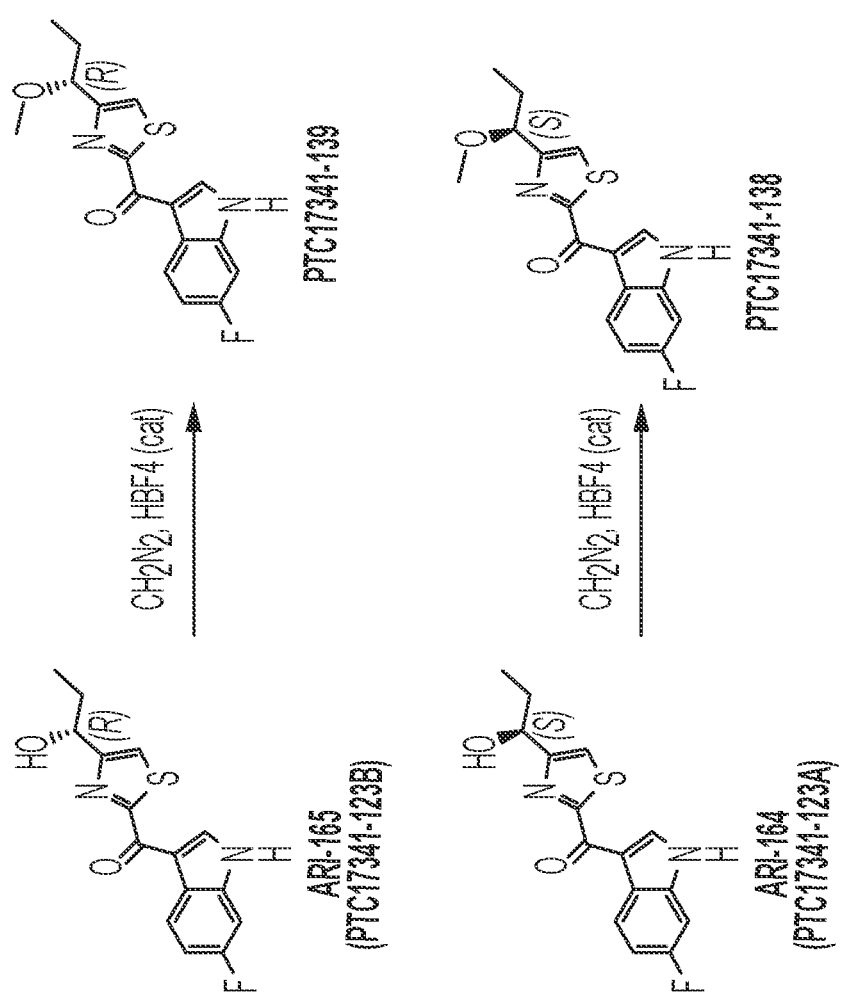
FIG. 5 shows a synthesis scheme for PTC17341-138 and PTC17341-139 according to Example 5.
Figure 6:
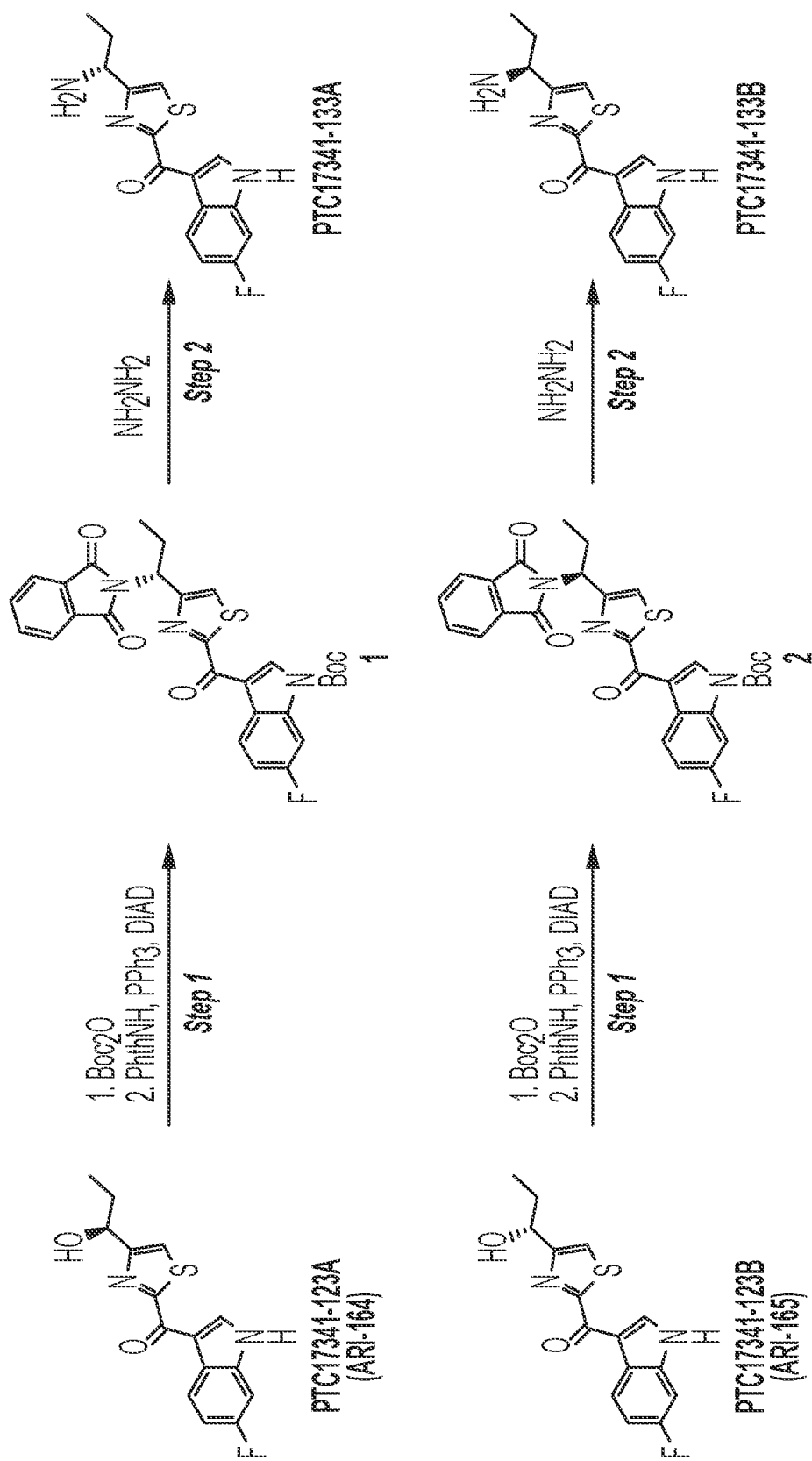
FIG. 6 shows a synthesis scheme for PTC17341-133A and PTC17341-133B according to Example 6.
Figure 7A:
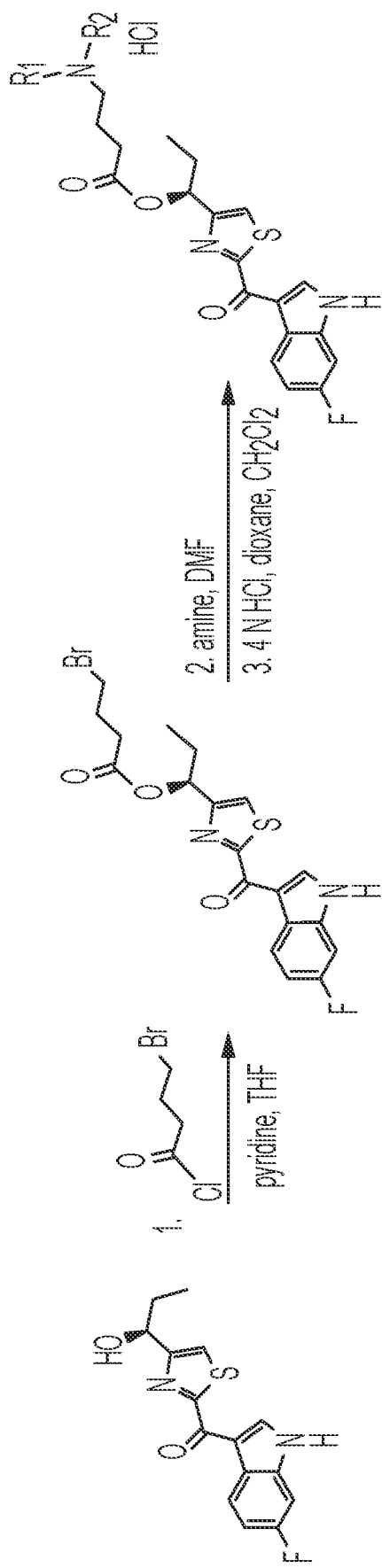
FIG. 7A shows a synthesis scheme for compounds ARI-196, ARI-197, ARI-198, ARI-199, and ARI-205 according to Examples 9-13.
Figure 7B:
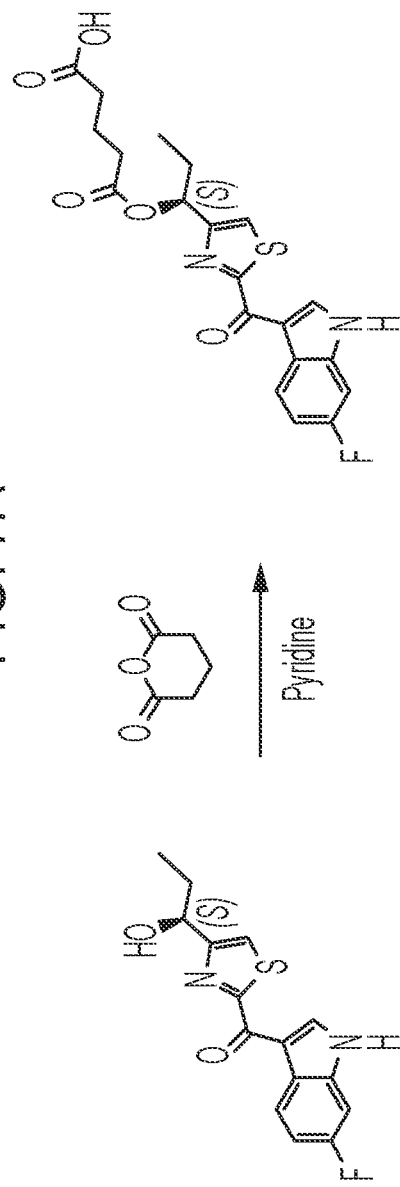
FIG. 7B shows a synthesis scheme for compound ARI-192 according to Example 14.
Figure 7C:
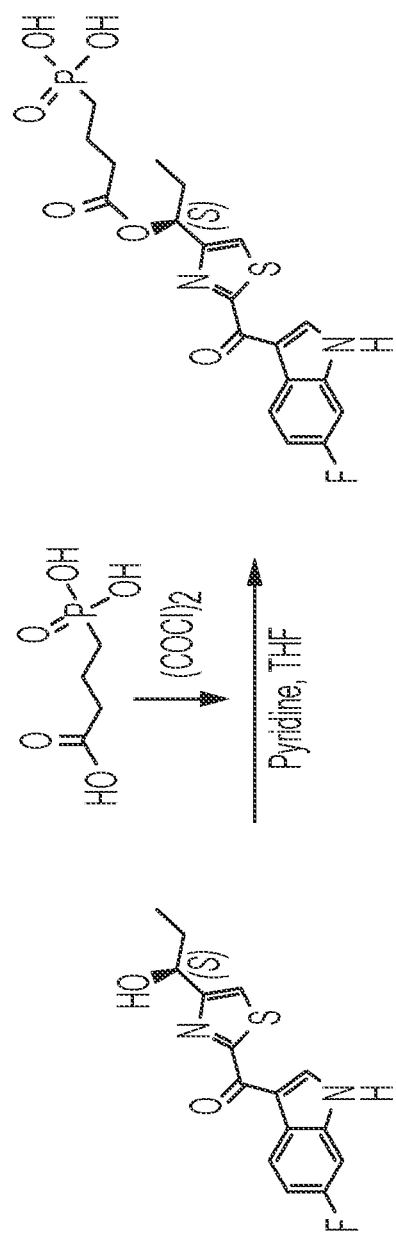
FIG. 7C shows a synthesis scheme for compound ARI-193 according to Example 15.
Figure 8:
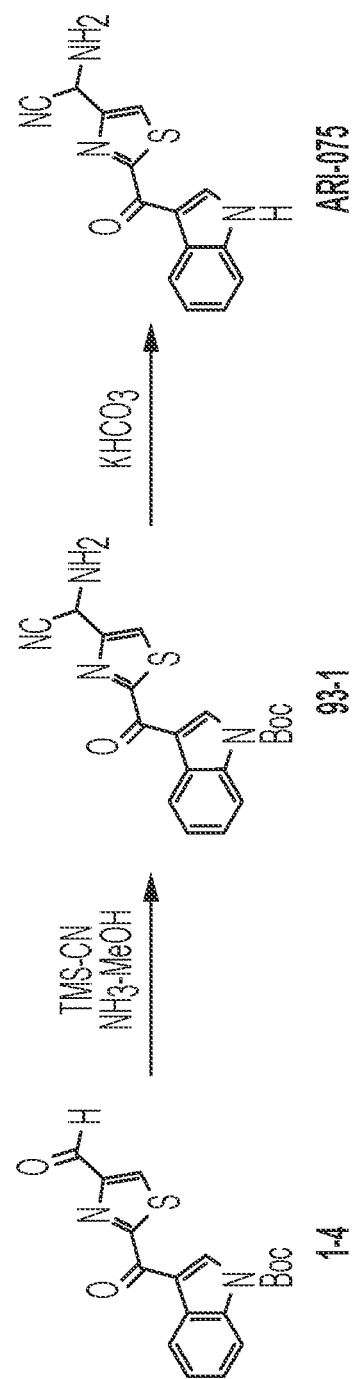
FIG. 8 shows a synthesis scheme for compound ARI-075 according to Example 16.
Figure 9:
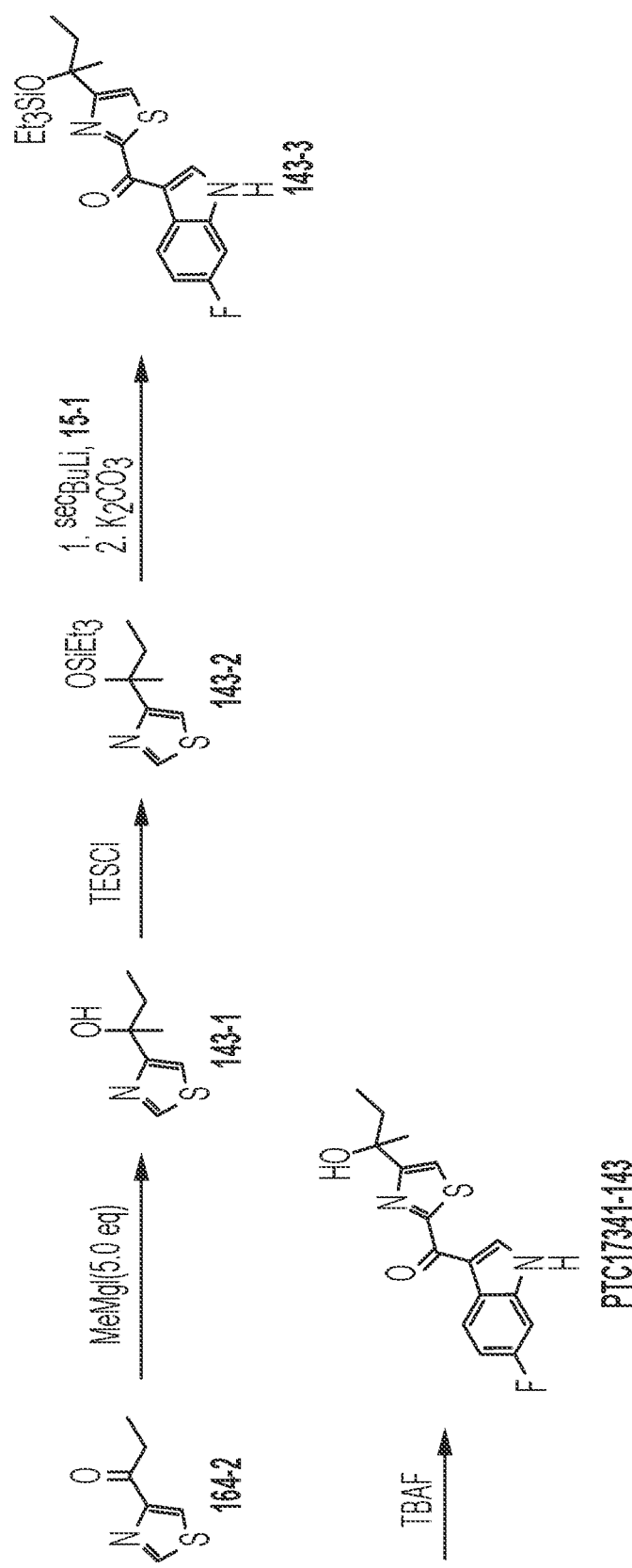
FIG. 9 shows a synthesis scheme for compound ARI-209 according to Example 18.
Figure 10:
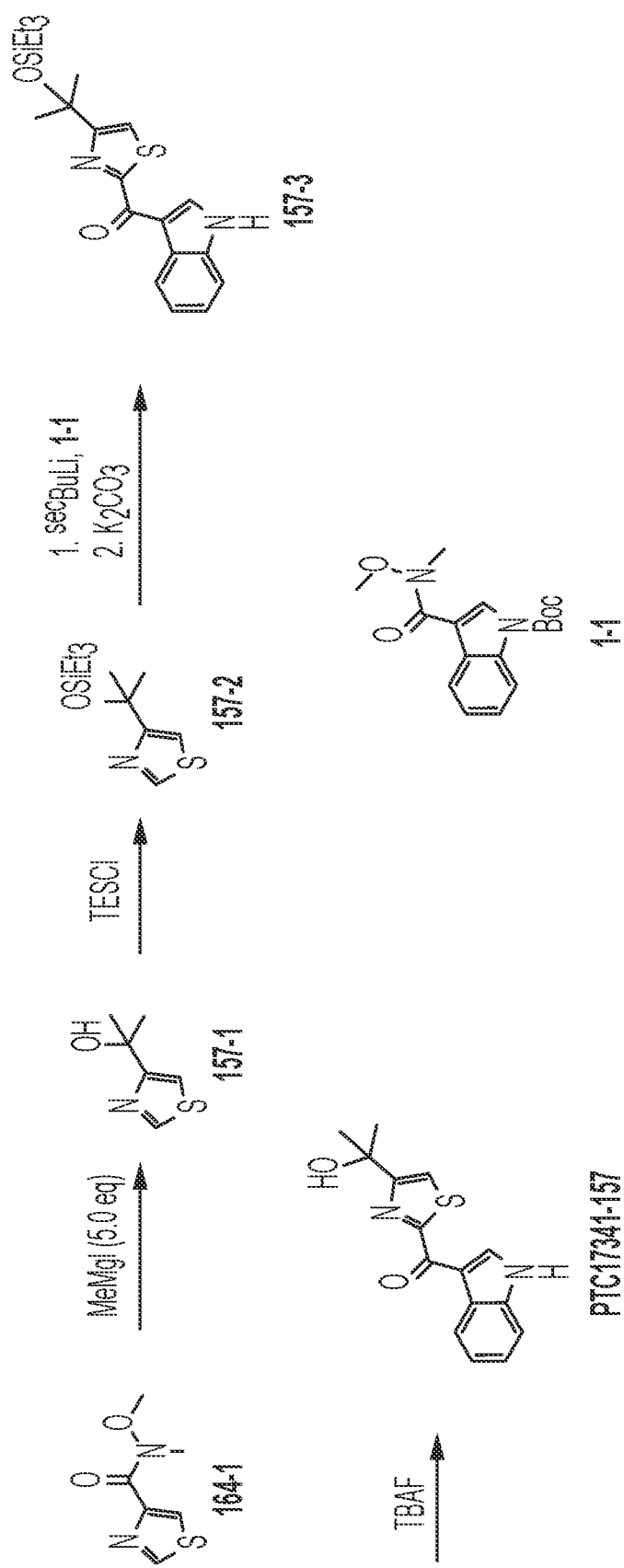
FIG. 10 shows a synthesis scheme for compound ARI-215 according to Example 20.
Figure 11:
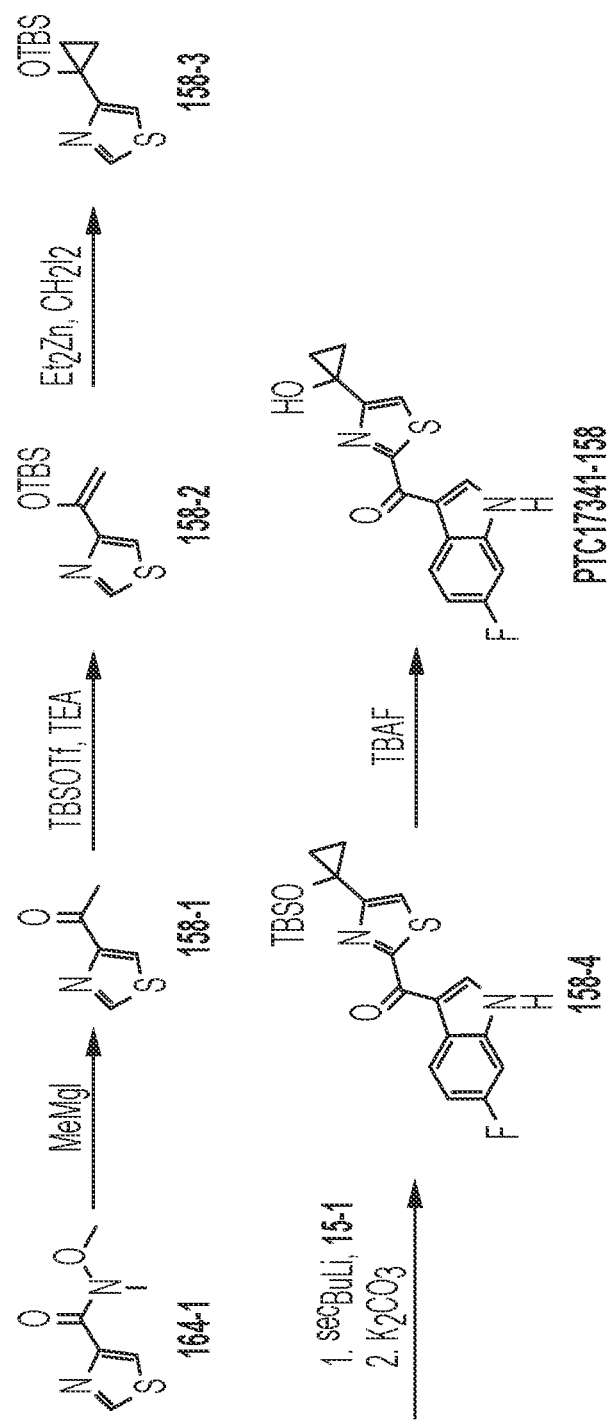
FIG. 11 shows a synthesis scheme for compound ARI-221 according to Example 22.
Figure 12:
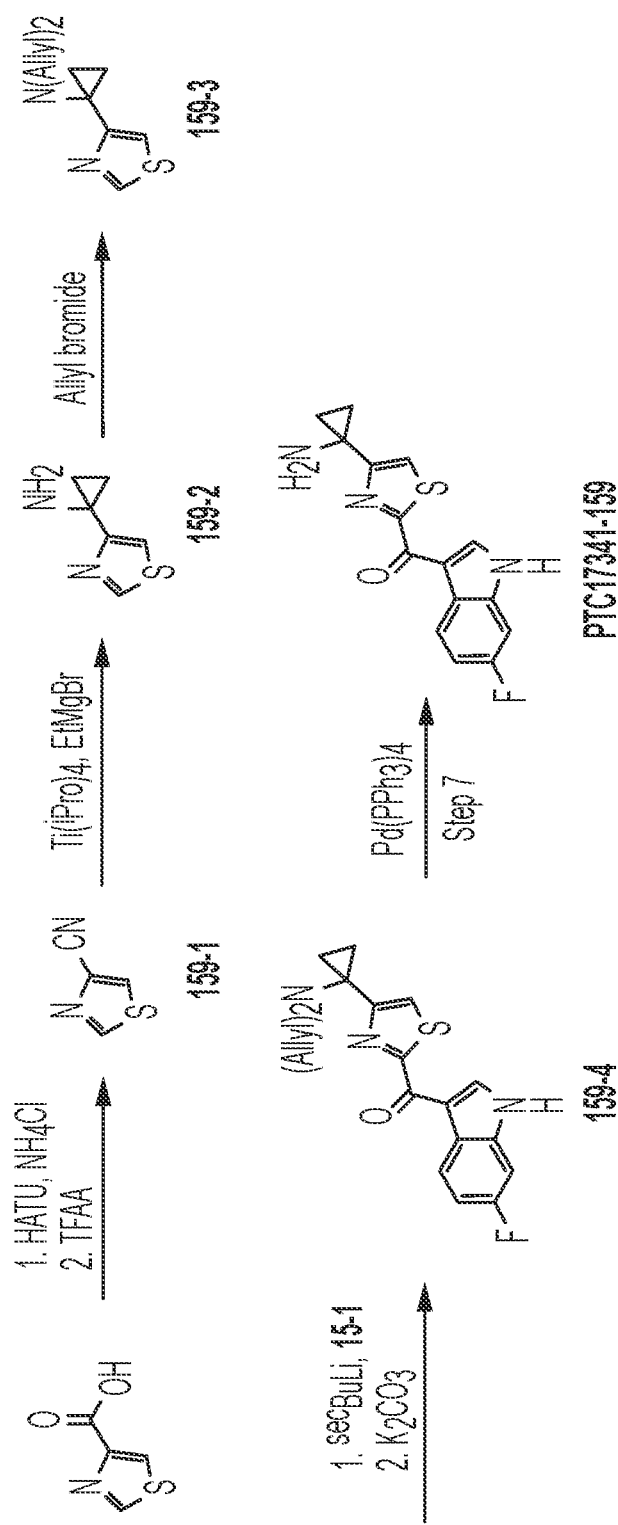
FIG. 12 shows a synthesis scheme for compound ARI-225 according to Example 23.
Figure 13:
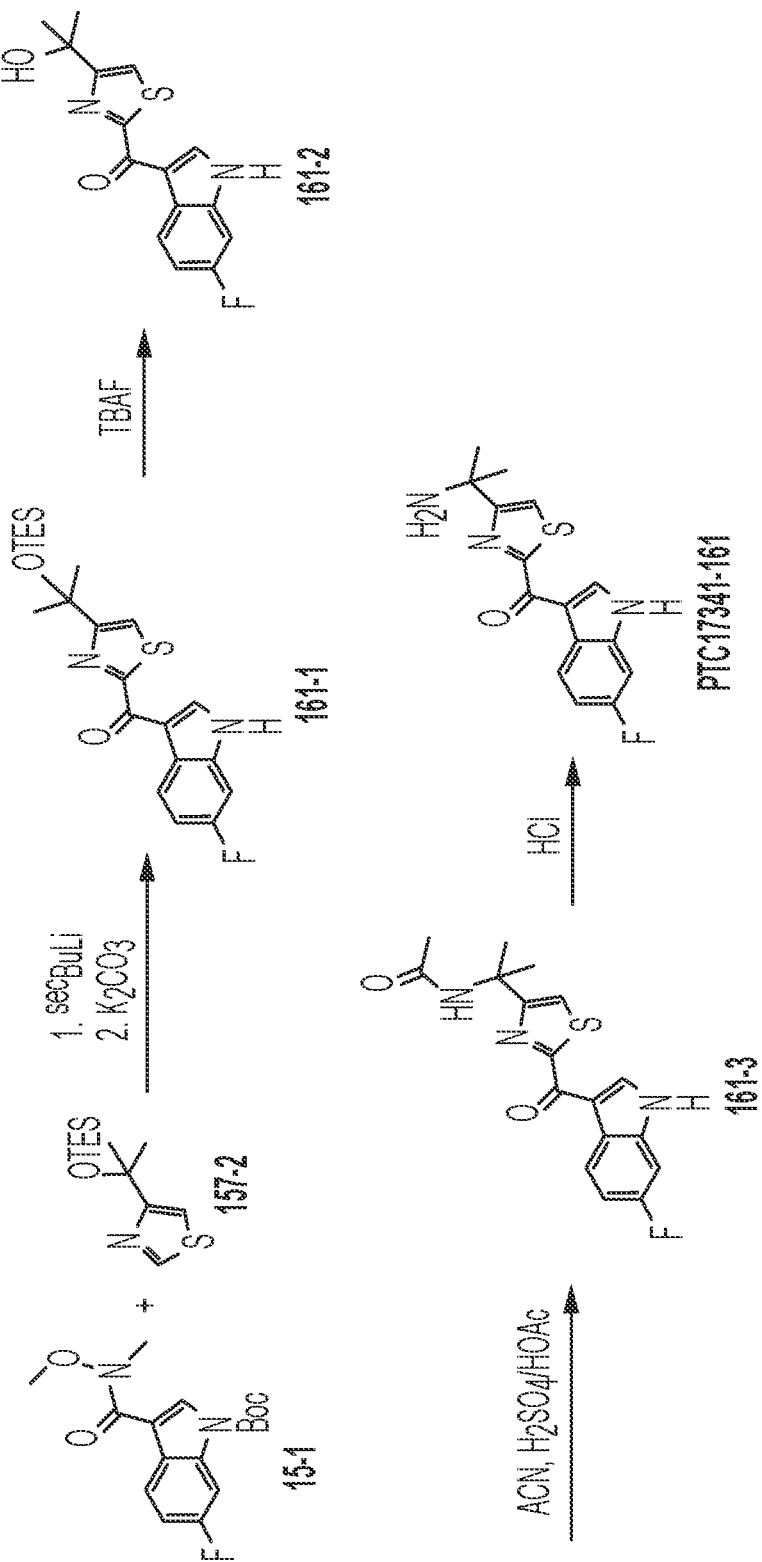
FIG. 13 shows a synthesis scheme for compound ARI-226 according to Example 24.
Figure 15B:
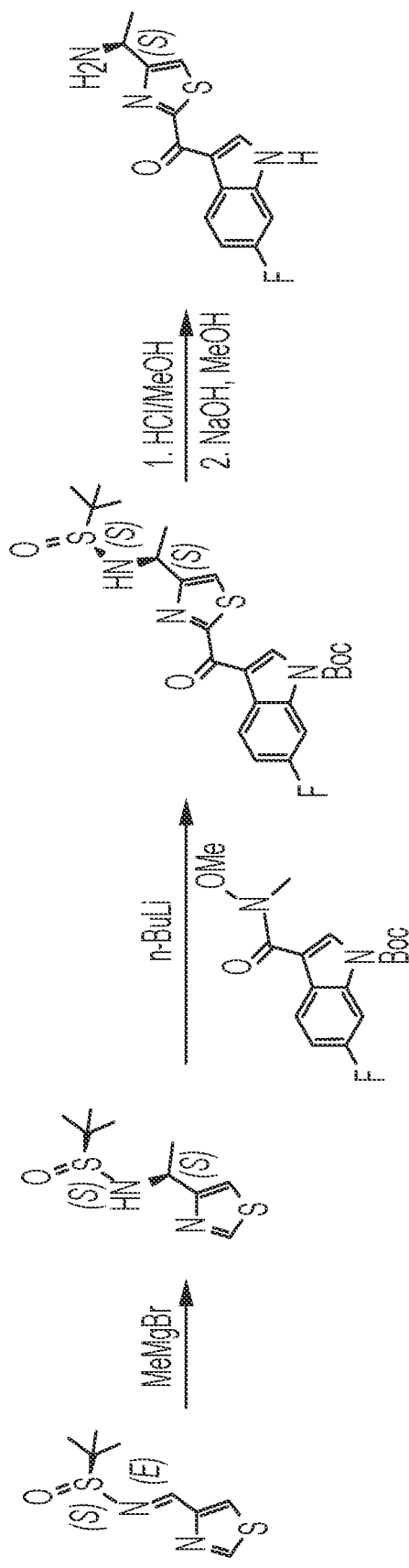
FIG. 15B shows a synthesis scheme for compound ARI-232 according to Example 27.
Figure 15C:
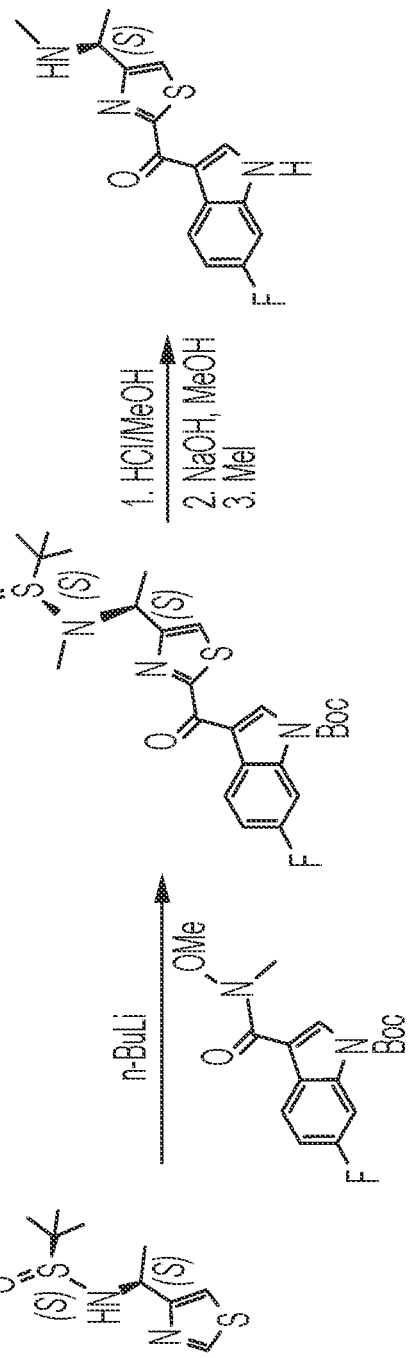
FIG. 15C shows a synthesis scheme for compound ARI-233 according to Example 28.
Figure 15D:
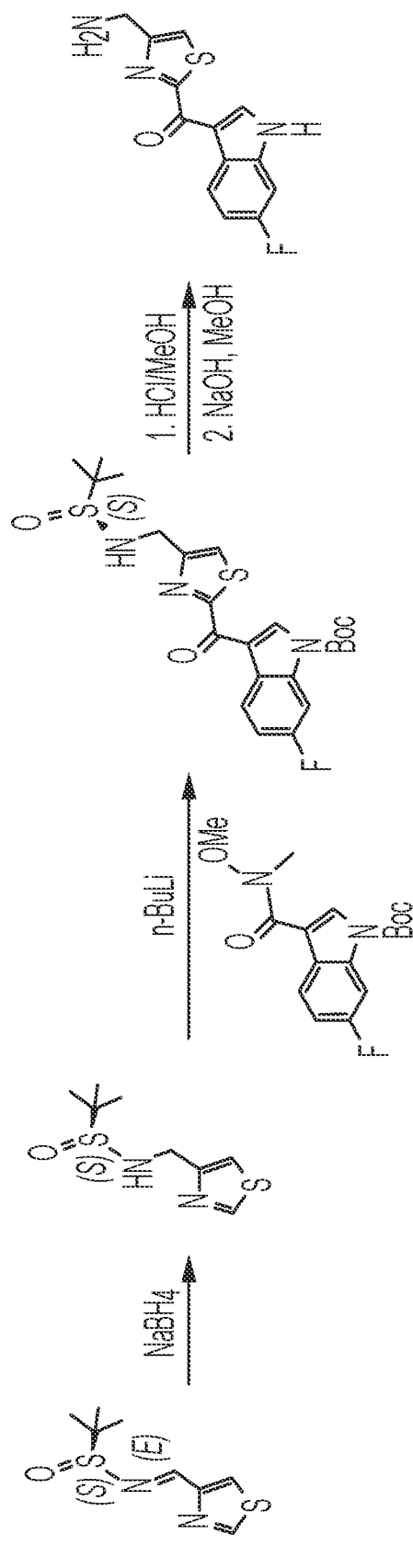
FIG. 15D shows a synthesis scheme for compound ARI-234 according to Example 29.
Figure 15E:
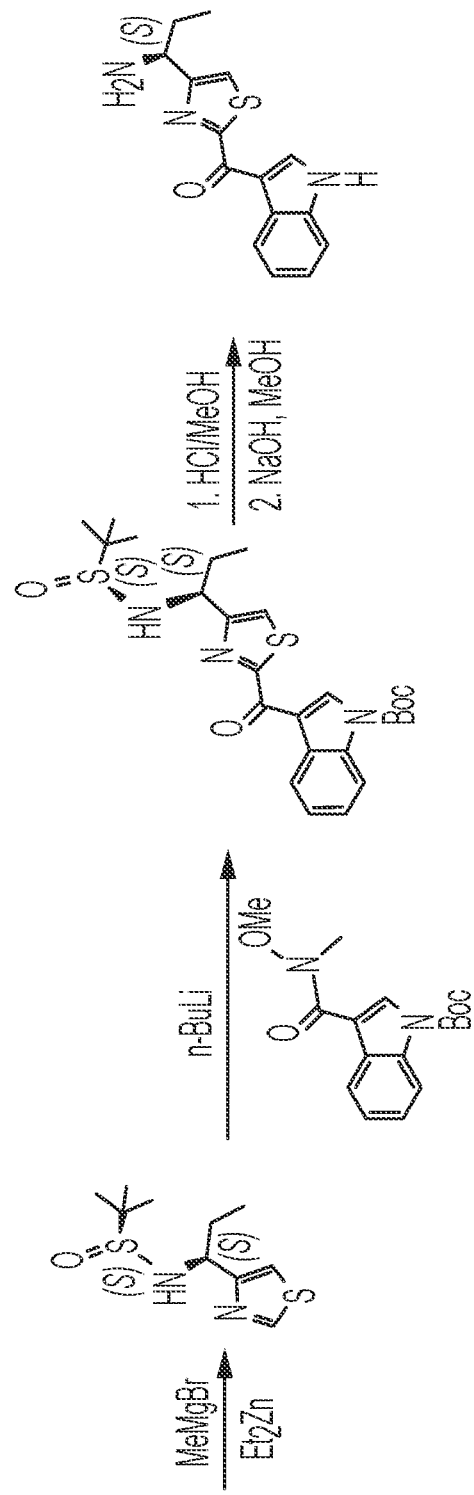
FIG. 15E shows a synthesis scheme for compound ARI-235 according to Example 30.
Figure 15F:
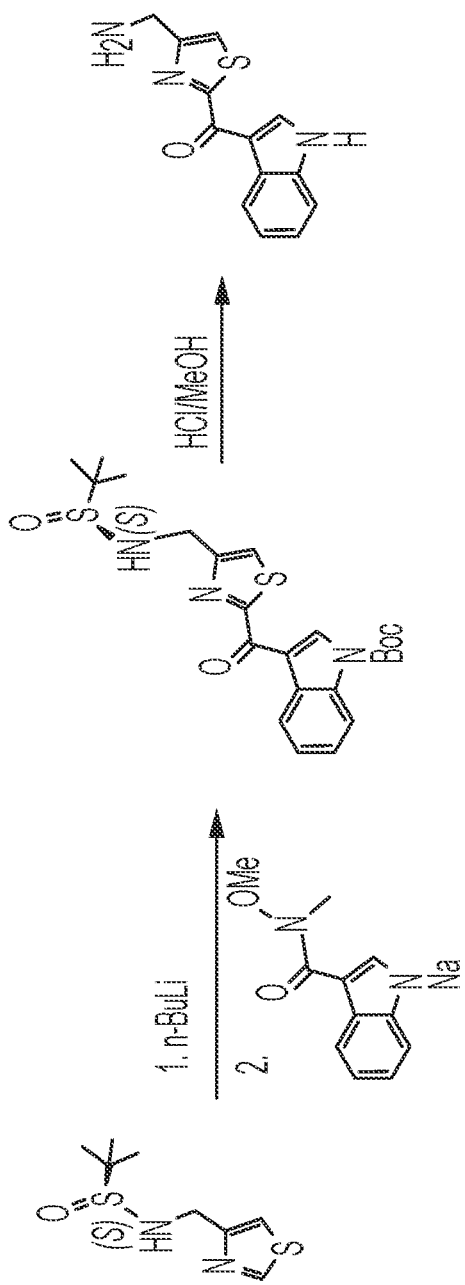
FIG. 15F shows a synthesis scheme for compound ARI-236 according to Example 31.
Figure 16A:
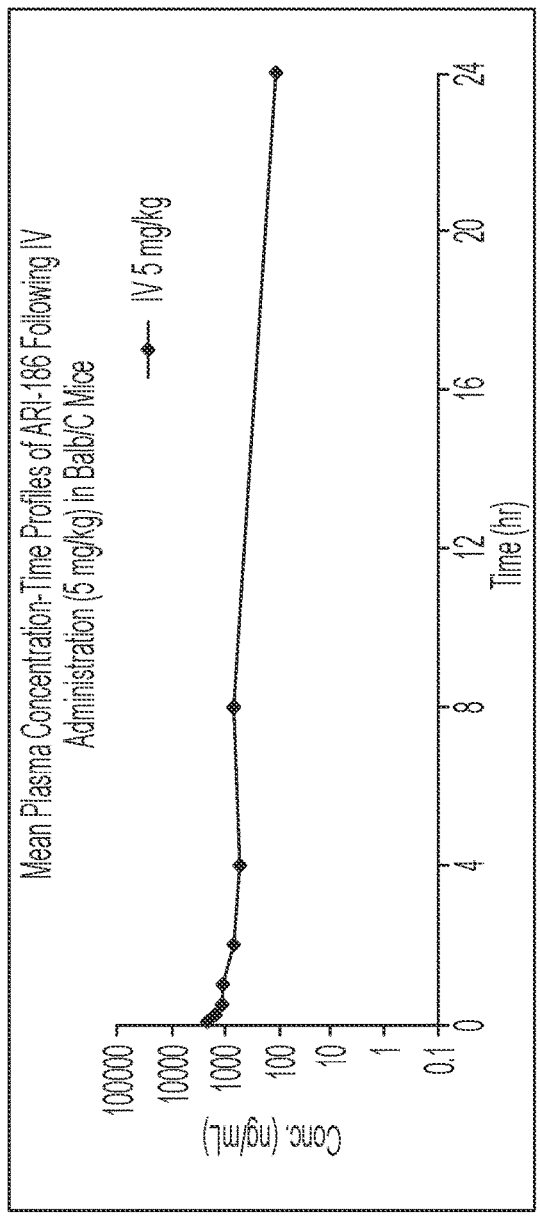
FIG. 16A is a plot showing the mean plasma concentration-time profile of ARI-186 following IV administration of 5 mg/kg in Balb/C mice.
Figure 16B:
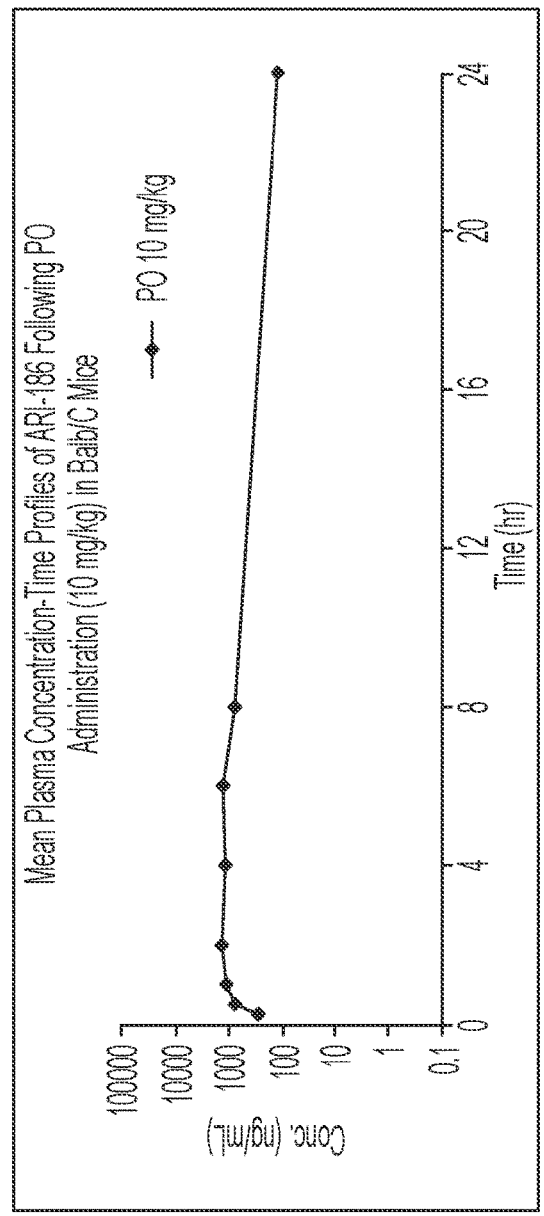
FIGS. 16B and 16C are plots showing the mean plasma concentration-time profiles of ARI-186 following PO administration of 10 mg/kg or 40 mg/kg in Balb/C mice.
Figure 16C:
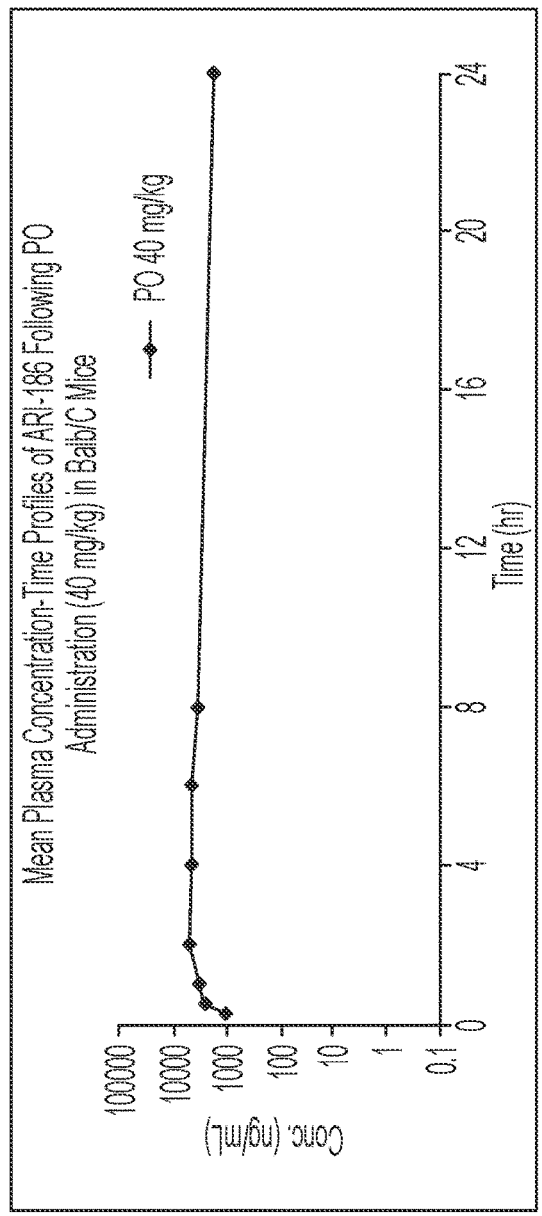
Figure 16D:
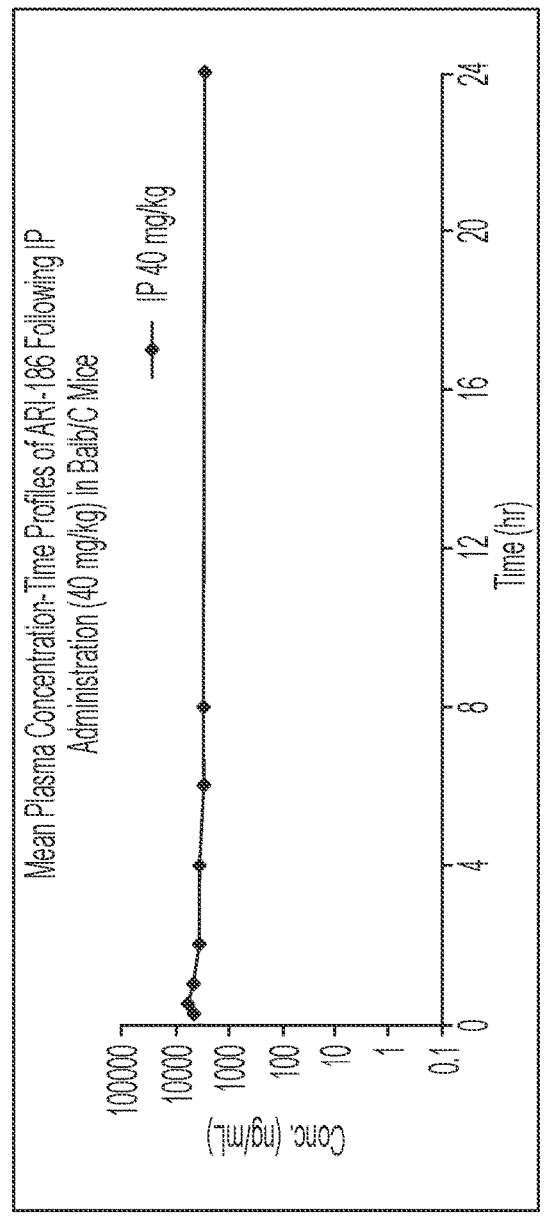
FIG. 16D is a plot showing the mean plasma concentration-time profile of ARI-186 following IP administration of 40 mg/kg in Balb/C mice.
Figure 17A:
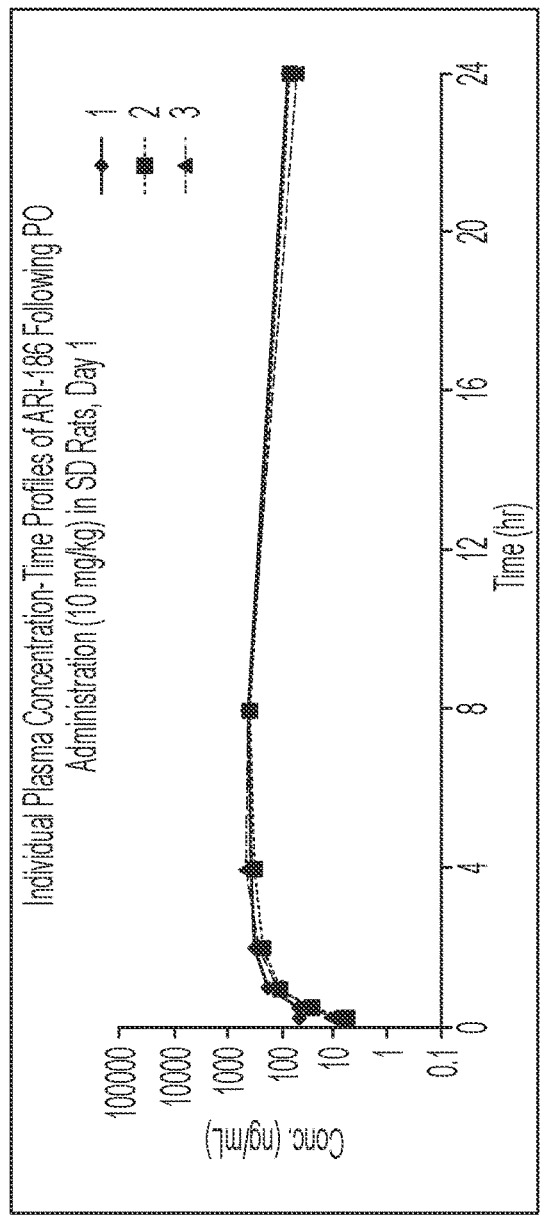
FIGS. 17A and 17B are plots showing individual plasma concentration-time profiles of ARI-186 following PO administration of 10 mg/kg in SD rats on days 1 and 5, respectively.
Figure 17B:
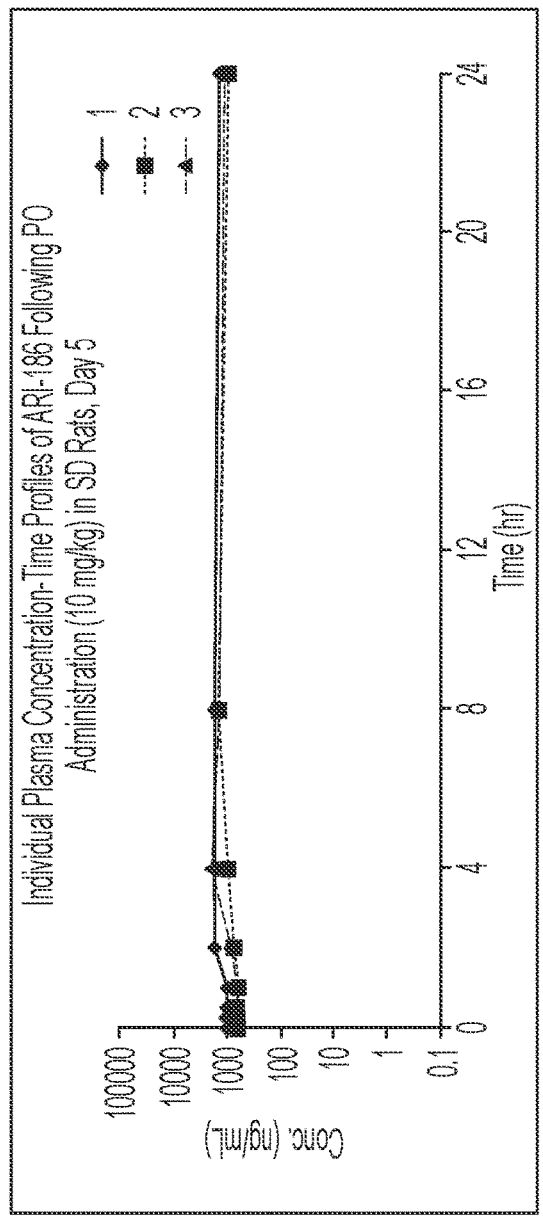
Figure 18A:
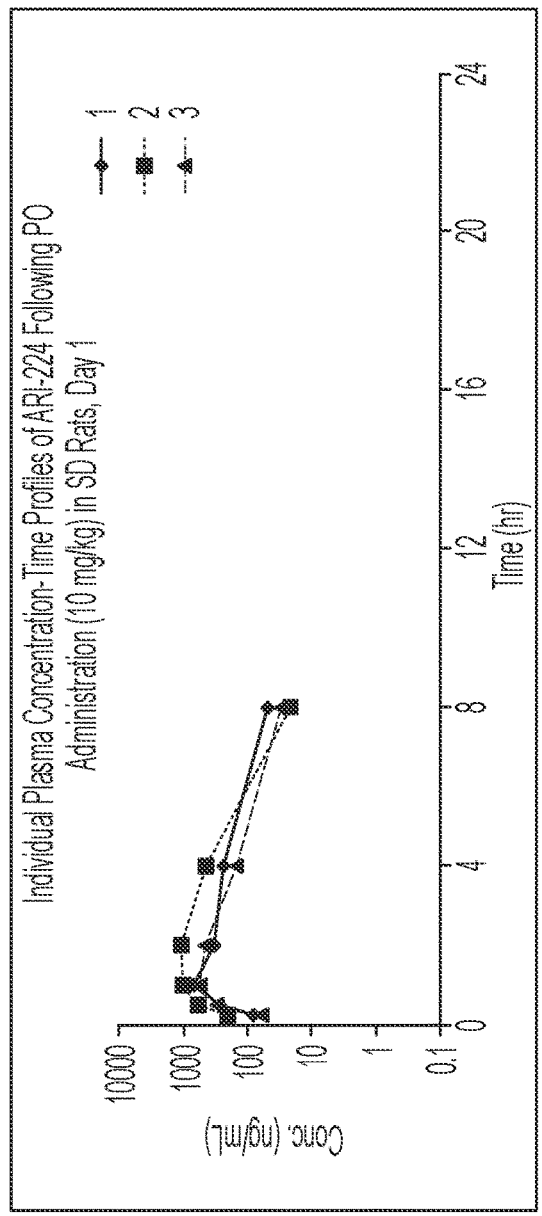
FIGS. 18A and 18B are plots showing individual plasma concentration-time profiles of ARI-224 following PO administration of 10 mg/kg in SD rats on days 1 and 5, respectively.
Figure 18B:
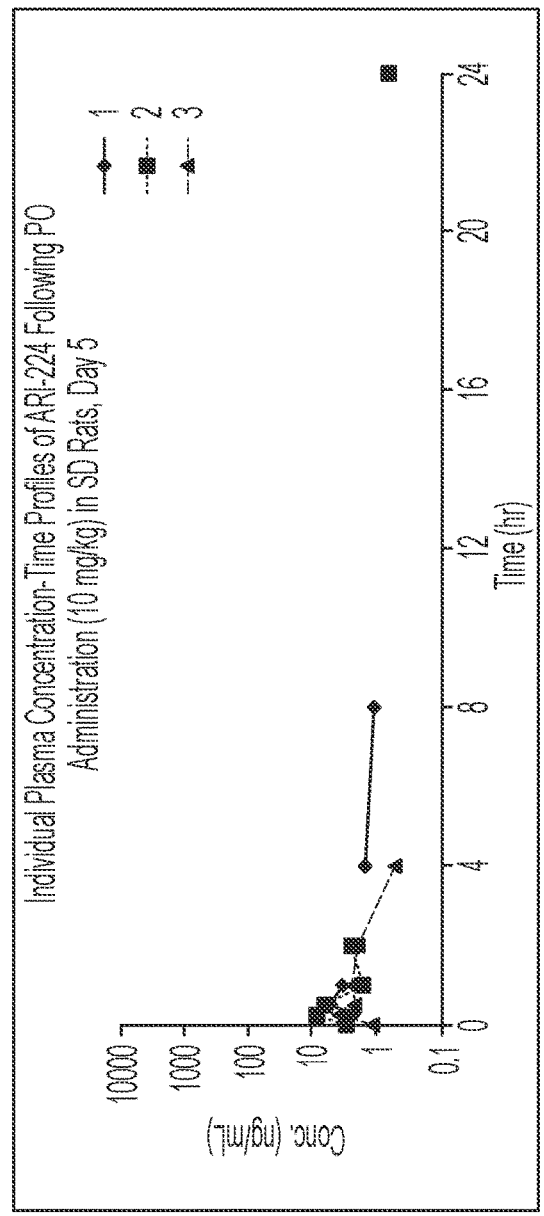
Figure 19A:
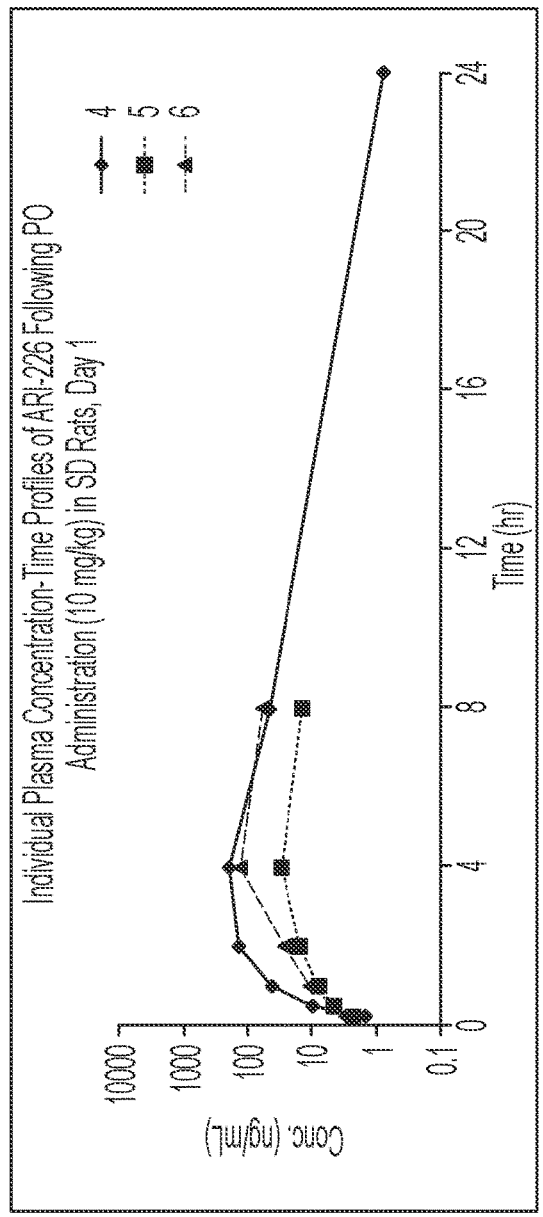
FIGS. 19A and B are plots showing individual plasma concentration-time profiles of ARI-226 following PO administration of 10 mg/kg in SD rats on days 1 and 5, respectively.
Figure 19B:
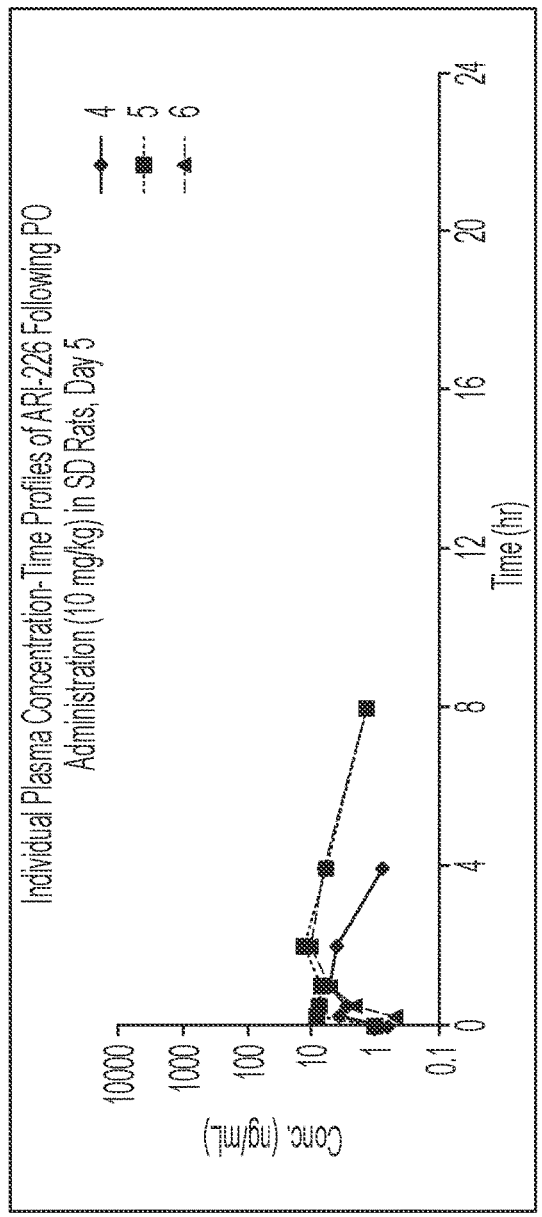

All technical and scientific terms used herein are the same as those commonly used by those ordinary skilled in the art to which the present invention pertains unless defined specifically otherwise.

The moieties described below can be substituted or unsubstituted. "Substituted" refers to replacement of a hydrogen atom of a molecule or an R-group with one or more additional R-groups such as deuterium, halogen, alkyl, haloalkyl, alkenyl, alkoxy, alkoxyalkyl, alkylthio, trifluoromethyl, acyloxy, hydroxy, hydroxyalkyl, mercapto, carboxy, cyano, acyl, aryloxy, aryl, arylalkyl, heteroaryl, amino, aminoalkyl, alkylamino, dialkylamino, morpholino, piperidino, pyrrolidin-1-yl, piperazin-1-yl, nitro, phosphine, phosphinate, phosphonate, sulfato, =O, =S, or other R-groups. Unless otherwise indicated, an optionally substituted group may have a substituent at each substitutable position of a group. Combinations of substituents contemplated herein are preferably those that result in the formation of stable (e.g., not substantially altered for a week or longer when kept at a temperature of 40° C. or lower in the absence of moisture or other chemically reactive conditions), or chemically feasible, compounds.

"Hydroxy", "thiol", "cyano", "nitro", and "formyl" refer, respectively, to —OH, —SH, —CN, —NO$_2$, and —CHO.

"Acyloxy" refers to a RC(=O)O— radical, wherein R is alkyl, cycloalkyl, aryl, heteroalkyl, heteroaryl, or heterocycloalkyl, which are as described herein. In some embodiments, it is a C$_1$-C$_4$ acyloxy radical, which refers to the total number of chain or ring atoms of the alkyl, cycloalkyl, aryl, heteroalkyl, heteroaryl, or heterocycloalkyl portion of the acyloxy group plus the carbonyl carbon of acyl, i.e., the other ring or chain atoms plus carbonyl. If the R radical is heteroaryl or heterocycloalkyl, the hetero ring or chain atoms contribute to the total number of chain or ring atoms.

"Alkyl" refers to a group of 1-18, 1-16, 1-12, 1-10, preferably 1-8, more preferably 1-6 unsubstituted or substituted hydrogen-saturated carbons connected in linear, branched, or cyclic fashion, including the combination in linear, branched, and cyclic connectivity. Non-limiting examples include methyl, ethyl, propyl, isopropyl, butyl, and pentyl.

"Cycloalkyl" refers to a monocyclic or polycyclic non-aromatic radical that contains carbon and hydrogen, and may be saturated, or partially unsaturated. Cycloalkyl groups include groups having from 3 to 10 ring atoms (e.g., C$_3$-C$_{10}$ cycloalkyl). Whenever it appears herein, a numerical range such as "3 to 10" refers to each integer in the given range; e.g., "3 to 10 carbon atoms" means that the cycloalkyl group may consist of 3 carbon ring atoms, 4 carbon ring atoms, carbon ring atoms, etc., up to and including 10 carbon ring atoms. In some embodiments, it is a C$_3$-C$_8$ cycloalkyl radical. In some embodiments, it is a C$_3$-C$_5$ cycloalkyl radical. Examples of cycloalkyl group include, but are not limited to, cyclopropyl, cyclobutyl, cyclopentyl, cyclopentenyl, cyclohexyl, cyclohexenyl, cycloseptyl, cyclooctyl, cyclononyl, cyclodecyl, and norbornyl. The term "cycloalkyl" also refers to spiral ring system, in which the cycloalkyl rings share one carbon atom.

"Heterocycloalkyl" refers to a 3- to 18-membered non-aromatic ring (e.g., C$_3$-C18 heterocycloalkyl) radical that comprises two to twelve ring carbon atoms and from one to six heteroatoms selected from nitrogen, oxygen and sulfur. Whenever it appears herein, a numerical range such as "3 to 18" refers to each integer in the given range; e.g., "3 to 18 ring atoms" means that the heterocycloalkyl group may consist of 3 ring atoms, 4 ring atoms, etc., up to and including 18 ring atoms. In some embodiments, it is a C$_5$-C$_{10}$ heterocycloalkyl. In some embodiments, it is a C$_4$-C$_{10}$ heterocycloalkyl. In some embodiments, it is a C$_3$-C$_{10}$ heterocycloalkyl. The heterocycloalkyl radical may be a monocyclic, bicyclic, tricyclic or tetracyclic ring system, which may include fused or bridged ring systems. The heteroatoms in the heterocycloalkyl radical may be optionally oxidized. One or more nitrogen atoms, if present, may optionally be quaternized. The heterocycloalkyl radical may be partially or fully saturated. The heterocycloalkyl may be attached to the rest of the molecule through any atom of the ring(s). Examples of such heterocycloalkyl radicals include, but are not limited to, 6,7-dihydro-5H-cyclopenta[b]pyridine, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. In some embodiments, the heterocycloalkyl group is aziridinyl, azetidinyl, pyrrolidinyl, piperidinyl, homopiperidinyl, morpholinyl, thiomorpholinyl, piperazinyl, tetrahydrofuranyl, tetrahydrothienyl, dihydrooxazolyl, tetrahydropyranyl, tetrahydrothiopyranyl, indolinyl, tetrahydroquinolyl, tetrahydroisoquinolin and benzoxazinyl, preferably dihydrooxazolyl and tetrahydrofuranyl.

"Halo" refers to any of halogen atoms fluorine (F), chlorine (Cl), bromine (Br), or iodine (I). A particular example of such halo groups is fluorine.

"Haloalkyl" refers to an alkyl substituted by one or more halo(s).

"Alkenyl" refers to a group of unsubstituted or substituted hydrocarbons containing 2-18, 2-16, 2-12, 2-10, for example, 2-8 (e.g., 2-6) carbons, which are linear, branched, cyclic, or in combination thereof, with at least one carbon-to-carbon double bond.

"Haloalkenyl" refers to an alkenyl substituted by one or more halo(s).

"Alkynyl" refers to a group of unsubstituted or substituted hydrocarbons containing 2-18, 2-16, 2-12, 2-10, for example, 2-8 (e.g., 2-6) carbons, which are linear, branched, cyclic, or in combination thereof, with at least one carbon-to-carbon triple bond.

"Haloalkynyl" refers to an alkynyl substituted by one or more halo(s).

"Amino protecting group" refers to those groups intended to protect an amino group against undesirable reactions during synthetic procedures and which can later be removed to reveal the amine. Commonly used amino protecting groups are disclosed in Protective Groups in Organic Synthesis, Greene, T. W.; Wuts, P. G. M., John Wiley & Sons, New York, N.Y., (3rd Edition, 1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, alpha-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, alpha,alpha-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amino protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz.

"Amino" refers to unsubstituted amino and substituted amino groups, for example, primary amines, secondary amines, tertiary amines and quaternary amines. Specifically, "amino" refers to —NR$_a$R$_b$, wherein R$_a$ and R$_b$, both directly connected to the N, can be independently selected from hydrogen, deuterium, halo, hydroxy, cyano, formyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, a nitrogen protective group, —(CO)-alkyl, —(CO)—O-alkyl, or —S(O)$_n$R$_c$ (n=0 to 2, R$_c$ is directly connected to S), wherein R is independently selected from hydrogen, deuterium, halo, amino, hydroxy, thiol, cyano, formyl, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, or halothiocarbonylthio.

"Aryl" refers to a $C_6$-$C_{14}$ aromatic hydrocarbon. For example, aryl can be phenyl, napthyl, or fluorenyl.

"Heteroaryl" refers to a $C_6$-$C_{14}$ aromatic hydrocarbon having one or more heteroatoms, such as N, O, or S. The heteroaryl can be substituted or unsubstituted. Examples of a heteroaryl include, but are not limited to, azepinyl, acridinyl, benzimidazolyl, benzindolyl, 1,3-benzodioxolyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzofurazanyl, benzothiazolyl, benzothienyl, benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazblinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). In some embodiments, the heteroaryl can be dithiazinyl, furyl, imidazolyl, indolyl, isoquinolinyl, isoxazolyl, oxadiazolyl (e.g., (1,3,4)-oxadiazolyl, or (1,2,4)-oxadiazolyl), oxazolyl, pyrazinyl, pyrazolyl, pyrazyl, pyridazinyl, pyridinyl, pyrimidinyl, pyrimidyl, pyrrolyl, quinolinyl, tetrazolyl, thiazolyl, thienyl, triazinyl, (1,2,3)-triazolyl, (1,2,4)-triazolyl, 1,3,4-oxadiazolyl, 1,2,4-oxadiazolyl, 1,2,4-triazolyl, 1,3,4-thiadiazolyl, 5-amino-1,2,4-oxadiazolyl, 5-amino-1,3,4-oxadiazolyl, 5-amino-1,3,4-oxadiazolyl, 3-methyl-1,2,4-oxadiazolyl, 5-methyl-1,2,4-oxadiazolyl, 5-(trifluoromethyl)-1,2,4-oxadiazolyl, 5-(methylamino)-1,2,4-oxadiazolyl, 5-(aminomethyl)-1,2,4-oxadiazolyl, 5-(aminomethyl)-1,3,4-oxadiazolyl, 5-amino-4-cyanooxazolyl, 5,6-dichloro-1H-indolyl, 5,6-difluoro-1H-indolyl, 5-chloro-1H-indolyl, 5,6-dibromo-1H-indolyl, 5-fluoro-1H-indolyl, 5-methoxy-1H-indolyl, 7-fluoro-1H-indolyl, 6-cyano-1H-indolyl, 5-cyano-1H-indolyl, 4-fluoro-1H-indolyl, 5,6-difluoro-1H-indolyl, 6-fluoro-1H-indolyl, or 5,7-difluoro-1h-indolyl.

The substituent on the heteroaryl group can be alkyl (e.g., C1-C6 alkyl), amino, cyano, halo (e.g., fluoro, bromo, and chloro), alkylamino (e.g., C1-C6 alkylamino), methyleneamino, nitro, or hydroxyl. The heteroaryl group can have two, three or four substituents.

"Carbocycle" refers to a $C_6$-$C_{14}$ cyclic hydrocarbon. For example, aryl can be phenyl, napthyl, or fluorenyl.

"Heterocycle" refers to a $C_6$-$C_{14}$ cyclic hydrocarbon having one or more heteroatoms, such as N, O, or S.

"Alkoxy" refers to an alkyl connected to an oxygen atom (—O-alkyl).

"Haloalkoxy" refers to a haloalkyl connected to an oxygen atom (—O-haloalkyl).

"Thioalkoxy" refers to an alkyl connected to a sulfur atom (—S-alkyl).

"Halothioalkoxy" refers to a haloalkyl connected to a sulfur atom (—S-haloalkyl).

"Carbonyl" refers to —(CO)—, wherein (CO) indicates that the oxygen is connected to the carbon with a double bond.

"Alkanoyl" or "acyl" refers to an alkyl connected to a carbonyl group [—(CO)-alkyl].

"Haloalkanoyl" or "haloacyl" refers to a haloalkyl connected to a carbonyl group [—(CO)-haloalkyl].

"Thiocarbonyl" refers to —(CS)—, wherein (CS) indicates that the sulfur is connected to the carbon with a double bond.

"Thioalkanoyl (or thioacyl)" refers to an alkyl connected to a thiocarbonyl group [—(CS)-alkyl].

"Halothioalkanoyl" or "halothioacyl" refers to a haloalkyl connected to a thiocarbonyl group [—(CS)-haloalkyl].

"Carbonyloxy" refers to an alkanoyl (or acyl) connected to an oxygen atom [—O—(CO)-alkyl].

"Halocarbonyloxy" refers to a haloalkanoyl (or haloacyl) connected to an oxygen atom [—O—(CO)-haloalkyl].

"Carbonylthio" refers to an alkanoyl (or acyl) connected to a sulfur atom [—S—(CO)-alkyl].

"Halocarbonylthio" refers to a haloalkanoyl (or haloacyl) connected to a sulfur atom [—S—(CO)-haloalkyl].

"Thiocarbonyloxy" refers to a thioalkanoyl (or thioacyl) connected to an oxygen atom [—O—(CS)-alkyl].

"Halothiocarbonyloxy" refers to a halothioalkanoyl (or halothioacyl) connected to an oxygen atom [—O—(CS)-haloalkyl].

"Thiocarbonylthio" refers to a thioalkanoyl (or thioacyl) connected to a sulfur atom [—S—(CS)-alkyl].

"Halothiocarbonylthio" refers to a halothioalkanoyl (or halothioacyl) connected to a sulfur atom [—S—(CS)-haloalkyl].

Indole Compounds

An aspect of the present disclosure relates to indole compounds that can modulate human aryl hydrocarbon receptor (AhR). These compounds bind specifically to AhR. Without wishing to be bound by theory, it is contemplated that AhR bound by one of the present compounds is agonized with respect to the receptor's immune-stimulatory activity.

In some embodiments, the compound has the structure of formula 2, or a pharmaceutically acceptable salt thereof:

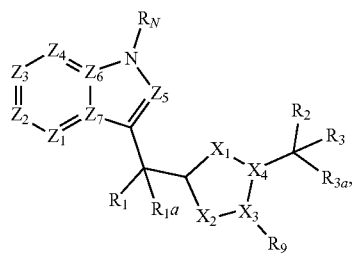

Structural Formula 2 wherein:

$X_1$ is N (nitrogen), O (oxygen), S (sulfur), or C (carbon); $X_2$ is N (nitrogen), O (oxygen) S (sulfur), or C (carbon); $X_3$ is N (nitrogen), O (oxygen), S (sulfur) or C (carbon); and $X_4$ is N (nitrogen) O (oxygen), S (sulfur), or C (carbon), such that at least one of $X_1$, $X_2$, $X_3$ and $X_4$ is N, each of $X_1$, $X_2$, $X_3$ and $X_4$ is optionally selected to form a heteroaromatic, wherein the bond between $X_1$ and the adjacent carbon, between $X_2$ and the adjacent carbon, between $X_1$ and $X_4$, between $X_2$ and $X_3$, and between $X_3$ and $X_4$ can be a single bond or a double bond and the valence of $X_1$, $X_2$, $X_3$ and $X_4$ is completed with H or $C_1$-$C_6$ alkyl (i.e., the ring can be aromatic, partially saturated, or saturated);

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_2$ is $OR_O$, $N(R_N)_2$, or $SR_S$;

$R_O$ is H, CN, substituted or unsubstituted alkyl, alkenyl, alkynyl, aryl, alkanoyl, carbonyloxy, carbonylthio, or carbonylamino, wherein the alkyl, alkenyl, alkynyl, or alkanoyl is optionally interrupted by O, S, or NR (in which NR can be N—C1-C6 alkyl), or a phosphate moiety;

$R_S$ is H, CN, alkyl, alkenyl, alkynyl, aryl, alkanoyl, carbonyloxy, carbonylthio, carbonylamino, or a phosphate moiety;

each $R_N$ is H, CN, alkyl, alkenyl, alkynyl, aryl, alkanoyl, carbonyloxy, carbonylthio, carbonylamino, or a phosphate moiety; and $R_{3a}$ is selected from the group consisting of hydrogen, deuterium, cyano, or C1-C6 alkyl;

$R_3$ is selected from the group consisting of deuterium, cyano, formyl, furyl, nitro, alkyl, haloalkyl, alkenyl, haloalkenyl, alkynyl, haloalkynyl, $C_1$-$C_6$ acyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_4$, $R_5$, $R_6$, $R_7$, $R_8$, and $R_9$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halocarbonyloxy, thiocarbonylthio, and halothiocarbonylthio;

$R_1$ and $R_{1a}$ are taken together to form =$NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, $R_2$ preferably can be =O, $R_3$ preferably can be —OR, wherein R is H or $C_1$-$C_6$ alkyl, or $R_1$ and $R_{1a}$ are taken together to form =$CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, $R_2$ preferably can be =O, $R_3$ preferably can be —OR, wherein R is H or $C_1$-$C_6$ alkyl, or $R_1$ and $R_{1a}$ are taken together to form =O, =NOR$_a$, or =S, $R_2$ and $R_3$ preferably can be each independently —OR or —NR$_a$R$_b$, wherein R, R$_a$, and R$_b$ are each independently H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

wherein the compound is enantiomerically pure at the carbon substituted with $R_2/R_3/R_{3a}$, and optionally, adjacent R groups, together, can form a three- to twelve-membered ring.

In some embodiments, the compound has the structure of formula 2a, or a pharmaceutically acceptable salt thereof:

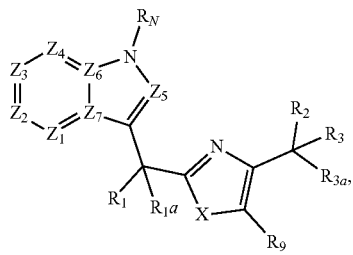

Structural Formula 2a wherein:

X is either O (oxygen) or S (sulfur);

$Z_1$ is N or CR$_4$, $Z_2$ is N or CR$_5$, $Z_3$ is N or CR$_6$, $Z_4$ is N or CR$_7$, $Z_5$ is N or CR$_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_2$ is OR$_O$, N(R$_N$)$_2$, or SR$_S$;

$R_O$ is H, CN, substituted or unsubstituted alkyl, alkenyl, alkynyl, aryl, alkanoyl, carbonyloxy, carbonylthio, or carbonylamino, wherein the alkyl, alkenyl, alkynyl, or alkanoyl is optionally interrupted by O, S, or NR (in which NR can be N—C1-C6 alkyl), or a phosphate moiety;

$R_S$ is H, CN, alkyl, alkenyl, alkynyl, aryl, alkanoyl, carbonyloxy, carbonylthio, carbonylamino, or a phosphate moiety;

each $R_N$ is H, CN, alkyl, alkenyl, alkynyl, aryl, alkanoyl, carbonyloxy, carbonylthio, carbonylamino, or a phosphate moiety; and $R_{3a}$ is selected from the group consisting of hydrogen, deuterium, cyano, or C1-C6 alkyl;

$R_3$ is selected from the group consisting of deuterium, cyano, formyl, furyl, nitro, alkyl, haloalkyl, alkenyl, haloalkenyl, alkynyl, haloalkynyl, $C_1$-$C_6$ acyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_4$, $R_5$, $R_6$, $R_7$, $R_8$, and $R_9$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_1$ and $R_{1a}$ are taken together to form —NR$_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, $R_2$ preferably can be =O, $R_3$ preferably can be —OR, wherein R is H or $C_1$-$C_6$ alkyl, or $R_1$ and $R_{1a}$ are taken together to form =CR$_b$R$_c$, wherein $R_b$ and $R_c$ are each independently H, $C_1$-$C_6$ alkyl, alkoxy (—O-alkyl), thioalkoxy (—S-alkyl), cyano (—CN), or amino, $R_2$ preferably can be =O, $R_3$ preferably can be —OR, wherein R is H or $C_1$-$C_6$ alkyl, or $R_1$ and $R_{1a}$ are taken together to form =O, =NOR$_a$, or =S, $R_2$ and $R_3$ preferably can be each independently —OR or —NR$_a$R$_b$, wherein R, R$_a$, and R$_b$ are each independently H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

wherein the compound is enantiomerically pure at the carbon substituted with $R_2/R_3/R_{3a}$, and optionally, adjacent R groups, together, can form a three- to twelve-membered ring.

In some embodiments, the compound has the structure of formula 3, or a pharmaceutically acceptable salt thereof:

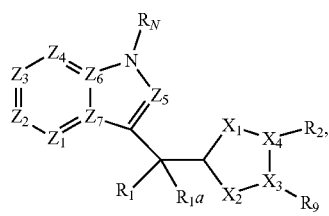

Structural Formula 3 wherein:

$X_1$ is N (nitrogen), O (oxygen), S (sulfur), or C (carbon); $X_2$ is N (nitrogen), O (oxygen) S (sulfur), or C (carbon); $X_3$ is N (nitrogen), O (oxygen), S (sulfur) or C (carbon); and $X_4$ is N (nitrogen) O (oxygen), S (sulfur), or C (carbon), such that at least one of $X_1$, $X_2$, $X_3$ and $X_4$ is N, each of $X_1$, $X_2$, $X_3$ and $X_4$ is optionally selected to form a heteroaromatic, wherein the bond between $X_1$ and the adjacent carbon, between $X_2$ and the adjacent carbon, between $X_1$ and $X_4$, between $X_2$ and $X_3$, and between $X_3$ and $X_4$ can be a single bond or a double bond and the valence of $X_1$, $X_2$, $X_3$ and $X_4$ is completed with H or $C_1$-$C_6$ alkyl (i.e., the ring can be aromatic, partially saturated, or saturated);

$Z_1$ is N or $CR_4$, $Z_2$ is N or $CR_5$, $Z_3$ is N or $CR_6$, $Z_4$ is N or $CR_7$, $Z_5$ is N or CRS, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_1$ and $R_{1a}$ are taken together to form =$NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, or $R_1$ and $R_{1a}$ are taken together to form =$CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, or $R_1$ and $R_{1a}$ are taken together to form =O, =$NOR_a$, or =S, wherein $R_a$ is H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and $R_2$ and $R_9$ are each independently selected from the group consisting of hydrogen, aryl, heteroaryl, cycloalkyl, heterocycloalkyl, alkyl, —NR$_{2a}$C(O)OR$_{2b}$, —NR$_{2a}$C(O)R$_{2b}$, —(C$_0$-C$_6$ alkyl)-CONHSO$_2$R$_2$, —(C$_0$-C$_6$ alkyl)-CONHSO$_2$NR$_{2a}$R$_{2b}$, —(C$_0$-C$_6$ alkyl)-SO$_2$NHCOR$_{2a}$, —(C$_0$-C$_6$ alkyl)-SO$_2$NHR$_{2a}$, —(C$_0$-C$_6$ alkyl)-CONR$_{2a}$OR$_{2b}$,

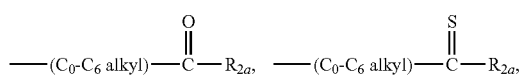

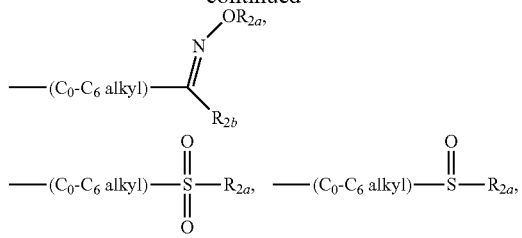

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino; wherein the compound is enantiomerically pure in the $R_2$ or $R_9$ moiety;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, alkyl, alkenyl, alkynyl, aryl, alkanoyl, carbonyloxy, carbonylthio, carbonylamino, or a phosphate moiety; and optionally, adjacent R groups, together, can form a three- to twelve-membered ring.

In some embodiments, the compound has the structure of formula 3a, or a pharmaceutically acceptable salt thereof:

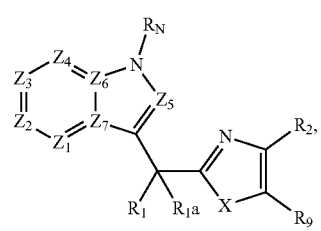

Structural Formula 3a wherein:

X is either O (oxygen) or S (sulfur);

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_1$ and $R_{1a}$ are taken together to form $=NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, or $R_1$ and $R_{1a}$ are taken together to form $=CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, or $R_1$ and $R_{1a}$ are taken together to form $=O$, $=NOR_a$, or $=S$, wherein $R_a$ is H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and $—S(O)_nR_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio; and $R_2$ and $R_9$ are each independently selected from the group consisting of hydrogen, aryl, heteroaryl, cycloalkyl, heterocycloalkyl, alkyl, $—NR_{2a}C(O)OR_{2b}$, $—NR_{2a}C(O)R_b$, $—(C_0$-$C_6$ alkyl)-$CONHSO_2R_{2a}$, $—(C_0$-$C_6$ alkyl)-$CONHSO_2NR_{2a}R_{2b}$, $—(C_0$-$C_6$ alkyl)-$SO_2NHCOR_{2a}$, $—(C_0$-$C_6$ alkyl)-$SO_2NHR_{2a}$, $—(C_0$-$C_6$ alkyl)-$CONR_{2a}OR_{2b}$,

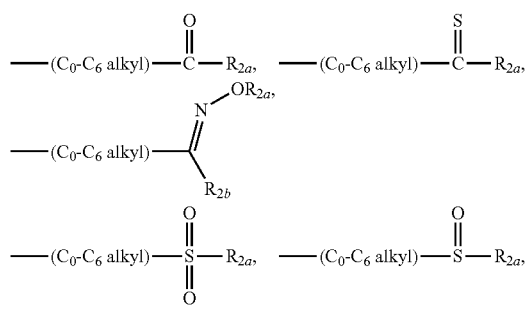

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and $—S(O)_nR_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino; wherein the compound is enantiomerically pure in the $R_2$ or $R_9$ moiety;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and $—S(O)_nR_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN; alkyl, alkenyl, alkynyl, aryl, alkanoyl, carbonyloxy, carbonylthio, carbonylamino, or a phosphate moiety; and optionally, adjacent R groups, together, can form a three- to twelve-membered ring.

In some embodiments, the compound has the structure of formula 3b, or a pharmaceutically acceptable salt thereof:

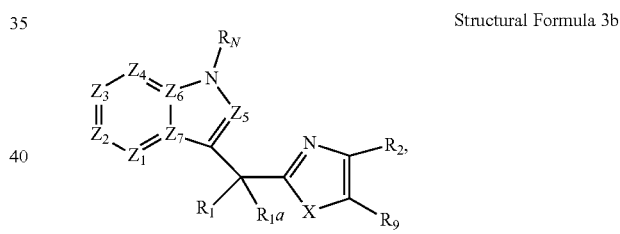

Structural Formula 3b wherein:

X is either O (oxygen) or S (sulfur);

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_1$ and $R_{1a}$ are taken together to form $=NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, or $R_1$ and $R_{1a}$ are taken together to form $=CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, or $R_1$ and $R_{1a}$ are taken together to form $=O$, $=NOR_a$, or $=S$, wherein R, is H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and $—S(O)_nR_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and $R_2$ and $R_9$ are each independently selected from the group consisting of hydrogen, aryl, heteroaryl, cycloalkyl, heterocycloalkyl, alkyl, —$NR_{2a}C(O)OR_{2b}$, —$NR_{2a}C(O)R_{2b}$, —($C_0$-$C_6$ alkyl)-$CONHSO_2R_{2a}$, —($C_0$-$C_6$ alkyl)-$CONHSO_2NR_{2a}R_{2b}$, —($C_0$-$C_6$ alkyl)-$SO_2NHCOR_{2a}$, —($C_0$-$C_6$ alkyl)-$SO_2NHR_{2a}$, —($C_0$-$C_6$ alkyl)-$CONR_{2a}OR_{2b}$,

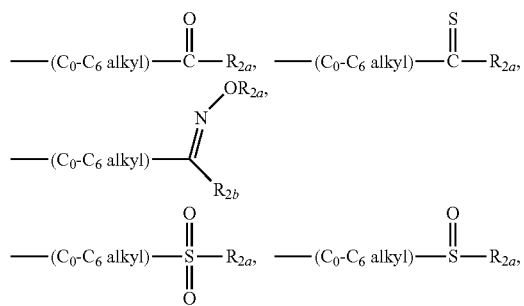

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino; wherein the compound is enantiomerically pure in the $R_2$ or $R_9$ moiety;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, alkyl, alkenyl, alkynyl, aryl, alkanoyl, carbonyloxy, carbonylthio, carbonylamino, or a phosphate moiety; and optionally, adjacent R groups, together, can form a three- to twelve-membered ring.

In some embodiments, the compound has the structure of formula 3c, or a pharmaceutically acceptable salt thereof:

Structural formula 3c

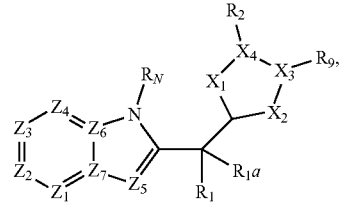

wherein:

$X_1$ is N (nitrogen), O (oxygen), S (sulfur), or C (carbon); $X_2$ is N (nitrogen), O (oxygen) S (sulfur), or C (carbon); $X_3$ is N (nitrogen), O (oxygen), S (sulfur) or C (carbon); and $X_4$ is N (nitrogen) O (oxygen), S (sulfur), or C (carbon), such that at least one of $X_1$, $X_2$, $X_3$ and $X_4$ is N, each of $X_1$, $X_2$, $X_3$ and $X_4$ is optionally selected to form a heteroaromatic, wherein the bond between $X_1$ and the adjacent carbon, between $X_2$ and the adjacent carbon, between $X_1$ and $X_4$, between $X_2$ and $X_3$, and between $X_3$ and $X_4$ can be a single bond or a double bond and the valence of $X_1$, $X_2$, $X_3$ and $X_4$ is completed with H or $C_1$-$C_6$ alkyl (i.e., the ring can be aromatic, partially saturated, or saturated);

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_1$ and $R_{1a}$ are taken together to form =$NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, or $R_1$ and $R_{1a}$ are taken together to form =$CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, or $R_1$ and $R_{1a}$ are taken together to form =O, =$NOR_a$, or =S, wherein $R_a$ is H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio; and $R_2$ and $R_9$ are each independently selected from the group consisting of hydrogen, aryl, heteroaryl, cycloalkyl, heterocycloalkyl, alkyl, —NR$_{2a}$C(O)OR$_{2b}$, —NR$_{2a}$C(O)R$_{2b}$, —(C$_0$-C$_6$ alkyl)-CONHSO$_2$R$_{2a}$, —(C$_0$-C$_6$ alkyl)-CONHSO$_2$NR$_{2a}$R$_{2b}$, —(C$_0$-C$_6$ alkyl)-SO$_2$NHCOR$_{2a}$, —(C$_0$-C$_6$ alkyl)-SO$_2$NHR$_{2a}$, —(C$_0$-C$_6$ alkyl)-CONR$_{2a}$OR$_{2b}$,

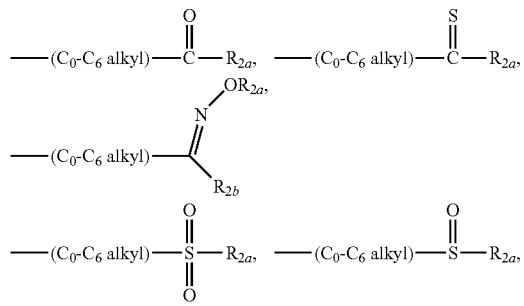

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, R$_{10}$ is directly connected to S), wherein R$_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein R$_{2a}$ and R$_{2b}$ are each independently H, C$_1$-C$_6$ alkyl, alkoxy (—O-alkyl), hydroxy, thioalkoxy (—S-alkyl), cyano (—CN), or amino; wherein the compound is enantiomerically pure in the R$_2$ or R$_9$ moiety;

R$_4$, R$_5$, R$_6$, R$_7$, and R$_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, R$_{11}$ is directly connected to S), wherein R$_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

R$_N$ is H, CN, alkyl, alkenyl, alkynyl, aryl, alkanoyl, carbonyloxy, carbonylthio, carbonylamino, or a phosphate moiety; and optionally, adjacent R groups, together, can form a three- to twelve-membered ring.

In still another embodiment, the compound has structural formula 4, or a pharmaceutically acceptable salt thereof:

Structural Formula 4

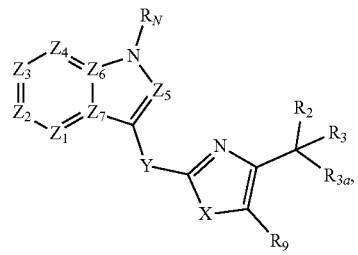

wherein:

X is O (oxygen) or S (sulfur);
Y is a bond, O (oxygen), S (sulfur), or

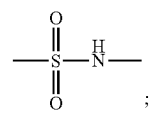

;

Z$_1$ is N or CR$_4$, Z$_2$ is N or CR$_5$, Z$_3$ is N or CR$_6$, Z$_4$ is N or CR$_7$, Z$_5$ is N or CR$_8$, Z$_6$ is N or C, Z$_7$ is N or C, wherein no more than two of Z$_1$, Z$_2$, Z$_3$, Z$_4$, Z$_5$, Z$_6$, and Z$_7$ are N;

R$_4$, R$_5$, R$_6$, R$_7$, and R$_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{11}$ (n=0 to 2, R$_{11}$ is directly connected to S), wherein R$_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

R$_2$ is OR$_O$, N(R$_N$)$_2$, or SR$_S$;

R$_O$ is H, CN, substituted or unsubstituted alkyl, alkenyl, alkynyl, aryl, alkanoyl, carbonyloxy, carbonylthio, or carbonylamino, wherein the alkyl, alkenyl, alkynyl, or alkanoyl is optionally interrupted by O, S, or NR in which NR can be N—C1-C6 alkyl), or a phosphate moiety;

R$_S$ is H, CN, alkyl, alkenyl, alkynyl, aryl, alkanoyl, carbonyloxy, carbonylthio, carbonylamino, or a phosphate moiety;

each R$_N$ is H, CN, alkyl, alkenyl, alkynyl, aryl, alkanoyl, carbonyloxy, carbonylthio, carbonylamino, or a phosphate moiety;

R$_{3a}$ is selected from the group consisting of hydrogen, deuterium, cyano, or C1-C6 alkyl;

R$_3$ is selected from the group consisting of deuterium, cyano, formyl, furyl, nitro, alkyl, haloalkyl, alkenyl, haloalkenyl, alkynyl, haloalkynyl, C$_1$-C$_6$ acyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_{10}$ (n=0 to 2, R$_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein the compound is enantiomerically pure at the carbon substituted with $R_2/R_3/R_{3a}$, and optionally, adjacent R groups, together, can form a three- to twelve-membered ring.

In some embodiments, the compound has structural formula 5, or a pharmaceutically acceptable salt thereof:

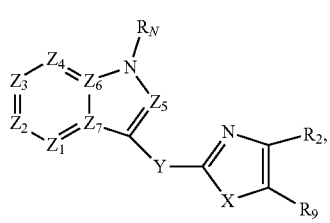

Structural Formula 5 wherein:
X is O (oxygen) or S (sulfur);
Y is a bond, O (oxygen), S (sulfur), or

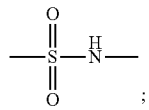

;

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and Z are N;

$R_2$ and $R_9$ are each independently selected from the group consisting of hydrogen, aryl, heteroaryl, cycloalkyl, heterocycloalkyl, alkyl, —$NR_{2a}C(O)OR_{2b}$, —$NR_{2a}C(O)R_{2b}$, —$(C_0$-$C_6$ alkyl)-$CONHSO_2R_{2a}$, —$(C_0$-$C_6$ alkyl)-$CONHSO_2NR_{2a}R_{2b}$, —$(C_0$-$C_6$ alkyl)-$SO_2NHCOR_{2a}$, —$(C_0$-$C_6$ alkyl)-$SO_2NHR_{2a}$, —$(C_0$-$C_6$ alkyl)-$CONR_{2a}OR_{2b}$,

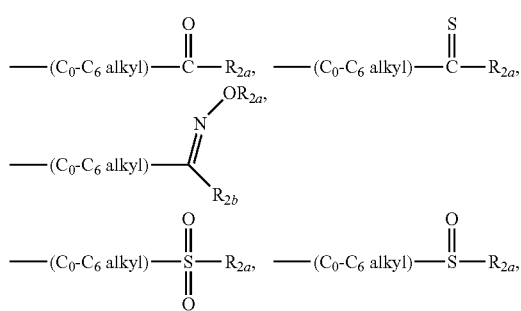

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino, wherein the compound is enantiomerically pure in the $R_2$ or $R_9$ moiety;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_N$ is H, CN, alkyl, alkenyl, alkynyl, aryl, alkanoyl, carbonyloxy, carbonylthio, carbonylamino, or a phosphate moiety; and optionally, adjacent R groups, together, can form a three- to twelve-membered ring.

In some embodiments, the compound has structural formula 6, or a pharmaceutically acceptable salt thereof:

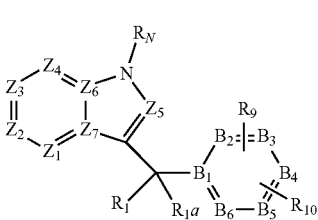

Structural Formula 6 wherein:
$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_5$, $Z_4$, and $Z_7$ are N;

$R_1$ and $R_{1a}$ are taken together to form =$NR_b$, wherein $R_b$ is H, $C_1$-$C_6$ alkyl, hydroxy, $C_1$-$C_6$ alkoxy (—O-alkyl), $C_1$-$C_6$ acyloxy, amino, or $C_1$-$C_6$ acyl, or $R_1$ and $R_{1a}$ are taken together to form =$CR_bR_c$, wherein $R_b$ and $R_c$ are each independently H, $C_1$-$C_6$ alkyl, alkoxy (—O-alkyl), thioalkoxy (—S-alkyl), cyano (—CN), or amino, or $R_1$ and $R_{1a}$ are taken together to form =O, =$NOR_1$, or =S, wherein $R_a$ is H, $C_1$-$C_6$ alkyl, or $C_1$-$C_6$ acyl, or $R_1$ and $R_{1a}$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and $—S(O)_nR_{14}$ (n=0 to 2, $R_{14}$ is directly connected to S), wherein $R_{14}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_4$, $R_5$, $R_6$, $R_7$, and $R_8$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and $—S(O)_nR_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halocarbonyloxy, thiocarbonylthio, and halothiocarbonylthio;

$R_N$ is H, CN, alkyl, alkenyl, alkynyl, aryl, alkanoyl, carbonyloxy, carbonylthio, carbonylamino, or a phosphate moiety;

$B_1$, $B_2$, $B_3$, $B_4$, $B_5$, and $B_6$ are each independently C or N;

$R_9$ and $R_{10}$, the number of which, together, complete the valence of each of $B_1$, $B_2$, $B_3$, $B_4$, $B_5$, and $B_6$, are each independently selected from the group consisting of hydrogen, aryl, heteroaryl, cycloalkyl, heterocycloalkyl, alkyl, $—NR_{2a}C(O)OR_{2b}$, $—NR_{2a}C(O)R_{2b}$, $—(C_0\text{-}C_6 \text{ alkyl})\text{-}CONHSO_2R_{2a}$, $—(C_0\text{-}C_6 \text{ alkyl})\text{-}CONHSO_2NR_{2a}R_{2b}$, $—(C_0\text{-}C_6 \text{ alkyl})\text{-}SO_2NHCOR_{2a}$, $—(C_0\text{-}C_6 \text{ alkyl})\text{-}SO_2NHR_{2a}$, $—(C_0\text{-}C_6 \text{ alkyl})\text{-}CONR_{2a}OR_{2b}$,

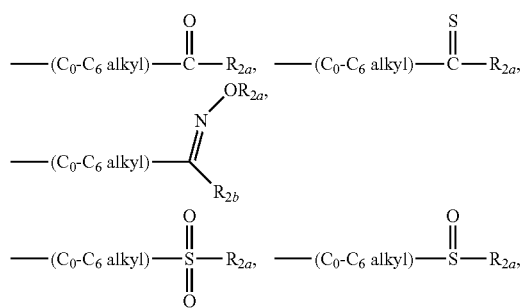

deuterium, halo, amino, hydroxy, cyano, formyl, nitro, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and $—S(O)_nR_{12}$ (n=0 to 2, $R_{12}$ is directly connected to S), wherein $R_{12}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and

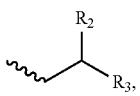

wherein $R_{2a}$ and $R_{2b}$ are each independently H, $C_1$-$C_6$ alkyl, alkoxy (—O-alkyl), hydroxy, thioalkoxy (—S-alkyl), cyano (—CN), or amino, $R_2$ and $R_3$ are each independently selected from the group consisting of $—NR_aR_b$ ($R_a$ and $R_b$ are each independently H, $C_1$-$C_6$ alkyl, or $C_1$-$C_6$ acyl), hydrogen, deuterium, halo, amino, hydroxy, cyano, formyl, furyl, nitro, alkyl, haloalkyl, alkenyl, haloalkenyl, alkynyl, haloalkynyl, $C_1$-$C_6$ acyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and $—S(O)R_{13}$ (n=0 to 2, $R_{13}$ is directly connected to S), wherein $R_{13}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio, wherein the compound is enantiomerically pure in the $R_9$ or $R_{10}$ moiety, and optionally, adjacent R groups, together, can form a three- to twelve-membered ring.

In each of formulae 2, 2a, 3, 3a, 3b, 3c, 4, 5, and 6, in some embodiments, each of $R_4$, $R_5$, $R_6$, and $R_7$ is hydrogen. In other embodiments, at least one of $R_4$, $R_5$, $R_6$, and $R_7$ can be F, Cl, or Br, and the others of $R_4$, $R_5$, $R_6$, and $R_7$ are hydrogen. In still other embodiments, at least two of $R_4$, $R_5$, $R_6$, and $R_7$, independently, can be F, Cl, or Br, and the others of $R_4$, $R_5$, $R_6$, and $R_7$ are hydrogen. The F, Cl, or Br can be at the indole ring carbon 5, 6, or 7.

In each of formulae 2a, 3, 3a, 3b, 3c, 4, 5, and 6, in certain embodiments, $R_9$ can be hydrogen. $R_2$ can be acyl, cyano, hydroxyl-substituted C1-C6 alkyl, amino-substituted C1-C6 alkyl, aryl, or heteroaryl. The aryl or heteroaryl can be substituted or unsubstituted. The substituted aryl or heteroaryl can be substituted with halo, amino, hydroxyl, or C1-C6 alkyl. The amino can be unsubstituted.

In each of formulae 2, 2a, and 4, in certain embodiments, $R_2$ can be an ester. In each of formulae 2, 2a, and 4, in certain embodiments, $R_2$ can be hydroxyl or amino and $R_3$ ran be alkyl, aryl, nitro, or cyano. $R_9$ can be hydrogen. The amino can be substituted or unsubstituted.

In some embodiments, the compound has a structural formula 8a, 8b, 8c, or 8d, or a pharmaceutically acceptable salt thereof:

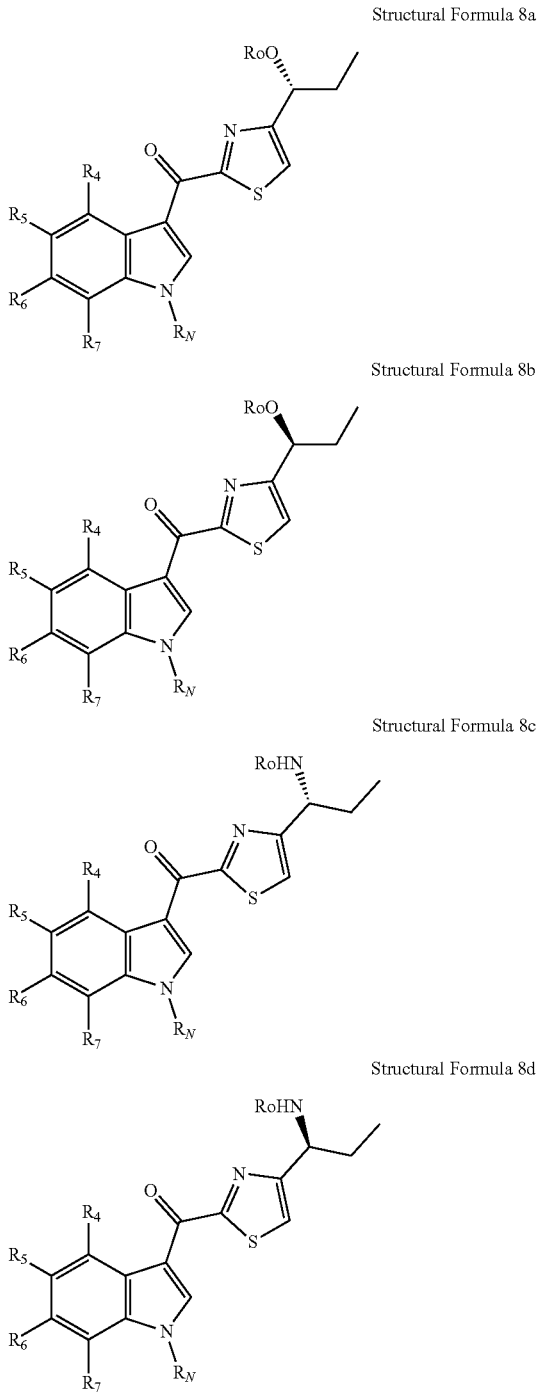

Structural Formula 8a

Structural Formula 8b

Structural Formula 8c

Structural Formula 8d wherein $R_4$, $R_5$, $R_6$, and $R_7$, are each independently selected from the group consisting of hydrogen and halo;

$R_o$ is hydrogen, deuterium, alkyl, aryl, or acyl; and $R_N$ is H, CN, alkyl, alkenyl, alkynyl, aryl, alkanoyl, carbonyloxy, carbonylthio, carbonylamino, or a phosphate moiety.

In one embodiment, $R_o$ is H or alkyl. In another embodiment, $R_o$ is acyl, for example, a substituted or unsubstituted $C_1$-$C_6$ acyl. The substituted or unsubstituted $C_1$-$C_6$ acyl can be a substituted $C_2$, $C_3$, $C_4$, $C_5$, or $C_6$ acyl, optionally interrupted by O, S, or NR (in which NR can be N—$C_1$-$C_6$ alkyl). The substituent can be a halo, carboxyl, amino, hydroxyl, alkoxy, or phosphonate moiety. The amino moiety can be a dialkylamino moiety, for example, dimethylamino, morpholino, methylpiperazinyl, piperazinyl or bipiperidinyl.

In one embodiment of the compound of structural formula 8a or 8b, at least one of $R_4$, $R_5$, $R_6$, and $R_7$ is F, Cl, or Br and the others of $R_4$, $R_5$, $R_6$, and $R_7$ are hydrogen. In another embodiment, at least two of $R_4$, $R_5$, $R_6$, and $R_7$ are F, Cl, or Br and the others of $R_4$, $R_5$, $R_6$, and $R_7$ are hydrogen.

In one embodiment, $R_5$ is F and $R_4$, $R_6$, and $R_7$ are hydrogen. In another embodiment, $R_6$ is F and $R_4$, $R_5$, and $R_7$ are hydrogen. In still another embodiment, $R_7$ is F and $R_4$, $R_5$, and $R_6$ are hydrogen.

In one embodiment, $R_5$ is Cl and $R_4$, $R_6$, and $R_7$ are hydrogen. In another embodiment, $R_6$ is Cl and $R_4$, $R_5$, and $R_7$ are hydrogen. In still another embodiment, $R_7$ is Cl and $R_4$, $R_5$, and $R_6$ are hydrogen.

In one embodiment, $R_5$ and $R_6$ are F and $R_4$ and $R_7$ are hydrogen. In another embodiment, $R_5$ and $R_7$ are F and $R_4$ and $R_6$ are hydrogen. In still another embodiment, $R_6$ and $R_7$ are F and $R_4$ and $R_5$ are hydrogen.

In one embodiment, $R_5$ and $R_6$ are Cl and $R_4$ and $R_7$ are hydrogen. In another embodiment, $R_5$ and $R_7$ are Cl and $R_4$ and $R_6$ are hydrogen. In still another embodiment, $R_6$ and $R_7$ are Cl and $R_4$ and $R_5$ are hydrogen.

In some embodiments, each of $R_4$, $R_5$, $R_6$, and $R_7$ is hydrogen.

In some embodiments, $R_N$ can be a phosphate moiety. The phosphate moiety can have the structure

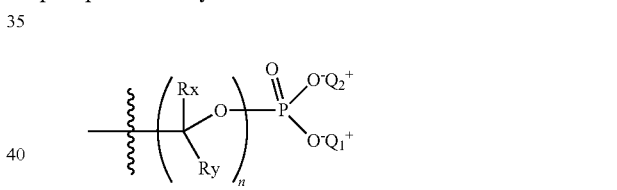

wherein n can be 0, 1, 2, 3, 4, 5, or 6, $R_x$ can be H or C1-C6 alkyl, $R_y$ can be H or C1-C6 alkyl, or, together, $R_x$ and $R_y$ form a C3-C8 cycloalkyl, and $Q_1^+$ and $Q_2^+$ can be each, independently, a monocation, or together can be a dication or one of $Q_1^+$ or $Q_2^+$ can be C1-C6 alkyl, benzyl, allyl or —(CR$_2$R$_3$—O)—R$_{23}$, and each of $R_2$, $R_3$ and $R_{23}$ can be, independently, H, or C1-C6 alkyl.

In some embodiments, n can be 0 or 1.

In certain circumstances, $Q_1^+$ and $Q_2^+$ can be each, independently, an alkali metal.

In certain circumstances, $Q_1^+$ and $Q_2^+$ can be each, independently, selected from the group consisting of lithium, sodium, potassium, ammonium, alkyl ammonium, and phosphonium.

In certain circumstances, $Q_1^+$ and $Q_2^+$ together can be selected from the group consisting of an alkaline earth metal salt.

In certain circumstances, $Q_1^+$ and $Q_2^+$ can be each independently selected from the group consisting of zinc, calcium and magnesium.

Exemplary indole compounds are shown in Table 1 below.
TABLE 1
| ARI-# | Structural Formula |
|---|---|
| 088 | 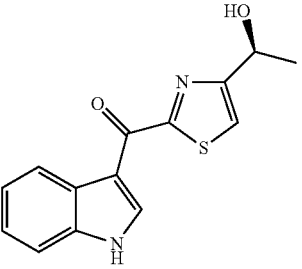 [SMILES: C[C@H](O)c1csc(C(=O)c2c[nH]c3ccccc23)n1] 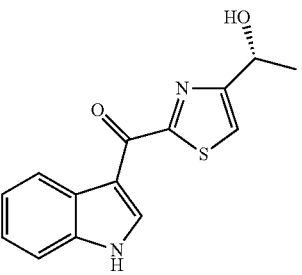 [SMILES: C[C@@H](O)c1csc(C(=O)c2c[nH]c3ccccc23)n1] 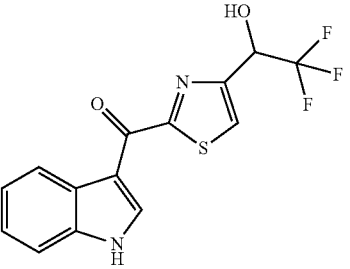 [SMILES: O=C(c1nc(C(O)C(F)(F)F)cs1)c1c[nH]c2ccccc12] 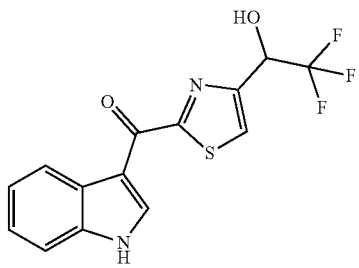 [SMILES: O=C(c1nc(C(O)C(F)(F)F)cs1)c1c[nH]c2ccccc12] 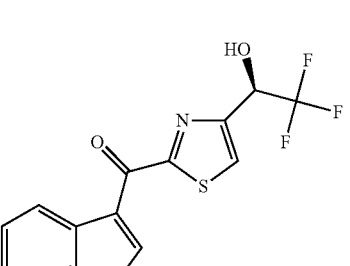 |
TABLE 1-continued
| ARI-# | Structural Formula |
|---|---|
| 215 | 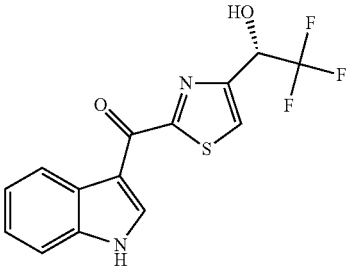 [SMILES: O=C(c1nc([C@H](O)C(F)(F)F)cs1)c1c[nH]c2ccccc12] |
| 092 | 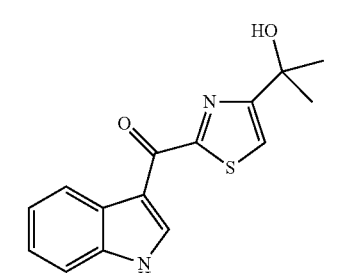 |
| 094 | 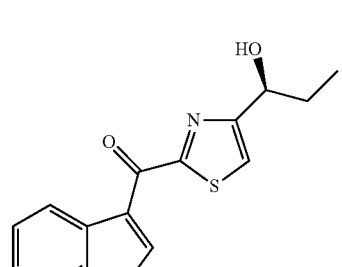 |
| 164 | 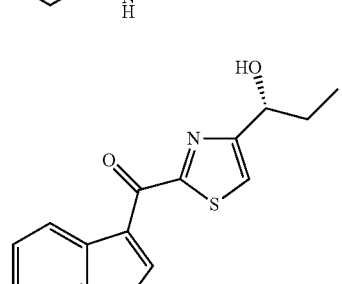 |

TABLE 1-continued

| ARI-# | Structural Formula |
|---|---|
| 165 | (structure: 6-fluoroindole-3-yl linked via C(=O) to thiazole-2-yl with (R)-1-hydroxypropyl at thiazole-4-position) |
| 194 | (structure: 5-fluoroindole-3-yl linked via C(=O) to thiazole-2-yl with 1-hydroxypropyl at thiazole-4-position) |
| 195 | (structure: 5-fluoroindole-3-yl linked via C(=O) to thiazole-2-yl with 1-hydroxypropyl at thiazole-4-position) |
| | (structure: 7-fluoroindole-3-yl linked via C(=O) to thiazole-2-yl with 1-hydroxypropyl at thiazole-4-position) |
| | (structure: 7-fluoroindole-3-yl linked via C(=O) to thiazole-2-yl with 1-hydroxypropyl at thiazole-4-position) |

TABLE 1-continued

| ARI-# | Structural Formula |
|---|---|
| | (structure: 4-fluoroindole-3-yl linked via C(=O) to thiazole-2-yl with 1-hydroxypropyl at thiazole-4-position) |
| | (structure: 4-fluoroindole-3-yl linked via C(=O) to thiazole-2-yl with 1-hydroxypropyl at thiazole-4-position) |
| 200 | (structure: 5,7-difluoroindole-3-yl linked via C(=O) to thiazole-2-yl with 1-hydroxypropyl at thiazole-4-position) |
| 201 | (structure: 5,7-difluoroindole-3-yl linked via C(=O) to thiazole-2-yl with 1-hydroxypropyl at thiazole-4-position) |
| 202 | (structure: 5,6-difluoroindole-3-yl linked via C(=O) to thiazole-2-yl with 1-hydroxypropyl at thiazole-4-position) |

TABLE 1-continued
| ARI-# | Structural Formula |
|---|---|
| 203 | 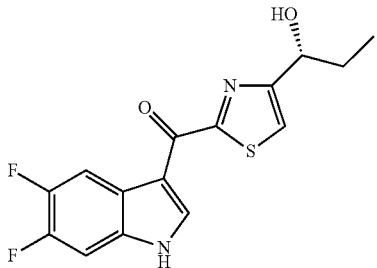 [SMILES: CC[C@@H](O)c1csc(C(=O)c2c[nH]c3cc(F)c(F)cc23)n1] |
| | 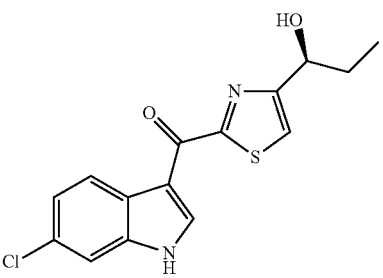 [SMILES: CC[C@H](O)c1csc(C(=O)c2c[nH]c3cc(Cl)ccc23)n1] |
| | 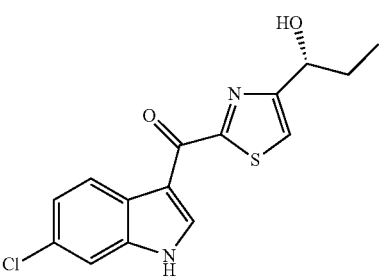 [SMILES: CC[C@@H](O)c1csc(C(=O)c2c[nH]c3cc(Cl)ccc23)n1] |
| | 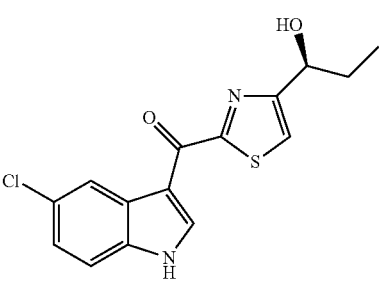 [SMILES: CC[C@H](O)c1csc(C(=O)c2c[nH]c3ccc(Cl)cc23)n1] |
| | 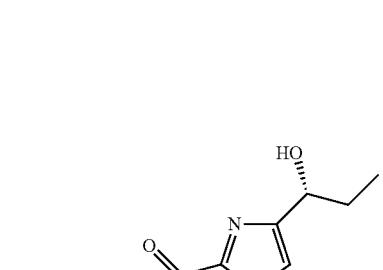 |
TABLE 1-continued
| ARI-# | Structural Formula |
|---|---|
| | 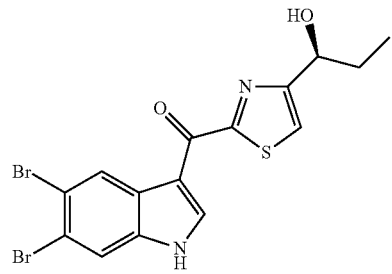 [SMILES: CC[C@H](O)c1csc(C(=O)c2c[nH]c3cc(Br)c(Br)cc23)n1] |
| | 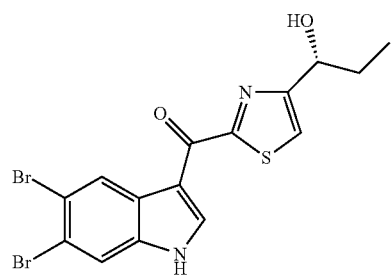 [SMILES: CC[C@@H](O)c1csc(C(=O)c2c[nH]c3cc(Br)c(Br)cc23)n1] |
| 220 | 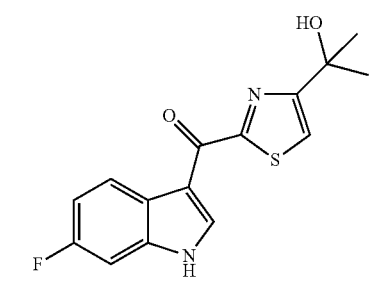 |
| 221 | 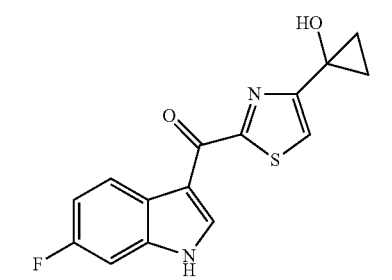 [SMILES: O=C(c1nc(C2(O)CC2)cs1)c1c[nH]c2cc(F)ccc12] |
| | 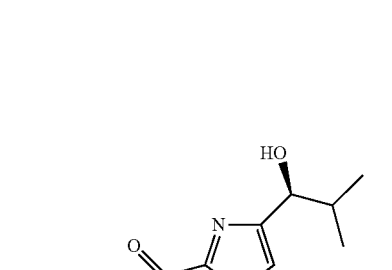 |

TABLE 1-continued

| ARI-# | Structural Formula |
|---|---|
| | (structure) |
| 209 | (structure) |
| 210 | (structure) |
| | (structure) |
| 211 | (structure) |

TABLE 1-continued

| ARI-# | Structural Formula |
|---|---|
| 212 | (structure) |
| 208 | (structure) |
| 213 | (structure) |
| 214 | (structure) |
| 217 | (structure) |

TABLE 1-continued

| ARI-# | Structural Formula |
|---|---|

TABLE 1-continued
| ARI-# | Structural Formula |
|---|---|
| | 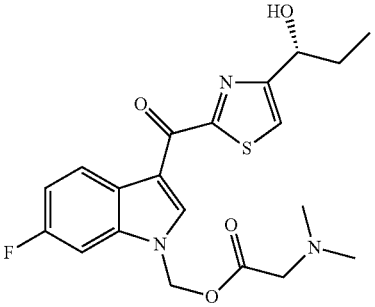 [SMILES: CC[C@@H](O)c1csc(C(=O)c2cn(COC(=O)CN(C)C)c3cc(F)ccc23)n1] |
| | 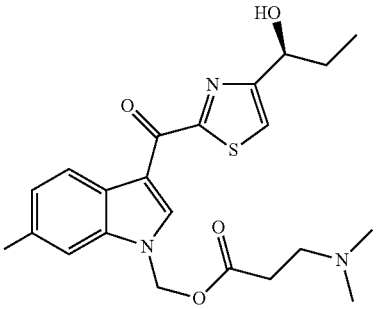 |
| | 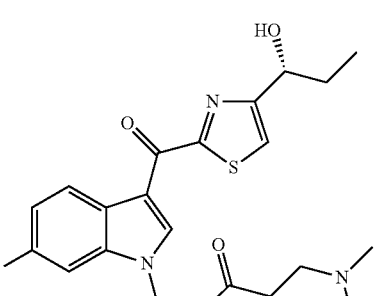 |
| | 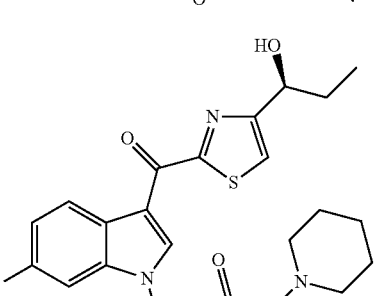 |
| | 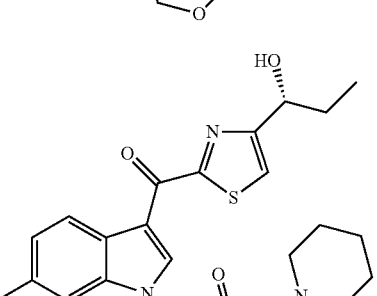 |
TABLE 1-continued
| ARI-# | Structural Formula |
|---|---|
| | 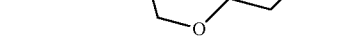 |
| | 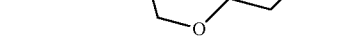 |
| | 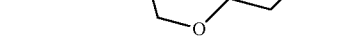 |

TABLE 1-continued
| ARI-# | Structural Formula |
|---|---|
| | 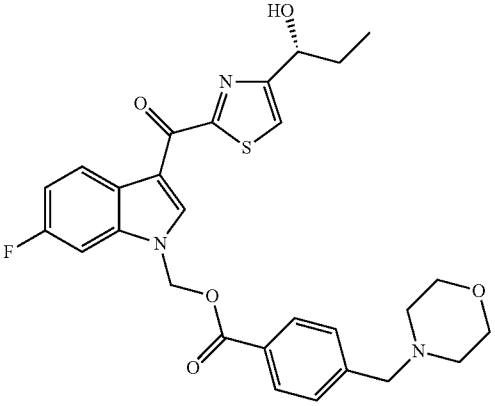 [SMILES: CC[C@@H](O)c1csc(C(=O)c2cn(COC(=O)c3ccc(CN4CCOCC4)cc3)c3cc(F)ccc23)n1] |
| | 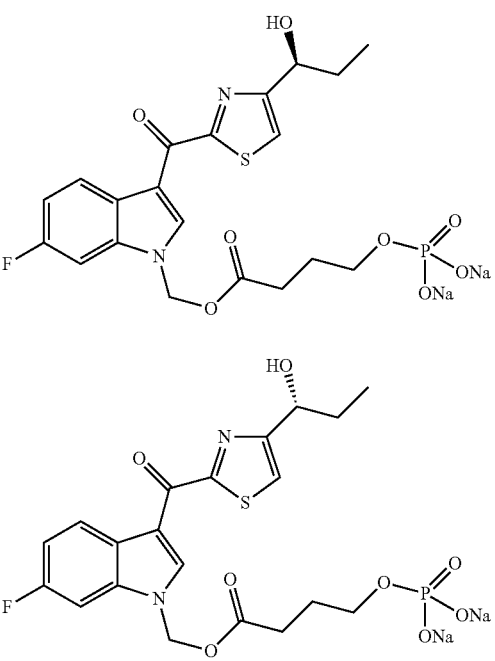 |
| | 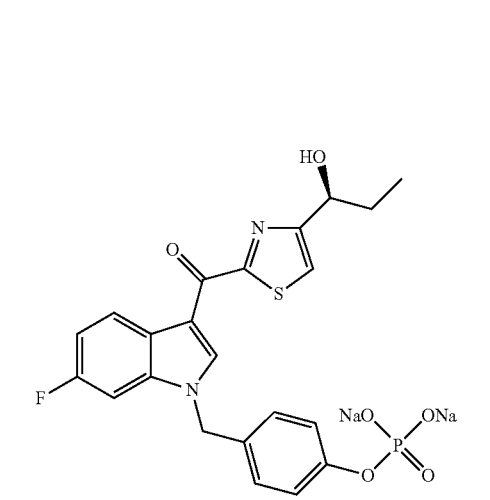 |
| | 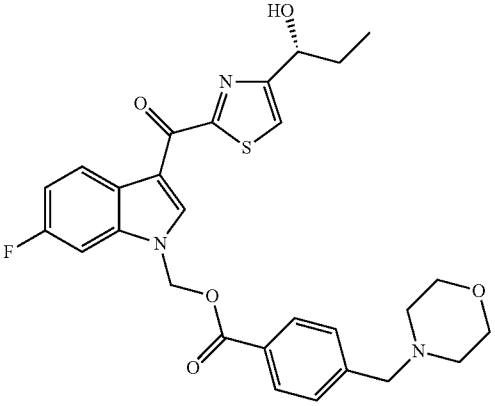 [SMILES: CC[C@@H](O)c1csc(C(=O)c2cn(COC(=O)c3ccc(CN4CCOCC4)cc3)c3cc(F)ccc23)n1] |
TABLE 1-continued
| ARI-# | Structural Formula |
|---|---|
| | 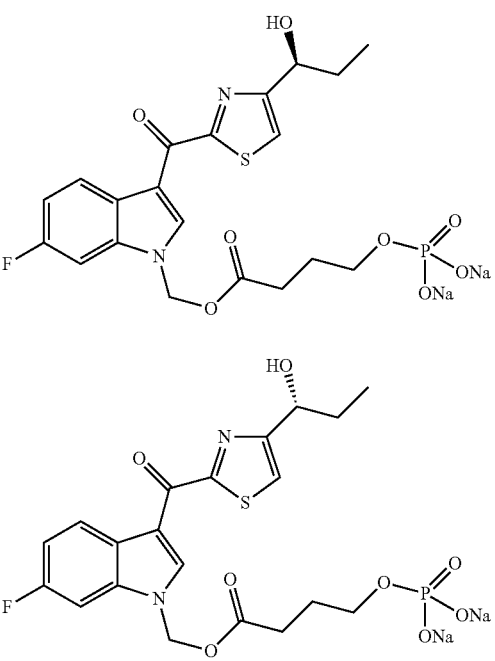 |
| | 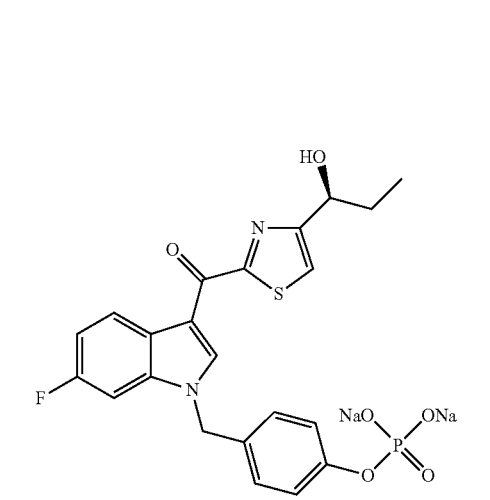 |
| | 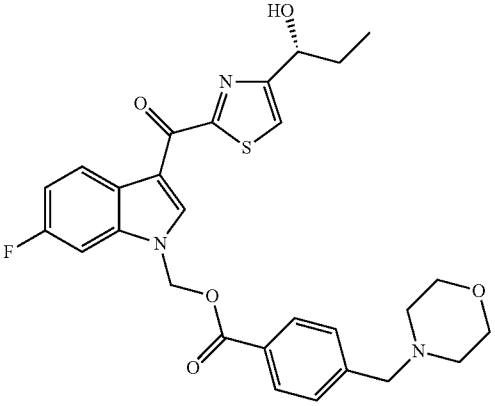 [SMILES: CC[C@@H](O)c1csc(C(=O)c2cn(COC(=O)c3ccc(CN4CCOCC4)cc3)c3cc(F)ccc23)n1] |
| | 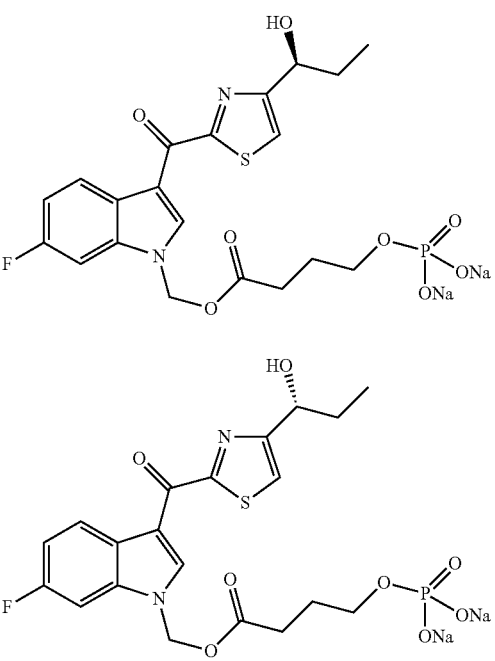 |

US 11,390,621 B2
61
TABLE 1-continued
| ARI-# | Structural Formula |
|---|---|
| | 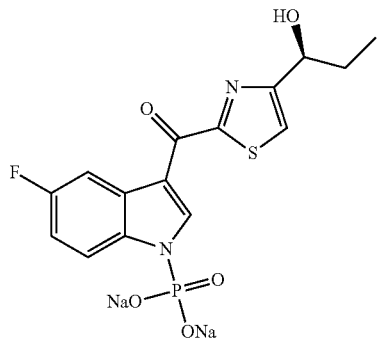 |
| 191 | 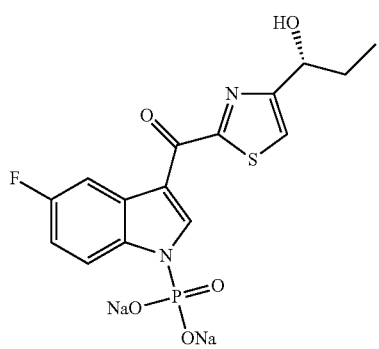 |
| | 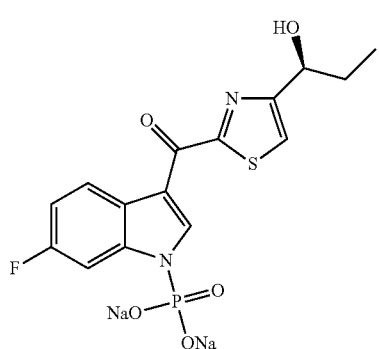 |
| | 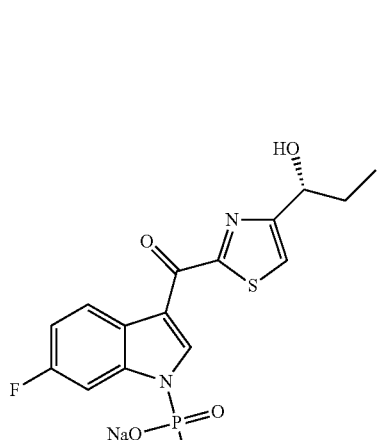 |
62
TABLE 1-continued
| ARI-# | Structural Formula |
|---|---|
| | 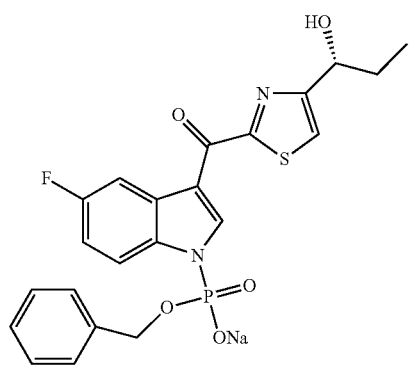 |
| | 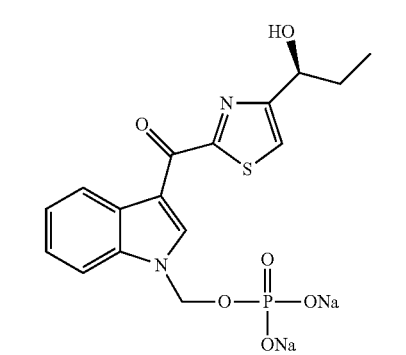 |
| | 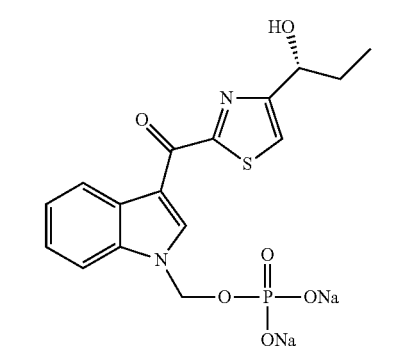 |
| | 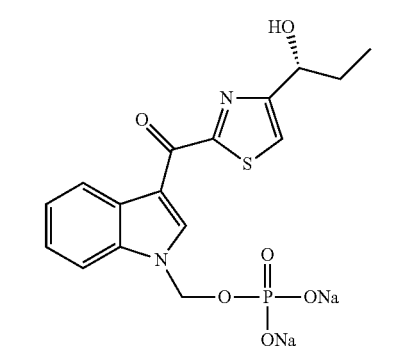 |

TABLE 1-continued

| ARI-# | Structural Formula |
|---|---|
| | (structure: 6-fluoroindole-3-yl connected via C=O to thiazole-2-yl, thiazole-4-yl bearing (R)-1-hydroxypropyl; indole N-CH2-OP(=O)(ONa)2) |
| | (structure: indole-3-yl connected via C=O to thiazole-2-yl, thiazole-4-yl bearing (R)-1-hydroxypropyl; indole N-CH2-P(=O)(ONa)2) |
| | (structure: indole-3-yl connected via C=O to thiazole-2-yl, thiazole-4-yl bearing (S)-1-hydroxypropyl; indole N-CH2-P(=O)(ONa)2) |
| | (structure: indole-3-yl connected via C=O to thiazole-2-yl, thiazole-4-yl bearing (R)-1-methoxypropyl) |

TABLE 1-continued

| ARI-# | Structural Formula |
|---|---|
| | (structure: 1H-indole-3-yl connected via C=O to thiazole-2-yl, thiazole-4-yl bearing (S)-1-methoxypropyl) |
| 178 | (structure: 6-fluoro-1H-indole-3-yl connected via C=O to thiazole-2-yl, thiazole-4-yl bearing (S)-1-methoxypropyl) |
| 184 | (structure: 6-fluoro-1H-indole-3-yl connected via C=O to thiazole-2-yl, thiazole-4-yl bearing (R)-1-methoxypropyl) |
| | (structure: 5-fluoro-1H-indole-3-yl connected via C=O to thiazole-2-yl, thiazole-4-yl bearing (R)-1-methoxypropyl) |
| | (structure: 5-fluoro-1H-indole-3-yl connected via C=O to thiazole-2-yl, thiazole-4-yl bearing (S)-1-methoxypropyl) |

TABLE 1-continued

| ARI-# | Structural Formula |
|---|---|
| 234 | (6-fluoro-1H-indol-3-yl)(4-(aminomethyl)thiazol-2-yl)methanone |
| 075 | 2-(2-(1H-indole-3-carbonyl)thiazol-4-yl)-2-aminoacetonitrile |
| 172 | 2-(2-(6-chloro-1H-indole-3-carbonyl)thiazol-4-yl)-2-aminoacetonitrile |
| 173 | 2-(2-(6-fluoro-1H-indole-3-carbonyl)thiazol-4-yl)-2-aminoacetonitrile |
| 232 | (S)-(6-fluoro-1H-indol-3-yl)(4-(1-aminoethyl)thiazol-2-yl)methanone |

TABLE 1-continued

| ARI-# | Structural Formula |
|---|---|
| 233 | (S)-(6-fluoro-1H-indol-3-yl)(4-(1-(methylamino)ethyl)thiazol-2-yl)methanone |
| 235 | (S)-(1H-indol-3-yl)(4-(1-aminopropyl)thiazol-2-yl)methanone |
| (no #) | (1H-indol-3-yl)(4-(1-aminopropyl)thiazol-2-yl)methanone |
| 179 | (6-fluoro-1H-indol-3-yl)(4-(1-aminopropyl)thiazol-2-yl)methanone |
| 186 | (S)-(6-fluoro-1H-indol-3-yl)(4-(1-aminopropyl)thiazol-2-yl)methanone |

TABLE 1-continued

| ARI-# | Structural Formula |
|---|---|
| 187 | (structure: 6-fluoro-1H-indol-3-yl connected via C(O) to thiazole bearing (S)-1-aminopropyl group) |
| 218 | (structure: 5-fluoro-1H-indol-3-yl connected via C(O) to thiazole bearing 1-aminopropyl group) |
| 219 | (structure: 5-fluoro-1H-indol-3-yl connected via C(O) to thiazole bearing (S)-1-aminopropyl group) |
| 100 | (structure: 1H-indol-3-yl connected via C(O) to thiazole bearing 1-amino-2,2,2-trifluoroethyl group) |
| 223 | (structure: 6-fluoro-1H-indol-3-yl connected via C(O) to thiazole bearing (R)-1-amino-2,2,2-trifluoroethyl group) |

TABLE 1-continued

| ARI-# | Structural Formula |
|---|---|
| 224 | (structure: 6-fluoro-1H-indol-3-yl connected via C(O) to thiazole bearing (S)-1-amino-2,2,2-trifluoroethyl group) |
| 225 | (structure: 6-fluoro-1H-indol-3-yl connected via C(O) to thiazole bearing 1-aminocyclopropyl group) |
| 226 | (structure: 6-fluoro-1H-indol-3-yl connected via C(O) to thiazole bearing 2-aminopropan-2-yl group) |
| 228 | (structure: 1H-indol-3-yl connected via C(O) to thiazole bearing (R)-1-amino-2,2,2-trifluoroethyl group) |
| 229 | (structure: 1H-indol-3-yl connected via C(O) to thiazole bearing (S)-1-amino-2,2,2-trifluoroethyl group) |

TABLE 1-continued
| ARI-# | Structural Formula |
|---|---|
| | 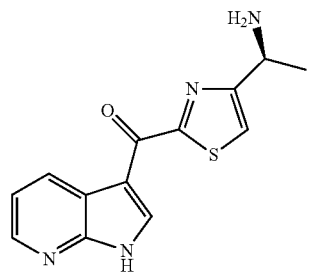 [SMILES: C[C@H](N)c1csc(C(=O)c2c[nH]c3ncccc23)n1] |
| | 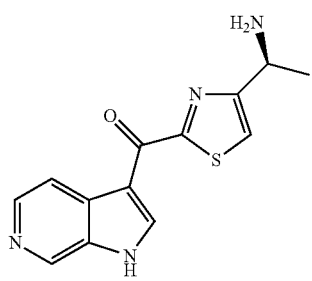 [SMILES: C[C@H](N)c1csc(C(=O)c2c[nH]c3cnccc23)n1] |
| | 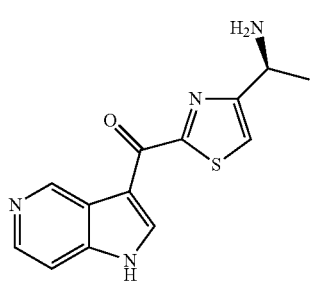 [SMILES: C[C@H](N)c1csc(C(=O)c2c[nH]c3ccncc23)n1] |
| | 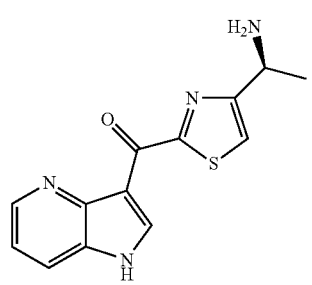 [SMILES: C[C@H](N)c1csc(C(=O)c2c[nH]c3cccnc23)n1] |
| | 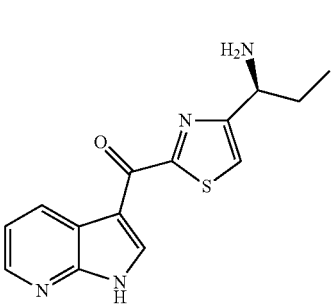 [SMILES: CC[C@H](N)c1csc(C(=O)c2c[nH]c3ncccc23)n1] |
TABLE 1-continued
| ARI-# | Structural Formula |
|---|---|
| | 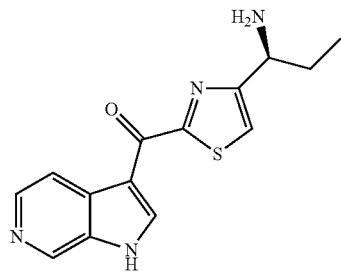 [SMILES: CC[C@H](N)c1csc(C(=O)c2c[nH]c3cnccc23)n1] |
| | 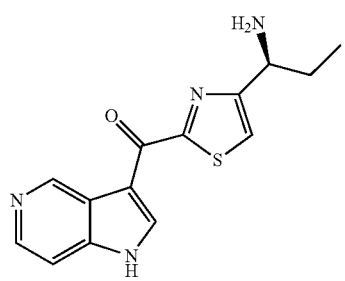 [SMILES: CC[C@H](N)c1csc(C(=O)c2c[nH]c3ccncc23)n1] |
| | 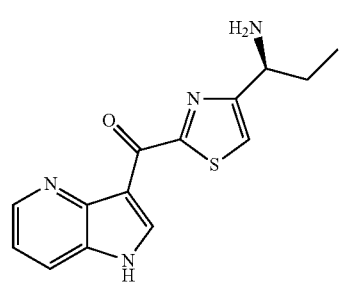 |
| | 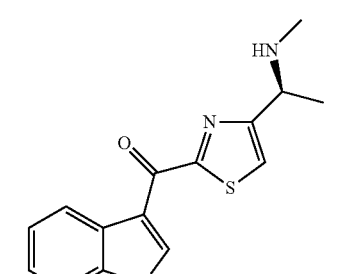 |
| | 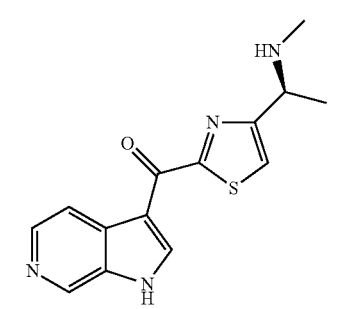 [SMILES: CN[C@@H](C)c1csc(C(=O)c2c[nH]c3cnccc23)n1] |

TABLE 1-continued
| ARI-# | Structural Formula |
|---|---|
| |  |
| 192 | |
| 185 | |
| 193 | |
TABLE 1-continued
| ARI-# | Structural Formula |
|---|---|
| 196 | 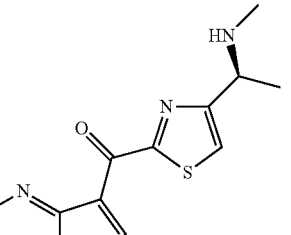 |
| 197 | |
| 198 | |
| 199 | |
| 204 | |

TABLE 1-continued

| ARI-# | Structural Formula |
|---|---|
| 205 | |
| 207 | |

Single stereochemical isomers, enantiomers, diastereomers, and pharmaceutically acceptable salts of the above exemplified compounds are also within the scope of the present disclosure. Where appropriate, pharmaceutically acceptable salts may be, for example, derived from suitable inorganic and organic acids and bases.

The compound described herein can be isolated as a pharmaceutically pure compound. The compound can be isolated as an oil, crystalline solid or a non-crystalline solid. When enantiomerically pure around the carbon substituted with $R_2/R_3/R_{3a}$, the compound can be at least 60%, at least 70%, at least 80%, at least 85%, at least 90%, at least 95%, at least 98%, at least 99% or at least 99.5% enantiomeric excess (ee). The enantiomeric configuration at the carbon substituted with $R_2/R_3/R_{3a}$ can be the (R) configuration. Alternatively, the enantiomeric configuration at the carbon substituted with $R_2/R_3/R_{3a}$ can be the (S) configuration. The enantiomeric configuration at the carbon substituted with $R_2/R_3/R_{3a}$ can be the (+) configuration. Alternatively, the enantiomeric configuration at the carbon substituted with $R_2/R_3/R_{3a}$ can be the (−) configuration.

Where appropriate, acid addition salts can be prepared by reacting the purified compound in its free-based form, if possible, with a suitable organic or inorganic acid and isolating the salt thus formed. Examples of pharmaceutically acceptable acid addition salts include, without limitations, salts of an amino group formed with inorganic acids such as hydrochloric acid, hydrobromic acid, phosphoric acid, sulfuric acid and perchloric acid, or with organic acids such as acetic acid, oxalic acid, maleic acid, tartaric acid, citric acid, succinic acid or malonic acid.

Where appropriate, base addition salts can be prepared by reacting the purified compound in its acid form with a suitable organic or inorganic base and isolating the salt thus formed. Such salts include, without limitations, alkali metal (e.g., sodium, lithium, and potassium), alkaline earth metal (e.g., magnesium and calcium), ammonium and $N^+(C_{1-4}$ alkyl$)_4$ salts.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, and valerate salts.

In some embodiments, the compound may be selected from ARI-164 or ARI-165, or a pharmaceutically acceptable salt thereof.

The indole compounds' activity in stimulating AhR can be measured by, for example, an EROD assay as described below. The EROD assay may be performed on, e.g., human or mouse hepatocyte cell lines. The indole compounds of the present disclosure may have an $EC_{50}$ of about 100 nM or less (e.g., 50 nM or less, 40 nM or less, 30 nM or less, 20 nM or less, 10 nM or less, 9 nM or less, 8 nM or less, 7 nM or less, 6 nM or less, 5 nM or less, 4 nM or less, 3 nM or less, 2 nM or less, 1 nM or less, or 0.1 nM or less) in a human or mouse EROD assay.

The indole compounds' agonistic effect on AhR's immune-stimulatory activity may be measured by the compounds' ability to inhibit IL-21 secretion from CD4$^+$ T cells, as described below. In such an assay, the indole compounds of the present disclosure may have an $IC_{50}$ of about 500 nM or less (e.g., 400 nM or less, 300 nM or less, 200 nM or less, 100 nM or less, 50 nM or less, 40 nM or less, 30 nM or less, 20 nM or less, 10 nM or less, 5 nM or less, 1 nM or less, or 0.1 nM or less).

The PK profiles of the present indole compounds are exemplified in the examples below. The compounds can have a $T_{max}$ of between 0.05 and 2 hours, a $C_{max}$ of between 300 and 50,000 ng/mL, a $T_{1/2}$ of between 0.5 and 5 hours, or AUC of between 1,000 and 25,000 hr ng/kg for a 2 mg/kg IV dose or 10 mg/kg oral dose.

The indole compounds of the present disclosure may be synthesized by methods known in the art or by methods illustrated in the examples below.

Synthesis of the phosphate derivatives is described in U.S. Provisional Application No. 62/734,989, filed Sep. 21, 2018, which is incorporated by reference in its entirety.

The classes of compounds described and claimed herein have been made by the methods described and have been tested in various in vitro incubations as well as in vivo studies in rat, dog and monkey.

The compounds described herein may contain one or more chiral centers, e.g., ARI-164, ARI-165, ARI-186, ARI-187, and the like. The chirality may confer enhanced potency and in vivo as well as in vitro stability to these compounds. As discussed in detail in the Examples, several chiral alcohol and chiral amines derivatives of the compounds described herein showed improved potency as well as reduced susceptibility to cellular oxidation. Further, the improved potency and/or stability of many of these chiral compounds was associated with a preferred enantiomeric form.

In certain embodiments, the present disclosure refers to a method of making a compound of Structural Formula 9, or an enantiomer, diastereomer, or pharmaceutically acceptable salt thereof:

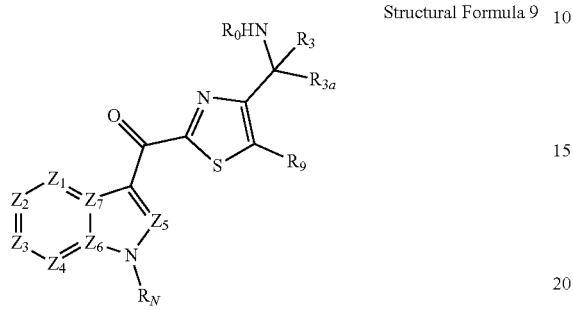

Structural Formula 9 wherein:

$Z_1$ is N or $CR_4$, $Z_2$ is N or $CR_5$, $Z_3$ is N or $CR_6$, $Z_4$ is N or $CR_7$, $Z_5$ is N or $CR_8$, $Z_6$ is N or C, $Z_7$ is N or C, wherein no more than two of $Z_1$, $Z_2$, $Z_3$, $Z_4$, $Z_5$, $Z_6$, and $Z_7$ are N;

$R_4$, $R_5$, $R_6$, $R_7$, $R_8$, and $R_9$ are each independently selected from the group consisting of hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and $-S(O)_nR_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_3$ is selected from the group consisting of deuterium, cyano, formyl, furyl, nitro, alkyl, haloalkyl, alkenyl, haloalkenyl, alkynyl, haloalkynyl, $C_1$-$C_6$ acyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and $-S(O)_nR_{10}$ (n=0 to 2, $R_{10}$ is directly connected to S), wherein $R_{10}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio;

$R_{3a}$ is selected from the group consisting of hydrogen, deuterium, cyano, or C1-C6 alkyl;

$R_o$ is hydrogen, deuterium, alkyl, aryl, or acyl;

each $R_N$ is H, CN, alkyl, alkenyl, alkynyl, aryl, alkanoyl, carbonyloxy, carbonylthio, carbonylamino, or a phosphate moiety;

and optionally, adjacent R groups, together, can form a three- to twelve-membered ring; comprising:

(i) contacting a compound of Structural Formula 10 with (S)-2-methylpropane-2-sulfinamide in the presence of a catalyst to yield a compound of Structural Formula 11;

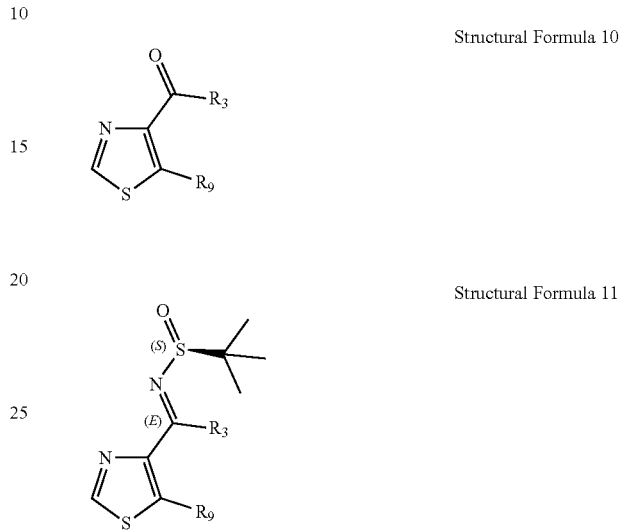

Structural Formula 10

Structural Formula 11

(ii) contacting a compound of Structural Formula 11 with one or more alkylating agent(s) to yield a compound of Structural Formula 12;

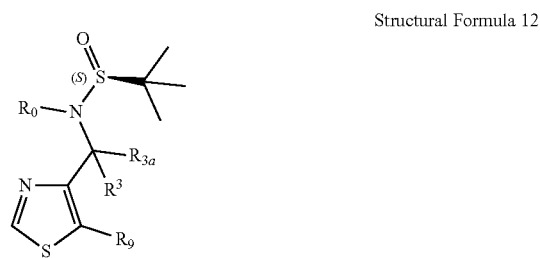

Structural Formula 12

(iii) contacting a compound of Structural Formula 12 with a compound of Structural Formula 13 in the presence of an organolithium base to yield a compound of Structural Formula 14;

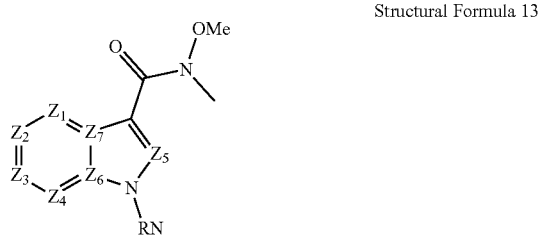

Structural Formula 13

Structural Formula 14

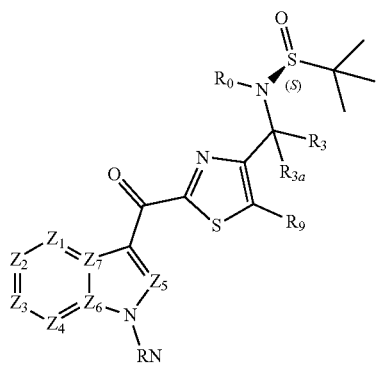

(iv) subjecting a compound of Structural Formula 14 to acid-base hydrolysis to obtain a compound of Structural Formula 9.

In particular embodiments, each of $R_4$, $R_5$, $R_6$, $R_7$, $R_8$, $R_9$, and $R_N$ is hydrogen.

In particular embodiments, at least one of $R_4$, $R_5$, $R_6$, and $R_7$ is F, Cl, or Br and the others of $R_4$, $R_5$, $R_6$, and $R_7$ are hydrogen.

In particular embodiments, $R_o$, $R_3$, and $R_{3a}$ are independently H or alkyl.

In particular embodiments, at least one of $Z_1$, $Z_2$, $Z_3$, $Z_4$, $Z_5$, $Z_6$, or $Z_7$ is N.

In particular embodiments, the compound of Structural formula 9 is enantiomerically pure at the carbon substituted with $NHR_o/R_3/R_{3a}$.

In some embodiments, $R_3$ and $R_{3a}$ together form a three- to twelve-membered ring, including a cyclopropyl, cyclobutyl, cyclopentyl, or cyclohexyl ring.

In some embodiments, the catalyst is a transition metal alkoxide.

In particular embodiments, the transition metal alkoxide is a titanium alkoxide, such as, for example, titanium isopropoxide.

In some embodiments, the alkylating agent is a metal alkyl, for example $R_{3a}MgX$, alone or in combination with $R_oX$ or $(R_o)_2Zn$, wherein X is F, Cl, Br, or I.

In some embodiments, this method can be used to make other compounds described herein, including compounds of Structural Formulae ARI-179, ARI-186, ARI-187, ARI-218, ARI-219, ARI-226, ARI-232, ARI-233, ARI-234, ARI-235, ARI-236, and the like.

Unless otherwise defined herein, scientific and technical terms used in connection with the present disclosure shall have the meanings that are commonly understood by those of ordinary skill in the art. Exemplary methods and materials are described below, although methods and materials similar or equivalent to those described herein can also be used in the practice or testing of the present disclosure. In case of conflict, the present specification, including definitions, will control. Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein. Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers. All publications and other references mentioned herein are incorporated by reference in their entirety. Although a number of documents are cited herein, this citation does not constitute an admission that any of these documents forms part of the common general knowledge in the art.

In order that this invention may be better understood, the following examples are set forth. These examples are for purposes of illustration only and are not to be construed as limiting the scope of the invention in any manner.

EXAMPLES

Example 1: Preparation of (S)-(6-Fluoro-1H-indol-3-yl)(4-(1-hydroxypropyl)thiazol-2-yl)methanone (PTC17341-123A, ARI-164) and (R)-(6-Fluoro-1H-indol-3-yl)(4-(1-hydroxypropyl)thiazol-2-yl)methanone (PTC17341-123B, ARI-165)

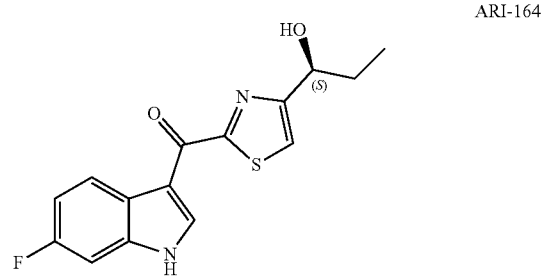

(PTC17341-123A)

ARI-164

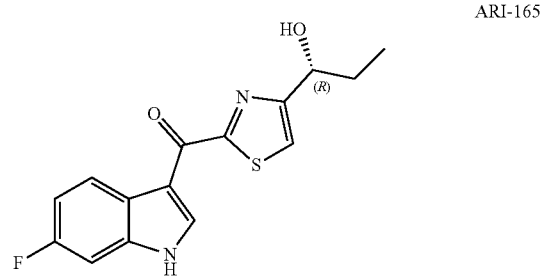

(PTC17341-123B)

ARI-165

Step 1: Preparation of (6-Fluoro-1H-indol-3-yl)(4-(1-hydroxypropyl)thiazol-2-yl)methanone (PTC17341-123, ARI-161)

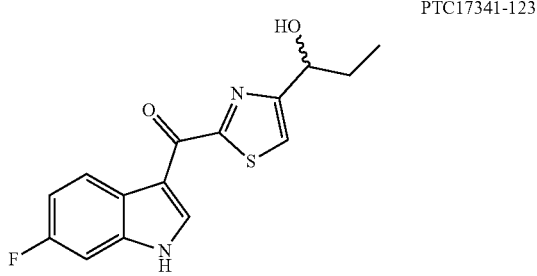 [SMILES: CCC(O)c1csc(C(=O)c2c[nH]c3cc(F)ccc23)n1]

(PTC17341-123)

To an ice-cold suspension of 1-(2-(6-fluoro-1H-indole-3-carbonyl)thiazol-4-yl)propan-1-one (ARI-143; 4.0 g, 13.2 mmol) in EtOH/THF (50 mL/50 mL), sodium borohydride (503 mg, 13.2 mmol) was added portionwise, and the reaction mixture was stirred for 1 h. Upon complete consumption of the starting material, as was indicated by TLC, the mixture was quenched with acetone (2 mL) and concentrated to remove the organic solvent. The residue was then diluted with water (100 mL), followed by extraction with EtOAc (100 mL×4). The combined organic phases were washed with brine, dried and concentrated. Trituration of the residue with EtOAc/hexane gave (6-Fluoro-1H-indol-3-yl)(4-(1-hydroxypropyl)thiazol-2-yl)methanone (3.9 g, 97% yield).

Step 2: Preparation of (S)-(6-Fluoro-1H-indol-3-yl)(4-(1-hydroxypropyl)thiazol-2-yl)methanone (PTC17341-123A, ARI-164) and (R)-1-(2-(6-fluoro-1H-indole-3-carbonyl)thiazol-4-yl)propyl acetate (Ac-ARI-165)

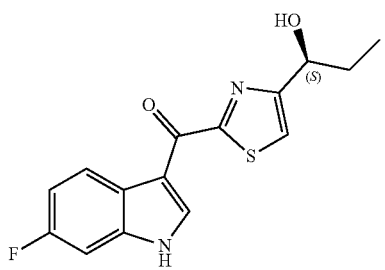

(PTC17341-123A)

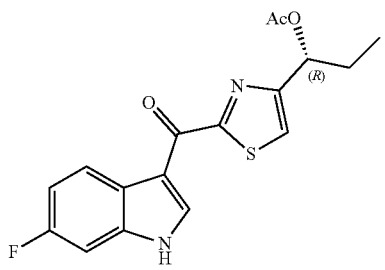

Ac-ARI-165

To a room-temperature solution of (6-Fluoro-1H-indol-3-yl)(4-(1-hydroxypropyl)thiazol-2-yl)methanone (6.0 g, 19.7 mmol) and vinyl acetate (8.5 g, 99 mmol) in acetone (200 mL), Novozym 435 (6.0 g, 10000 PLU/g) was added, and the resulting suspension was stirred for 48 h at 25° C. Upon completion, the mixture was filtered, and the filtrate was concentrated. Purification of the residue by silica gel column chromatography (hexane/EtOAc-3:1 to 1:1) gave (S)-(6-Fluoro-1H-indol-3-yl)(4-(1-hydroxypropyl)thiazol-2-yl)methanone (2.3 g, 38% yield) and (R)-1-(2-(6-fluoro-1H-indole-3-carbonyl)thiazol-4-yl)propyl acetate (2.8 g, 41% yield) as yellow solids.

ARI-164: $^1$H-NMR (400 MHz, DMSO-d6): δ 12.24 (bs, 1H), 9.11 (s, 1H), 8.28~8.32 (dd, J=5.6 and 9.6 Hz, 1H), 7.83 (s, 1H), 7.37~7.41 (dd, J=2.4 and 9.6 Hz, 1H), 7.11~7.18 (m, 1H), 5.48 (m, 1H), 4.74 (m, 1H), 1.90~2.00 (m, 1H), 1.75-1.83 (m, 1H), 0.93 (t, J=7.2 Hz, 3H)

LC-MS: m/z 302.9 [M−H]$^-$

Chiral-HPLC purity: 100% (Rt 10.826 min)

Optical Rotation: −39.7° (CH$_3$CN, c=0.310, 20° C.)

Step 3: Preparation of (R)-(6-Fluoro-1H-indol-3-yl)(4-(1-hydroxypropyl)thiazol-2-yl)methanone (PTC17341-123B, ARI-165)

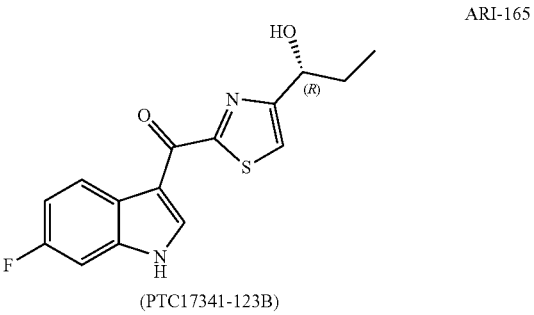

(PTC17341-123B)

Lithium hydroxide monohydrate (0.8 g, 19 mmol) was added to an ice-cold solution of (R)-1-(2-(6-fluoro-1H-indole-3-carbonyl)thiazol-4-yl)propyl acetate (2.0 g, 5.8 mmol) in THF (10 mL) and H$_2$O (10 mL). The resulting mixture was stirred for 2 h at room temperature, and then acidified with 1M HCl aqueous to a pH of 6, followed by extraction with EtOAc (20 mL×3). The combined organic phases were washed with brine, dried over Na$_2$SO$_4$, filtered and concentrated to dryness. Trituration of the residue with EtOAc/hexane (1:5, 20 mL), and subsequent filtration and drying, gave (R)-(6-Fluoro-1H-indol-3-yl)(4-(1-hydroxypropyl)thiazol-2-yl)methanone (1.5 g, 85% yield) as a yellow solid.

ARI-165: 1H-NMR (400 MHz, DMSO-d6): δ 12.25 (bs, 1H), 9.11 (s, 1H), 8.28~8.32 (dd, J=5.6 and 9.6 Hz, 1H), 7.84 (s, 1H), 7.37~7.41 (dd, J=2.4 and 9.6 Hz, 1H), 7.11~7.18 (m, 1H), 5.46~5.50 (m, 1H), 4.72~4.76 (t, J=6.0 Hz, 1H), 1.89~1.99 (m, 1H), 1.76~1.85 (m, 1H), 0.92~0.96 (t, J=7.2 Hz, 3H)

LC-MS: m/z 302.9 [M−H]$^-$

Chiral-HPLC purity: 97.9% (Rt 13.547 min)

Optical Rotation: +40.3° (CH$_3$CN, c=0.330, 20° C.)

Example 2: Separation of (S)-(6-Fluoro-1H-indol-3-yl)(4-(1-hydroxypropyl)thiazol-2-yl)methanone (PTC17341-123A, ARI-164) and (R)-(6-Fluoro-1H-indol-3-yl)(4-(1-hydroxypropyl)thiazol-2-yl)methanone (PTC17341-123B, ARI-165) by SFC SFC separation of racemic (6-Fluoro-1H-indol-3-yl)(4-(1-hydroxypropyl)thiazol-2-yl)methanone (4.9 g) derived from reduction of 1-(2-(6-fluoro-1H-indole-3-carbonyl)thiazol-4-yl)propan-1-one (ARI-143; 5.5 g) gave (S)-(6-Fluoro-1H-indol-3-yl)(4-(1-hydroxypropyl)thiazol-2-yl)methanone (1.60 g, 100% ee, 33% yield) and (R)-(6-Fluoro-1H-indol-3-yl)(4-(1-hydroxypropyl)thiazol-2-yl)methanone (1.75 g, 96.7% ee, 37% yield).

Example 3: Preparation of (S)-(4-(1-hydroxypropyl)thiazol-2-yl)(1H-indol-3-yl)methanone (PTC17341-16A, ARI-092) and (R)-(4-(1-hydroxypropyl)thiazol-2-yl)(1H-indol-3-yl)methanone (PTC17341-16A, ARI-094)

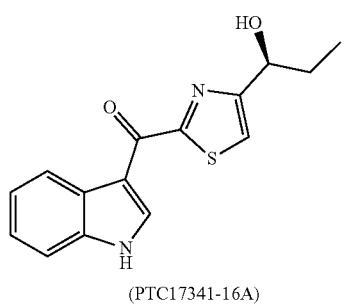

(PTC17341-16A) ARI-092

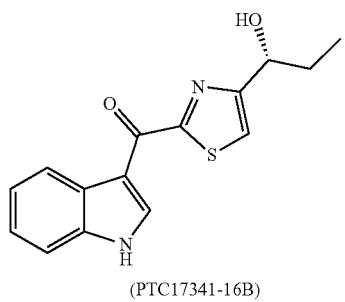

(PTC17341-16B) ARI-094

Step 1: Preparation of (4-(1-hydroxypropyl)thiazol-2-yl)(1H-indol-3-yl)methanone (PTC17341-16)

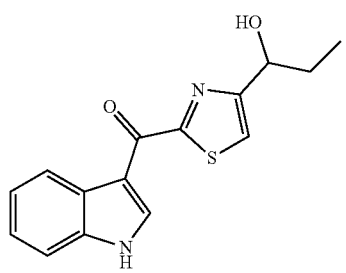

PTC17341-16

To an ice-cold suspension of 1-(2-(1H-indole-3-carbonyl)thiazol-4-yl)propan-1-one (ARI-002; 1.4 g. 5 mmol) in EtOH/THF (50 mL/50 mL), sodium borohydride (190 mg, 5 mmol) was added portion wise, and the mixture was then stirred for 1 h. Upon complete consumption of the starting material, as was indicated by TLC, the mixture was quenched with acetone (2 mL) and concentrated to remove the organic solvent. The residue was then diluted with water (100 mL), followed by extraction with EtOAc (100 mL×4). The combined organic phases were washed with brine, dried and concentrated. Purification of the residue by silica gel column chromatography (hexane/EtOAc=2:1 to 1:1) gave racemic (4-(1-hydroxypropyl)thiazol-2-yl)(1H-indol-3-yl)methanone (690 mg, 49% yield).

Step 2: Chiral Separation of (4-(1-hydroxypropyl)thiazol-2-yl)(1H-indol-3-yl)methanone (PTC17341-16) into (S) (4-(1-hydroxypropyl)thiazol-2-yl(1H-indol-yl)methanone (PTC17341-16A, ARI-092) and (R) (4-(1-hydroxypropyl)thiazol-2-yl)(1H-indol-3-yl)methanone (PTC17341-16B, ARI-094)

Separation of racemic (4-(1-hydroxypropyl)thiazol-2-yl)(1H-indol-3-yl)methanone (690 mg) by chiral prep-HPLC gave (S) (4-(1-hydroxypropyl)thiazol-2-yl)(1H-indol-yl)methanone (115 mg, 100% ee, 173% yield, Rt 12.138 min) and (R) (4-(1-hydroxypropyl)thiazol-2-yl)(1H-indol-yl)methanone (135 mg, 96.7% ee, 19% yield, Rt 15.243 min).

Example 4: Chiral Synthesis of (S)-(6-Fluoro-1H-indol-3-yl)(4-(1-hydroxypropyl)thiazol-2-yl)methanone (ARI-164; Major Product) and (R)-(6-Fluoro-1H-indol-3-yl)(4-(1-hydroxypropyl)thiazol-2-yl)methanone (ARI-165; Minor Product)

To an ice-cold solution of 1-(2-(6-fluoro-1H-indole-3-carbonyl)thiazol-4-yl)propan-1-one (150 mg, 0.5 mmol) in THF (20 mL), (R)-(+)-2-methyl-CBS-oxazaborolidine (1M in toluene, 0.1 mL, 0.1 mmol) was added, followed by the dropwise addition of $BH_3$-THF solution (1M, 0.5 mL, 0.5 mmol). The reaction mixture was stirred for 3 h at 0° C., allowed to warm to room temperature, and then stirred overnight. The mixture was quenched with acetone (2 mL) and concentrated to remove the organic solvent. The residue was then diluted with water (100 mL), followed by extraction with EtOAc (100 mL×4). The combined organic phases were washed with brine, dried and concentrated. Purification of the residue by silica gel column chromatography (hexane/EtOAc=3:1 to 1:1) gave compound (S)-(6-Fluoro-1H-indol-3-yl)(4-(1-hydroxypropyl)thiazol-2-yl)methanone (50 mg, 34% yield, chiral HPLC purity of 93.5%).

Example 5: Preparation of (S)-(6-Fluoro-1H-indol-3-yl)(4-(1-methoxypropyl)thiazol yl)methanone (PTC17341-138; ARI-184)

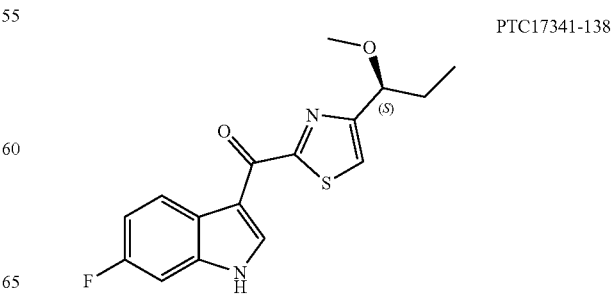

PTC17341-138

To an ice-cold solution of (S)-(6-Fluoro-1H-indol-3-yl) (4-(1-hydroxypropyl)thiazol-2-yl)methanone (1.0 g, 3.3 mmol) and tetrafluoroboric acid (50% aqueous, 0.1 mL) in THF (50 mL), a freshly prepared diazomethane solution (in ethyl ether, 50 mmol) was added dropwise. Upon complete consumption of the starting material, as was indicated by TLC, the reaction mixture was quenched with acetic acid (0.5 mL) and then concentrated to remove the organic solvent. The resulting residue was diluted with water (100 mL), and then extracted with EtOAc (100 mL×4). The combined organic phases were washed with brine, dried and concentrated. Purification of the residue by silica gel column chromatography (hexane/EtOAc=3:1 to 1:1) gave (S)-(6-Fluoro-1H-indol-3-yl)(4-(1-methoxypropyl)thiazol yl)methanone (550 mg, 52% yield) as a yellow solid.

$^1$H-NMR (400 MHz, DMSO-d6): δ 12.24 (bs, 1H), 9.05 (s, 1H), 8.27~8.33 (dd, J=5.6 and 8.4 Hz, 1H), 7.95 (s, 1H), 7.38~7.41 (d, J=9.2 Hz, 1H), 7.11~7.18 (m, 1H), 4.40~4.45 (m, 1H), 3.26 (s, 3H), 1.89~1.95 (m, 2H), 0.86~0.93 (t, J=7.2 Hz, 3H). DEPT135 (100 MHz, DMSO-d6): δ 138.80, 123.00, 122.83, 111.32, 99.65, 99.39, 80.63, 66.79, 28.29, 10.13

LC-MS: m/z 318.9 [M+H]$^+$;

Chiral-HPLC purity: 99.8% (Rt 24.148 min)

Example 6: Preparation of (R)-(6-Fluoro-1H-indol-3-yl)(4-(1-methoxypropyl)thiazol-2-yl)methanone (PTC17341-139; ARI-178

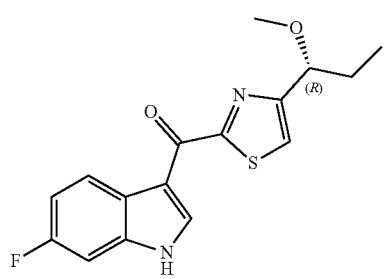

PTC17341-139

(R)-(6-Fluoro-1H-indol-3-yl)(4-(1-methoxypropyl)thiazol-2-yl)methanone (450 mg, 45% yield) was synthesized according to the method described in Example 5 except that (R)-(6-Fluoro-1H-indol-3-yl)(4-(1-hydroxypropyl)thiazol-2-yl)methanone was used instead of (S)-(6-Fluoro-1H-indol-3-yl)(4-(1-hydroxypropyl)thiazol-2-yl)methanone.

$^1$H-NMR (400 MHz, DMSO-d6): δ 12.24 (bs, 1H), 9.04~9.06 (d, J=2.8, 1H), 8.27~8.30 (dd, J=6.0 and 8.8 Hz, 1H), 7.95 (s, 1H), 7.38~7.41 (dd, J=2.8 and 9.2 Hz, 1H), 7.11~7.18 (m, 1H), 4.40~4.43 (m, 1H), 3.26 (s, 3H), 1.89~1.95 (m, 2H), 0.86~0.93 (t, J=7.2 Hz, 3H)

LC-MS: m/z 316.9 [M−H]$^−$ (Chiral-HPLC purity: 98.1% (Rt 25.706 min)

Example 7: Preparation of PTC17341-133A (R)-(4-(1-aminopropyl)thiazol-2-yl)(6-fluoro-1H-indol-3-yl)methanone (PTC3AU-187)

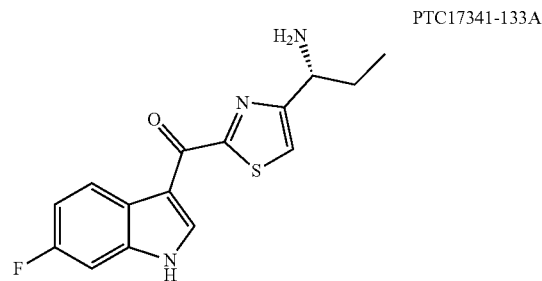 [SMILES: CC[C@@H](N)c1csc(C(=O)c2c[nH]c3cc(F)ccc23)n1]

PTC17341-133A

Step 1: Preparation of (R)-tert-Butyl 3-(4-(1-(1,3-dioxoisoindolin-2-yl)propyl)thiazole-2-carbonyl)-6-fluoro-1H-indole-1-carboxylate (1)

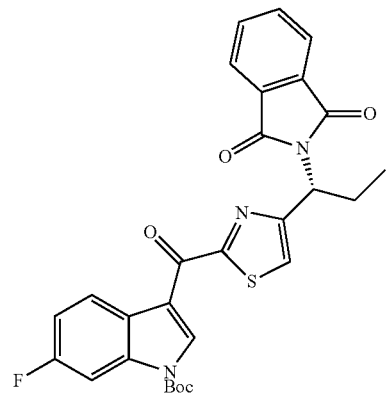

2

(S)-(6-Fluoro-1H-indol-3-yl)(4-(1-hydroxypropyl)thiazol-2-yl)methanone (1.6 g, 5 mmol) and Boc$_2$O (1.2 g, 5.6 mmol) were dissolved in THF (50 mL), followed by the addition of DMAP (20 mg, cat.) and TEA (2 mL). After stirring the resulting mixture for 12 at room temperature, it was diluted with water (100 mL), and extracted with ethyl acetate (100 mL×3). The combined organic layer was then washed with 1N HCl aqueous (100 mL×2) and brine, dried over magnesium sulfate and concentrated to yield Boc-ARI-165 (1.65 g), which was used without further purification.

Next, to an ice-cold solution of triphenylphosphine (1.6 g, 6.4 mmol), compound Boc-ARI-165 (1.65 g, 4 mmol) and phthalimide (0.8 g, 5 mmol) in THF (40 mL), DIAD (1.2 g, 6 mmol) was added dropwise. After stirring for 1 h at 0° C., the reaction mixture was allowed to warm to room temperature and further stirred for 16 h. Thereafter, the reaction mixture was concentrated, diluted with ethyl acetate (100 mL), washed with water (100 mL×2) followed by a 5% solution of sodium bisulphate (100 mL×2), dried and concentrated to dryness. Purification of the residue by flash chromatography (Hexane/EtOAc=5:1 to 3:1) gave (R)-tert-Butyl 3-(4-(1-(1,3-dioxoisoindolin-2-yl)propyl)thiazole-2-carbonyl)-6-fluoro-1H-indole-1-carboxylate (520 mg, 19% yield).

Step 2. Preparation of (R)-(4-(1-aminopropyl)thiazol-2-yl)(6-fluoro-1H-indol-3-yl)methanone (PTC17341-133A; ARI-187)

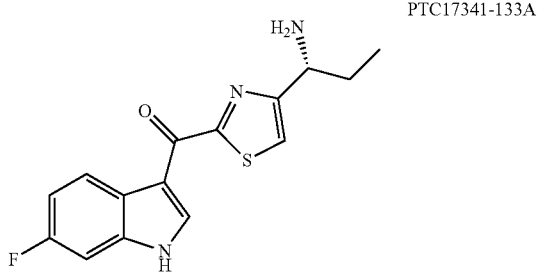 [SMILES: CC[C@@H](N)c1csc(C(=O)c2c[nH]c3cc(F)ccc23)n1]

PTC17341-133A (R)-tert-Butyl 3-(4-(1-(1,3-dioxoisoindolin-2-yl)propyl)thiazole-2-carbonyl)-6-fluoro-1H-indole-1-carboxylate (500 mg, 0.94 mmol) was suspended in hydrazine hydrate (80% solution, 60 mL) and EtOH (15 mL), and the resulting mixture was heated under reflux for 10 h. The reaction mixture was then cooled to room temperature, followed by filtration. The filtrate was concentrated to dryness, and trituration of the residue with EtOAc/hexane gave compound (R)-(4-(1-aminopropyl)thiazol-2-yl)(6-fluoro-1H-indol-3-yl)methanone (160 mg, 56% yield) as a yellow solid.

¹H-NMR (400 MHz, DMSO-d6): δ 9.15 (s, 1H), 8.26~8.33 (dd, J=5.6 and 8.4 Hz, 1H), 7.86 (s, 1H), 7.34~7.39 (dd, J=2.4 and 9.6 Hz, 1H), 7.11~7.17 (m, 1H), 4.02~4.06 (t, J=6.4 Hz, 2H), 1.82~1.95 (m, 1H), 1.70~1.80 (m, 1H), 0.88~0.93 (t, J=7.2 Hz, 3H)

LC-MS: m/z 303.9 [M+H]⁺;

Chiral-HPLC purity: 100% (Rt 12.890 min).

Example 8: Preparation of (S)-(4-(1-aminopropyl)thiazol-2-yl)(6-fluoro-1H-indol-3-yl)methanone (PTC17341-133B; ARI-186)

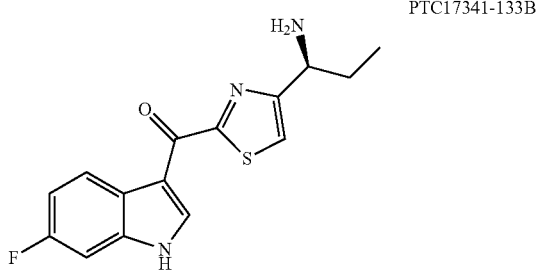 [SMILES: CC[C@H](N)c1csc(C(=O)c2c[nH]c3cc(F)ccc23)n1]

PTC17341-133B

Step 1: Preparation of (S)-tert-butyl 3-(4-(1-(1,3-dioxoisoindolin-2-yl)propyl)thiazole-2-carbonyl)-6-fluoro-1H-indole-1-carboxylate (2)

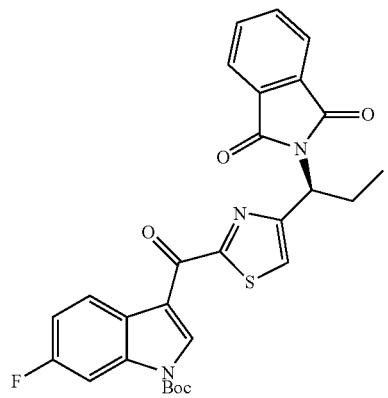

1

(S)-tert-Butyl 3-(4-(1-(1,3-dioxoisoindolin-2-yl)propyl)thiazole-2-carbonyl)-6-fluoro-1H-indole-1-carboxylate was synthesized according to the method described in Step 1 of Example 7, except that (R)-(6-Fluoro-1H-indol-3-yl)(4-(1-hydroxypropyl)thiazol-2-yl)methanone was used instead of (S)-(6-Fluoro-1H-indol-3-yl)(4-(1-hydroxypropyl)thiazol-2-yl)methanone.

Step 2: Preparation of (S)-(4-(1-aminopropyl)thiazol-2-yl)(6-fluoro-1H-indol-3-yl)methanone (PTC17341-133B)

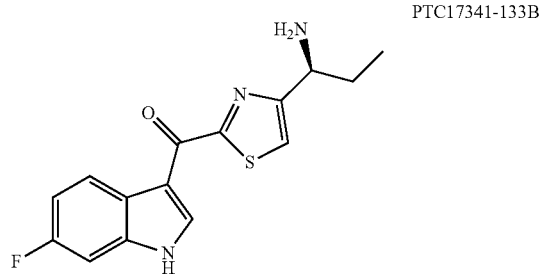 [SMILES: CC[C@H](N)c1csc(C(=O)c2c[nH]c3cc(F)ccc23)n1]

PTC17341-133B (S)-(4-(1-Aminopropyl)thiazol-2-yl)(6-fluoro-1H-indol-3-yl)methanone (410 mg, 78% yield) was synthesized according to the method described in Step. 3 of Example 7, except that (S)-tert-Butyl 3-(4-(1-(1,3-dioxoisoindolin-2-yl)propyl)thiazole-2-carbonyl)-6-fluoro-1H-indole-1-carboxylate was used instead of (R)-tert-Butyl 3-(4-(1-(1,3-dioxoisoindolin-2-yl)propyl)thiazole-2-carbonyl)-6-fluoro-1H-indole-1-carboxylate.

¹H-NMR (400 MHz, DMSO-d6): δ 9.11 (s, 1H), 8.25~8.30 (dd, J=5.6 and 8.8 Hz, 1H), 7.90 (s, 1H), 7.34~7.38 (dd, J=2.4 and 9.6 Hz, 1H), 7.08~7.14 (m, 1H), 3.94~3.99 (t, J=6.4 Hz, 2H), 1.82~2.00 (m, 1H), 1.68~1.74 (m, 1H), 0.83~0.93 (t, J=7.2 Hz, 3H);

LC-MS: m/z 304.0 [M+H]⁺

Chiral-HPLC purity: 100% (Rt 11.890 min)

Example 9: Preparation of (S)-1-(2-(6-fluoro-1H-indole-3-carbonyl)thiazol-4-yl)propyl 4-morpholinobutanoate hydrochloride (ARI-197)

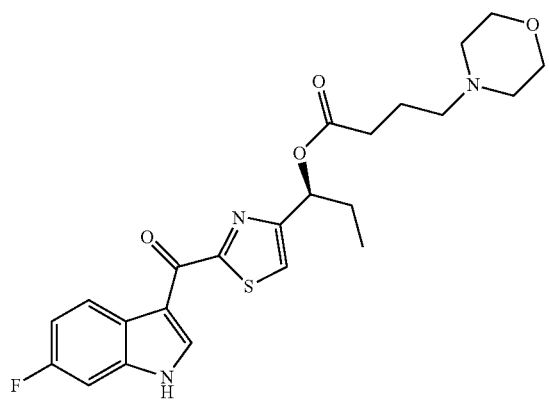 [SMILES: CC[C@H](OC(=O)CCCN1CCOCC1)c1csc(C(=O)c2c[nH]c3cc(F)ccc23)n1]

To an ice-cold solution of (S)-(6-fluoro-1H-indol-3-yl)(4-(1-hydroxypropyl)thiazol-2-yl)methanone (4.09 g, 13.44 mmol) in THF (67.2 mL) and pyridine (6.52 mL, 81 mmol), 4-bromobutanoyl chloride (1.968 mL, 16.13 mmol) was added dropwise over 5-10 minutes with a syringe. After 5 min, the cold bath was removed and the reaction was allowed to slowly warm to ambient temperature. Upon completion, as was determined by LC-MS (ESI-MS: m/z 453/455 [M+H]$^+$), the reaction mixture was concentrated under reduced pressure with no heat, followed by partitioning between EtOAc and a saturated aqueous solution of NaHCO$_3$. The organic phase was washed with brine, dried over Na$_2$SO$_4$, filtered, and concentrated to a yellow solid. The solid was co-evaporated with two portions of toluene, briefly placed on the high vacuum, and then used without further purification.

To a solution of the crude (S)-1-(2-(6-fluoro-1H-indole-3-carbonyl)thiazol-4-yl)propyl 4-bromobutanoate (13.44 mmol) in DMF (25 mL), morpholine (7.05 mL, 81 mmol) was added. Upon completion of the reaction, as was determined by LC-MS (ESI-MS: m/z 460 [M+H]$^+$), the reaction mixture was poured into a saturated aqueous solution of NaHCO$_3$ and then extracted with EtOAc. The organic phase was washed with water followed by brine, dried over Na$_2$SO$_4$, and filtered. Celite was added to the filtrate and the mixture was concentrated to dryness. Chromatographic separation (330 g silica gel, CH$_2$Cl$_2$ to 40% 80:18:2 CH$_2$Cl$_2$:MeOH:NH$_4$OH) yielded the amine free base (S)-1-(2-(6-fluoro-1H-indole-3-carbonyl)thiazol-4-yl)propyl 4-morpholinobutanoate as a yellow solid. The solid was placed on the high vacuum for several hours and then dissolved in CH$_2$Cl$_2$ (50 mL). To this solution, a slight excess of HCl (4N in dioxane; 3.70 mL, 14.78 mmol) (confirmed acidic by pH paper) was added with stirring. The reaction mixture was concentrated under reduced pressure to dryness to give a yellow solid. A smaller batch (3.29 mmol) of the free base previously prepared by the same procedure was combined at this point. The combined batch was dissolved in water and acetonitrile, filtered through a 0.2 micron nylon filter, and then lyophilized to give (S)-1-(2-(6-fluoro-1H-indole-3-carbonyl)thiazol-4-yl)propyl 4-morpholinobutanoate hydrochloride (7.53 g, 15.19 mmol) as a pale yellow solid. The overall yield from the alcohol (total of 16.73 mmol) was 90%.

ARI-197: $^1$H NMR (500 MHz, DMSO-d6) δ 12.30 (s, 1H), 10.07 (br. s, 1H), 9.03 (d, J=3.1 Hz, 1H), 8.29 (dd, J=8.7, 5.7 Hz, 1H), 8.04 (s, 1H), 7.40 (dd, J=9.5, 2.3 Hz, 1H), 7.17-7.12 (m, 1H), 5.95 (t, J=6.6 Hz, 1H), 3.94 (d, J=12.5 Hz, 2H), 3.68 (t, J=12.4 Hz, 2H), 3.41 (d, J=12.4 Hz, 2H), 3.13-3.08 (m, 2H), 3.06-2.97 (m, 2H), 2.56 (app t, 7.07 Hz, 2H), 2.15-1.92 (m, 4H), 0.93 (t, J=7.1 Hz, 3H);

$^{19}$F NMR (470 MHz, D$_2$O) δ −118.22;

ESI-MS: m/z 460 [M+H]$^+$;

Specific Rotation: −67.8° (CH$_3$CN, c=0.12, 20° C.).

Example 10: Preparation of (S)-1-(2-(6-fluoro-1H-indole-3-carbonyl)thiazol-4-yl)propyl 4-(4-methylpiperazin-1-yl)butanoate dihydrochloride (ARI-196)

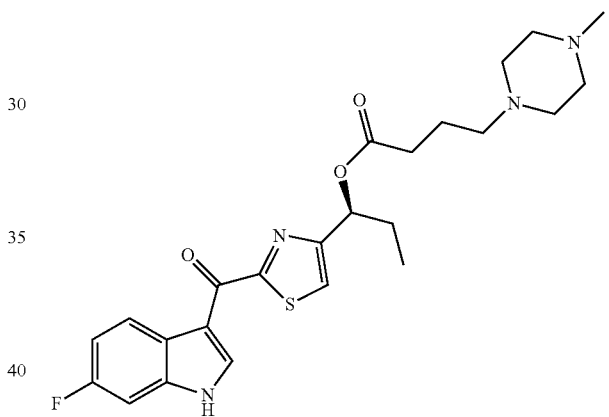

(S)-1-(2-(6-fluoro-1H-indole-3-carbonyl)thiazol-4-yl)propyl 4-(4-methylpiperazin-1-yl)butanoate dihydrochloride (902 mg, 1.65 mmol) was synthesized from (S)-(6-fluoro-1H-indol-3-yl)(4-(1-hydroxypropyl)thiazol-2-yl)methanone (1.046 g 3.44 mmol) according to the method described in Example 9, except that 1-methylpiperazine was used instead of morpholine.

ARI-196: $^1$H NMR (500 MHz, D$_2$O) δ 8.68 (s, 1H), 8.15 (dd, J=8.8, 5.5 Hz, 1H), 7.83 (s, 1H), 7.28 (dd, J=9.5, 2.1 Hz, 1H), 7.13-7.09 (m, 1H), 5.87 (t, J=6.8 Hz, 1H), 3.30 (br m, 9H), 2.96-2.93 (m, 1H), 2.81 (s, 3H), 2.50 (app t, J=7.0 Hz, 2H), 2.07-2.01 (m, 2H), 1.94-1.88 (m, 2H), 0.88 (t, J=7.4 Hz, 3H);

$^{19}$F NMR (470 MHz, D$_2$O) δ −118.24;

ESI-MS: m/z 473 [M+H]$^+$;

Specific Rotation: −63.6° (CH$_3$CN, c=0.055, 20° C.).

Elemental analysis of C$_{24}$H$_{29}$FN$_4$O$_3$S.2HCl.1.45 H$_2$O:

Theoretical: C—50.43; H—5.98; Cl—12.4; N—9.8.

Experimental: C—50.16; H—5.67; Cl—12.56; N—9.68.

Example 11: Preparation of (S)-1-(2-(6-fluoro-1H-indole-3-carbonyl)thiazol-4-yl)propyl 4-(dimethylamino)butanoate hydrochloride (ARI-198)

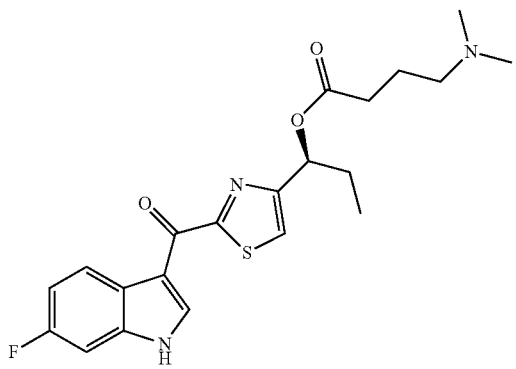 [SMILES: CC[C@H](OC(=O)CCCN(C)C)c1csc(C(=O)c2c[nH]c3cc(F)ccc23)n1]

(S)-1-(2-(6-fluoro-1H-indole-3-carbonyl)thiazol-4-yl)propyl 4-(dimethylamino)butanoate hydrochloride (125 mg, 0.275 mmol, 53% yield) was synthesized from (S)-(6-fluoro-1H-indol-3-yl)(4-(1-hydroxypropyl)thiazol-2-yl)methanone (0.512 mmol) according to the method described in Example 9, except that dimethylamine (2M in THF) was used instead of morpholine.

ARI-198: $^1$H NMR (500 MHz, D$_2$O) δ 8.65 (s, 1H), 8.12 (dd, J=8.9, 5.4 Hz, 1H), 7.81 (s, 1H), 7.25 (dd, J=11.8, 2.2 Hz, 1H), 7.10-7.06 (m, 1H), 5.87 (t, J=7.2 Hz, 1H), 3.02 (dd, J=9.4, 6.8 Hz, 2H), 2.72 (s, 6H), 2.51 (dt, J=10.4, 2.8 Hz, 2H), 2.06-2.01 (m, 2H), 1.97-1.91 (m, 2H), 0.88 (t, J=7.4 Hz, 3H);
$^{19}$F NMR (470 MHz, D$_2$O) 8-118.35;
ESI-MS: m/z 418 [M+H]$^+$.

Example 12: Preparation of ((S)-1-(2-(6-fluoro-1H-indole-3-carbonyl)thiazol-4-yl)propyl 4-([1,4'-bipiperidin]-1'-yl)butanoate dihydrochloride (ARI-199)

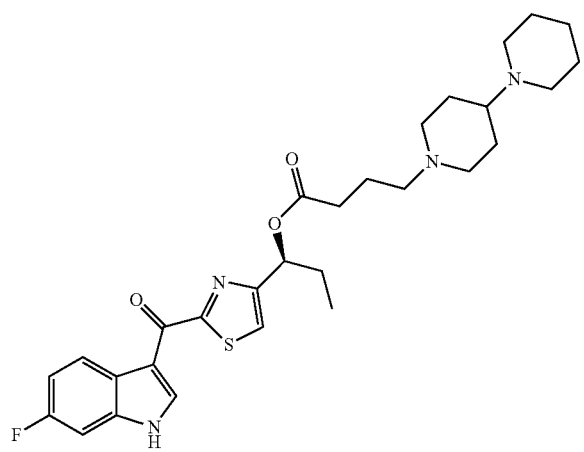 [SMILES: CC[C@H](OC(=O)CCCN1CCC(N2CCCCC2)CC1)c1csc(C(=O)c2c[nH]c3cc(F)ccc23)n1]

(S)-1-(2-(6-fluoro-1H-indole-3-carbonyl)thiazol-4-yl)propyl 4-(dimethylamino)butanoate dihydrochloride (204 mg, 0.329 mmol, 96% yield) was synthesized from (S)-(6-fluoro-1H-indol-3-yl)(4-(1-hydroxypropyl)thiazol-2-yl)methanone (0.493 mmol) according to the method described in Example 9, except that 4-piperidinopiperidine was used instead of morpholine.

ARI-199: $^1$H NMR (500 MHz, DMSO-d6) δ 12.33 (s, 1H), 10.23 (br. s, 1H), 10.11 (br. s, 1H), 9.03 (d, J=3.1 Hz, 1H), 8.29 (dd, J=8.8, 5.7 Hz, 1H), 8.04 (s, 1H), 7.40 (dd, J=9.5, 2.4 Hz, 1H), 7.17-7.12 (m, 1H), 5.95 (t, J=6.6 Hz, 1H), 3.61 (d, J=11.0 Hz, 2H), 3.42-3.34 (m, 2H), 3.08-3.01 (m, 2H), 2.98-2.85 (m, 4H), 2.59-2.53 (m, 2H), 2.26 (d, J=13.1 Hz, 2H), 2.15-1.94 (m, 6H), 1.84-1.65 (m, 5H), 1.46-1.35 (m, 1H), 0.93 (t, J=7.3 Hz, 3H);
$^{19}$F NMR (470 MHz, DMSO-d6) δ -118.59;
ESI-MS: m/z 541 [M+H]$^+$.

Example 13: Preparation of (S)-1-(2-(6-fluoro-1H-indole-3-carbonyl)thiazol-4-yl)propyl 2-morpholinoacetate hydrochloride (ARI-205)

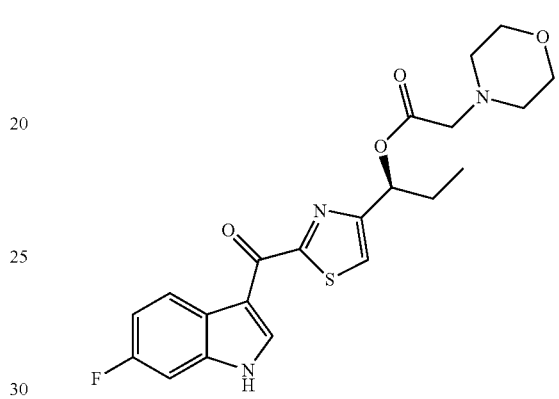

(S)-1-(2-(6-fluoro-1H-indole-3-carbonyl)thiazol-4-yl)propyl 2-morpholinoacetate hydrochloride was synthesized from (S)-(6-fluoro-1H-indol-3-yl)(4-(1-hydroxypropyl)thiazol-2-yl)methanone according to the method described in Example 9, except that chloroacetyl chloride was used in place of 4-bromobutanoyl chloride.

ARI-205: $^1$H NMR (500 MHz, DMSO-d6) δ 12.33 (br. s, 1H), 10.79 (br. s, 1H), 9.03 (d, J=3.2 Hz, 1H), 8.29 (dd, J=8.8, 5.6 Hz, 1H), 8.14 (s. 1H), 7.44 (dd, J=9.5, 2.2 Hz, 1H), 7.18-7.12 (m, 1H), 6.12-6.02 (m, 1H), 4.63-2.94 (Obs. m, 10H, morpholine), 2.21-2.03 (m, 1H), 0.95 (t, J=7.3 Hz, 3H);
$^{19}$F NMR (470 MHz, DMSO-d6) δ -118.58;
ESI MS m/z 430 [M-H]$^-$.

Example 14: Preparation of Sodium (S)-5-(1-(2-(6-fluoro-1H-indole-3-carbonyl)thiazol-4-yl)propoxy)-5-oxopentanoate (ARI-192)

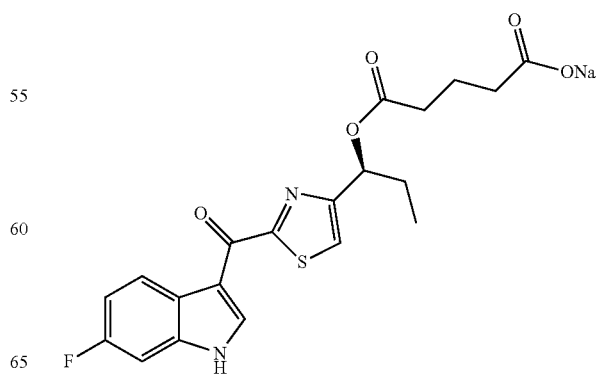

Pyridine (0.12 mL, 1.484 mmol) was added to a mixture of (S)-(6-fluoro-1H-indol-3-yl)(4-(1-hydroxypropyl)thiazol-2-yl)methanone (105 mg, 0.345 mmol) and glutaric anhydride (39.4 mg, 0.345 mmol), and the resulting solution was heated to 60° C. Upon completion, the reaction mixture was treated with 1:1 MeOH/H$_2$O (10 mL), followed by addition of 1.5 mL of a saturated aqueous solution of NaHCO$_3$. Next, the solution was concentrated and using MeOH, the sample was adsorbed onto celite. Chromatographic separation (100 g C18, 10% CH$_3$CN/H$_2$O to CH$_3$CN+0.1% TFA, dry loaded celite) yielded the product as a pale yellow solid which was contaminated with TFA. The material was then combined with another previous batch (50 mg) which was also contaminated with TFA. The combined material was adsorbed onto celite using MeOH. Further chromatographic separation (100 g C18, 10% CH$_3$CN/H$_2$O to CH$_3$CN, dry loaded celite) yielded the product, which was then taken up in 1:1 MeOH/H$_2$O and passed through Dowex 50W×8, 50-100 mesh ion exchange resin (1.5 g, 0.191 mmol) in the Na$^+$ form. The residue was concentrated and lyophilized from H$_2$O/CH$_3$CN to give sodium (S)-5-(1-(2-(6-fluoro-1H-indole-3-carbonyl)thiazol-4-yl)propoxy)-5-oxopentanoate (84 mg, 0.191 mmol) as a yellow solid. The overall yield was 24% from 0.789 mmol of alcohol.

ARI-192: $^1$H NMR (500 MHz, DMSO-d6) δ 12.63 (br. s, 0.5H), 12.08 (br. s, 0.5H), 9.04 (s, 1H), 8.27 (dd, J=8.7, 5.6 Hz, 1H), 8.00 (s, 1H), 7.37 (dd, J=9.6, 2.2 Hz, 1H), 7.15-7.11 (m, 1H), 5.93 (dd, J=7.4, 5.6 Hz, 1H), 2.47-2.44 (obscured m, 2H), 2.23 (app t, J=7.3 Hz, 2H), 2.14-1.95 (m, 2H), 1.81-1.75 (m, 2H), 0.93 (t, J=7.3 Hz, 3H);
$^{19}$F NMR (470 MHz, D$_2$O) δ −118.38;
ESI-MS: m/z 419 [M+H]$^+$.

Example 15: Preparation of sodium (S)-(4-(1-(2-(6-fluoro-1H-indole-3-carbonyl)thiazol-4-yl)propoxy)-4-oxobutyl)phosphonate (ARI-193)

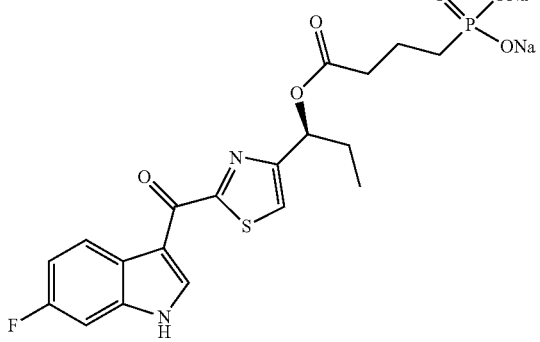

Step 1

To an ice-cold suspension of 4-phosphonobutanoic acid (168 mg, 0.999 mmol) in CH$_2$Cl$_2$ (5 mL), oxalyl chloride (0.338 mL, 4.00 mmol) was added followed by addition of 2 drops of DMF. After 3 hrs, bubbling ceased and the solvent was evaporated to a solid. The solid was co-evaporated with toluene, dried under high vacuum, and then used directly as is.

Step 2

To an ice-cold solution of (S)-(6-fluoro-1H-indol-3-yl)(4-(1-hydroxypropyl)thiazol-2-yl)methanone (215 mg, 0.706 mmol) in THF (10 mL) and pyridine (0.457 mL, 5.65 mmol), 5.67 mL of the reagent prepared in Step 1 (23.25 mg/mL in 3:1 THF:DCM) (132 mg, 0.706 mmol) was added dropwise. Later on, an additional 2 mL of the reagent prepared in Step 1 (23.25 mg/mL in 3:1 THF:DCM) was added as LC-MS indicated an incomplete reaction. Upon completion, the reaction mixture was treated with water and the majority of the solvent was concentrated under reduced pressure. The residue was then partitioned between EtOAc and 1N HCl (aq). Since the organic layer became a thick slurry, it was treated with water followed by brine. The emulsion was then filtered using a Buchner funnel and the solid was dried overnight on the filter. The EtOAc layer of the filtrate was concentrated and the resulting residue was recombined with the solid using MeOH. After addition of water and a saturated aqueous solution of NaHCO$_3$, the mixture was adsorbed onto celite and then concentrated to dryness. Chromatographic separation (100 g C18, 10% CH$_3$CN/H$_2$O to CH$_3$CN, dry loaded celite) yielded sodium (S)-(4-(1-(2-(6-fluoro-1H-indole-3-carbonyl)thiazol-4-yl)propoxy)-4-oxobutyl)phosphonate (143 mg, 0.287 mmol) as a yellow solid after lyophilization from water and acetonitrile.

ARI-193: $^1$H NMR (500 MHz, D$_2$O) δ 8.61 (s, 1H), 8.14-8.11 (m, 1H), 7.80 (s, 1H), 7.30-7.28 (m, 1H), 7.09-7.05 (m, 1H), 5.85 (t, J=6.86 Hz, 1H), 2.30 (app t, J=7.6 Hz, 2H), 2.02-1.97 (m, 2H), 1.85-1.76 (m, 2H), 1.44-1.37 (m, 2H), 0.87 (t, J=7.3 Hz, 3H);
$^{31}$P NMR (202 MHz, D$_2$O) δ 21.47;
$^{19}$F NMR (470 MHz, D$_2$O) δ −118.50;
ESI-MS: m/z 453 [M−H]$^-$.

Example 16: Preparation of 2-(2-(1H-indole-3-carbonyl)thiazol-4-yl)-2-aminoacetonitrile

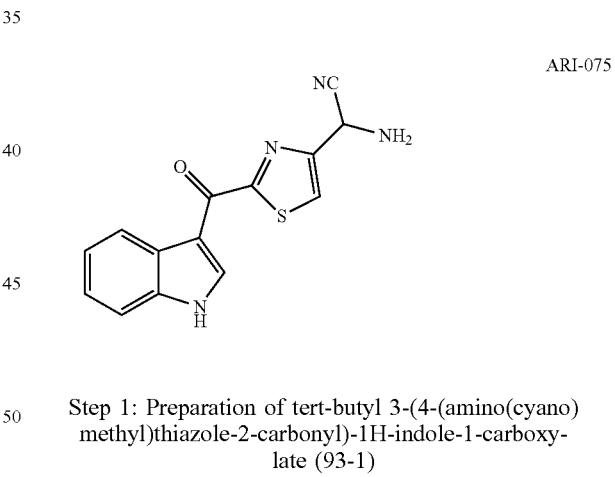

ARI-075

Step 1: Preparation of tert-butyl 3-(4-(amino(cyano)methyl)thiazole-2-carbonyl)-1H-indole-1-carboxylate (93-1)

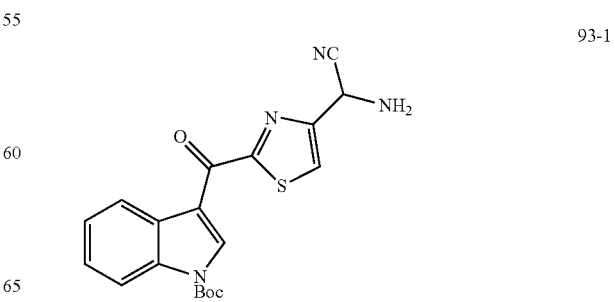

93-1

Trimethylsilyl cyanide (0.74 mL, 5.5 mmol) was added to a solution of tert-butyl-3-(4-formylthiazole-2-carbonyl)-1H-indole-1-carboxylate (1.40 g, 4 mmol) in THF (5 mL) and NH$_3$-MeOH (7M solution, 20 mL) at room temperature. The mixture was stirred for 2 h and then concentrated to dryness to afford compound 93-1 (2.0 g, ~100% yield), which was used for next step without further purification.

Step 2: Preparation of 2-(2-(1H-indole-3-carbonyl)thiazol-4-yl)-2-aminoacetonitrile (ARI-075)

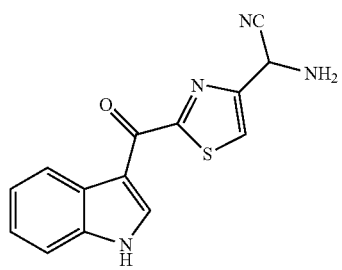

ARI-075

Compound 93-1 (2.00 g, 5 mmol) was dissolved in TFA/DCM (10 mL/10 mL) at 0° C. Then the mixture was allowed to warm to room temperate and stirred for 2 h. Next, the residue was concentrated to dryness. The residue was suspended in saturated aqueous KHCO$_3$ (50 mL) and EtOAc (50 mL), stirred for 0.5 h, then filtered to collect the solid. The solid was washed with water (30 mL×3) and EtOAc (30 mL×3), and then dried to afford compound ARI-075 (680 mg, 43% yield) as a yellow solid.

$^1$H-NMR (400 MHz, DMSO-d6): δ 12.37 (bs, 1H), 9.17 (s, 1H), 8.31-8.35 (m, 1H), 8.07 (s, 1H), 7.56~7.59 (d, J=6.0 Hz, 1H), 7.28~7.33 (m, 2H), 5.34~5.39 (t, J=8.0 Hz, 1H), 3.05~3.08 (d, J=8.0 Hz, 1H).

LC-MS: m/z 281.0 [M–H]$^-$.

Example 17: Preparation of 2-amino-2-(2-(6-fluoro-1H-indole-3-carbonyl)thiazol-4-yl)acetonitrile (ARI-173)

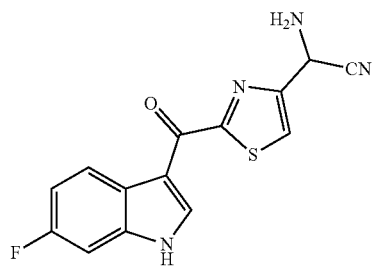 [SMILES: N#CC(N)c1csc(C(=O)c2c[nH]c3cc(F)ccc23)n1]

2-amino-2-(2-(6-fluoro-1H-indole-3-carbonyl)thiazol-4-yl)acetonitrile was synthesized according to the method described in Example 16 except that tert-butyl-3-(4-formylthiazole-2-carbonyl)-6-fluoro-1H-indole-1-carboxylate was used instead of tert-butyl-3-(4-formylthiazole-2-carbonyl)-1H-indole-1-carboxylate.

$^1$H-NMR (400 MHz, DMSO-d6): δ 12.15 (bs, 1H), 9.17 (s, 1H), 8.28-8.32 (dd, J=5.6 and 8.8 Hz, 1H), 8.08 (s, 1H), 7.37-7.41 (dd, J=2.0 and 8.8 Hz, 1H), 7.12-7.19 (m, 1H), 5.33-5.39 (t, J=8.4 Hz, 1H), 3.06-3.08 (d, J=8.4, 2H).

LC-MS: m/z 298.9 [M–H]$^-$.

Example 18: Preparation of (6-fluoro-1H-indol-3-yl)(4-(2-hydroxybutan-2-yl)thiazol-2-yl)methanone (PTC17341-143; ARI-209)

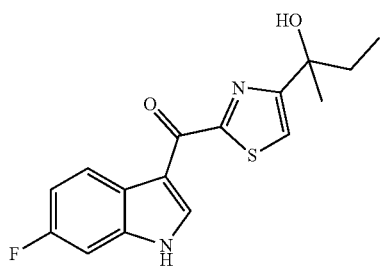 [SMILES: CCC(O)(CC)c1csc(C(=O)c2c[nH]c3cc(F)ccc23)n1]

PTC17341-143

Step 1: Preparation of 2-(thiazol-4-yl)butan-2-ol (143-1)

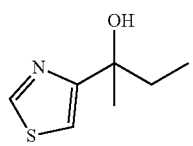

143-1

A solution of 1-(thiazol-4-yl)propan-1-one (3.0 g, 21 mmol) in THF (100 mL) was stirred and cooled to −10° C. under N$_2$. Next, MeMgI (3 M in Et$_2$O, 33 mL, 0.1 mol) was added dropwise at 0~10° C. over 30 min. The mixture was allowed to warm to room temperature and stirred for 2 h, and then quenched with saturated NH$_4$Cl aqueous (100 mL). The mixture was extracted with EtOAc (100 mL×3). The combined organic phases were washed with brine (100 mL×2), dried, and concentrated to dryness. The residue was purified by silica gel chromatography (EtOAc/Hexane=1:5) and afforded 2-(thiazol-4-yl)butan-2-ol (1.9 g, 57% yield) as an oil.

Step 2: Preparation of (S)-4-(2-(triethylsilyloxy)butan-2-yl)thiazole (143-2)

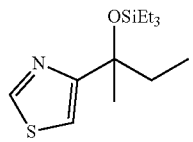

143-2

Compound 143-1 (1.9 g, 12.08 mmol) was dissolved in DCM (21 ml) and cooled to 0° C. Imidazole (1.33 g, 19.9 mmol) was added followed by addition of a solution of TES-Cl (2.2 g, 14.6 mmol) in DCM (8 mL) dropwise at 0-20° C. The reaction mixture was stirred overnight at room temperature, then washed with water, aqueous 5% KHSO$_4$ (×3), saturated aqueous NaHCO$_3$ (×3), and brine, dried over anhydrous Na$_2$SO$_4$ and concentrated to dryness. The residue was purified by distillation under reduced pressure to afford compound 143-2 (2.5 g, 76% yield) as an oil Step 3: Preparation of (6-fluoro-1H-indol-3-yl)(4-(2-(triethylsilyloxy)butan-2-yl)thiazol-2-yl) methanone (143-3)

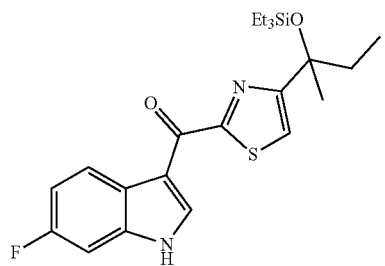

143-3

A solution of 143-2 (1.45 g, 5.34 mmol) in THF (13 mL) and toluene (13 mL) was cooled to −78° C., and sec-BuLi (1.3 M solution in hexane, 5.1 mL, 6.6 mmol) was added dropwise at −78° C. over 10 min. The mixture was stirred for 0.5 h at this temperature, then a solution of compound tert-butyl 6-fluoro-3-(methoxy(methyl)carbamoyl)-1H-indole-1-carboxylate (2.15 g, 6.68 mmol) in THF (14 mL) was added dropwise over 10 min. The mixture was stirred at −78° C. for 1 h then allowed to warm to 0° C. and quenched with aqueous 10% NH$_4$Cl. The organic phase was collected and washed with water (×2), saturated aqueous NaHCO$_3$ (×2), and brine (×1), dried (Na$_2$SO$_4$), filtered and concentrated to dryness. The residue was dissolved in MeOH, and K$_2$CO$_3$ (0.74 g, 5.34 mmol) was added. The mixture was stirred for 2 h at room temperature. The mixture was filtered, and the filtrate was concentrated to dryness. The residue was triturated in EtOH to afford compound 143-3 (1.5 g, 65% yield).

Step 4: Preparation of (6-Fluoro-1H-indol-3-yl)(4-(2-hydroxybutan-2-yl)thiazol-2-yl)methanone (PTC17341-143; ARI-209)

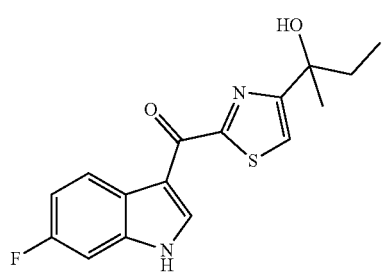

PTC17341-143

Tetrabutylammonium fluoride trihydrate (TBAF, 9.0 g, 28.7 mmol) was added to a solution of compound 143-3 (1.5 g, 3.5 mmol) in THF (15 mL) at room temperature. The mixture was stirred for 10 h at room temperature and then quenched with H$_2$O. The mixture was extracted with EtOAc (×3). The organic phase was collected and washed with water (×2), saturated aqueous NaHCO$_3$ (×2), and brine, dried over Na$_2$SO$_4$, filtered, and concentrated to dryness.

The residue was recrystallized with EtOH/H$_2$O (9:1) to afford compound PTC17341-143 (ARI-209; 735 mg, 66% yield) as a yellowish solid.
$^1$H-NMR (400 MHz, DMSO-d6): δ 12.21 (bs, 1H), 9.09 (s, 1H), 8.28~8.32 (dd, J=5.6 and 8.8 Hz, 1H), 7.80 (s, 1H), 7.37~7.40 (dd, J=2.4 and 9.6 Hz, 1H), 7.11~7.17 (m, 1H), 5.23 (bs, 1H), 1.81~2.00 (m, 2H), 1.54 (s, 3H), 0.75~0.80 (t, J=7.2 Hz, 3H). LC-MS: m/z 341.0 [M+Na]$^+$.

Example 19: Preparation of (6-fluoro-1H-indol-3-yl)(4-(3-hydroxypentan-3-yl)thiazol-2-yl)methanone (PTC17341-142; ARI-210)

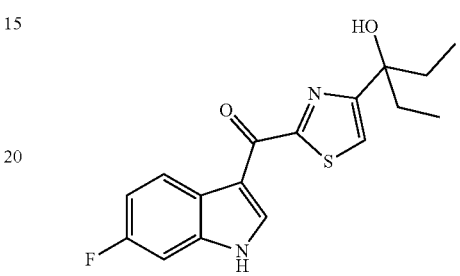

(6-fluoro-1H-indol-3-yl)(4-(3-hydroxypentan-3-yl)thiazol-2-yl)methanone was synthesized according to the method described in Example 18 except that EtMgI was used instead of MeMgI.
$^1$H-NMR (400 MHz, DMSO-d6): δ 12.19 (bs, 1H), 9.05 (s, 1H), 8.29~8.32 (dd, J=5.6 and 8.8 Hz, 1H), 7.78 (s, 1H), 7.37~7.41 (dd, J=2.4 and 8.8 Hz, 1H), 7.11~7.18 (m, 1H), 4.97 (bs, 1H), 1.91~2.00 (m, 2H) 1.77~1.87 (m, 2H), 0.72~0.77 (m, 6H).

Example 20: Preparation of (1H-indol-3-yl)(4-(2-hydroxypropan-2-yl)thiazol-2-yl)methanone (PTC17341-157; ARI-215)

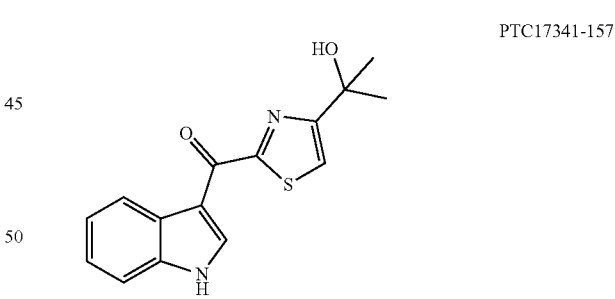

PTC17341-157

Step 1: Preparation of thiazole-4-carbonitrile (157-1)

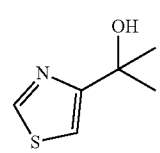

157-1

A solution of N-methoxy-N-methylthiazole-4-carboxamide (17.2 g, 0.10 mol) in THF (500 mL) was stirred and cooled to −10° C. under N₂. Next, MeMgI (3 M in Et₂O, 200 mL, 0.60 mol) was added dropwise at 0~10° C. over 30 min. The mixture was allowed to warm to room temperature and stirred for 2 h, and then quenched with saturated NH₄Cl aqueous (500 mL). The mixture was extracted with EtOAc (500 mL×3). The combined organic phases were washed with brine (500 mL×2), dried, and concentrated to dryness. The residue was purified by silica gel chromatography (EtOAc/Hexane=1:5) and afforded compound 157-1 (9.3 g, 65% yield) as an oil.

Step 2: Preparation of 4-(2-(triethylsilyloxy)propan-2-yl)thiazole (157-2)

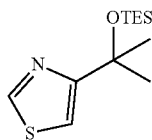

157-2

157-1 (9.4 g, 65.6 mmol) was dissolved in DCM (113 ml) and cooled to 0° C. Imidazole (72.0 g, 1.06 mol) was added, and then a solution of TES-Cl (11.9 g, 79 mmol) in DCM (85 mL) was added dropwise at 0~20° C. The reaction mixture was stirred overnight at room temperature, then washed with water, aqueous 5% KHSO₄ (×3), saturated aqueous NaHCO₃ (×3), and brine, dried over anhydrous Na₂SO₄ and concentrated to dryness. The residue was purified by distillation under reduced pressure to afford compound 157-2 (9.6 g, 57% yield) as an oil.

Step 3: Preparation of (1H-indol-3-yl)(4-(2-(triethylsilyloxy)propan-2-yl)thiazol-2-yl) methanone (157-3)

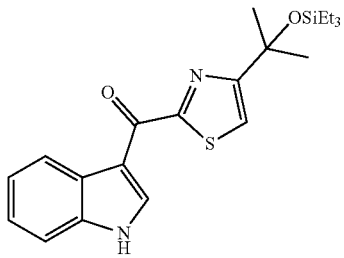

157-3

A solution of 4-(2-(triethylsilyloxy)propan-2-yl)thiazole (7.2 g, 28 mmol) in THF (8 mL) and toluene (8 mL) was cooled to −78° C., and sec-BuLi (1.3 M solution in hexane, 28 mL, 36.4 mmol) was added dropwise at −78° C. over 10 min. The mixture was stirred for 0.5 h at this temperature, then a solution of tert-butyl 3-(methoxy(methyl)carbamoyl)-1H-indole-1-carboxylate (10.65 g, 35 mmol) in THF (100 mL) was added dropwise over 10 min. The mixture was stirred at −78° C. for 1 h, and allowed to warm to 0° C., and quenched with aqueous 10% NH₄Cl. The organic phase was collected and washed with water (×2), saturated aqueous NaHCO₃ (×4), and brine, dried (Na₂SO₄), filtered and concentrated to dryness. The residue was dissolved in MeOH, and K₂CO₃ (3.87 g, 28 mmol) was added. The mixture was stirred for 2 h at room temperature. The mixture was filtered, and the filtrate was concentrated to dryness. The residue was triturated in EtOH to afford compound 157-3 (6.5 g, 58% yield).

Step 4: Preparation of (1H-indol-3-yl)(4-(2-hydroxypropan-2-yl)thiazol-2-yl)methanone (PTC17341-157)

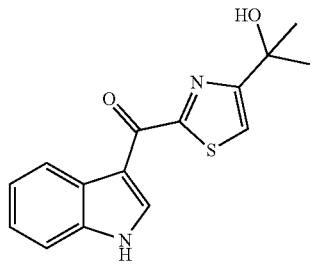

PTC17341-157

Tetrabutylammonium fluoride trihydrate (TBAF, 9.0 g, 28.7 mmol) was added to a solution of compound 157-3 (4.8 g, 11.5 mmol) in THF (50 mL) at room temperature, the mixture was stirred for 10 h at room temperature, then quenched with H₂O (100 mL). The mixture was extracted with EtOAc (100 mL×3). The organic phase was collected and washed with water (500 mL×2), saturated aqueous NaHCO₃ (100 mL×2), and brine (100 mL×1), dried over Na₂SO₄, filtered, and concentrated to dryness. The residue was recrystallized with EtOH/H₂O (9:1, 300 mL) to afford compound PTC17341-157 as a yellowish solid.

¹H-NMR (400 MHz, DMSO-d6): δ 12.21 (bs, 1H), 9.14~9.15 (d, J=3.2 Hz, 1H), 8.31~8.34 (dd, J=4.0 and 8.4 Hz, 1H), 7.81 (s, 1H), 7.55~7.59 (m, 1H), 7.25~7.32 (m, 1H), 5.39 (bs, 1H), 1.58 (s, 6H).
LC-MS: m/z 287.0 [M+H]⁺.

Example 21: Preparation of (6-fluoro-1H-indol-3-yl)(4-(2-hydroxypropan-2-yl)thiazol-2-yl)methanone (ARI-220)

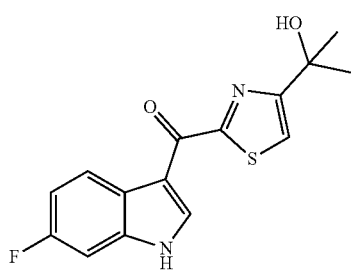 [SMILES: CC(C)(O)c1csc(C(=O)c2c[nH]c3cc(F)ccc23)n1]

(6-Fluoro-1H-indol-3-yl)(4-(2-hydroxypropan-2-yl)thiazol-2-yl)methanone was synthesized according to the method described in Example 20 except that tert-butyl 3-(methoxy(methyl)carbamoyl)-6-fluoro-1H-indole-1-carboxylate was used instead of tert-butyl 3-(methoxy(methyl)carbamoyl)-1H-indole-1-carboxylate.

¹H-NMR (400 MHz, DMSO-d6): δ 12.19 (bs, 1H), 9.12~9.14 (d, J=3.2 Hz, 1H), 8.27~8.32 (dd, J=5.6 and 8.8

Hz, 1H), 7.82 (s, 1H), 7.36~7.40 (dd, J=2.4 and 8.8 Hz, 1H), 7.10~7.17 (m, 1H), 5.37 (bs, 1H), 1.18 (s, 6H);
LC-MS: m/z 303.1 [M−H]⁻.

Example 22: Preparation of (6-fluoro-1H-indol-3-yl)(4-(1-hydroxycyclopropyl)thiazol-2-yl)methanone (PTC17341-158; ARI-221)

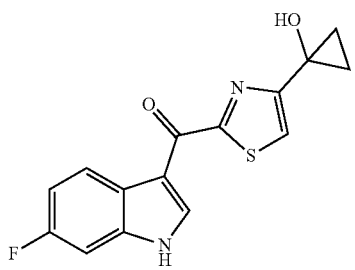

PTC17341-158

Step 1: Preparation of 1-(Thiazol-4-yl)ethanone (158-1)

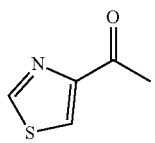

158-1

A solution of compound N-methoxy-N-methylthiazole-4-carboxamide (110.0 g, 0.643 mol) in THF (1 L) was stirred and cooled to −10° C. under $N_2$, MeMgBr (1M) was added dropwise at 0~10° C. over 1 h. The mixture was stirred for 2 h at this temperature, and then quenched with saturated $NH_4Cl$ aqueous (500 mL). The mixture was warmed to room temperature, then extracted with EtOAc (1 L×3). The combined organic phases were washed with brine (500 mL×2), dried, concentrated to dryness. The residue was purified by distillation under reduced pressure to afford compound 158-1 (12.1 g, 69% yield) as an oil.

Step 2: Preparation of 4-(1-(tert-butyldimethylsilyloxy)vinyl)thiazole (158-2)

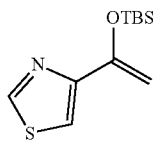

158-2 tert-Butyldimethylsilyl trifluoromethanesulfonate (TBS-OTf, 15 mL, 56.3 mmol) was added dropwise to a solution of compound 158-1 (5.5 g, 43.3 mmol) and TEA (6.6 g, 65 mmol) in DCM (100 mL) at 0° C. The reaction mixture was stirred overnight at room temperature, then washed with water (50 mL×1) and brine (50 mL×1), dried over anhydrous $Na_2SO_4$ and concentrated to dryness. The residue was purified by silica gel chromatography (EtOAc/Hexane=1:30) and afforded compound 158-2 (6.8 g, 65% yield) as an oil.

Step 3: Preparation of 4-(1-(tert-butyldimethylsilyloxy)cyclopropyl)thiazole (158-3)

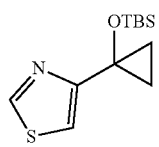

158-3

Diethylzinc solution (1.0 M in hexanes, 15.6 mL, 15.6 mmol) was added dropwise to a solution of compound 158-2 (780 mg, 3.9 mmol) and diiodomethane (4.2 g, 15.6 mmol) in DCM (100 mL) at 0° C. over 10 min. The solution was stirred for 0.5 h at 0° C., then allowed to warm to room temperature. The mixture was quenched with sat aqueous $NH_4Cl$ (50 mL) and extracted with DCM (50 mL×3). The combined organic layers were washed with brine, dried, and concentrated to dryness. The residue was purified by silica gel chromatography (EtOAc/Hexane=1:20) and afforded compound 158-3 (350 mg, 45% yield) as an oil.

Step 4: Preparation of (4-(1-(tert-Butyldimethylsilyloxy)cyclopropyl)thiazol-2-yl)(6-fluoro-1H-indol-3-yl)methanone (158-4)

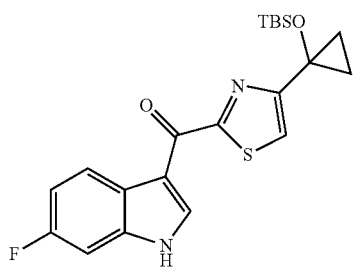

158-4

A solution of 158-3 (3.23 g, 12.7 mmol) in THF (44 mL) and toluene (44 mL) was cooled to −78° C., and sec-BuLi (1.3 M solution in hexane, 12.1 mL, 15.7 mmol) was added dropwise at −78° C. over 10 min. The mixture was stirred for 0.5 h at this temperature, then a solution of compound tert-butyl-6-fluoro-3-(methoxy(methyl)carbamoyl)-1H-indole-1-carboxylate (5.1 g, 15.8 mmol) in THF (43 mL) was added dropwise over 10 min. The mixture was stirred at −78° C. for 1 h, then allowed to warm to 0° C. and quenched with aqueous 10% $NH_4Cl$. The organic phase was collected and washed with water (×2), saturated aqueous $NaHCO_3$ (×2), and brine, dried ($Na_2SO_4$), filtered and concentrated to dryness. The residue was dissolved in MeOH, and $K_2CO_3$ (1.75 g, 12.7 mmol) was added. The mixture was stirred for 2 h at room temperature. The mixture was filtered, and the filtrate was concentrated to dryness. The residue was triturated in EtOH to afford compound 158-4 (2.9 g, 55% yield) as a yellow solid.

Step 5: Preparation of (6-Fluoro-1H-indol-3-yl)(4-(1-hydroxycyclopropyl)thiazol-2-yl)methanone (PTC17341-158)

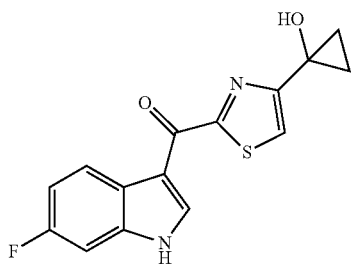

PTC17341-158

Tetrabutylammonium fluoride trihydrate (TBAF, 4.83 g, 17.3 mmol) was added to a solution of compound 158-4 (2.88 g, 6.91 mmol) in THF (30 mL) at room temperature, the mixture was stirred for 10 h at room temperature, then quenched with H$_2$O. The mixture was extracted with EtOAc (×3). The organic phase was collected and washed with water (×2), saturated aqueous NaHCO$_3$ (×2), and brine, dried (Na$_2$SO$_4$), filtered and concentrated to dryness. The residue was recrystallized with EtOH/H$_2$O (9:1) to afford PTC17341-158 (1.8 g, 86% yield) as a yellow solid.

$^1$H-NMR (400 MHz, DMSO-d6): δ 12.17 (bs, 1H), 8.92 (s, 1H), 8.26~8.30 (dd, J=5.6 and 8.8 Hz, 1H), 7.80 (s, 1H), 7.35~7.39 (dd, J=2.4 and 8.8 Hz, 1H), 7.10~7.16 (m, 1H), 6.36 (m, 1H), 1.22~1.30 (m, 2H), 1.18~1.20 (m, 2H); LC-MS: m/z 303.1 [M+H]$^+$.

Example 23: Preparation of (4-(1-aminocyclopropyl)thiazol-2-yl)(6-fluoro-1H-indol-3-yl)methanone (PTC17341-159; ARI-225)

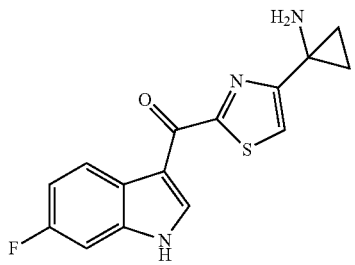

PTC17341-159

Step 1: Preparation of thiazole-4-carbonitrile (159-1)

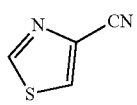

159-1

TEA (76 g, 748 mmol) and TFAA (108 g, 512 mmol) were added to a suspension of thiazole-4-carboxylic acid (21.46 & 166.2 mmol) in DCM (800 mL) at 0° C. The mixture was allowed to warm to room temperature and stirred for 6 h, then diluted with H$_2$O and EtOAc. The mixture was stirred for 0.5 h, then filtered to collect the solid. The solid was washed with water (×3) and EtOAc (×3), dried to afford compound 159-1 (15.2 g, 83% yield) as an oil.

Step 2: Preparation of 1-(thiazol-4-yl)cyclopropanamine (159-2)

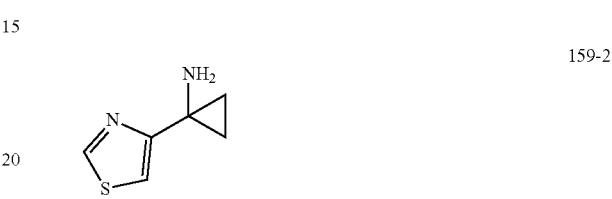

Titanium (IV) isopropoxide (15.1 mL, 55 mmol) was added to a solution of compound 159-1 (5.5 g, 50 mmol) in THF (100 mL) at 0° C. The mixture was stirred for 15 min, then EtMgBr (2 M Et2O solution, 50 mL, 0.1 mol) was added dropwise over 30 min at 0° C. The deep black solution was stirred for 2 h at room temperature, then BF$_3$.Et$_2$O (12.5 mL, 0.1 mol) was added dropwise and stirred for 15 min. The reaction was quenched with 1 N aqueous HCl (18 mL), stirred for 30 min, then alkalized with 1 N aqueous NaOH to pH of 9. The mixture was extracted with DCM (200 mL×3). The combined organic layers were washed with brine, dried, concentrated to dryness to afford crude compound 159-2 (3.1 g, 44% yield) as an oil, which was used for next step without further purification.

Step 3: Preparation of N,N-Diallyl-1-(thiazol-4-yl)cyclopropanamine (159-3)

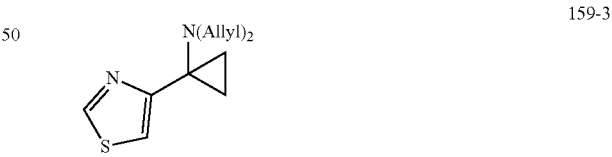

KOH (7.9 g, 142 mmol) and allyl bromide (19.3 g, 142 mmol) were added to a solution of compound 159-2 (3.1 g, 22 mmol) in DMF (20 mL). The reaction mixture was heated to 60° C. and stirred for 4 h. After cooled to room temperature, the mixture was quenched with H$_2$O (50 mL), extracted with DCM (50 mL×3). The combined organic layers were washed with brine, dried, concentrated to dryness. The residue was purified by silica gel chromatography (EtOAc/Hexane=1:3) and afforded compound 159-3 (2.2 g, 45% yield) as an oil.

Step 4: Preparation of (4-(1-(diallylamino)cyclopropyl)thiazol-2-yl)(6-fluoro-1H-indol-3-yl) methanone (159-4)

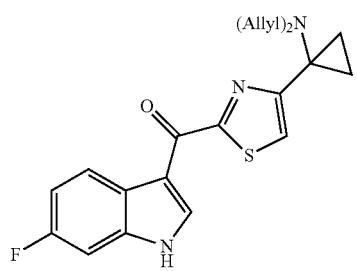

159-4

A solution of compound 159-3 (4.43 g, 20.1 mmol) in THF (65 mL) and toluene (65 mL) was cooled to −78° C., and sec-BuLi (1.3 M solution in hexane, 19.2 mL, 25 mmol) was added dropwise at −78° C. over 10 min. The mixture was stirred for 0.5 h at this temperature, then a solution of compound tert-butyl 6-fluoro-3-(methoxy(methyl)carbamoyl)-1H-indole-1-carboxylate (8.1 g, 25.1 mmol) in THF (68 mL) was added dropwise over 10 min. The mixture was stirred at −78° C. for 1 h then allowed to warm to 0° C. and quenched with aqueous 10% NH$_4$Cl. The organic phase was collected and washed with water (×2), saturated aqueous NaHCO$_3$ (×2), and brine, dried (Na$_2$SO$_4$), filtered and concentrated to dryness. The residue was dissolved in MeOH, and K$_2$CO$_3$ (2.78 g, 20.1 mmol) was added. The mixture was stirred for 2 h at room temperature. The mixture was filtered, and the filtrate was concentrated to dryness. The residue was triturated in EtOH to afford compound 159-4 (3.3 g, 43% yield) as a yellow solid.

Step 5: Preparation of (4-(1-aminocyclopropyl)thiazol-2-yl)(6-fluoro-1H-indol-3-yl)methanone (PTC17341-159)

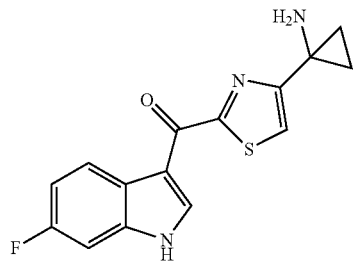

PTC17341-159

Pd(PPh$_3$)$_4$(0) (1 g) was added to a solution of compound 159-4 (2.0 g, 4.1 mmol) in DCM (20 mL). Piperidine (2 drops) and AcOH (20 drops) were added, then the mixture was heated under reflux for 5 h under N$_2$. After cooled to room temperature, the mixture was concentrated to dryness. The residue was purified by silica gel chromatography (EtOAc/DCM/MeOH=10:10:1) and afforded compound PTC17341-159 in the form of a yellow solid (460 mg, 28% yield).

$^1$H-NMR (400 MHz, DMSO-d6): δ 12.17 (bs, 1H), 8.96 (s, 1H), 8.26~8.29 (dd, J=5.6 and 8.8 Hz, 1H), 7.84 (s, 1H), 7.34~7.38 (dd, J=2.4 and 9.6 Hz, 1H), 7.09~7.16 (m, 1H), 2.50 (bs, 2H) 1.74~1.78 (m, 2H), 1.05~1.10 (m, 2H);

LC-MS: m/z 302.0 [M+H]$^+$.

Example 24: Preparation of (4-(2-aminopropan-2-yl)thiazol-2-yl)(6-fluoro-1H-indol-3-yl)methanone (PTC17341-161; ARI-226)

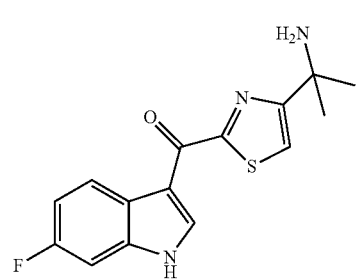

PTC17341-161

Step 1: Preparation of (6-Fluoro-1H-indol-3-yl)(4-(2-(triethylsilyloxy)propan-2-yl)thiazol-2-yl) methanone (161-1)

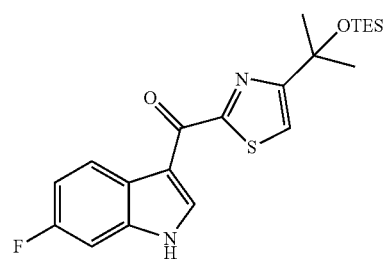

161-1

A solution of 4-(2-(triethylsilyloxy)propan-2-yl)thiazole (10.1 g, 39.3 mmol) in THF (130 mL) and toluene (130 mL) was cooled to −78° C., and sec-BuLi (1.3 M solution in hexane, 37.4 mL, 48.7 mmol) was added dropwise at −78° C. over 10 min. The mixture was stirred for 0.5 h at this temperature, then a solution of tert-butyl-6-fluoro-3-(methoxy(methyl)carbamoyl)-1H-indole-1-carboxylate (15.8 g, 49.1 mmol) in THF (130 mL) was added dropwise over 10 min. The mixture was stirred at −78° C. for 1 h then allowed to warm to 0° C. and quenched with aqueous 10% NH$_4$Cl. The organic phase was collected and washed with water (×2), saturated aqueous NaHCO$_3$ (×2), and brine, dried (Na$_2$SO$_4$), filtered and concentrated to dryness. The residue was dissolved in MeOH, and K$_2$CO$_3$ (5.4 g, 39.3 mmol) was added. The mixture was stirred for 2 h at room temperature. The mixture was filtered, and the filtrate was concentrated to dryness. The residue was triturated in EtOH to afford compound 161-1 (11.0 g, 67% yield) as a yellow solid.

Step 2: Preparation of (6-Fluoro-1H-indol-3-yl)(4-(2-hydroxypropan-2-yl)thiazol-2-yl) methanone (161-2)

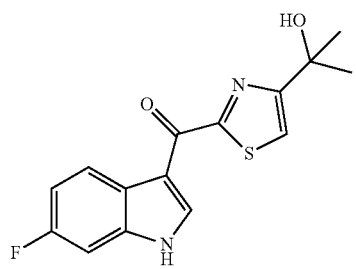

161-2

Tetrabutylammonium fluoride trihydrate (TBAF, 9.0 g, 28.7 mmol) was added to a solution of compound 161-1 (4.8 g, 11.5 mmol) in THF (50 mL) at room temperature, the mixture was stirred for 10 h at room temperature, then quenched with $H_2O$ (100 mL). The mixture was extracted with EtOAc (100 mL×3). The organic phase was collected and washed with water (500 mL×2), saturated aqueous $NaHCO_3$ (100 mL×2), and brine (100 mL×1), dried ($Na_2SO_4$), filtered and concentrated to dryness. The residue was recrystallized with EtOH/$H_2O$ (9:1, 300 mL) to afford 161-2 (4.9 g, 90% yield) as a yellow solid.

Step 3: Preparation of N-(2-(2-(6-Fluoro-1H-indole-3-carbonyl)thiazol-4-yl)propan-2-yl) acetamide (161-3)

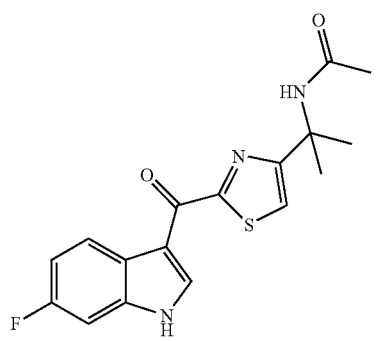

161-3

A solution of compound 161-2 (3.9 g, 7.5 mmol) in AcOH (40 mL) was cooled to 0° C. Acetonitrile (1 mL) and conc. $H_2SO_4$ (20 mL) were added, then the mixture was heated to 60° C. and stirred for 5 h under $N_2$. After cooled to room temperature, the mixture was diluted with $H_2O$ (100 mL), extracted with EtOAc (100 mL×3). The combined organic layers were washed with brine, dried, concentrated to dryness. The residue was purified by silica gel chromatography (EtOAc/DCM/THF=3:3:1) and afforded compound 161-3 (1.6 g, 62% yield).

Step 4: Preparation of (4-(2-Aminopropan-2-yl)thiazol-2-yl)(6-fluoro-1H-indol-3-yl)methanone (PTC17341-161)

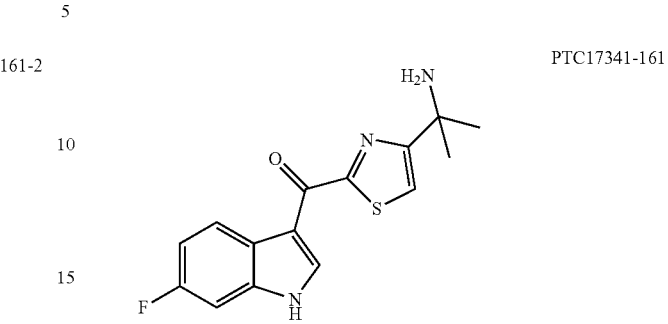

PTC17341-161

KOH (2.6 g, 46 mmol) was added to solution of compound 161-3 (1.6 g, 4.6 mmol) in glycol (50 mL). The mixture was heated to 175° C. and stirred for 8 h. After cooled to room temperature, the mixture was diluted with $H_2O$ (100 mL), extracted with EtOAc (100 mL×3). The combined organic layers were washed with brine, dried, concentrated to dryness. The residue was purified by silica gel chromatography (EtOAc/DCM/THF/MeOH=3:3:1:1) and afforded compound PTC17341-161 (900 mg, 64% yield) as yellow solid.

$^1$H-NMR (400 MHz, DMSO-d6): δ 9.15 (s, 1H), 8.27~8.32 (dd, J=5.6 and 8.8 Hz, 1H), 7.83 (s, 1H), 7.36~7.39 (dd, J=2.4 and 9.6 Hz, 1H), 7.10~7.16 (m, 1H), 1.49 (s, 6H);

LC-MS: m/z 326.0 [M+Na]$^+$.

Example 25: Preparation of D$_3$-ARI-164 (ARI-217)

Step 1: Preparation of D$_3$-ARI-143

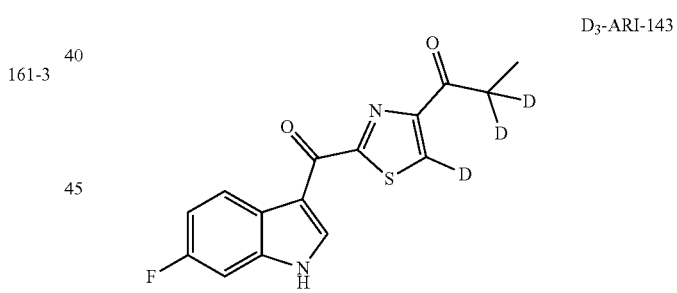

D$_3$-ARI-143

NaOH (2.65 g, 66 mmol) was added to solution of 1-(2-(6-fluoro-1H-indole-3-carbonyl)thiazol-4-yl)propan-1-one (2.0 g, 6.6 mmol) in DMSO-d6 (20 mL) and D$_2$O (3 mL). The mixture was heated to 95° C. and stirred for 8 h. After cooled to room temperature, the mixture was diluted with H$_2$O (100 mL). The solid was collected, dissolved in in DMSO-d6 (20 mL) and D$_2$O (3 mL) and NaOH (2.65 g, 66 mmol) was added. The mixture was heated to 95° C. and stirred for 8 h. This process was repeated 2-3 times until NMR indicated deuterated ratio >99%. Finally, the solid was collected and washed with EtOAc, dried to afford D$_3$-ARI-143 (1.1 g, 55% yield, deuterated ratio 99% by NMR) as yellow solid.

$^1$H-NMR (400 MHz, DMSO-d6): δ 12.35 (bs, 1H), 9.15~9.17 (d, J=3.2 Hz, 1H), 8.27~8.32 (dd, J=5.6 and 8.4 Hz, 1H), 7.39~7.42 (dd, J=2.4 and 9.6 Hz, 1H), 7.13~7.19 (m, 1H), 1.41 (s, 3H);

LC-MS: m/z 304.0 [M−H]$^−$.

Step 2: Preparation of D₃-ARI-164

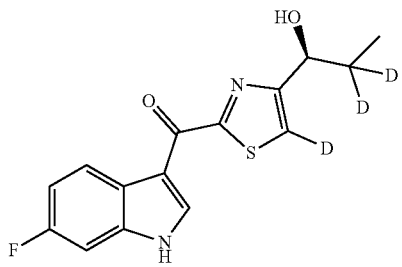

D₃-ARI-164

Compound D₃-ARI-143 (150 g, 0.50 mol) was dissolved THF (1 L). The mixture was cooled to 0° C., then (R)-(+)-2-methyl-CBS-oxazaborolidine (1M in toluene, 100 mL, 0.1 mol) was added, then BH₃-THF solution (1M, 500 mL, 0.5 mol) was added dropwise over 2 h. The mixture was stirred for 3 h at 0° C., then allowed to warm to room temperature and stirred overnight. Chiral HPLC indicated about 90% D₃-ARI-143 was consumed and gave two isomers (S:R=8:2). The mixture was carefully quenched with addition of acetone (200 mL), then concentrated to removal the organic solvent, the residue was dissolved in acetone (2 L), vinyl acetate (500 mL and Novozym 435 (100.0 g, 10000 u/g) were added. The resulting suspension was stirred 48 h at 40° C.

This mixture was filtered to collect Novozym 435 (to be recycled) and the filtrate was concentrated. The residue was triturated with EtOAc/EtOH to afford D₃-ARI-164 (1.18 g, 50% yield, ee 98.2% by chiral HPLC, deuterated ratio 99% by NMR) as a yellow solid and the mother liquor was further purified by silica gel column chromatography, (DCM/EtOAc/THF=3:1:1) to give another batch of D₃-ARI-164 (15.7 g, 10% yield. Two batches gave 80.2 g as 53% yield) and compound Ac-D₃-ARI-164 (16.3 g, 10% yield).

¹H-NMR (400 MHz, DMSO-d6): δ12.24-12.25 (d, J=2.0 Hz, 1H), 9.10-9.12 (d, J=3.2 Hz, 1H), 8.27-8.32 (dd, J=5.6 and 8.4 Hz, 1H), 7.37-7.41 (dd, J=2.4 and 9.6 Hz, 1H), 7.11-7.17 (m, 1H), 5.47 (bs, 1H), 4.73 (s, 1H), 0.91-0.93 (d, J=6.8 Hz, 3H);

LC-MS: m/z 306.0 [M−H]⁻.

Example 26: Preparation of (S)-(4-(1-aminopropyl)thiazol-2-yl)(6-fluoro-1H-indol-3-yl)methanone (ARI-186)

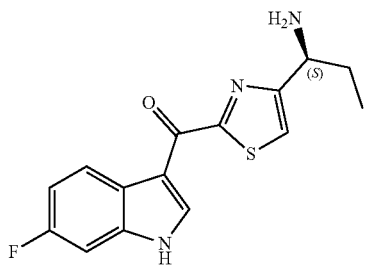

Step 1: Preparation of (S,E)-2-methyl-N-(thiazol-4-ylmethylene)propane-2-sulfinamide

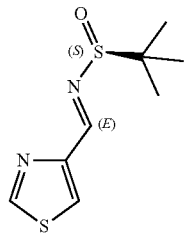

In a 20 mL microwave vessel, thiazole-4-carbaldehyde (1.27 g, 11.23 mmol) was combined with (S)-2-methylpropane-2-sulfinamide (1.36 g, 11.23 mmol), then titanium isopropoxide (6.65 ml, 22.45 mmol) was added. The vessel was heated in a microwave reactor to 70° C. for 15 min. Upon completion, the suspension had completely gone into solution. The cooled reaction mixture and a parallel reaction mixture (previously derived from 18.83 mmol of aldehyde 1) were added to a rapidly stirring solution of 300 mL of EtOAc and 5 mL of satd NaCl. A fine white ppt resulted that was removed by filtration over a celite pad. TLC (EtOAc/heptane) showed the reaction to be complete. Adsorbed onto celite, and then concentrated to dryness. Chromatography (40 g silica gel, heptane to 80% EtOAc/heptane) gave an off-white solid. The solid was co-evaporated with CH₂Cl₂ and heptane twice, then placed on the high vacuum to give (S,E)-2-methyl-N-(thiazol-4-ylmethylene)propane-2-sulfinamide (5.46 g, 25.2 mmol, 84% yield) as an off-white solid.

¹H NMR (500 MHz, CDCl3) δ 8.93 (d, J=2.0 Hz, 1H), 8.74 (s, 1H), 8.02 (d, J=2.0 Hz, 1H), 1.29 (s, 9H);
ESI MS m/z 217 [M+H]⁺.

Step 2: Preparation of (S)-2-methyl-N-(1-(thiazol-4-yl)propyl)propane-2-sulfinamide

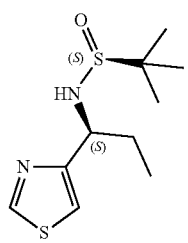

To a −78° C. solution of (S,E)-2-methyl-N-(thiazol-4-ylmethylene)propane-2-sulfinamide (5-11 mg, 2.36 mmol) in THF (24 mL) was added ethylmagnesium bromide (1.0 M in THF) (2.60 mL, 2.60 mmol) dropwise. The solution remained clear and colorless upon addition. The reaction was allowed to slowly warm to room temperature overnight. In the morning, satd NH₄Cl was added. HPLC indicated a 5.69:1 ratio. Also, a minor product formed which was identified as the reduction product (S)-2-methyl-N-(thiazol-4-ylmethyl)propane-2-sulfinamide. The reaction was quenched by addition of saturated NH₄Cl followed by EtOAc. The aqueous layer was extracted twice with EtOAc. The combined organic layers were washed with brine, dried over Na₂SO₄, filtered, and concentrated. Chromatography (24 g silica gel, heptane to EtOAc, dry load silica gel) gave the desired product (493 mg, 85%) as a mixture of diastereomers by $^1$H NMR (5.8:1 diastereomeric ratio) and as a white solid after co-evaporation with CH$_2$Cl$_2$/heptane. A portion of this mixture was evaluated for crystallization. To the solid sulfinamide (304 mg) was added dichloromethane (2 mL) and upon dissolution, heptane (8.00 mL) was added. The colorless solution was stirred at room temp under N$_2$ with a bleed needle to let the DCM slowly escape. A solid started forming on the edges. The mixture was briefly sonicated to give significant solids. After 1 hr, the solid was isolated by filtration to yield 53.9 mg after vacuum drying. $^1$H NMR estimated only 1% of the minor diastereomer was present. A second crop of crystals from the concentrated filtrate was isolated using a slower crystallization process. Excess CH$_2$Cl$_2$ (10 mL) was combined with heptane (25 ml). This was allowed to slowly concentrate by evaporation overnight. The resulting solid was isolated as white needles (83.4 mg). $^1$H NMR estimated only 1% of the minor diastereomer was present. This was combined with batch 1 to give a 45% overall yield.

Major Diastereomer: $^1$H NMR (500 MHz, CDCl$_3$) δ 8.78 (d, J=2.0 Hz, 1H), 7.27 (d, J=2.0 Hz, 1H), 4.43 (app q, J=7.0 Hz, 1H), 3.87 (d, J=7.2 Hz, 1H), 1.98 (m, 2H), 1.24 (s, 9H), 0.90 (t, J=7.4 Hz, 3H); ESI MS m/z 247 [M+H]$^+$; HPLC=4.74 min, C18 Kinetex.

Minor Diastereomer (only distinctly separated signals provide for reference): $^1$H NMR (500 MHz, CDCl3) δ 8.79 (d, J=2.0 Hz, 1H), 7.19 (d, J=2.0 Hz, 1H), 4.54 (m, 1H), 3.64 (m, 1H), 1.18 (s, 9H). HPLC=4.47 min, C18 Kinetex.

Step 3: Preparation of (S)—N—((S)-1-(2-(6-fluoro-1H-indole-3-carbonyl)thiazol-4-yl)propyl)-2-methyl-propane-2-sulfinamide

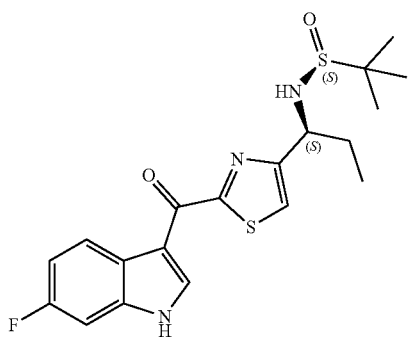

To a −78° C. solution of (S)-2-methyl-N-(1-(thiazol-4-yl)propyl)propane-2-sulfinamide (59.5 mg, 0.241 mmol) in 500 uL of THF was added n-butyllithium (1.6 M in hexanes) (0.309 mL, 0.495 mmol) with a gastight syringe. The solution remained clear for the first 1 eq of BuLi. Upon addition of the second equivalent the solution turned a pale yellow. The reaction mixture warmed to −40° C. over 40 min. This solution was cannulated dropwise into a −15° C. solution of tert-butyl 6-fluoro-3-(methoxy(methyl)carbamoyl)-1H-indole-1-carboxylate (89 mg, 0.276 mmol) in THF (0.5 mL). The dianion vessel was rinsed with 500 uL of THF and transferred into the Weinreb vessel via the cannula. Upon addition of the dianion, the solution turned an emerald green. After ~15 min, the green color became a dull olive green. After another 20 min, the reaction was quenched with satd. NH$_4$Cl and stirred. Subsequently, 0.5 mL of 3 N HCl was added to ensure the Weinreb intermediate completely decomposed. The work-up solution eventually went from olive green to a yellow/orange color. The mixture was extracted with EtOAc, dried over Na$_2$SO$_4$, filtered, and concentrated to give crude (S)—N—((S)-1-(2-(6-fluoro-1H-indole-3-carbonyl)thiazol-4-yl)propyl)-2-methylpropane-2-sulfinamide (assumed 0.241 mmol). LCMS shows both desired Boc product (ESI MS m/z 508 [M+H]$^+$) and des-Boc product (ESI MS m/z 408 [M+H])). The product was used without further purification.

Step 4: Preparation of (S)-(4-(1-aminopropyl)thiazol-2-yl)(6-fluoro-1H-indol-3-yl)methanone

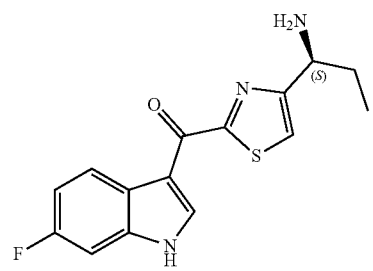

To crude tert-butyl 3-(4-(1-(((S)-tert-butylsulfinyl)amino)propyl)thiazole-2-carbonyl)-6-fluoro-1H-indole-1-carboxylate (122 mg, 0.241 mmol) was added MeOH (10 ml) followed by HCl (4 M in dioxane) (1 ml, 4.00 mmol). LCMS shows mainly sulfinamide deprotection. The reaction was concentrated to dryness. The residue was treated with MeOH and 1 mL of 2 N NaOH was added. The residue adsorbed to celite using MeOH then concentrated to dryness. Reverse phase chromatography (30 g C18, 10% H$_2$O/CH$_3$CN+0.1% NH$_4$OH to 50% CH$_3$CN, dry load) gave a clean separation to give (4-(1-aminopropyl)thiazol-2-yl)(6-fluoro-1H-indol-3-yl)methanone (48.2 mg, 66%) as a yellow solid after lyophilization.

LCMS showed both desired Boc product (ESI MS m/z 304 [M+H]). Major diastereomer retention time=4.38 min (ARI-186), OJ-X, 4.6×150 mm, 5 micron, 25% MeOH+0.05% DEA/CO2 isocratic, 2.2 mL/min, column temperature: 35° C., 254 nM uv and mass detection. Minor Diastereomer=4.13 min (ARI-187).

Example 27: Preparation of (S)-(4-(1-aminoethyl)thiazol-2-yl)(6-fluoro-1H-indol-3-yl)methanone (ARI-232)

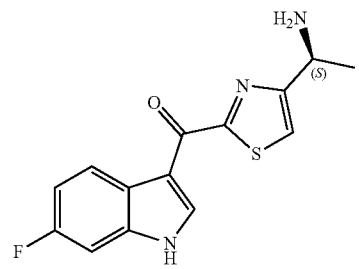

Step 1: Preparation of (S)-2-methyl-N—((S)-1-(thiazol-4-yl)ethyl)propane-2-sulfinamide

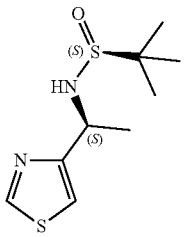

To a −78° C. solution of (S,E)-2-methyl-N-(thiazol-4-ylmethylene)propane-2-sulfinamide (506 mg, 2.339 mmol) in $CH_2Cl_2$ (20 mL) was added methylmagnesium bromide (3.0 M in $Et_2O$) (0.858 mL, 2.57 mmol) dropwise. The solution became increasingly yellow upon addition with no obvious exotherm. The reaction was allowed to slowly warm to room temperature overnight. The reaction was quenched by addition of saturated $NH_4Cl$. The aqueous layer was extracted with $CH_2Cl_2$. The combined organic layers were washed with brine, dried ($Na_2SO_4$), filtered and concentrated. $^1H$ NMR indicates an 8:1 ratio of diastereomers. The stereochemistry is tentatively assigned assuming the Grignard behaved similarly to the EtMgBr case. Chromatography (24 g silica gel, heptane to EtOAc, dry load silica gel) gave a poorly shaped elution profile. The fractions were combined. The solid (466 mg, 8:1 diastereomeric ratio) was dissolved using $CH_2Cl_2$ (15 mL) then 50 mL of heptane was added. Continuous stirring gave crystals. Needles (396.5 mg, 73% yield) were isolated by filtration. $^1H$ NMR estimates 3.8% of the minor diastereomer present. The solid (396.5 mg) was dissolved in a minimum of $CH_2Cl_2$ (~2 mL) then 8 mL of heptane was added. The mixture was stirred. Crystals formed within 5 min. The mixture was briefly sonicated to make the crystals smaller then stirred overnight with the vessel capped. The fine white needles were isolated by filtration to give (S)-2-methyl-N—((S)-1-(thiazol-4-yl)ethyl)propane-2-sulfinamide (318 mg, 58.5% overall yield). $^1H$ NMR estimated <1% of the minor diastereomer is present.

Major Diastereomer: $^1H$ NMR (500 MHz, DMSO-$d_6$) δ 9.04 (d, J=2.0 Hz, 1H), 7.55 (dd, J=0.9, 2.0 Hz, 1H), 5.61 (d, J=7.5 Hz, 1H), 4.53 (app pentet, J=6.9 Hz, 1H), 1.48 (d, J=6.8 Hz, 3H), 1.12 (s, 9H); ESI MS m/z 233 [M+H]$^+$, HPLC=4.09 min, C18 Kinetex;

Minor Diastereomer (only select distinctly separated signals provide for reference): $^1H$ NMR (500 MHz, $CDCl_3$) δ 7.47 (dd, J=0.8, 2.0 Hz, 1H), 5.44 (d, J=6.6 Hz, 1H); HPLC=3.78 min, C18 Kinetex.

Step 2: Preparation of tert-butyl 3-(4-((S)-1-(((S)-tert-butylsulfinyl)amino)ethyl)thiazole-2-carbonyl)-6-fluoro-1H-indole-1-carboxylate

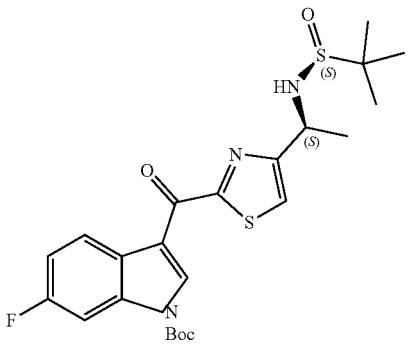

To a −78° C. suspension of (S)-2-methyl-N-(1-(thiazol-4-yl)ethyl)propane-2-sulfinamide (156 mg, 0.671 mmol) in 1.5 mL of THF was added n-butyllithium (1.6 Min hexanes) (0.860 mL, 1.376 mmol) with a syringe. The suspension turned pale pink and fully dissolved after warming to −50° C. This solution was cannulated dropwise into a −35° C. solution of tert-butyl 6-fluoro-3-(methoxy(methyl)carbamoyl)-1H-indole-1-carboxylate (238 mg, 0.738 mmol) in THF (0.5 mL). The dianion vessel was rinsed with 500 uL of THF and transferred into the Weinreb vessel via the cannula. Upon addition of the dianion, the solution turned an olive then to an emerald green. After ~20 min, the green color became a dark olive green (now at −15° C.). After another 20 min, the reaction was quenched with satd $NH_4Cl$ and stirred. Subsequently, 0.5 mL of 3 N HCl was added to ensure the Weinreb intermediate completely decomposed. The work-up solution eventually went from olive green to a yellow/orange color. The mixture was extracted with EtOAc, dried over $Na_2SO_4$, filtered and concentrated to give crude tert-butyl 3-(4-((S)-1-(((S)-tert-butylsulfinyl)amino)ethyl)thiazole-2-carbonyl)-6-fluoro-1H-indole-1-carboxylate (0.671 mmol). LCMS shows both desired Boc product (ESI MS m/z 494 [M+H]$^+$) and des-Boc product (ESI MS m/z 394 [M+H]$^+$). The product was used without further purification.

Step 3: (S)-(4-(1-aminoethyl)thiazol-2-yl)(6-fluoro-1H-indol-3-yl)methanone

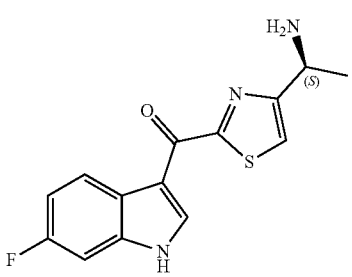

To crude tert-butyl 3-(4-((S)-1-(((S)-tert-butylsulfinyl)amino)ethyl)thiazole-2-carbonyl)-6-fluoro-1H-indole-1-carboxylate (0.671 mmol) was added MeOH (10 ml) then HCl (4 M in dioxane) (1 ml, 4.00 mmol). LCMS shows mainly sulfinamide deprotection. The reaction was concentrated to dryness. The residue was treated with MeOH (10 mL) and 1 mL of 2 N NaOH was added. Upon completion, the residue adsorbed to celite using MeOH then concentrated to dryness. Reverse phase chromatography (100 g C18, 10% $H_2O/CH_3CN$+0.1% $NH_4OH$ to 50% $CH_3CN$, dry load) and then by normal phase chromatography (24 g silica gel, $CH_2Cl_2$ to 18:2:80 MeOH:$NH_4OH$:$CH_2Cl_2$, dry load) gave (S)-(4-(1-aminoethyl)thiazol-2-yl)(6-fluoro-1H-indol-3-yl)methanone (151 mg, 78%) as a yellow solid after lyophilization. $^1$H NMR (500 MHz, DMSO-$d_6$) δ 9.13 (s, 1H), 8.28 (dd, J=8.7, 5.6 Hz, 1H), 7.81 (d, J=0.8 Hz, 1H), 7.37 (dd, J=9.6, 2.3 Hz, 1H), 7.15-7.10 (m, 1H), 4.22-4.18 (m, 1H), 1.43 (d, J=6.7 Hz, 3H); $^{19}$F NMR (470 MHz, DMSO-$d_6$) δ -118.87; ESI MS m/z 288 [M-H]$^-$ Example 28: Preparation of (S)-(6-fluoro-1H-indol-3-yl)(4-(1-(methylamino)ethyl)thiazol-2-yl)methanone (ARI-233)

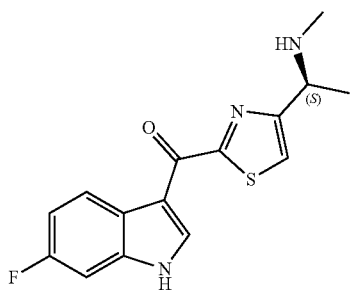

Step 1: Preparation of tert-butyl 3-(4-((S)-1-(((S)-tert-butylsufinyl)(methyl)amino)ethyl)thiazole-2-carbonyl)-6-fluoro-1H-indole-1-carboxylate

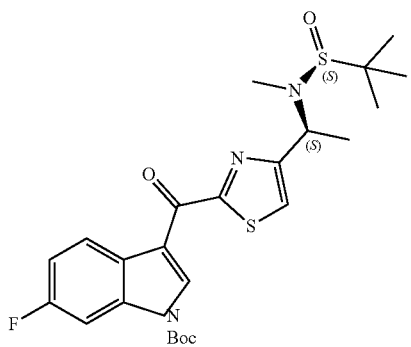

To a -78° C. suspension of (S)-2-methyl-N-(1-(thiazol-4-yl)ethyl)propane-2-sulfinamide (144 mg, 0.620 mmol) in 2 mL of THF was added n-butyllithium (1.6 M in hexanes) (0.794 mL, 1.27 mmol) with a syringe. This yellow solution was slowly warmed to -40° C. over 40 min. The dianion was cannulated dropwise into a -15° C. solution of tert-butyl 6-fluoro-3-(methoxy(methyl)carbamoyl)-1H-indole-1-carboxylate (220 mg, 0.682 mmol) in THF (0.5 mL). The dianion vessel was rinsed with 500 uL of THF and transferred into the Weinreb vessel via the cannula. Upon addition of the dianion, the solution turned an olive then to an emerald green. After ~15 min, the green color became a dark olive green. After another 20 min, iodomethane (0.039 mL, 0.620 mmol) was added at 0° C. The reaction was allowed to warm to room temperature overnight and then was quenched by addition of satd $NH_4Cl$. The mixture was stirred. Subsequently, 0.5 mL of 3 N HCl was added to ensure the Weinreb intermediate completely decomposed. The work-up solution eventually went from olive green to a yellow/orange color. The mixture was extracted with EtOAc, dried over $Na_2SO_4$, filtered and concentrated to give crude tert-butyl 3-(4-((S)-1-(((S)-tert-butylsulfinyl(methyl)amino)ethyl)thiazole-2-carbonyl)-6-fluoro-1H-indole-1-carboxylate (0.620 mmol). LCMS shows both desired Boc product (ESI MS m/z 508 [M+H]$^+$) and des-Boc product (ESI MS m/z 408 [M+H]$^+$). The product was used without further purification.

Step 2: Preparation of (S)-(6-fluoro-1H-indol-3-yl)(4-(1-(methylamino)ethyl)thiazol-2-yl) ethanone

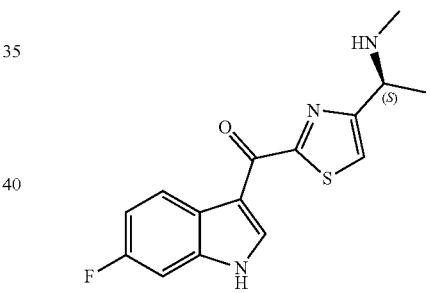

To crude tert-butyl 3-(4-((S)-1-(((S)-tert-butylsulfinyl)(methyl)amino)ethyl)thiazole-2-carbonyl)(6-fluoro-1H-indole-1-carboxylate (0.621 mmol) was added MeOH (10 ml) followed by HCl (4 M in dioxane) (2 ml, 8.00 mmol). LCMS showed mainly sulfinamide deprotection. The reaction was concentrated to dryness. The residue was treated with MeOH (10 mL) and 2 mL of 2 N NaOH was added. Upon completion (<1 hr), the residue adsorbed to silica gel using MeOH then concentrated to dryness. Chromatography (40 g silica gel, $CH_2Cl_2$ to 18:2:80 MeOH:$NH_4OH$:$CH_2Cl_2$, dry load) gave (S)-(6-fluoro-1H-indol-3-yl)(4-(1-(methylamino)ethyl)thiazol-2-yl)methanone (68.4 mg, 36%) as a yellow solid after lyophilization from acetonitrile and water.

$^1$H NMR (500 MHz, DMSO-$d_6$) δ 12.20 (s, 1H), 9.12 (s, 1H), 8.29 (dd, J=8.7, 5.6 Hz, 1H), 7.81 (s, 1H), 7.37 (dd, J=9.6, 2.3 Hz, 1H), 7.15-7.11 (m, 1H), 3.88 (q, J=6.6 Hz, 1H), 2.25 (s, 3H), 1.40 (d, J=6.7 Hz, 3H); $^{19}$F NMR (470 MHz, DMSO-$d_6$) δ -118.86;

ESI MS m/z 302 [M-H]$^-$.

Example 29: Preparation of Preparation of (4-(aminomethyl)thiazol-2-yl)(6-fluoro-1H-indol-3-yl)methanone (ARI-234)

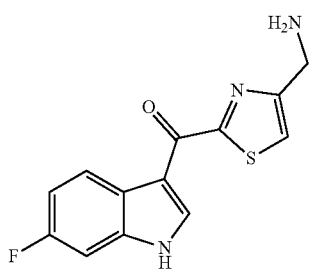 [SMILES: NCc1csc(C(=O)c2c[nH]c3cc(F)ccc23)n1]

Step 1: Preparation of (S)-2-methyl-N-(thiazol-4-ylmethyl)propane-2-sulfinamide

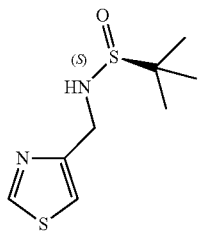

To a solution of (S,E)-2-methyl-N-(thiazol-4-ylmethylene)propane-2-sulfinamide (361 mg, 1.669 mmol) in MeOH (20 mL) was added sodium borohydride (126 mg, 3.34 mmol). After 1 hr, water (5 mL) was added and combined with crude material from a parallel reaction which used 0.328 mmol of (S,E)-2-methyl-N-(thiazol-4-ylmethylene)propane-2-sulfinamide. After stirring for 1 hr, the reaction was concentrated to dryness, then adsorbed onto silica gel using MeOH, and then concentrated to dryness. Chromatography (24 g silica gel, $CH_2Cl_2$ to 80:18:2 $CH_2Cl_2$:MeOH:$NH_4OH$, dry load) gave (S)-2-methyl-N-(thiazol-4-ylmethyl)propane-2-sulfinamide (415 mg, 95%) as a white solid after co-evaporation with $CH_2Cl_2$/heptane.

$^1$H NMR (500 MHz, $CDCl_3$) δ 8.79 (d, J=2.0 Hz, 1H), 7.30 (m, 1H), 4.51 (ABq, J=3.1, 14.6 Hz, 2H), 3.74 (bs, 1H), 1.24 (s, 9H);

ESI MS m/z 219 [M+H]$^+$.

Step 2: Preparation of tert-butyl (S)-3-(4-(((tert-butylsulfinyl)amino)methyl)thiazole-2-carbonyl)-6-fluoro-1H-indole-1-carboxylate

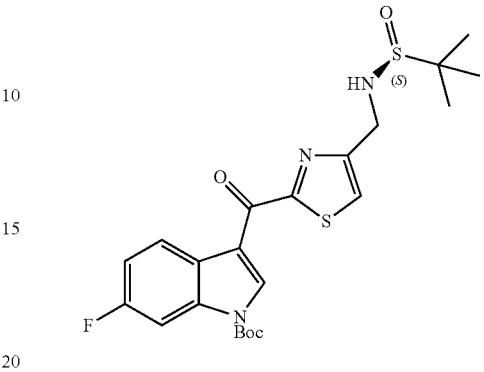

To a −78° C. solution of (S)-2-methyl-N-(thiazol-4-ylmethyl)propane-2-sulfinamide (415 mg, 1.901 mmol) in 5 mL of THF was added n-butyllithium (1.6 M in hexanes) (2.435 mL, 3.90 mmol) with a syringe. The solution turned pale pink and then yellow. After warming to −40° C. over 40 min, this solution was cannulated dropwise into a −15° C. solution of tert-butyl 6-fluoro-3-(methoxy(methyl)carbamoyl)-1H-indole-1-carboxylate (674 mg, 2.091 mmol) in THF (3 mL). The dianion vessel was rinsed with 2 mL of THF and transferred into the Weinreb vessel via the cannula. Upon addition of the dianion, the solution turned an olive. After ~15 min, the reaction turned an orange brown. The reaction was allowed to warm to 5° C. over 1 hour, then the reaction was quenched with satd $NH_4Cl$. Subsequently, 1 mL of 3 N HCl was added to ensure the Weinreb intermediate completely decomposed. The mixture was extracted with EtOAc, dried over $Na_2SO_4$, filtered and concentrated to give crude crude tert-butyl (S)-3-(4-(((tert-butylsulfinyl)amino)methyl)thiazole-2-carbonyl)-6-fluoro-1H-indole-1-carboxylate (1.901 mmol). LCMS shows both desired Boc product (ESI MS m/z 480 [M+H]$^+$) and des-Boc product (ESI MS m/z 380 [M+H]$^+$). The product was used without further purification.

Step 3: (4-(aminomethyl)thiazol-2-yl)(6-fluoro-1H-indol-3-yl)methanone

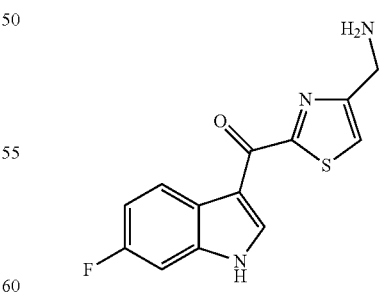

To crude tert-butyl (S)-3-(4-(((tert-butylsulfinyl)amino)methyl)thiazole-2-carbonyl)-6-fluoro-1H-indole-1-carboxylate (1.901 mmol) was added MeOH (10 ml) then HCl (4 M in dioxane) (2 ml, 8.00 mmol). LCMS shows mainly sulfinamide deprotection. Upon completion (<1 hr), the reaction was concentrated to dryness. The residue was treated with MeOH (15 mL) and 4 mL of 2 N NaOH was added. Upon completion (<1 hr), the residue adsorbed to silica gel using MeOH then concentrated to dryness. Chromatography (40 g silica gel, $CH_2Cl_2$ to 18:2:80 MeOH:$NH_4OH$:$CH_2Cl_2$, dry load) gave a yellow solid. The solid was taken up in hot MeOH then treated with activated carbon. Filtration gave (4-(aminomethyl)thiazol-2-yl)(6-fluoro-1H-indol-3-yl) methanone (404 mg, 77%) as a yellow solid after lyophilization from acetonitrile and water. $^1$H NMR (500 MHz, DMSO-$d_6$) δ 9.14 (s, 1H), 8.29 (dd, J=8.7, 5.6 Hz, 1H), 7.81 (m, 1H), 7.36 (dd, J=9.6, 2.3 Hz, 1H), 7.15-7.10 (m, 1H), 3.95 (d, J=0.9 Hz, 2H); $^{19}$F NMR (470 MHz, DMSO-$d_6$) δ −118.89;

ESI MS m/z 276 [M+H]$^+$.

Example 30: Preparation of (S)-(4-(1-aminopropyl) thiazol-2-yl)(1H-indol-3-yl)methanone (ARI-235)

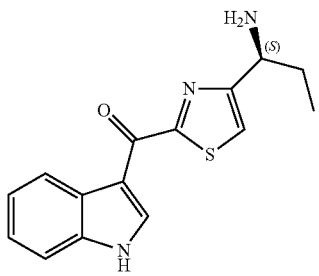

Step 1: Preparation of (S)-2-methyl-N—((S)-1-(thiazol-4-yl)propyl)propane-2-sulfinamide

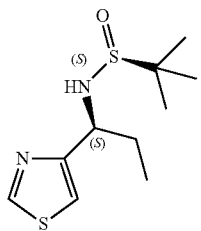

A mixture of methylmagnesium bromide (3 M in diethylether) (1.200 ml, 3.60 mmol) and diethylzinc (15 wt % in toluene) (1.079 ml, 1.200 mmol) was stirred for 10 min at room temperature, then cooled to −78° C. Then a solution of (S,E)-2-methyl-N-(thiazol-4-ylmethylene)propane-2-sulfinamide (519 mg, 2.399 mmol) in THF (15 ml) was added dropwise slowly over 40 min and stirred at −78° C. for another 20 min. Satd $NH_4Cl$ was added and the bath removed. EtOAc was added and the layers were separated. The aqueous layer was extracted with EtOAc. The combined organics were washed with brine, dried ($Na_2SO_4$), filtered and concentrated to give 581 mg of a white solid which consists of 5.8:1 ratio of the desired (S,S) to (S:R) product and only 1.7% of the reduced imine (i.e. (S)-2-methyl-N-(thiazol-4-ylmethyl)propane-2-sulfinamide). The crude solid was dissolved with boiling heptane (50 mL). The heat was removed and the mixture was stirred. A white solid subsequently appeared. The mixture was briefly sonicated and the solid collected by filtration to give 430 mg. $^1$H NMR shows predominantly the (S,S) diastereomer plus 1.9% of the (S,R) diastereomer and a trace of (S)-2-methyl-N-(thiazol-4-ylmethyl)propane-2-sulfinamide. A second crystallization was effected by treatment of the white solid (430 mg) with boiling heptane (10 mL). The hot solution was allowed to cool to ambient temperature. The resulting solids were briefly sonicated then isolated by vacuum filtration to give (S)-2-methyl-N—((S)-1-(thiazol-4-yl)propyl)propane-2-sulfinamide (399 mg, 67% yield) as a white solid. $^1$H NMR indicates <1% of the (S, R) diastereomer.

$^1$H NMR (500 MHz, CDCl$_3$) δ 8.78 (d, J=2.0 Hz, 1H), 7.27 (d, J=2.0 Hz, 1H), 4.43 (app q, J=7.0 Hz, 1H), 3.87 (d, J=7.2 Hz, 1H), 1.98 (m, 2H), 1.24 (s, 9H), 0.90 (t, J=7.4 Hz, 3H);

ESI MS m/z 247 [M+H]$^+$.

Step 2: Preparation of tert-butyl 3-(4-((S)-1-(((S)-tert-butylsulfinyl)amino)propyl)thiazole-2-carbonyl)-1H-indole-1-carboxylate

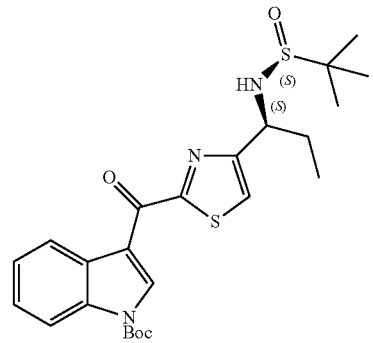

To a −78° C. suspension of (S)-2-methyl-N—((S)-1-(thiazol-4-yl)propyl)propane-2-sulfinamide (658 mg, 2.67 mmol) in 8 mL of THF was added n-butyllithium (1.6 M in hexanes) (3.42 mL, 5.48 mmol) with a syringe. The suspension became a yellow solution and, after warming to −40° C. over 40 min, this solution was cannulated dropwise into a −15° C. solution of tert-butyl 3-(methoxy(methyl)carbamoyl)-1H-indole-1-carboxylate (895 mg, 2.94 mmol) in THF (3 mL). The dianion vessel was rinsed with 2 mL of THF and transferred into the Weinreb vessel via the cannula. Upon addition of the dianion, the solution turned a green color. After ~15 min, the reaction turned an orange brown. The reaction was allowed to warm to 5° C. over 1 hour afterwards the reaction was quenched with satd $NH_4Cl$. Subsequently, 1 mL of 3 N HCl was added to ensure the Weinreb intermediate completely decomposed. The mixture was extracted with EtOAc, dried over $Na_2SO_4$, filtered and concentrated to give crude tert-butyl 3-(4-((S)-1-(((S)-tert-butylsulfinyl)amino)propyl)thiazole-2-carbonyl)-1H-indole-1-carboxylate (2.67 mmol). LCMS shows both desired Boc product (ESI MS m/z 490 [M+H]$^+$) and des-Boc product (ESI MS m/z 388 [M−H]$^−$). The product was used without further purification.

Step 3: Preparation of (S)-(4-(1-aminopropyl)thiazol-2-yl)(1H-indol-3-yl)methanone

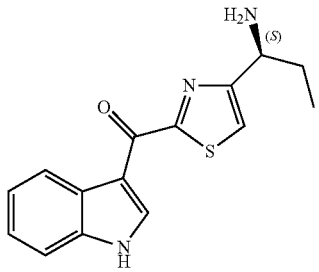

To crude tert-butyl 3-(4-((S)-1-(((S)-tert-butylsulfinyl)amino)propyl)thiazole-2-carbonyl)-1H-indole-1-carboxylate (2.67 mmol) was added MeOH (15 ml) then HCl (4 M in dioxane) (3 ml, 12.00 mmol). LCMS shows mainly sulfinamide deprotection. Upon completion (<1 hr), the reaction was concentrated to dryness. The residue was treated with MeOH (15 mL) and 4 mL of 2 N NaOH was added. Upon completion, the residue was treated with 3 N HCl until neutral. The solvent was concentrated to dryness. Then the crude material was adsorbed to silica gel using MeOH then concentrated to dryness. Chromatography (40 g silica gel, $CH_2Cl_2$ to 18:2:80 MeOH:$NH_4$OH:$CH_2Cl_2$, dry load) gave (S)-(4-(1-aminopropyl)thiazol-2-yl)(1H-indol-3-yl)methanone a yellow solid after lyophilization from acetonitrile and water.

$^1$H NMR (500 MHz, DMSO-$d_6$) δ 12.18 (bs, 1H), 9.12 (s, 1H), 8.32-8.30 (m, 1H), 7.80 (d, J=0.6 Hz, 1H), 7.57-7.55 (m, 1H), 7.29-7.24 (m, 2H), 3.98 (app t, J=6.5 Hz, 1H), 2.20 (bs, 2H), 1.90-1.82 (m, 1H), 1.75-1.66 (m, 1H), 0.90 (t, J=7.3 Hz, 3H);

ESI MS m/z 284 [M−H]$^−$.

Example 31: Preparation of (S)—N-((2-(1H-indole-3-carbonyl)thiazol-4-yl)methyl)-2-methylpropane-2-sulfinamide (ARI-236)

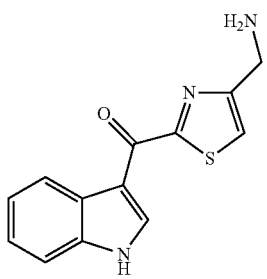 [SMILES: NCc1csc(C(=O)c2c[nH]c3ccccc23)n1]

Step 1: Preparation of (S)—N-((2-(1H-indole-3-carbonyl)thiazol-4-yl)methyl)-2-methylpropane-2-sulfinamide

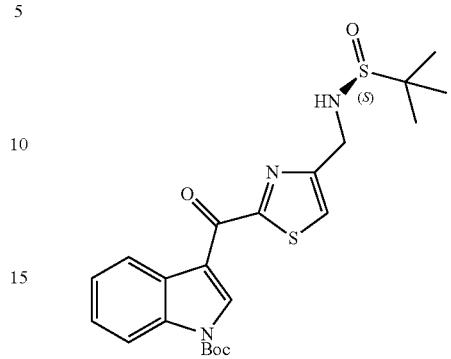

To a −78° C. suspension of (S)-2-methyl-N-(thiazol-4-ylmethyl)propane-2-sulfinamide (298 mg, 1.365 mmol) in THF (3900 μl) was added n-butyllithium (1.6 M in hexanes) (1749 μl, 2.80 mmol). The suspension became a pale yellow solution and was warmed to −40° C. over 40 min. Separately, N-methoxy-N-methyl-1H-indole-3-carboxamide (307 mg, 1.501 mmol) in THF (4 mL) at room temperature was treated with sodium hydride (85 mg, 2.125 mmol) to give a thick suspension of a grey solid. Cooled this mixture to −40° C. and then the dianion previously prepared above was added by cannula. The reaction mixture was allowed to warm to room temperature overnight with stirring. A tan solution resulted which was treated with satd $NH_4Cl$. EtOAc and 3 N HCl (1 mL) were added and the layers were separated. The organic was washed with brine, dried ($Na_2SO_4$), filtered and concentrated to a solid (1.365 mmol; ESI MS m/z 362 [M+H]$^+$). The crude was taken as is.

Step 2: Preparation of (4-(aminomethyl)thiazol-2-yl)(1H-indol-3-yl)methanone

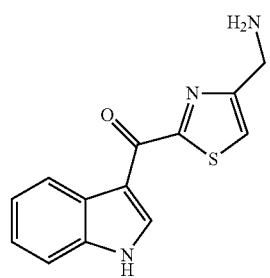 [SMILES: NCc1csc(C(=O)c2c[nH]c3ccccc23)n1]

To crude (S)—N-((2-(1H-indole-3-carbonyl)thiazol-4-yl)methyl)-2-methylpropane-2-sulfinamide (1.365 mmol) was added MeOH (15 ml) then HCl (4 M in dioxane, 3 ml, 12.00 mmol). Upon completion (<1 hr), the reaction was concentrated to dryness. The residue was treated with MeOH (15 mL) and satd $NaHCO_3$ was added until neutral. The solvent was concentrated to dryness. Then the crude material was adsorbed to silica gel using MeOH then concentrated to dryness. Chromatography (25 g silica gel, $CH_2Cl_2$ to 18:2:80 MeOH:$NH_4$OH:$CH_2Cl_2$, dry load) gave (4-(aminomethyl)thiazol-2-yl)(1H-indol-3-yl)methanone (231 mg, 65% yield) as a yellow solid after lyophilization from acetonitrile and water.

$^1$H NMR (500 MHz, DMSO-d6) δ 12.20 (bs, 1H), 9.14 (s, 1H), 8.32-8.30 (m, 1H), 7.80 (s, 1H), 7.57-7.55 (m, 1H), 7.29-7.24 (m, 2H), 3.94 (app d, J=0.9 Hz, 2H), 2.07 (bs, 2H); ESI MS m/z 258 [M+H]$^+$.

Example 32: Preparation of (S)-(4-(1-aminopropyl) thiazol-2-yl)(1H-pyrrolo[2,3-b]pyridin-3-yl)methanone

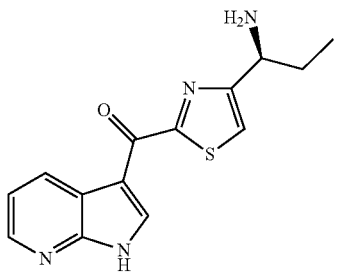 [SMILES: CC[C@H](N)c1csc(C(=O)c2c[nH]c3ncccc23)n1]

(S)-(4-(1-aminopropyl)thiazol-2-yl)(1H-pyrrolo[2,3-b] pyridin-3-yl)methanone can be synthesized from (S)-2-methyl-N—((S)-1-(thiazol-4-yl)propyl)propane-2-sulfinamide and N-methoxy-N-methyl-1H-pyrrolo[2,3-b]pyridine-3-carboxamide according to the method described in Example 31, except that N-methoxy-N-methyl-1H-pyrrolo[2,3-b]pyridine-3-carboxamide would be used instead of N-methoxy-N-methyl-1H-indole-3-carboxamide.

Example 33: Preparation of (S)-(4-(1-aminopropyl) thiazol-2-yl)(1H-pyrrolo[2,3-c]pyridin-3-yl)methanone

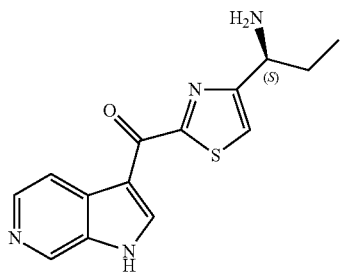

(S)-(4-(1-aminopropyl)thiazol-2-yl)(1H-pyrrolo[2,3-c] pyridin-3-yl)methanone can be synthesized from (S)-2-methyl-N—((S)-1-(thiazol-4-yl)propyl)propane-2-sulfinamide and N-methoxy-N-methyl-1H-pyrrolo[2,3-c]pyridine-3-carboxamide according to the method described in Example 31, except that N-methoxy-N-methyl-1H-pyrrolo[2,3-c]pyridine-3-carboxamide would be used instead of N-methoxy-N-methyl-1H-indole-3-carboxamide.

Example 34: Preparation of (S)-(4-(1-aminopropyl) thiazol-2-yl)(1H-pyrrolo[3,2-c]pyridin-3-yl)methanone

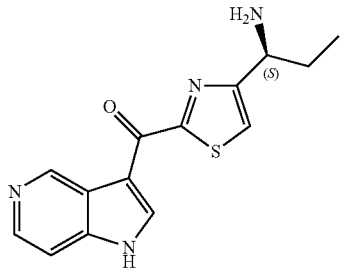

(S)-(4-(1-aminopropyl)thiazol-2-yl)(1H-pyrrolo[3,2-c] pyridin-3-yl)methanone can be synthesized from (S)-2-methyl-N—((S)-1-(thiazol-4-yl)propyl)propane-2-sulfinamide and N-methoxy-N-methyl-1H-pyrrolo[3,2-c]pyridine-3-carboxamide according to the method described in Example 31, except that N-methoxy-N-methyl-1H-pyrrolo[3,2-c]pyridine-3-carboxamide would be used instead of N-methoxy-N-methyl-1H-indole-3-carboxamide.

Example 35: Preparation of (S)-(4-(1-aminopropyl) thiazol-2-yl)(1H-pyrrolo[3,2-b]pyridin-3-yl)methanone

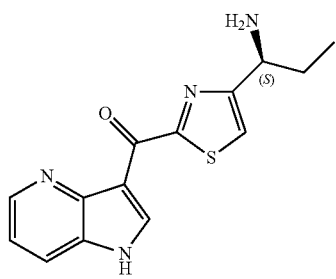

(S)-(4-(1-aminopropyl)thiazol-2-yl)(1H-pyrrolo[3,2-b] pyridin-3-yl)methanone can be synthesized from (S)-2-methyl-N—((S)-1-(thiazol-4-yl)propyl)propane-2-sulfinamide and N-methoxy-N-methyl-1H-pyrrolo[3,2-b]pyridine-3-carboxamide according to the method described in Example 31, except that N-methoxy-N-methyl-1H-pyrrolo[3,2-b]pyridine-3-carboxamide would be used instead of N-methoxy-N-methyl-1H-indole-3-carboxamide.

Example 36: Preparation of (S)-(4-(1-aminoethyl) thiazol-2-yl)(1H-pyrrolo[2,3-b]pyridin-3-yl)methanone

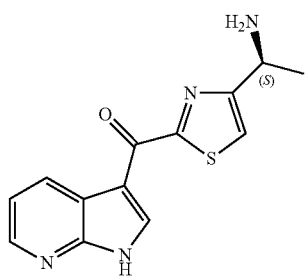

(S)-(4-(1-aminoethyl)thiazol-2-yl)(1H-pyrrolo[2,3-b] pyridin-3-yl)methanone can be prepared from (S)-2-methyl-N-(1-(thiazol-4-yl)ethyl)propane-2-sulfinamide and N-methoxy-N-methyl-1H-pyrrolo[2,3-b]pyridine-3-carboxamide according to the method described in Example 31, except that N-methoxy-N-methyl-1H-pyrrolo[2,3-b]pyridine-3-carboxamide would be used instead of N-methoxy-N-methyl-1H-indole-3-carboxamide.

Example 37: Preparation of (S)-(4-(1-aminoethyl)thiazol-2-yl)(1H-pyrrolo[2,3-c]pyridin-3-yl)methanone

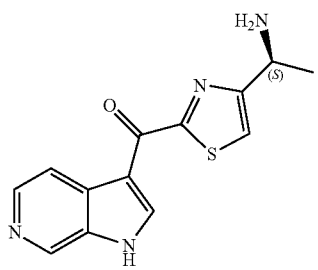

(S)-(4-(1-aminoethyl)thiazol-2-yl)(1H-pyrrolo[2,3-c]pyridin-3-yl)methanone can be prepared from (S)-2-methyl-N-(1-(thiazol-4-yl)ethyl)propane-2-sulfinamide and N-methoxy-N-methyl-1H-pyrrolo[2,3-c]pyridine-3-carboxamide according to the method described in Example 31, except that N-methoxy-N-methyl-1H-pyrrolo[2,3-c]pyridine-3-carboxamide would be used instead of N-methoxy-N-methyl-1H-indole-3-carboxamide.

Example 38: Preparation of (S)-(4-(1-aminoethyl)thiazol-2-yl)(1H-pyrrolo[3,2-c]pyridin-3-yl)methanone

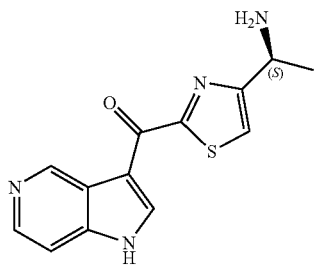

(S)-(4-(1-aminoethyl)thiazol-2-yl)(1H-pyrrolo[3,2-c]pyridin-3-yl)methanone can be prepared from (S)-2-methyl-N-(1-(thiazol-4-yl)ethyl)propane-2-sulfinamide and N-methoxy-N-methyl-1H-pyrrolo[3,2-c]pyridine-3-carboxamide according to the method described in Example 31, except that N-methoxy-N-methyl-1H-pyrrolo[3,2-c]pyridine-3-carboxamide would be used instead of N-methoxy-N-methyl-1H-indole-3-carboxamide.

Example 39: Preparation of (S)-(4-(1-aminoethyl)thiazol-2-yl)(1H-pyrrolo[3,2-b]pyridin-3-yl)methanone

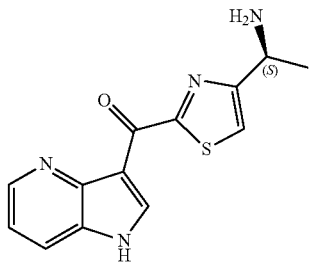

(S)-(4-(1-aminoethyl)thiazol-2-yl)(1H-pyrrolo[3,2-b]pyridin-3-yl)methanone can be prepared from (S)-2-methyl-N-(1-(thiazol-4-yl)ethyl)propane-2-sulfinamide and N-methoxy-N-methyl-1H-pyrrolo[3,2-b]pyridine-3-carboxamide according to the method described in Example 31, except that N-methoxy-N-methyl-1H-pyrrolo[3,2-b]pyridine-3-carboxamide would be used instead of N-methoxy-N-methyl-1H-indole-3-carboxamide.

Example 40: Preparation of (4-((S)-1-(methylamino)ethyl)thiazol-2-yl)(1H-pyrrolo[2,3-b]pyridin-3-yl)methanone

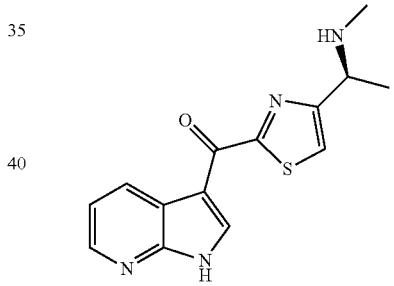

(S)-2-methyl-N-(1-(thiazol-4-yl)ethyl)propane-2-sulfinamide would be dissolved in dry THF cooled to −20° C. and to it would be added one equivalent of sodium hydride. The solution would be stirred for 10 min and then to it would be added 1.2 equivalents of methyliodide. The solution would be stirred for 2 hours, then evaporated to dryness, and then redissolved in dry THF and the solution would be filtered under a nitrogen atmosphere. The THF solution would then be cooled to −78° C. and to it would be added 1.1 equivalents of n-BuLi. The solution would then be warmed to −40° C. This solution would be added by cannula to the preformed solution of the sodium salt of N-methoxy-N-methyl-1H-pyrrolo[2,3-b]pyridine-3-carboxamide in THF held at −15° (prepared by the addition of 1 equivalent of sodium hydride to a THF solution of (4-(aminomethyl)thiazol-2-yl)(1H-indol-3-yl)methanone). After warming overnight to room temperature, the solution would be worked up as described in Example 31.

Example 41: Preparation of (4-((S)-1-(methyl-amino)ethyl)thiazol-2-yl)(1H-pyrrolo[2,3-c]pyridin-3-yl)methanone

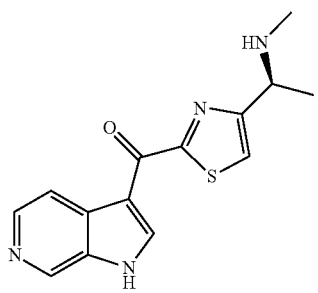 [SMILES: CN[C@@H](C)c1csc(C(=O)c2c[nH]c3cnccc23)n1]

(S)-2-methyl-N-(1-(thiazol-4-yl)ethyl)propane-2-sulfinamide would be dissolved in dry THF cooled to −20° C. and to it would be added one equivalent of sodium hydride. The solution would be stirred for 10 min and then to it would be added 1.2 equivalents of methyliodide. The solution would be stirred for 2 hours, then evaporated to dryness, and then redissolved in dry THF and the solution would be filtered under a nitrogen atmosphere. The THF solution would then be cooled to −78° C. and to it would be added 1.1 equivalents of n-BuLi. The solution would then be warmed to −40° C. This solution would be added by cannula to the preformed solution of the sodium salt of N-methoxy-N-methyl-1H-pyrrolo[2,3-c]pyridine-3-carboxamide in THF held at −15° C. (prepared by the addition of 1 equivalent of sodium hydride to a THF solution of (4-(aminomethyl)thiazol-2-yl)(1H-indol-3-yl)methanone). After warming overnight to room temperature, the solution would be worked up as described in Example 31.

Example 42: Preparation of (4-((S)-1-(methyl-amino)ethyl)thiazol-2-yl)(1H-pyrrolo[3,2-c]pyridin-3-yl)methanone

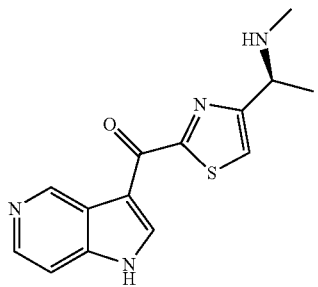 [SMILES: CN[C@@H](C)c1csc(C(=O)c2c[nH]c3ccncc23)n1]

(S)-2-methyl-N-(1-(thiazol-4-yl)ethyl)propane-2-sulfinamide would be dissolved in dry THF cooled to −20° C. and to it would be added one equivalent of sodium hydride. The solution would be stirred for 10 min and then to it would be added 1.2 equivalents of methyliodide. The solution would be stirred for 2 hours, then evaporated to dryness, and then redissolved in dry THF and the solution would be filtered under a nitrogen atmosphere. The THF solution would then be cooled to −78° C. and to it would be added 1.1 equivalents of n-BuLi. The solution would then be warmed to −40° C. This solution would be added by cannula to the preformed solution of the sodium salt of N-methoxy-N-methyl-1H-pyrrolo[3,2-c]pyridine-3-carboxamide in THF held at −15° C. (prepared by the addition of 1 equivalent of sodium hydride to a THF solution of (4-(aminomethyl)thiazol-2-yl)(1H-indol-3-yl)methanone). After warming overnight to room temperature, the solution is worked up as described in Example 31.

Example 43: Preparation of (4-((S)-1-(methyl-amino)ethyl)thiazol-2-yl)(1H-pyrrolo[3,2-b]pyridin-3-yl)methanone

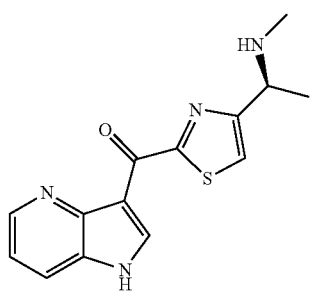 [SMILES: CN[C@@H](C)c1csc(C(=O)c2c[nH]c3cccnc23)n1]

(S)-2-methyl-N-(1-(thiazol-4-yl)ethyl)propane-2-sulfinamide would be dissolved in dry THF cooled to −20° C. and to it would be added one equivalent of sodium hydride. The solution would be stirred for 10 min and then to it would be added 1.2 equivalents of methyliodide. The solution would be stirred for 2 hours, then evaporated to dryness, and then redissolved in dry THF and the solution would be filtered under a nitrogen atmosphere. The THF solution would then be cooled to −78° C. and to it would be added 1.1 equivalents of n-BuLi. The solution would then be warmed to −40° C. This solution would be added by cannula to the preformed solution of the sodium salt of N-methoxy-N-methyl-1H-pyrrolo[3,2-b]pyridine-3-carboxamide in THF held at −15° C. (prepared by the addition of 1 equivalent of sodium hydride to a THF solution of (4-(aminomethyl)thiazol-2-yl)(1H-indol-3-yl)methanone). After warming overnight to room temperature, the solution would worked up as described in Example 31.

Example 44: Stimulation of CYP1A1 in Human HepG2 Cells

CYP1A1 induction is under the control of the AhR signaling pathway. This Example describes an in vitro assay (7-ethoxy-resorufin-O-deethylase (EROD) assay) that evaluated the AhR modulating activities of the indole compounds described herein. In this assay, the indole compounds were incubated with human HepG2 cells or mouse Hepa1-6 cells. The activity of CYP1A1 in the cells was measured by the conversion of substrate 7-ethoxyresorufin, with the readout being a fluorescence signal associated with the conversion product. The $EC_{50}$ values of the indole compounds as well as the maximum luminescence induced by them in the assay were determined.

Materials

Human HepG2 cells were obtained from Sigma Aldrich (Catalog 85011430-1VL).

Methods

Human HepG2 cells were grown to 60-80% confluency in tissue culture flasks, lifted with non-enzymatic cell dissociation solution (cell stripper), seeded in a 384-well plate at 5,000 cells per well, treated with the test compounds, and incubated for 20 hours overnight at 37° C. The treatment medium was removed and a solution of substrate 7-ethoxy-resorufin (ETX) was added to initiate the reaction. The plate was incubated at 37° C. for 30 minutes. The reaction was subsequently terminated by adding tempered methanol. Fluorescent emission was measured at 590 nm with excitation at 530 nm in a FLEXSTATION III instrument (Molecular Devices).

Results

Table 2 shows the EROD assay data of ARI-001 (ITE), ARI-143, ARI-145, ARI-146, ARI-164, ARI-186, ARI-187, ARI-194, ARI-195, ARI-210, ARI-211, ARI-212, ARI-213, ARI-214, ARI-215, ARI-218, ARI-219, ARI-220, ARI-221, ARI-222, ARI-223, ARI-224, ARI-225, ARI-226, ARI-228, and ARI-229 derivatives using human HepG2 cells.

TABLE 2

EROD Assay Data in human HepG2 cells

| Plate 1 | | | Plate 2 | | |
|---|---|---|---|---|---|
| Compound ID | $EC_{50}$ nM | $EC_{90}$ nM | Compound ID | $EC_{50}$ nM | $EC_{90}$ nM |
| ARI-186 | 5.8 | 7.4 | ARI-143 | 95.2 | 347.1 |
| ARI-187 | 55.6 | 152.3 | ARI-218 | 6.3 | 7.9 |
| ARI-194 | 409.2 | 517.4 | ARI-219 | 124.1 | 418.8 |
| ARI-195 | 289.3 | 847.3 | ARI-220 | 371.8 | 475.9 |
| ARI-210 | 240.5 | 626.6 | ARI-221 | 26.1 | 34.5 |
| ARI-211 | 35.9 | 183.0 | ARI-222 | 32.7 | 218.2 |
| ARI-212 | 21.9 | 149.6 | ARI-223 | 22.6 | 102.6 |
| ARI-213 | 476.3 | 671.7 | ARI-224 | 33.7 | 151.9 |
| ARI-214 | 581.6 | 2,806.0 | ARI-225 | 46.8 | 108.7 |
| ARI-215 | 119.0 | 135.1 | ARI-226 | 24.6 | 33.0 |
| ARI-145 | 19.3 | 80.5 | ARI-228 | 65.6 | 216.7 |
| ARI-146 | 52.0 | 152.7 | ARI-229 | 50.3 | 204.3 |
| ARI-001 (ITE) | 4,442.0 | 13,220.0 | ARI-001 (ITE) | 28,950.0 | 457,900.0 |
| ARI-164 | 104.1 | 133.6 | ARI-164 | 103.7 | 138.2 |

The results from the above table show that several chiral alcohols and chiral amines showed potency as well as chiral preference, especially, in human HepG2 cells:

ARI-186 was 9.5× more potent than ARI-187 by $EC_{50}$, and 20.5× more potent by $EC_{90}$;

ARI-186 was 17.8× more potent than ARI-164 by $EC_{50}$, and 18.0× more potent by $EC_{90}$;

ARI-224 was 3.1× more potent than ARI-164 by $EC_{50}$, and 0.90× as potent by $EC_{90}$; and ARI-226 was 4.2× more potent than ARI-164 by $EC_{50}$, and 4.2× more potent by $EC_{90}$.

Surprisingly, chiral preference for S vs R was maintained in several instances. For example, ARI-186 was more 9.6× more potent than ARI-187 by $EC_{50}$, and 20.6× more potent by $EC_{90}$. Similarly, ARI-218 was 19.7× more potent than ARI-219 by $EC_{50}$, and 53× more potent by $EC_{90}$.

Example 45: Determination of Metabolic Stability of Indole Compounds

The liver is an important organ in the body for drug metabolism. This Example describes hepatocyte intrinsic clearance assays using both human and rat hepatocytes to evaluate the metabolic stability of the indole compounds disclosed herein. The parameters measured include $t_{1/2}$ (half-life), $CL_{int}$ (intrinsic clearance), and EH (hepatic extraction ratio).

Materials

Testosterone (Lot FE111011-01) was obtained from Cerilliant (Round Rock, Tex.). 7-hydroxycoumarin (Lot 11631ED) was obtained from Sigma Aldrich (St. Louis, Mo.). Cryopreserved human hepatocytes pooled from ten donor males (X008001), cryopreserved male IRC/CD-1 mouse hepatocytes (M005052), INVITROGRO HI Medium (incubation), and INVITROGRO HT Medium (thawing) were obtained from Bioreclamation IVT (Baltimore, Md.). All solvents were obtained from commercial sources and used without further purification.

Methods

Metabolic Stability in Hepatocytes

Each test compound was prepared as a 1 mM stock solution in DMSO. A 2 µM solution of test compound and positive controls were prepared in INVITROGRO HI Medium (incubation). These solutions were pre-warmed in a sterile incubator set to maintain 37° C., 5% $CO_2$, and 98% humidity. Cryopreserved hepatocytes were prepared at a concentration of $2 \times 10^6$ living cells/mL in incubation media and pre-warmed in the incubator. The compound solutions and hepatocyte mixtures were then combined at a ratio of 1:1 (v:v). The final volume of the reaction mixture was 750 µL, containing 1 µM test compound (10 µM for 7-hydroxycoumarin) and $1 \times 10^6$ cells. The reaction mixture was placed in the incubator on a plate shaker. After 0, 15, 30, 60, 90, and 120 minutes of incubation, 100 µL of reaction mixtures were removed from the incubation plate and mixed with 150 µL of ice-cold acetonitrile in a designated well of a 96-well crash plate. The 96-well crash plate was placed on ice for 15 min, and samples were centrifuged (3,600 RPM, 10 min, 4° C.) to precipitate protein. The supernatants were diluted 1:1 (v:v) with water containing 0.15 µM verapamil and/or 1 µM tolbutamide (internal standards for positive and negative modes, respectively) in a 96-well shallow injection plate. This plate was sealed for LC-MS analysis. All measurements were done in duplicate.

LC-MS Analysis

Liquid Chromatography

Column: Waters Atlantis T3 Column, 100 Å, 3 µm, 2.1 nm×50 mm (Part #186003717). Mobile Phase A: Water with 0.1% formic acid. Mobile Phase B: Acetonitrile with 0.1% formic acid. Flow Rate: 0.7 mL/minute. Gradient Program:

| Time (min) | % A | % B |
|---|---|---|
| 0.0 | 90 | 10 |
| 0.4 | 90 | 10 |
| 1.2 | 10 | 90 |
| 2.0 | 10 | 90 |
| 2.1 | 90 | 10 |
| 3.0 | 90 | 10 |

Total Run Time: 3 minutes. Autosampler: 10 µL injection volume. Autosampler Wash: A: 90% water, 10% acetonitrile; B: 90° % acetonitrile, 10% water.

Mass Spectrometer

Instrument: AB SCIEX API4000. Interface: Turbo Ionspray. Mode: Q1 Multiple Ions. Method: 3.0 minute duration. Mass Spectrometer Source Settings:

| IS | TEM | CUR | GS1 | GS2 |
|---|---|---|---|---|
| 5500 | 550 | 20 | 50 | 50 |

Data and Calculations

Determination of $t_{1/2}$, $CL_{int}$, $E_H$, and % R at 60 Minutes

The residual compound remaining (% R) was determined from LC-MS peak areas by comparison to the zero time point. Metabolic half-life ($t_{1/2}$) and intrinsic clearance ($CL_{int}$) values were calculated from the slope of the plot of ln (% R) vs. time and the concentration of hepatocytes present in the incubation. Percent remaining at 60 minutes was calculated by plugging in the 60 minute value into the slope equation generated by the percent remaining time points.

Calculation of In Vivo Hepatic Clearance

In vivo hepatic clearance $CL_H$ was calculated using the well stirred liver model according to the following equation:

$$CL_H = \frac{Q_H \cdot f_u \cdot CL'_{int}}{Q_H + f_u \cdot CL'_{int}},$$

where $Q_H$ is the total liver blood flow, $f_u$ is unbound fraction of the drug, and $CL'_{int}$ is defined as follows:

$$CL'_{int} = CL_{int} \times (10^6 \text{ cells/g of liver weight}) \times (\text{g liver weight/kg of body weight}).$$

In the first approximation, used in this study, $f_u = 1$.

Hepatic extraction ratio $E_H$ was calculated using the following equation:

$$E_H = \frac{CL_H}{Q_H}$$

Corresponding physiological parameters used in calculations for all species are shown below in Table 3.

TABLE 3

Physiological Parameters of Mammalian Species Used for Calculation of $CL_H$

| Species | g liver wt/ kg body wt | 10⁶ cells/ g liver wt | $Q_H$ (mL/min/ kg body wt) |
|---|---|---|---|
| Human | 26 | 99 | 21 |
| Mouse | 55 | 128 | 120 |

Results

Table 4 shows the $t_{1/2}$, $CL_{int}$, and $E_H$ of various indole compounds described herein as assayed on human and rat hepatocytes.

TABLE 4

Metabolism of Indole Compounds

| Compound ID | Human Hepatocytes | | | Rat Hepatocytes | | |
|---|---|---|---|---|---|---|
| | $t_{1/2}$ (min) | $CL_{int}$ (μL/min/ 10⁶ cells) | $E_H$ (%) | $t_{1/2}$ (min) | $CL_{int}$ (μL/min/ 10⁶ cells) | $E_H$ (%) |
| Batch 1, Part 1 | | | | | | |
| ARI088 | 0.9 | 12.366 | 24.1 | 1.0 | 11.594 | 43.7 |
| ARI100 | 46.1 | 0.251 | 1.9 | 1.3 | 8.733 | 36.9 |
| ARI143 | 0.6 | 18.494 | 26.1 | 0.8 | 13.820 | 48.0 |
| ARI164 | 0.7 | 15.696 | 25.3 | 1.5 | 7.454 | 33.3 |
| ARI186 | 7.9 | 1.453 | 8.7 | 2.8 | 4.127 | 21.6 |
| ARI187 | 18.6 | 0.621 | 4.4 | 2.3 | 4.926 | 24.8 |
| ARI194 | 0.6 | 20.465 | 26.5 | 0.6 | 18.246 | 55.0 |
| ARI195 | 0.6 | 20.584 | 26.5 | 1.3 | 9.164 | 38.0 |
| Batch 1, Part 2 | | | | | | |
| ARI143 | 0.7 | 16.203 | 25.5 | 0.8 | 13.708 | 47.8 |
| ARI164 | 0.9 | 13.556 | 24.6 | 1.5 | 7.900 | 34.6 |
| ARI209 | 0.8 | 14.727 | 25.0 | 0.9 | 12.167 | 44.9 |
| ARI210 | 0.7 | 16.016 | 25.4 | 0.4 | 29.925 | 66.7 |
| ARI211 | 1.0 | 11.349 | 23.6 | 3.6 | 3.208 | 17.7 |
| ARI212 | 0.3 | 44.086 | 28.9 | 3.0 | 3.850 | 20.5 |
| ARI213 | 0.8 | 13.989 | 24.7 | 0.8 | 13.881 | 48.1 |
| ARI214 | 0.5 | 21.539 | 26.7 | 1.4 | 8.005 | 34.9 |
| ARI215 | 0.6 | 17.944 | 25.9 | 0.9 | 13.439 | 47.3 |
| Batch 2, Part 1 | | | | | | |
| ARI143 | 0.6 | 18.445 | 26.1 | 0.8 | 14.086 | 48.5 |
| ARI164 | 0.7 | 15.446 | 25.2 | 1.9 | 6.042 | 28.8 |
| ARI001 | 0.0 | 767.365 | 31.3 | 0.1 | 89.786 | 85.7 |
| ARI218 | 1.3 | 9.165 | 22.2 | 1.0 | 11.067 | 42.5 |
| ARI219 | 5.3 | 2.174 | 11.5 | 0.5 | 21.417 | 58.9 |
| ARI220 | 1.4 | 8.330 | 21.6 | 2.4 | 4.774 | 24.2 |
| ARI221 | 0.5 | 25.251 | 27.3 | 2.1 | 5.550 | 27.1 |
| ARI222 | 0.4 | 27.669 | 27.6 | 0.7 | 16.981 | 53.2 |
| Batch 2, Part 2 | | | | | | |
| ARI143 | 0.7 | 16.920 | 25.7 | 0.8 | 14.792 | 49.7 |
| ARI164 | 0.8 | 13.712 | 24.6 | 1.4 | 8.050 | 35.0 |
| ARI223 | 1.0 | 11.626 | 23.7 | 0.5 | 25.589 | 63.1 |
| ARI224 | 3.0 | 3.850 | 15.8 | 1.9 | 6.123 | 29.0 |
| ARI225 | 2.3 | 4.965 | 17.8 | 0.5 | 23.158 | 60.8 |
| ARI226 | 3.0 | 3.850 | 15.8 | 1.8 | 6.540 | 30.4 |
| ARI227 | 0.8 | 13.943 | 24.7 | 0.3 | 42.587 | 74.0 |
| Batch 2, Part 3 | | | | | | |
| ARI143 | 0.3 | 43.661 | 26.1 | 0.3 | 43.829 | 74.6 |
| ARI164 | 0.8 | 15.383 | 19.9 | 0.8 | 14.236 | 48.8 |
| ARI228 | 0.2 | 64.371 | 27.6 | 0.1 | 112.145 | 88.2 |
| ARI229 | 2.3 | 5.028 | 11.4 | 1.0 | 11.728 | 43.9 |

These results indicate that in rats, ARI-186 was found to be extremely low clearance, with a $CL_{int}$ of 4.1 μl/min/10⁶ cells and a hepatic extraction ratio of 21.6%. This CLint value is 1.8× lower than that of ARIA 64. In humans, AR-186 was also low clearance, with a $CL_{int}$ of 1.5 μl/min/10⁶ cells and 8.7% hepatic extraction ratio. This $CL_{int}$ value is 10.8× lower than that of ARI-164. ARI-224 and ARI-226 had values slightly lower than ARI-164 in rats. In human cells, however, both compounds had at least a 4× improvement in $CL_{int}$ compared to ARI-164.

Example 46: CYP Profiling of Indole Compounds

In order to investigate the contributions of CYP1A2 and CYP3A4 to the metabolism of the compounds of the present disclosure, human liver microsomes were incubated with the test compounds for 30 minutes in the presence of selective chemical inhibitors furafylline (1A2) and ketoconazole (3A4).

Results:

Table 5 shows the metabolic turnover rate of the tested compounds.

TABLE 5

CYP Profiling of indole compounds

| HLMs Compound ID | % Compound Metabolized at 30 min | | | % Inhibition Relative to Negative Control | |
|---|---|---|---|---|---|
| | No Inhibitor | CYP1A2 Inhibitor | CYP3A4 Inhibitor | 1A2 | 3A4 |
| Batch 1 | | | | | |
| Phenacitin | 31% | 1% | — | 97% | N/A |
| Midazolam | 97% | — | 0% | N/A | 100% |
| ARI-100 | 2% | 0% | 8% | 100% | None |
| ARI-143 | 69% | 32% | 82% | 54% | None |
| ARI-186 | 13% | 10% | 12% | 23% | 8% |
| ARI-187 | 4% | 7% | 3% | None | 25% |
| ARI-211 | 50% | 67% | 59% | None | None |
| ARI-212 | 43% | 51% | 24% | None | 44% |
| Batch 2 | | | | | |
| Phenacitin | 36% | 3% | 23% | 92% | 36% |
| Midazolam | 98% | 96% | 1% | 2% | 99% |
| ARI-143 | 91% | 17% | 92% | 81% | None |
| ARI-164 | 37% | 4% | 34% | 89% | 8% |
| ARI-218 | 16% | 17% | 0% | None | 100% |
| ARI-219 | 13% | 5% | 23% | 62% | None |
| ARI-220 | 41% | 0% | 27% | 100% | 34% |
| ARI-221 | 95% | 28% | 82% | 71% | 14% |
| ARI-223 | 79% | 12% | 42% | 85% | 47% |
| ARI-224 | 9% | 7% | 8% | 22% | 11% |
| ARI-225 | 39% | 10% | 29% | 74% | 26% |
| ARI-226 | 6% | 16% | 11% | None | None |
| ARI-228 | 89% | 23% | 75% | 74% | 16% |
| ARI-229 | 0% | 0% | 0% | None | None |

Confirming prior studies, ARI-164 was shown to have metabolic turnover in 30 minutes, with 37% metabolized. In the presence of furafylline, only 4% of ARI-164 was metabolized, demonstrating 89% inhibition by a 1A2 inhibitor. However, in the presence of ketoconazole, there was only an 8% inhibitory effect. Thus, ARI-164 is selectively metabolized by CYP1A2.

ARI-186 was shown to be a very low turnover compound, with only 13% metabolized in 30 minutes. Importantly, neither furafylline nor ketoconazole had much effect on ARI-186 metabolism.

ARI-224 and ARI-226 similarly were low turnover, with little to no impact on metabolism in the presence of furafylline or ketoconazole.

Therefore, ARI-186, ARI-224, and ARI-226 are compounds that appear to have selectively removed the CYP1A1/1A2-mediated oxidation of ARI-164, while preserving or improving potency.

Surprisingly, several chiral pairs appeared to demonstrate clear differences in terms of turnover and CYP metabolic liability. For example, ARI-223 was high turnover with CYP1A2 metabolic contribution while ARI-224 was not. Similarly, ARI-225 was high turnover with CYP1A2 metabolic contribution while ARI-226 was not. Also, ARI-228 was high turnover with CYP1A2 metabolic contribution while ARI-229 was not.

Example 47: In Vivo Pharmacokinetic Studies in Mice and Rats

This example describes pharmacokinetic (PK) studies of ARI-164, ARI-165, ARI-186, ARI-224, and ARI-226 in mice and rats. In the present studies, the test compounds were given to groups of mice and/or rats (N=3 in each group), intravenously (IV) at 2 mg/kg or orally (PO) at 10, 30, or 40 mg/kg. ARI-186, ARI-224 and ARI-226 were given orally to rats QD for 5 days at 10 mg/kg to assess whether decreased susceptibility to CYP1A1/1A2 metabolism would lead to increased accumulation. IV doses were formulated in DMSO, while PO doses were formulated in a 50/50 mixture of PEG400 and Tween 80 (single dose mouse and rat studies for ARI-164, ARI-165, ARI-186, ARI-224, ARI-226) or PEG400/Kolliphor HS15/Oleic Acid 45/45/10 (ARI-164 repeat dose rat study). Blood samples were collected at pre-dose and over a period of 24 hours post-dose. Plasma concentrations of the test compounds were determined by HPLC.

Results:

Tables 6a-h below show the results of PK studies on the select compounds in rats and mice.

TABLE 6a

Single Dose PK Studies in Rats Following a 2 mg/kg IV or 10 mg/kg Oral Dose of ARI-164

ARI-164 PK Parameters

| Dosed Compound | Group_ID | Route | Dosage (mg/kg) | Animal_ID | Tmax (hr) | Cmax (ng/mL) | T1/2 (hr) | MRTlast (hr) | MRTinf (hr) | AUClast (hr*ng/mL) | AUCinf (hr*ng/mL) | Cl (mL/hr/kg) | Vss (mL/kg) |
|---|---|---|---|---|---|---|---|---|---|---|---|---|---|
| ARI-164 | 1 | IV | 2 | 1 | 0.083 | 44500 | 2.24 | 1.03 | 1.04 | 21000 | 21000 | 95.1 | 98.6 |
| | | | | 2 | 0.083 | 42200 | 3.91 | 1.38 | 1.53 | 20300 | 20500 | 97.8 | 149 |
| | | | | 3 | 0.083 | 35400 | 2.39 | 2.49 | 2.5 | 23000 | 23000 | 87.1 | 218 |
| | | | | Mean | 0.083 | 40700 | 2.85 | 1.63 | 1.69 | 21400 | 21500 | 93.3 | 155 |
| | | | | SD | 0 | 4730 | 0.926 | 0.76 | 0.744 | 1350 | 1310 | 5.56 | 59.7 |
| | | | | CV% | 0 | 11.6 | 32.5 | 46.5 | 44.1 | 6.3 | 6.11 | 5.95 | 38.5 |

| Dosed Compound | Group_ID | Route | Dosage (mg/kg) | Animal_ID | Tmax (hr) | Cmax (ng/mL) | T1/2 (hr) | MRTlast (hr) | MRTinf (hr) | AUClast (hr*ng/mL) | AUCinf (hr*ng/mL) | F (%) |
|---|---|---|---|---|---|---|---|---|---|---|---|---|
| ARI-164 | 2 | PO | 10 | 4 | 2 | 532 | 0.56 | 2.64 | 2.65 | 2110 | 2110 | |
| | | | | 5 | 2 | 646 | 0.746 | 3.02 | 3.05 | 2650 | 2660 | |
| | | | | 6 | 1 | 354 | 2.82 | 2.88 | 2.92 | 1500 | 1500 | |
| | | | | Mean | 1.67 | 511 | 1.37 | 2.85 | 2.87 | 2090 | 2090 | 1.94 |
| | | | | SD | 0.577 | 147 | 1.25 | 0.19 | 0.203 | 574 | 578 | |
| | | | | CV% | 34.6 | 28.8 | 91.2 | 6.68 | 7.07 | 27.5 | 27.6 | |

F %: Bioavailability

TABLE 6b

Single Dose PK Studies in Rats Following a 2 mg/kg IV or 10 mg/kg Oral Dose of ARI-165

ARI-165 PK Parameters

| Dosed Compound | Group | Route | Dosage (mg/kg) | Animal_ID | Tmax (hr) | Cmax (ng/mL) | T1/2 (hr) | MRTlast (hr) | MRTinf (hr) | AUClast (hr*ng/mL) | AUCinf (hr*ng/mL) | Cl (mL/hr/kg) | Vss (mL/kg) |
|---|---|---|---|---|---|---|---|---|---|---|---|---|---|
| ARI-165 | 1 | IV | 2 | 1 | 0.083 | 3880 | 0.83 | 0.8 | 0.91 | 2620 | 2690 | 744 | 677 |
| | | | | 2 | 0.083 | 36500 | 1.07 | 0.79 | 0.81 | 19500 | 19500 | 103 | 83.2 |
| | | | | 3 | 0.083 | 17100 | 2.11 | 1.28 | 1.61 | 15700 | 16300 | 123 | 198 |
| | | | | Mean | 0.083 | 19200 | 1.33 | 0.959 | 1.11 | 12600 | 12800 | 323 | 320 |
| | | | | SD | 0 | 16400 | 0.68 | 0.28 | 0.436 | 8840 | 8930 | 365 | 315 |
| | | | | CV% | 0 | 85.6 | 51.1 | 29.2 | 39.2 | 70.2 | 69.6 | 113 | 98.7 |

| Dosed Compound | Group_ID | Route | Dosage (mg/kg) | Animal_ID | Tmax (hr) | Cmax (ng/mL) | T1/2 (hr) | MRTlast (hr) | MRTinf (hr) | AUClast (hr*ng/mL) | AUCinf (hr*ng/mL) | F (%) |
|---|---|---|---|---|---|---|---|---|---|---|---|---|
| ARI-165 | 2 | PO | 10 | 4 | 2 | 1250 | 1.87 | 2.71 | 3.41 | 4260 | 4680 | |
| | | | | 5 | 2 | 1070 | 0.541 | 3.12 | 3.12 | 4640 | 4650 | |
| | | | | 6 | 2 | 1040 | 0.87 | 2.64 | 2.71 | 3560 | 3620 | |
| | | | | Mean | 2 | 1120 | 1.09 | 2.82 | 3.08 | 4160 | 4310 | 6.73 |
| | | | | SD | 0 | 114 | 0.692 | 0.259 | 0.355 | 548 | 604 | |
| | | | | CV% | 0 | 10.1 | 63.2 | 9.17 | 11.5 | 13.2 | 14 | |

F %: Bioavailability

TABLE 6c

Repeat Dose PK Studies in Rats Following a 30 mg/kg Oral Dose of ARI-164

| Analyte | Dose (mg/kg) | Day | Gender | Statistic | $C_{max}$ (ng/mL) | $C_{max}$/Dose (kg*ng/mL/mg) | $T_{max}^a$ (hr) | $T_{last}^a$ (hr) | $AUC_{Tlast}$ (hr*ng/mL) | $AUC_{0-24hr}$/Dose (hr*ng/mL) | $AUC_{0-24hr}$/Dose (hr*kg*ng/mL/mg) | $R^b$ | $R^c$ | $F:M^d$ |
|---|---|---|---|---|---|---|---|---|---|---|---|---|---|---|
| ARI-164 | 30 | 1 | Male | N | 5 | 5 | 5 | 5 | 5 | 5 | 5 | NA | NA | NA |
| | | | | Mean | 499 | 16.6 | 1 | 8 | 1430 | 1510 | 50.3 | NA | NA | NA |
| | | | | SD | 445 | 14.8 | (1-1) | (8-8) | 1120 | 1110 | 37.1 | NA | NA | NA |
| | | | | CV % | 89.1 | 89.1 | NA | NA | 78.5 | 73.7 | 73.7 | NA | NA | NA |

TABLE 6c-continued

Repeat Dose PK Studies in Rats Following a 30 mg/kg Oral Dose of ARI-164

| Analyte | Dose (mg/kg) | Day | Gender | Statistic | $C_{max}$ (ng/mL) | $C_{max}$/Dose (kg*ng/mL/mg) | $T_{max}{}^a$ (hr) | $T_{last}{}^a$ (hr) | $AUC_{Tlast}$ (hr*ng/mL) | $AUC_{0-24hr}$/Dose (hr*ng/mL) | $AUC_{0-24hr}$/Dose (hr*kg*ng/mL/mg) | $R^b$ | $R^c$ | $F:M^d$ |
|---|---|---|---|---|---|---|---|---|---|---|---|---|---|---|
| ARI-164 | 30 | 7 | Male | N | 5 | 2 | 2 | 2 | NA | NA | NA | NA | NA | NA |
| | | | | Mean | 2.93 | 0.245 | 1 | NA | NA | NA | NA | NA | NA | NA |
| | | | | SD | 5.29 | NA | (1-1) | (1-4) | NA | NA | NA | NA | NA | NA |
| | | | | CV % | 180 | NA | NA | NA | NA | NA | NA | NA | NA | NA |

TABLE 6d

Repeat Dose PK Studies in Rats Following a 10 mg/kg Oral Dose of ARI-186

| Compound | Day | Route | Dosage (mg/kg) | Animal_ID | Tmax (hr) | Cmax (ng/mL) | T1/2 (hr) | MRTlast (hr) | MRTinf (hr) | AUClast (hr*ng/mL) | AUCinf (hr*ng/mL) |
|---|---|---|---|---|---|---|---|---|---|---|---|
| ARI-186 | 1 | PO | 10 | 1 | 8 | 397 | 6.44 | 8.14 | 10.5 | 6260 | 6920 |
| | | | | 2 | 8 | 359 | 6.45 | 8.40 | 10.9 | 5400 | 6000 |
| | | | | 3 | 4 | 441 | 5.22 | 7.63 | 8.93 | 6150 | 6510 |
| | | | | Mean | 6.67 | 399 | 6.04 | 8.06 | 10.1 | 5940 | 6480 |
| | | | | SD | 2.31 | 41 | 0.71 | 0.395 | 1.04 | 469 | 461 |
| | | | | CV % | 34.6 | 10.3 | 11.8 | 4.9 | 10.3 | 7.89 | 7.11 |

| Compound | Day | Route | Dosage (mg/kg) | Animal_ID | Tmax (hr) | Cmax (ng/mL) | T1/2 (hr) | MRTlast (hr) | MRTinf (hr) | AUClast (hr*ng/mL) | AUCinf (hr*ng/mL) |
|---|---|---|---|---|---|---|---|---|---|---|---|
| ARI-186 | 5 | PO | 10 | 1 | 2 | 1610 | NC | 11.6 | NC | 33600 | NC |
| | | | | 2 | 8 | 1310 | NC | 11.6 | NC | 24600 | NC |
| | | | | 3 | 4 | 1810 | NC | 11.4 | NC | 29100 | NC |
| | | | | Mean | 4.67 | 1580 | NC | 11.5 | NC | 29100 | NC |
| | | | | SD | 3.06 | 252 | | 0.116 | | 4480 | |
| | | | | CV % | 65.5 | 16 | | 1.01 | | 15.4 | |

TABLE 6e

Single Dose PK Studies in Mice Following a 40 mg/kg Oral Dose of ARI-164

| Time (hr) | M1 | M2 | M3 | Mean | | S.D. | CV (%) |
|---|---|---|---|---|---|---|---|
| 0.083 | 330 | 202 | 88 | 206.7 | ± | 121 | 58.6 |
| 0.25 | 1780 | 1740 | 1350 | 1623 | ± | 238 | 14.6 |
| 0.5 | 1960 | 2020 | 1620 | 1867 | ± | 216 | 11.6 |
| 1 | 1050 | 1600 | 930 | 1193 | ± | 357 | 29.9 |
| 2 | 463 | 572 | 482 | 506 | ± | 58 | 11.5 |
| 4 | 101 | 79.3 | 68.2 | 82.8 | ± | 16.7 | 20.1 |
| 8 | 7.1 | BLQ | BLQ | 7.1 | ± | NA | NA |
| 12 | 7.5 | BLQ | 5.6 | 6.5 | ± | 1.35 | 20.7 |

TABLE 6e-continued

Single Dose PK Studies in Mice Following a 40 mg/kg Oral Dose of ARI-164

| Time (hr) | M1 | M2 | M3 | Mean | | S.D. | CV (%) |
|---|---|---|---|---|---|---|---|
| 24 | BLQ | BLQ | BLQ | NA | ± | NA | NA |
| $t_{1/2}$ (hr) | | | | 1.4 | | | |
| $T_{max}$ (hr) | | | | 0.5 | | | |
| $C_{max}$ (ng/mL) | | | | 1867 | | | |
| $AUC_{0-t}$ (ng · hr/mL) | | | | 3008 | | | |
| $AUC_{0-\infty}$ (ng · hr/mL) | | | | 3021 | | | |
| Bioavailability (%) | | | | 15.1% | | | |

TABLE 6f

Single Dose PK Studies of ARI-186 in Mice

| Compound | Group ID | Route | Dosage (mg/kg) | Tmax (hr) | Cmax (ng/mL) | T1/2 (hr) | MRT last (hr) | MRT inf (hr) | AUClast (hr*ng/mL) | AUCinf (hr*ng/mL) | Cl (mL/hr/kg) | Vss (mL/kg) | F* (%) |
|---|---|---|---|---|---|---|---|---|---|---|---|---|---|
| ARI-186 | 1 | IV | 5 | 0.083 | 2130 | 7.62 | 6.99 | 9.55 | 12200 | 13500 | 371 | 3550 | |
| ARI-186 | 2 | PO | 10 | 2 | 1380 | 5.56 | 6.76 | 8.21 | 16100 | 17000 | | | 63.0 |
| ARI-186 | 3 | PO | 40 | 2 | 5000 | NC | 9.35 | NC | 73900 | NC | | | 75.7** |
| ARI-186 | 4 | IP | 40 | 0.5 | 6230 | NC | 11.2 | NC | 79400 | NC | | | 81.4** |

TABLE 6g

Repeat Dose PK Studies in Rats Following a 10 mg/kg Oral Dose of ARI-224

| Compound | Route | Dosage (mg/kg) | Day | Animal_ID | Tmax (hr) | Cmax (ng/mL) | T1/2 (hr) | MRTlast (hr) | MRTinf (hr) | AUClast (hr*ng/mL) | AUCinf (hr*ng/mL) |
|---|---|---|---|---|---|---|---|---|---|---|---|
| ARI-224 | PO | 10 | 1 | 1 | 1 | 699 | 2.05 | 2.66 | 3.23 | 1990 | 2140 |
|  |  |  |  | 2 | 2 | 1090 | 1.04 | 2.42 | 2.48 | 4030 | 4070 |
|  |  |  |  | 3 | 1 | 587 | 1.57 | 2.36 | 2.66 | 1770 | 1840 |
|  |  |  |  | Mean | 1.33 | 792 | 1.55 | 2.48 | 2.79 | 2600 | 2680 |
|  |  |  |  | SD | 0.577 | 264 | 0.507 | 0.159 | 0.389 | 1250 | 1210 |
|  |  |  |  | CV % | 43.3 | 33.3 | 32.6 | 6.4 | 14 | 48.1 | 45.2 |

| Compound | Route | Dosage (mg/kg) | Day | Animal_ID | Tmax (hr) | Cmax (ng/mL) | T1/2 (hr) | MRTlast (hr) | MRTinf (hr) | AUClast (hr*ng/mL) | AUCinf (hr*ng/mL) |
|---|---|---|---|---|---|---|---|---|---|---|---|
| ARI-224 | PO | 10 | 5 | 1 | 0.5 | 5.53 | NA | 3.29 | NA | 11.9 | NA |
|  |  |  |  | 2 | 0.25 | 8.36 | NA | 8.95 | NA | 14.9 | NA |
|  |  |  |  | 3 | 0.25 | 3.98 | 1.28 | 1.44 | 1.95 | 7.28 | 8.24 |
|  |  |  |  | Mean | 0.333 | 5.96 | 1.28 | 4.56 | 1.95 | 11.4 | 8.24 |
|  |  |  |  | SD | 0.144 | 2.22 | NA | 3.91 | NA | 3.84 | NA |
|  |  |  |  | CV % | 43.3 | 37.3 | NA | 85.7 | NA | 33.7 | NA |

TABLE 6h

Repeat Dose PK Studies in Rats Following a 10 mg/kg Oral Dose of ARI-226

| Compound | Route | Dosage (mg/kg) | Day | Animal_ID | Tmax (hr) | Cmax (ng/mL) | T1/2 (hr) | MRTlast (hr) | MRTinf (hr) | AUClast (hr*ng/mL) | AUCinf (hr*ng/mL) |
|---|---|---|---|---|---|---|---|---|---|---|---|
| ARI-226 | PO | 10 | 1 | 4 | 4 | 188 | 2.55 | 5.18 | 5.23 | 1280 | 1280 |
|  |  |  |  | 5 | 4 | 28.4 | 2.39 | 5.96 | 5.99 | 253 | 253 |
|  |  |  |  | 6 | 4 | 119 | 1.89 | 6.21 | 6.22 | 963 | 963 |
|  |  |  |  | Mean | 4 | 112 | 2.28 | 5.78 | 5.81 | 831 | 832 |
|  |  |  |  | SD | 0 | 80 | 0.342 | 0.537 | 0.517 | 525 | 526 |
|  |  |  |  | CV% | 0 | 71.6 | 15.0 | 9.28 | 8.90 | 63.2 | 63.2 |

| Compound | Route | Dosage (mg/kg) | Day | Animal_ID | Tmax (hr) | Cmax (ng/mL) | T1/2 (hr) | MRTlast (hr) | MRTinf (hr) | AUClast (hr*ng/mL) | AUCinf (hr*ng/mL) |
|---|---|---|---|---|---|---|---|---|---|---|---|
| ARI-226 | PO | 10 | 5 | 4 | 1 | 5.33 | 1.05 | 1.56 | 1.89 | 13.0 | 14.2 |
|  |  |  |  | 5 | 2 | 13.2 | 1.87 | 2.76 | 3.31 | 50.9 | 54.7 |
|  |  |  |  | 6 | 2 | 10.8 | 2.01 | 3.15 | 3.82 | 43.2 | 47.3 |
|  |  |  |  | Mean | 1.67 | 9.78 | 1.64 | 2.49 | 3.01 | 35.7 | 38.7 |
|  |  |  |  | SD | 0.577 | 4.03 | 0.519 | 0.831 | 1 | 20.0 | 21.5 |
|  |  |  |  | CV% | 34.6 | 41.3 | 31.6 | 33.4 | 33.2 | 56.1 | 55.6 |

This study showed that surprisingly, after a single 40 mg/kg oral dose of ARI-186, the AUC was 73,900 ng*hr/ml with 75.7% oral bioavailability (Table 6f). This is a major improvement over a single 40 mg/kg oral dose of ARI-164, which achieved only 3,008 ng*hr/ml with 15.1% oral bioavailability (Table 6e). This is a 24.6× improvement in AUC and a 5.0× improvement in oral bioavailability. Half-lives for ARI-186 were in the 7.6 hour range, significantly longer than ARI-164 half-life in mice of 1.4 hours.

It was also surprising that while ARI-164 showed a greater than 90% decrease in exposure after repeat oral dosing in rats at 30 mg/kg QD, ARI-186 saw a 4.9× accumulation, from 5,940 ng*hr/ml on day 1 to 29,100 ng*hr/ml on day 5, thereby confirming the in vitro results with ARI-186 and suggesting that ARI-186 was achieving steady-state pharmacokinetics after 5 doses.

Furthermore, while ARI-186 showed accumulation towards steady state after-5 days of repeat dosing, surprisingly, ARI-224 and ARI-226 did not (Tables 6g and 6h). In fact, ARI-224 and ARI-226 showed increased elimination after induction of CYP1A1/1A2. This suggests that although each of these compounds possess the same 6-fluoro indole moiety as well as the same chiral amino group, the structural changes on the thiazole end of the molecule contribute significantly to the CYP metabolic profiles of these molecules.

Example 48: Anti-Tumor Activity of ARI-143, ARI-164 and ARI-165 in Animal Models This example describes in vivo studies that evaluated the anti-cancer efficacy of ARI-143, ARI-164, ARI-165, and ARI-186 in syngeneic mouse tumor models. Mice implanted subcutaneously with EMT-6 or Pan02 cancer cells were treated with ARI-143, ARI-164, ARI-165, ARI-186, or vehicle controls, as described below.

Materials and Methods

Cell Culture

A monolayer culture of tumor cells was maintained in vitro in DMEM or RPMI1640 medium supplemented with 10% fetal bovine serum at 37° C. in an atmosphere of 5% $CO_2$. Cells in exponential growth phase were harvested and quantitated by cell counter before tumor inoculation. The cell lines used are described in the table below.

| Cell Line | Cancer Type | Culture Medium |
|---|---|---|
| EMT-6 | breast cancer | DMEM + 10% FBS |
| Pan02 | pancreatic cancer | RPMI1640 + 10% FBS |

Subcutaneous Syngeneic Mouse Tumor Models

Two subcutaneous syngeneic mouse tumor models were generated by innoculating female BALB/C or C57BL/6 mice with cancer cells at their right lower or front flank as detailed in the table below:

| Cell line | Cell Number | Inoculation site | MouseStrain |
|---|---|---|---|
| EMT-6 | $5 \times 10^5$ | right lower flank | BALB/C |
| Pan02 | $3 \times 10^6$ | right front flank | C57BL/6 |

Each mouse was inoculated subcutaneously with tumor cells in 0.1 mL of PBS. Treatments were started when the mean tumor size reached approximately 80-120 mm$^3$ (around 100 mm$^3$). The administration of the test compounds and the animal number in each study group are shown in the study design. The date of tumor cell inoculation was denoted as day 0.

Formulation of Test Compounds

ARI-143, ARI-164, and ARI-165 were dissolved in DMSO at the final concentration of 26.7 mg/ml and stored at room temperature. In Pan02 studies of ARI-164 and ARI-186, both compounds were dissolved in 100% PEG400.

Study Design

Randomization of animals was started when the mean tumor size reached approximately 90 mm$^3$ to form the mouse study groups. The randomization was performed based on "Matched distribution" method using the multi-task method (StudyDirector™ software, version 3.1.399.19)/randomized block design. The mouse groups (ten in each group) were treated with vehicle (DMSO or PEG400) or the test compounds at a dose of 26-80 mg/kg by intraperitoneal (i.p.). injection, QD for 28 days or longer.

Observation and Data Collection

After tumor cell inoculation, the mice were checked daily for morbidity and mortality. During routine monitoring, the mice were checked for tumor growth and any effects of the treatment on behavior such as mobility, food and water consumption, body weight gain/loss (body weights were measured twice per week after randomization), eye/hair matting, and any other abnormalities. Mortality and observed clinical signs were recorded for individual mice in detail.

Tumor volumes were measured twice per week in two dimensions using a caliper, and the volume was expressed in mm$^3$ using the formula:

$$V=(L \times W \times W)/2,$$

where V is tumor volume, L is tumor length (the longest tumor dimension) and W is tumor width (the longest tumor dimension perpendicular to L). Dosing as well as tumor and body weight measurements was conducted in a Laminar Flow Cabinet. The body weights and tumor volumes were measured by using StudyDirector™ software (version 3.1.399.19).

Dosing Holiday

A dosing holiday was given to the mice after one measurement of body weight loss (BWL) >30%. The length of the dosing holiday was long enough for the body weight to recover to BWL <30%, at which time the treatment was resumed. The mice were not fed any additional nutrient supplement during the dosing holiday.

Experimental Termination

Tumor growth inhibition percentage (TGI %) is an indicator for antitumor activity of a drug compound, and expressed as:

$$TGI(\%)=100 \times (1-T/C),$$

where T and C are the mean tumor volume (or weight) of the treated and control groups, respectively, on a given day. Statistical analysis of the difference in mean tumor volume (MTV) among the groups was conducted using the data collected on the day when the MTV of the vehicle group reached the humane endpoints, so that TGI could be derived for all or most mice enrolled in the study.

The body weight of all animals was monitored throughout the study and animals were euthanized if they lost over 20% of their body weight relative to the weight at the start of the study and could not recover within 72 hours.

All of the mice in the same group would be sacrificed when the MTV reached 2000 mm$^3$, or an individual mouse would be sacrificed when the tumor volume reached 3000 mm$^3$.

To deter cannibalization, any animal exhibiting an ulcerated or necrotic tumor would be separated immediately and singly housed and monitored daily before the animal was euthanized or until tumor regression was complete. Mouse with tumor ulceration of approximately 25% or greater on the surface of the tumor would be euthanized.

Statistical Analysis

For comparison between two groups, a Student's t-test was performed. All data were analyzed using SPSS 18.0 and/or GraphPad Prism 5.0. P<0.05 was considered statistically significant.

Results

In vivo studies were performed in the above-described syngeneic mouse tumor models to evaluate the anti-tumor activity of ARI-143, ARI-164, ARI-165, and ARI-186.

TABLE 7

TGI data-ARI-164 vs ARI-165

| | Study Days | | | | | | | |
|---|---|---|---|---|---|---|---|---|
| | 6 | 10 | 13 | 17 | 20 | 24 | 27 | 31 |
| ARI-164, 40 mg/kg, IP | 0.1% | −10.8% | −2.4% | 20.8% | 41.6% | 54.7% | 54.3% | 56.2% |
| ARI-165, 40 mg/kg, IP | 0.0% | −7.9% | −8.6% | 14.5% | 23.1% | 25.8% | 12.5% | 9.1% |

TABLE 8

TGI data-ARI-143 vs AM-164 vs ARI-165

| | Study Days | | | | | | |
|---|---|---|---|---|---|---|---|
| | 6 | 10 | 13 | 17 | 20 | 24 | 27 | 31 |
| ARI-164, 40 mg/kg, IP | 0.1% | −10.8% | −2.4% | 20.8% | 41.6% | 54.7% | 54.3% | 56.2% |
| ARI-165, 40 mg/kg, IP | 0.0% | −7.9% | −8.6% | 14.5% | 23.1% | 25.8% | 12.5% | 9.1% |
| ARI-143 (susp), 40 mg/kg, IP | 0.1% | −10.1% | 0.6% | 30.9% | 41.0% | 53.2% | 51.8% | 54.8% |

TABLE 9

TGI data-ARI-164 vs ARI-186

| | Study Days | | | | | |
|---|---|---|---|---|---|---|
| | 0 | 4 | 7 | 11 | 14 | 18 |
| ARI-164, 80 mg/kg, IP | −0.6% | −4.4% | −8.4% | 26.6% | 40.6% | 35.3% |
| ARI-186, 20 mg/kg, IP | −2.0% | −13.0% | −0.3% | 27.0% | 49.5% | 61.9% |

Figure 20A:
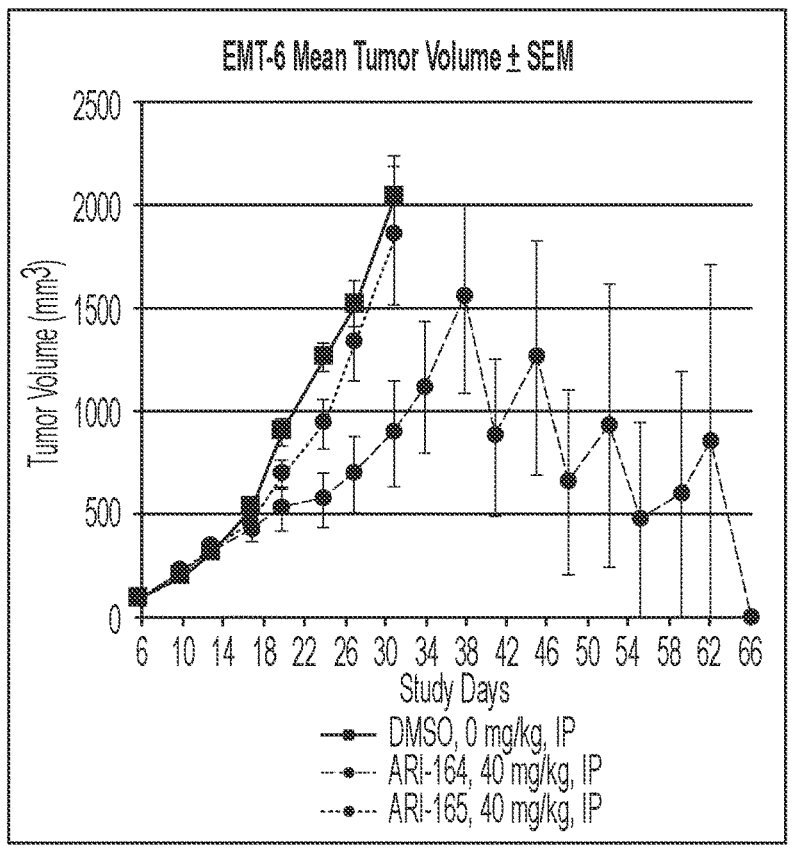
FIGS. 20A and 20B are plots comparing the tumor inhibitory activities of ARI-143, ARI-164 and ARI-165 in the EMT-6 syngeneic mouse tumor model.
Figure 20B:
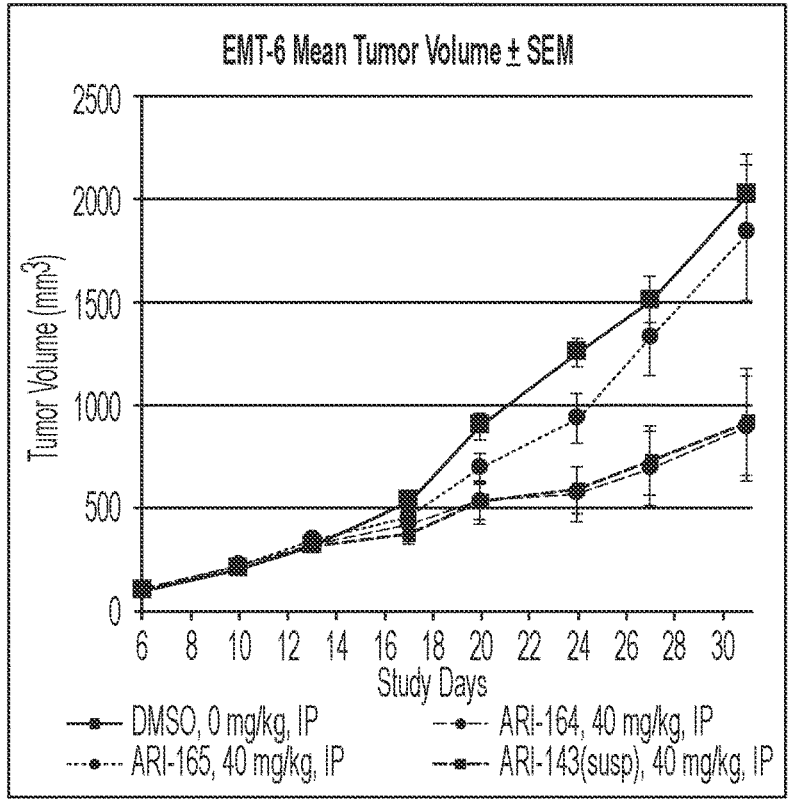
Figure 20C:
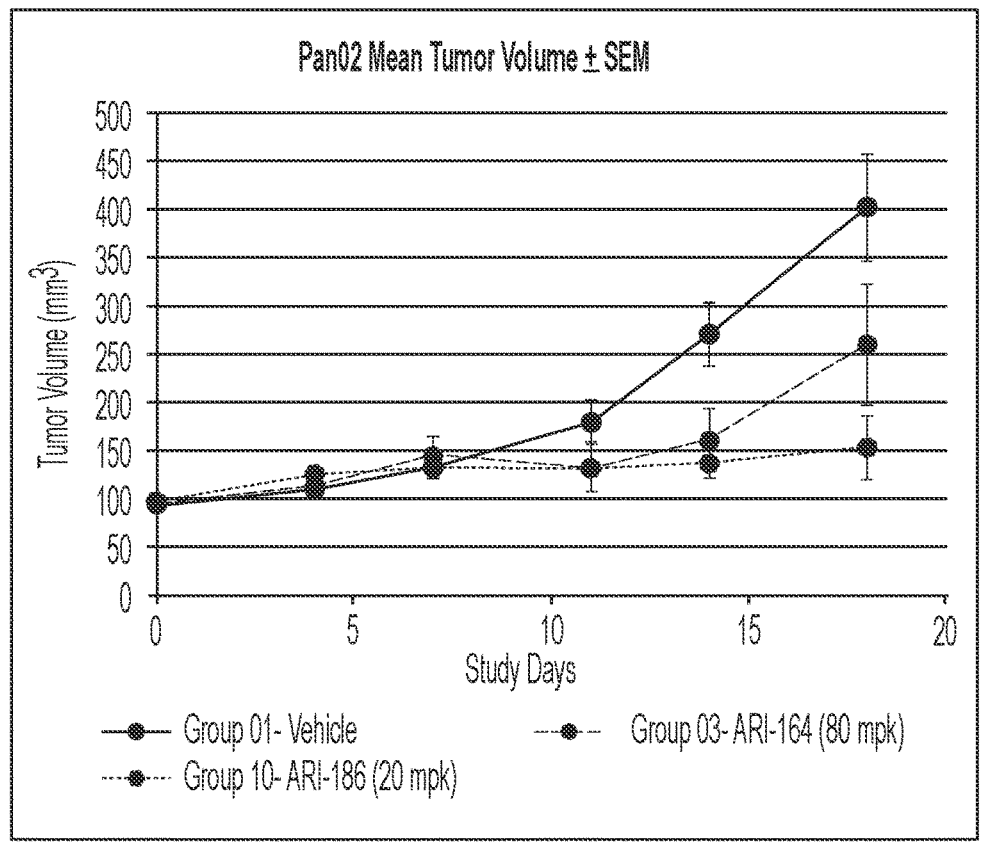
FIG. 20C is a plot comparing the tumor inhibitory activities of ARI-164 (80 mpk) and ARI-186 (20 mpk) in the Pan02 syngeneic mouse tumor model.

Surprisingly, ARI-186 was much more effective at suppressing Pan02 tumors at 20 mpk than ARI-164 was at 80 mpk. At study day 18, ARI-186 20 mpk resulted in 62% tumor inhibition versus vehicle as compared to ARI-164 80 mpk which resulted in 35% tumor inhibition versus vehicle (FIG. 20C).

Example 49: In Vivo Anti-Tumor Activity of ARI-164 in Combination with an Anti-PD-1 Antibody In this example, the in vivo anti-tumor efficacy of a combination of ARI-164 with an anti-PD-1 antibody was evaluated using a panel of seven subcutaneous syngeneic mouse tumor models.

Materials and Methods

Subcutaneous Syngeneic Mouse Tumor Models

Seven subcutaneous syngeneic mouse tumor models were generated by innoculating female BALB/C or C57BL/6 mice with cancer cells at their right lower or right front flank followed by randomization as detailed in Table 10 below.

TABLE 10

| Mouse Strain | Cell line | Cancer Type | Cell Number | Inoculation site | Age at Tumor Inno-culation (weeks) | Random-ization on Day |
|---|---|---|---|---|---|---|
| BALB/C | 4T-1 | Breast | $3 \times 10^5$ | Breast orthotopic | 7-9 | 8 |
| BALB/C | A20 | Lymphoma | $5 \times 10^5$ | right lower flank | 7-9 | 12 |
| BALB/C | EMT-6 | Breast | $5 \times 10^5$ | right lower flank | 7-9 | 6 |
| C57BL/6 | Pan02 | Pancreatic | $3 \times 10^6$ | right front flank | 6-8 | 4 |
| BALB/C | H22 | Liver | $1 \times 10^6$ | right front flank | 6-8 | 5 |
| C57BL/6 | LL/2 | Lung | $3 \times 10^5$ | right lower flank | 7-9 | 16 |

TABLE 10-continued

| Mouse Strain | Cell line | Cancer Type | Cell Number | Inoculation site | Age at Tumor Inno-culation (weeks) | Random-ization on Day |
|---|---|---|---|---|---|---|
| C57BL/6 | MC38 | Colon | $1 \times 10^6$ | right lower flank | 7-9 | 9 |

Formulation of Anti-PD-1 Antibody, ARI-164

A solution of a rat monoclonal anti-mouse PD-1 antibody (isotype $IgG_{2a}$, κ) at a concentration of 6.61 mg/ml was obtained from BioXcell (InVivoMAb anti-mouse PD-1 (CD279), Clone RMP1-14, Cat #BE0146)) and store at 4° C. The antibody solution was diluted with PBS to obtain a 1 mg/ml dosing solution.

ARI-164 powder was stored at −20° C. The powder of the compound was dissolved in DMSO to obtain dosing solutions at 26.7 mg/ml for administration to mice at 40 mg/kg, respectively.

Study Design and Randomization

Seven studies using the seven subcutaneous syngeneic mouse tumor models were performed. In each study, 80 mice were enrolled and randomly allocated to eight different study groups, with 10 mice in each study group. The mean tumor size at randomization was approximately 80-120 mm³ (around 100 mm³). Randomization was performed based on "Matched distribution" randomization method (StudyDirector™ software, version 3.1.399.19). Table 6 shows the study design and the actual dosing frequency and number of doses. All the drugs and vehicle controls were injected to the mice intraperitoneally.

TABLE 11

| Group No. | Treatment | Dose (mg/kg) | Dose Vol. (ml/kg) | Dose Freq. & Numbers |
|---|---|---|---|---|
| Study 1-4T-1 | | | | |
| 1 | Vehicle (DMSO) | 0 | 10 | QD × 23 doses |
| 2 | Anti-PD-1 | 10 | 10 | BIW × 7 doses |
| 3 | ARI-164 | 40 | 1.5 | QD × 23 doses |
| 4 | Anti-PD-1 | 10 | 10 | BIW × 7 doses |
|   | ARI-164 | 40 | 1.5 | QD × 21 doses |
| Study 2-A20 | | | | |
| 1 | Vehicle (DMSO) | 0 | 10 | QD × 17 doses |
| 2 | Anti-PD-1 | 10 | 10 | BIW × 6 doses |
| 3 | ARI-164 | 40 | 1.5 | QD × 17 doses |
| 4 | Anti-PD-1 | 10 | 10 | BIW × 6 doses |
|   | ARI-164 | 40 | 1.5 | QD × 17 doses |

TABLE 11-continued

| Group No. | Treatment | Dose (mg/kg) | Dose Vol. (ml/kg) | Dose Freq. & Numbers |
|---|---|---|---|---|
| | | Study 3-EMT-6 | | |
| 1 | Vehicle (DMSO) | 0 | 10 | QD × 24 doses |
| 2 | Anti-PD-1 | 10 | 10 | BIW × 8 doses |
| 3 | ARI-164 | 40 | 1.5 | QD × 24 doses |
| 4 | Anti-PD-1 | 10 | 10 | BIW × 8 doses |
| | ARI-164 | 40 | 1.5 | QD × 24 doses |
| | | Study 4-Pan02 | | |
| 1 | Vehicle (DMSO) | 0 | 10 | QD × 49 doses |
| 2 | Anti-PD-1 | 10 | 10 | BIW × 14 doses |
| 3 | ARI-164 | 40 | 1.5 | QD × 49 doses |
| 4 | Anti-PD-1 | 10 | 10 | BIW × 14 doses |
| | ARI-164 | 40 | 1.5 | QD × 49 doses |
| | | Study 5-H22 | | |
| 1 | Vehicle (DMSO) | 0 | 10 | QD × 18 doses |
| 2 | Anti-PD-1 | 10 | 10 | BIW × 6 doses |
| 3 | ARI-164 | 40 | 1.5 | QD × 18 doses |
| 4 | Anti-PD-1 | 10 | 10 | BIW × 6 doses |
| | ARI-164 | 40 | 1.5 | QD × 18 doses |
| | | Study 6-LL/2 | | |
| 1 | Vehicle (DMSO) | 0 | 10 | QD × 20 doses |
| 2 | Anti-PD-1 | 10 | 10 | BIW × 6 doses |
| 3 | ARI-164 | 40 | 1.5 | QD × 20 doses |
| 4 | Anti-PD-1 | 10 | 10 | BIW × 6 doses |
| | ARI-164 | 40 | 1.5 | QD × 20 doses |
| | | Study 7-MC38 | | |
| 1 | Vehicle (DMSO) | 0 | 10 | QD × 20 doses |
| 2 | Anti-PD-1 | 10 | 10 | BIW × 4 doses |
| 3 | ARI-164 | 160 | 1.5 | QD × 20 doses |
| 4 | Anti-PD-1 | 10 | 10 | BIW × 4 doses |
| | ARI-164 | 160 | 1.5 | QD × 20 doses |

The data was collected and analyzed as described above in Example 48.

Results

Tumor Growth Inhibition

FIGS. 21A-G are graphs showing mean tumor volumes on different study days in the study groups as indicated according to studies 1-7, respectively. The TGI data are summarized in Table 12.

TABLE 11

TGI in Tumor Models

| | | TGI (%) | | | | | |
|---|---|---|---|---|---|---|---|
| Group | Treatment | 4T-1 | A20 | EMT-6 | Pan02 | H22 | LL/2 | MC38 |
| 1 | Vehicle (PBS) | — | — | — | — | — | — | — |
| 2 | Anti-PD-1 | 4.8 | 3.7 | 55.5 | 23.8 | 50.1 | 1.3 | 29.0 |
| 3 | ARI-164 | 45.3 | 28.1 | 57.2 | 61.1 | 46.9 | 42.5 | 18.8 |
| 4 | Anti-PD-1 + ARI-164 | 64.6 | 68.9 | 91.6 | 75.4 | 82.9 | 43.0 | 59.1 |

Figure 21A:
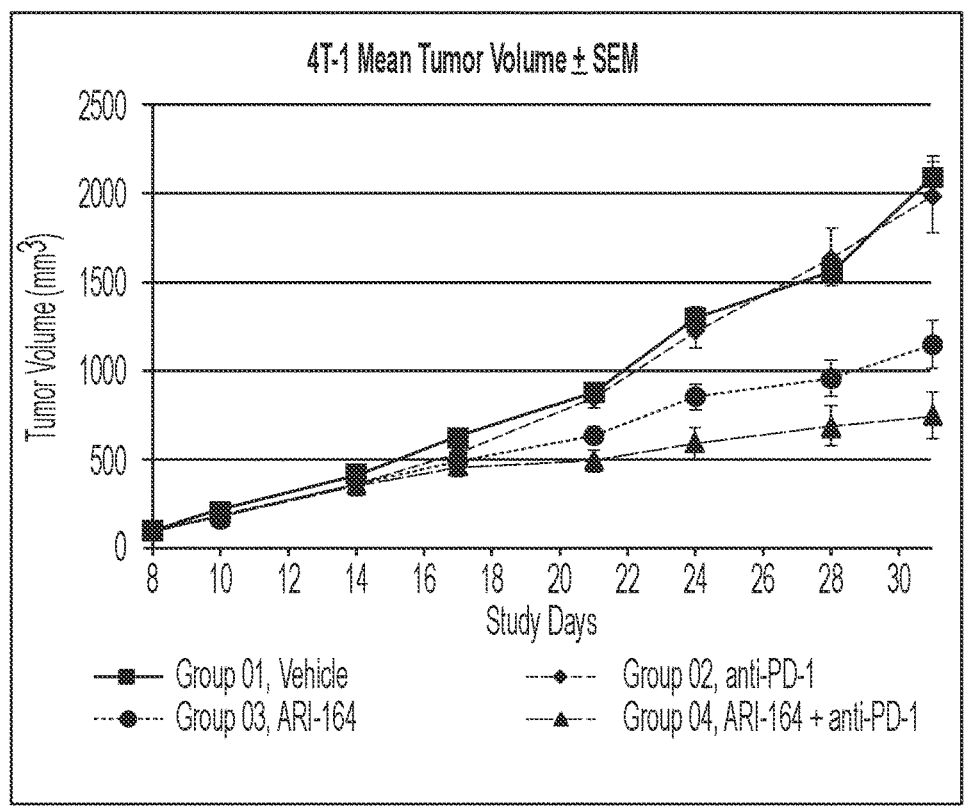
FIGS. 21A-G are plots comparing the tumor inhibitory activities of ARI-164, anti-PD-1, and their combination in the 4T-1, A20, EMT-6, Pan02, H22, LL/2, and MC38 syngeneic mouse tumor models.

4T-1 is a very aggressive breast line that is resistant to anti-PD-1. Surprisingly, not only did ARI-164 delay tumor growth, thereby improving survival curves, but its combination with an anti-PD-1 antibody resulted in a statistically significant delta in tumor growth inhibition at study day 31-(FIG. 21A).

Figure 21B:
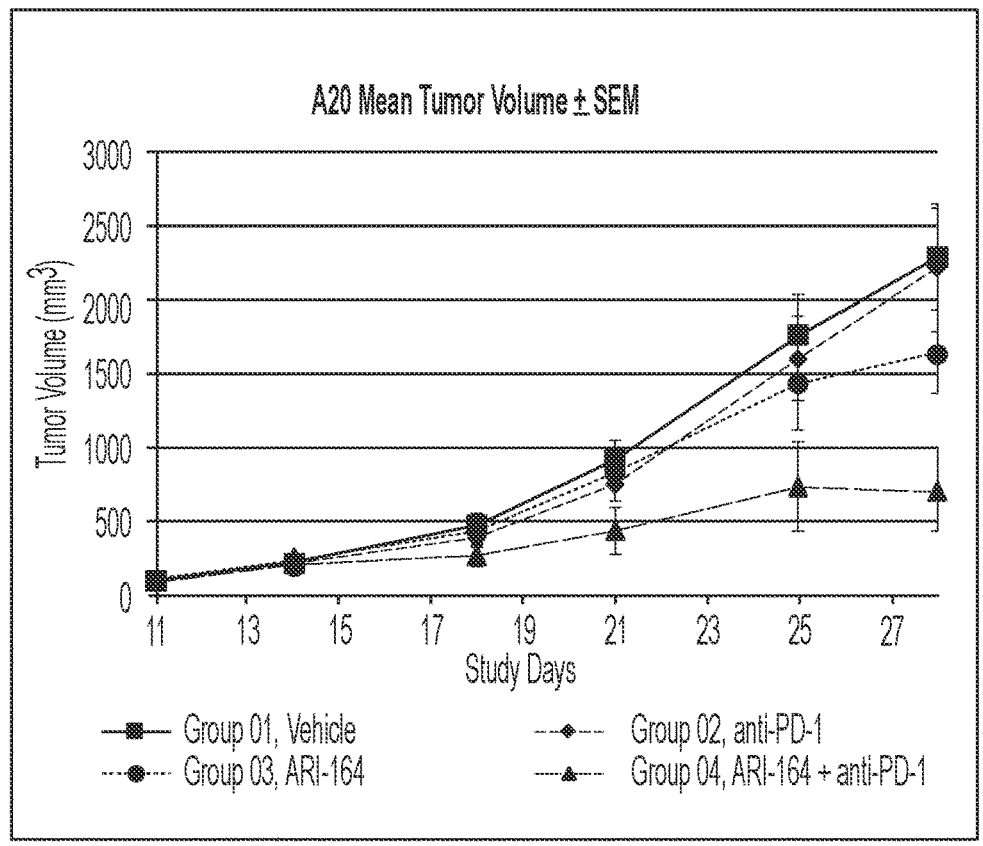

Combination of ARI-164 with an anti-PD-1 antibody led to significant tumor inhibition at study day 28 in the A20 model (FIG. 21B).

Figure 21C:
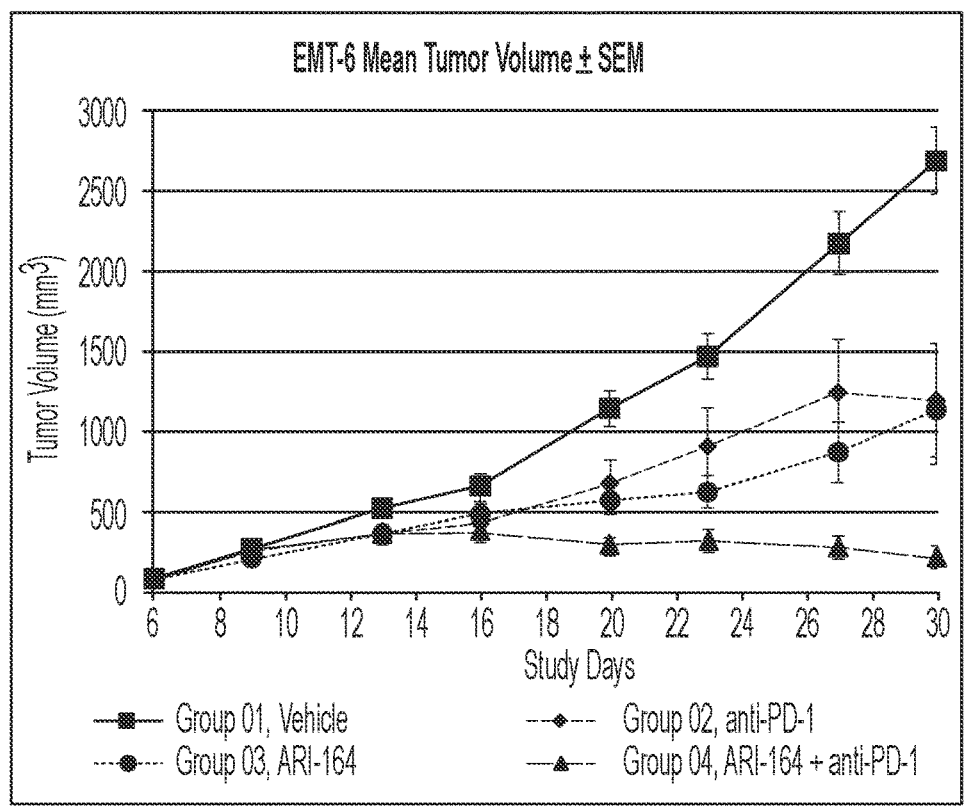

Combination of ARI-164 with an anti-PD-1 antibody led to significant tumor inhibition at study day 30 in the EMT-6 model (FIG. 21C).

Figure 21D:
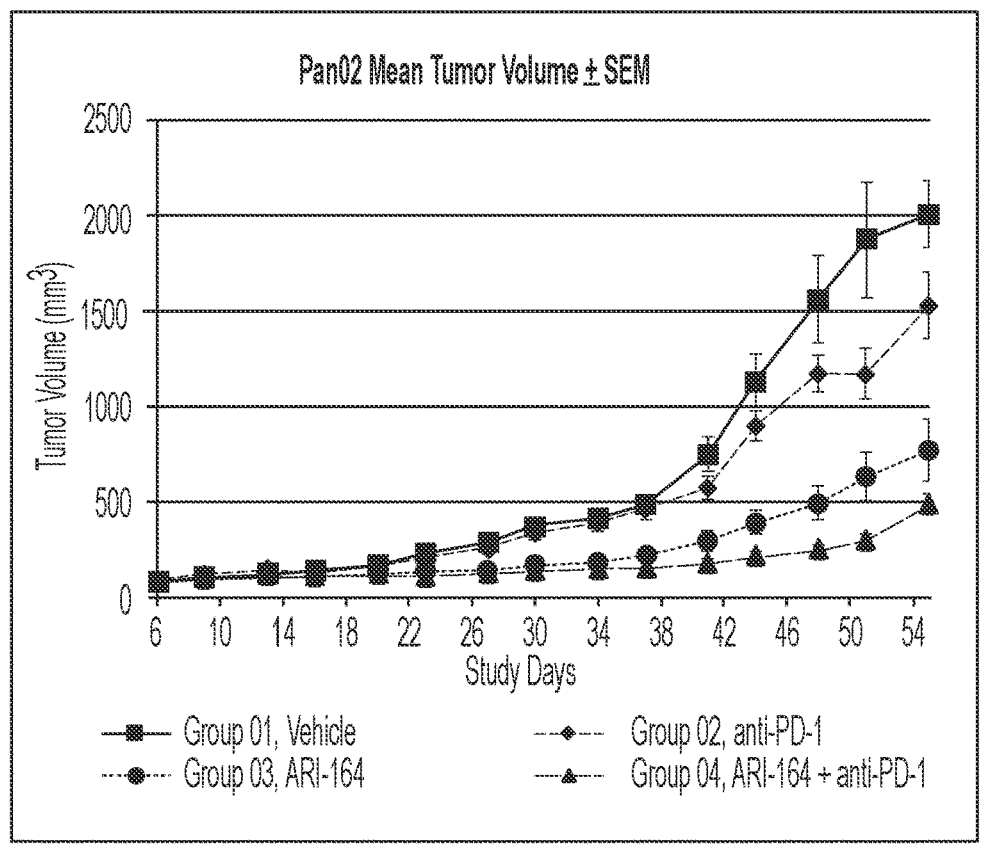

Combination of ARI-164 with an anti-PD-1 antibody led to increased tumor inhibition at study day 55 in Pan02, though given Pan02 is almost completely insensitive to anti-PD-1, the vast majority of this-activity was likely due to ARI-164 (FIG. 21D).

Figure 21E:
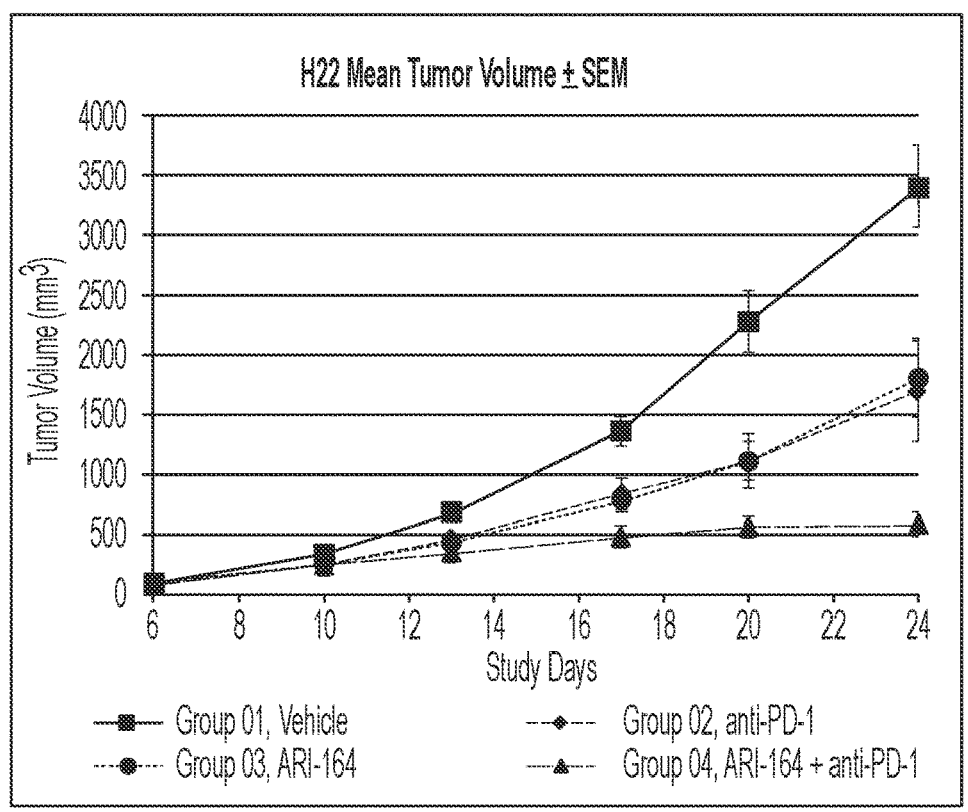

Combination of ARI-164 with an anti-PD-1 antibody led to significant tumor inhibition at study day 24 in the H22 model (FIG. 21E).

Figure 21F:
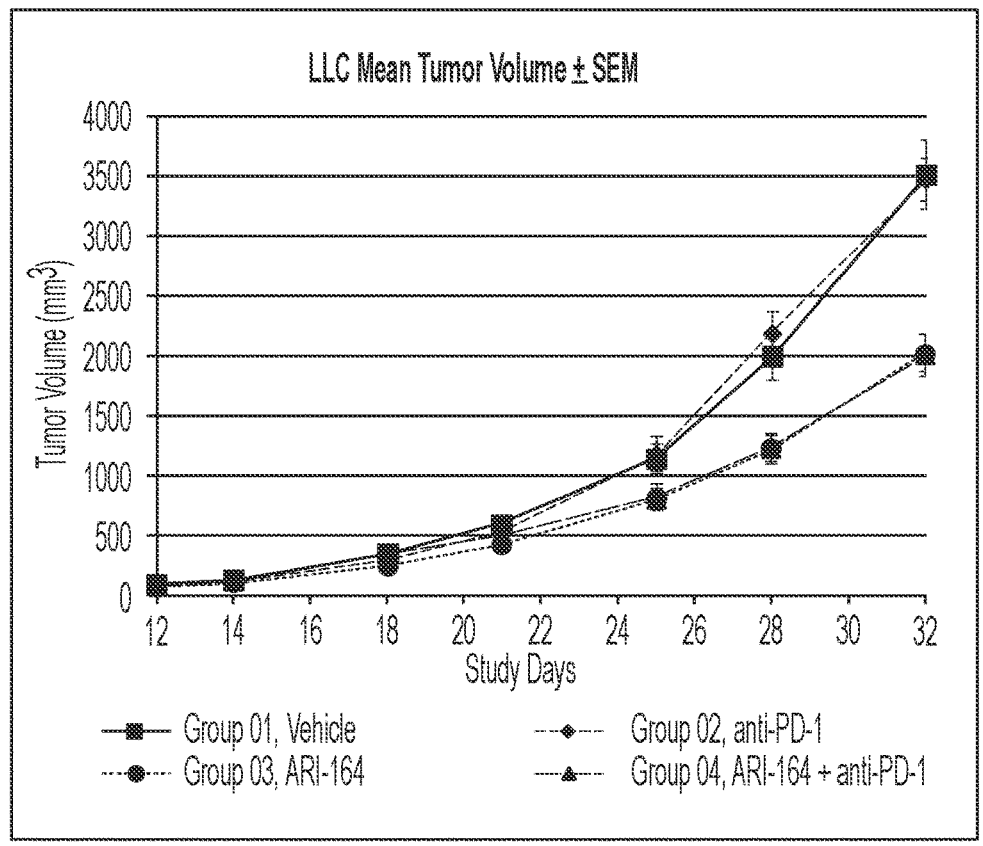

Combination of ARI-164 with an anti-PD-1 antibody led to tumor inhibition at study day 32, but the vast majority of this activity was likely due to ARI-164 (FIG. 21F).

Figure 21G:
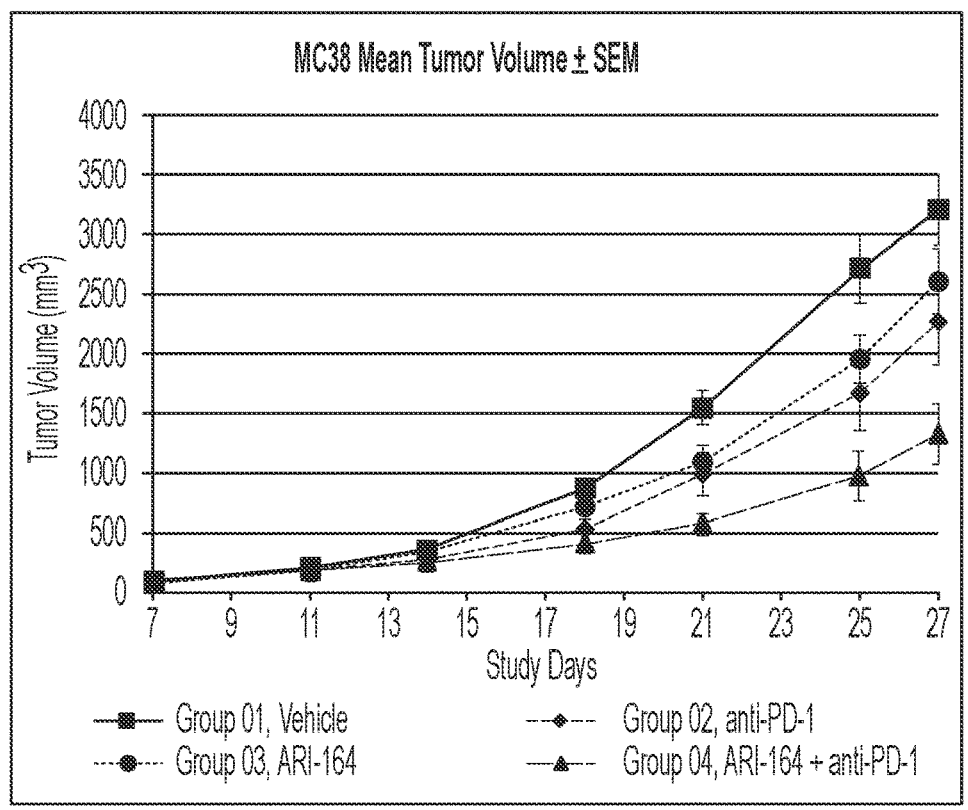

Combination of ARI-164 with an anti-PD-1 antibody led to significant tumor inhibition at study day 27 in the MC38 model (FIG. 21G).

The invention claimed is:

1. A compound of Structural Formula 8c or Structural Formula 8d, or a pharmaceutically acceptable salt thereof,

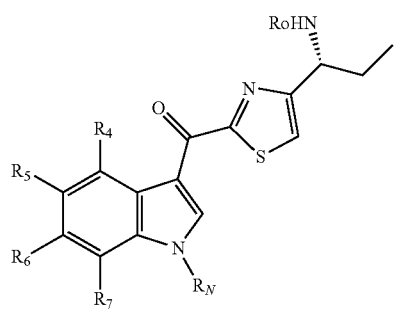

Structural Formula 8c

-continued

Structural Formula 8d

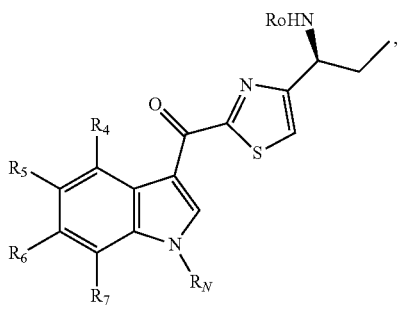

wherein
$R_4$ is H, at least one of $R_5$, $R_6$, and $R_7$ is F or Cl, and the others of $R_5$, $R_6$, and $R_7$ are each hydrogen;
$R_o$ is hydrogen, deuterium, or C1-C6 alkyl; and
$R_N$ is H, C1-C6 alkyl, or C2-C6 alkanoyl.

2. The compound of claim 1, wherein $R_o$ is H or C1-6 alkyl.

3. The compound of claim 1, wherein $R_5$ is F or Cl, and $R_4$, $R_6$, and $R_7$ are hydrogen.

4. The compound of claim 1, wherein $R_6$ is F or Cl, and $R_4$, $R_5$, and $R_7$ are hydrogen.

5. The compound of claim 1, wherein $R_7$ is F or Cl, and $R_4$, $R_5$, and $R_6$ are hydrogen.

6. The compound of claim 1, wherein $R_5$ and $R_6$ are F or Cl, and $R_4$ and $R_7$ are hydrogen.

7. The compound of claim 1, wherein $R_5$ and $R_7$ are F or Cl, and $R_4$ and $R_6$ are hydrogen.

8. The compound of claim 1, wherein $R_6$ and $R_7$ are F or Cl, and $R_4$ and $R_5$ are hydrogen.

9. A compound having the structure

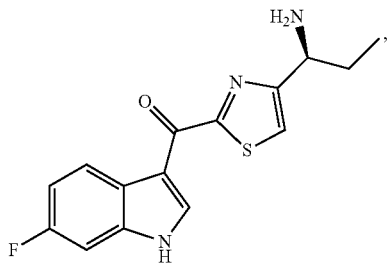 [SMILES: CC[C@@H](N)c1csc(C(=O)c2c[nH]c3cc(F)ccc23)n1]

or a pharmaceutically acceptable salt thereof.

10. A compound having the structure

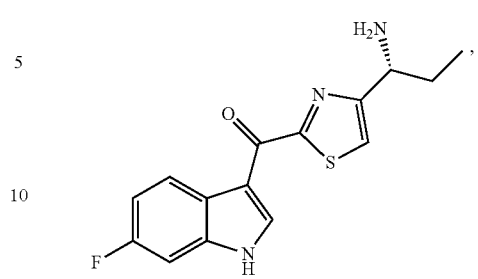

or a pharmaceutically acceptable salt thereof.

11. A pharmaceutical composition comprising the compound of claim 1 and a pharmaceutically acceptable carrier.

12. A pharmaceutical composition comprising the compound of claim 2 and a pharmaceutically acceptable carrier.

13. A pharmaceutical composition comprising the compound of claim 3 and a pharmaceutically acceptable carrier.

14. A pharmaceutical composition comprising the compound of claim 4 and a pharmaceutically acceptable carrier.

15. A pharmaceutical composition comprising the compound of claim 5 and a pharmaceutically acceptable carrier.

16. A pharmaceutical composition comprising the compound of claim 6 and a pharmaceutically acceptable carrier.

17. A pharmaceutical composition comprising the compound of claim 7 and a pharmaceutically acceptable carrier.

18. A pharmaceutical composition comprising the compound of claim 8 and a pharmaceutically acceptable carrier.

19. A pharmaceutical composition comprising the compound of claim 9 and a pharmaceutically acceptable carrier.

20. A pharmaceutical composition comprising the compound of claim 10 and a pharmaceutically acceptable carrier.

* * * * *